US012280105B2

(12) United States Patent
Ananthaswamy et al.

(10) Patent No.: US 12,280,105 B2
(45) Date of Patent: Apr. 22, 2025

(54) COMPOSITIONS AND METHODS OF mRNA VACCINES AGAINST NOVEL CORONAVIRUS INFECTION

(71) Applicant: RNAimmune, Inc., Gaithersburg, MD (US)

(72) Inventors: Neeti Ananthaswamy, Gaithersburg, MD (US); Yong-Sik Bong, Gaithersburg, MD (US); David Brown, Gaithersburg, MD (US); Renxiang Chen, Gaithersburg, MD (US); Ju Hyeong Jeon, Gaithersburg, MD (US); Zhifeng Long, Gaithersburg, MD (US); Dong Shen, Baltimore, MD (US); Chun Lu, Montreal (CA); Patrick Y. Lu, Potomac, MD (US); Shenggao Tang, Guangzhou (CN); Jiaxi He, Guangzhou (CN); Ziyang He, Potomac, MD (US)

(73) Assignee: RNAIMMUNE, INC., Gaithersburg, MD (US)

( * ) Notice: Subject to any disclaimer, the term of this patent is extended or adjusted under 35 U.S.C. 154(b) by 0 days.

(21) Appl. No.: 18/438,342

(22) Filed: Feb. 9, 2024

(65) Prior Publication Data

US 2024/0226275 A1 Jul. 11, 2024

Related U.S. Application Data

(63) Continuation of application No. PCT/US2022/039997, filed on Aug. 10, 2022.

(60) Provisional application No. 63/232,101, filed on Aug. 11, 2021.

(51) Int. Cl.

| | |
|---|---|
| ***A61K 39/215*** | (2006.01) |
| ***A61K 9/1271*** | (2025.01) |
| ***A61P 37/04*** | (2006.01) |
| ***C07K 14/005*** | (2006.01) |
| *A61K 39/00* | (2006.01) |

(52) U.S. Cl.

CPC .......... *A61K 39/215* (2013.01); *A61K 9/1271* (2013.01); *A61P 37/04* (2018.01); *C07K 14/005* (2013.01); *A61K 2039/53* (2013.01); *C12N 2770/18022* (2013.01); *C12N 2770/18034* (2013.01)

(58) Field of Classification Search

None

See application file for complete search history.

(56) References Cited

U.S. PATENT DOCUMENTS

| | | | |
|---|---|---|---|
| 10,973,909 | B1 | 4/2021 | Csiszovszki et al. |
| 12,029,786 | B2 | 7/2024 | Tang et al. |
| 2017/0340725 | A1 | 11/2017 | Ciaramella et al. |
| 2019/0240317 | A1 | 8/2019 | Ciaramella et al. |
| 2019/0351048 | A1 | 11/2019 | Rauch |
| 2021/0316002 | A1 | 10/2021 | Ellis |
| 2021/0388032 | A1 | 12/2021 | Langedijk et al. |
| 2022/0040292 | A1 | 2/2022 | Tang et al. |
| 2022/0064631 | A1 | 3/2022 | Barna et al. |
| 2023/0108926 | A1 | 4/2023 | Tang et al. |
| 2023/0117167 | A1 | 4/2023 | Mueller et al. |
| 2024/0156947 | A1 | 5/2024 | Brown et al. |

FOREIGN PATENT DOCUMENTS

| | | | | |
|---|---|---|---|---|
| CN | 115160413 A | 10/2022 | | |
| JP | 2004-536598 A | 12/2004 | | |
| JP | 2009-509516 A | 3/2009 | | |
| JP | 2015-513897 A | 5/2015 | | |
| WO | WO-2017049245 A2 * | 3/2017 | ......... | A61K 31/7105 |
| WO | WO-2018/160690 A1 | 9/2018 | | |
| WO | WO-2019/226940 A1 | 11/2019 | | |
| WO | WO-2021/159118 | 8/2021 | | |
| WO | WO-2021/247779 A1 | 12/2021 | | |
| WO | WO-2022/072910 A1 | 4/2022 | | |
| WO | WO-2023/018831 | 2/2023 | | |
| WO | WO-2023/079507 A1 | 5/2023 | | |
| WO | WO-2023/091766 A2 | 5/2023 | | |
| WO | WO-2024/094881 A1 | 5/2024 | | |

OTHER PUBLICATIONS

Final Office Action on U.S. Appl. No. 18/385,879 DTD Jul. 5, 2024.
International Search Report and Written Opinion on PCT/US2023/036540 DTD Feb. 27, 2024, 16 pages.
CDC COVID-19 Treatment Guidelines, Dec. 2023, pp. 18-21, available from https://files.covid19treatmentguidelines. nih.gov/guidelines/section/section_53.pdf (2023).
Kon et al., "Principles for designing an optimal mRNA lipid nanoparticle vaccine," Curr. Opin. Biotechnol., 73:329-336 (2022).
Nicholson et al., "Tales of Detailed Poly(A) Tails," Trends in Cell Biology, 29(3):191-200 (Mar. 2019).
Shi et al., "RBD-mRNA vaccine induces broadly neutralizing antibodies against Omicron and multiple other variants and protects mice from SARS-CoV-2 challenge," Transl. Res., 248:11-21 (Oct. 2022).
U.S. Appl. No. 18/385,879, filed Oct. 31, 2023, David Brown et al.
PCT/US2023/036540, Oct. 31, 2023, Rnaimmune, Inc.
Chan et al., "A familial cluster of pneumonia associated with the 2019 novel coronavirus indicating person-to-person transmission: a study of a family cluster", Lancet, 2020, vol. 395, pp. 514-523, Epub Jan. 24, 2020.

(Continued)

*Primary Examiner* — Stacy B Chen
(74) *Attorney, Agent, or Firm* — Foley & Lardner LLP

(57) ABSTRACT

Provided herein is a ribonucleic acid (RNA) encoding a spike (S) protein or an immunogenic fragment thereof of a severe acute respiratory syndrome coronavirus 2 (SARS-CoV-2) comprising at least one non-naturally occurring amino acid mutation. In some embodiments, the S protein is derived from a delta variant. Additionally provided are relevant polynucleotides, vectors, cells, compositions, kits, production methods and methods of use.

30 Claims, 33 Drawing Sheets

Specification includes a Sequence Listing.

(56) References Cited

OTHER PUBLICATIONS

Declaration of Non-Establishment of International Search Report, Written Opinion on PCT/US2022/039997 DTD Feb. 17, 2023, 6 pages.

Genbank, Accession: QHD43416.1, Surface Glycoprotein [Wuhan searfood market pneumonia virus], Jan. 23, 2020, www.ncbi.nlm.nih.gov/protein/1791269090?sat=48&satkey=1085346.

Genbank_CP006842, Corynebacterium glyciniphilum AJ3170, complete genome GenBank Accession No. CP006842, Apr. 8, 2015, www.ncbi.nlm.nih.gov/nuccore/CP006842.

Huang et al, "Clinical features of patients infected with 2019 novel coronavirus in Wuhan, China", Lancet, Feb. 15, 2020, vol. 395, pp. 497-506.

Liu et al., "Potential inhibitors against 2019-nCOV coronavirus M protease from clinically approved medicines", J. Genet Genomics, Feb. 20, 2020, vol. 47(2), pp. 119-121.

Ljungberg et al., "Self-Replicating Alphavirus RNA Vaccines," Expert Rev Vaccines, 14(2):177-94 (Feb. 2015).

Lu et al., "Genomic characterisation and epidemiology of 2019 novel coronavirus: implications for virus origins and receptor binding", Lancet, 2020, vol. 395, pp. 565-574, epub 2020.

Menachery et al., "A SARS-like cluster of circulating bat coronaviruses shows potential for human emergence", Nat Med. 2015, vol. 21(12), pp. 1508-1513.

Midoux et al., "Lipid-based mRNA Vaccine Delivery Systems," Expert Rev. Vaccines 14(2):221-234 (2015).

NCBI_NC_045512.2, Wuhan seafood market pneumonia virus isolate Wuhan-Hu-1, complete genome, NCBI accession No. NC_045512.2, Jan. 28, 2020, www.ncbi.nlm.nih.gov/nuccore/1798174254?sat=4&satkey=350670880.

SEQ ID# 1, U.S. Appl. No. 17/794,862, prior art year of search 2023, https://dav.uspto.gov/webapp/applicationViewer.html?casenumber=17170876, 3 pages.

Zhou et al., "A pneumonia outbreak associated with a new coronavirus of probably bat origin", Nature, 2020, vol. 579, pp. 270-273, Epub Feb. 3, 2020.

Notice of Allowance on U.S. Appl. No. 18/385,879 DTD Aug. 23, 2024.

Lancet, Jan. 2020, and vol. 395 and pp. 565-574, <Https://Doi.Org/10.1016/S0140-6736 (20) 30251-8> (Document Showing a Well-known Technique). 10 pgs.

Zhang YZ et al. and Wuhan seafood market pneumoniavirus isolate Wuhan-Hu-1, complete genome and Database DDBJ/EMBL/GenBank[online], Jan. 14, 2020, AccessionNo.MN908947, and <https://www.ncbi.nlm.nih.gov/nuccore/1796487982?sat=47&satkey=151862760> [Date of search Jan. 28, 2025] (Document showing a well-known technique). 10 pgs.

* cited by examiner

| A549 | SARS-CoV-2 S WT(SBI) | SARS-CoV-2 S WT(100%) | SARS-CoV-2 S2P WT | SARS-CoV-2 S2P D614G | SARS-CoV-2 D614G WT | SARS-CoV-2 S6P_UK | SARS-CoV-2 S6P_SA | SARS-CoV-2 S6P_SA_GS | SARS-CoV-2 S RBD |
|---|---|---|---|---|---|---|---|---|---|
| 1 | 2 | 3 | 4 | 5 | 6 | 7 | 8 | 9 | 10 |
| 0 | 10.60345 | 0 | 0 | 0 | 0 | 0 | 0 | 0 | |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |
| 0 | 0 | 0 | 0 | 0 | 0 | 0 | 0 | 0 | 0 |

IFN-α concentration secreted = 10.6 pg/100ul supernatant × 10 = 106 pg/ml

FIG. 5B

| A549 | SARS-CoV-2 S WT(SBI) | SARS-CoV-2 S WT(100%) | SARS-CoV-2 S2P WT | SARS-CoV-2 S2P D614G | SARS-CoV-2 D614G WT | SARS-CoV-2 S6P_UK | SARS-CoV-2 S6P_SA | SARS-CoV-2 S6P_SA_GS | SARS-CoV-2 S RBD |
|---|---|---|---|---|---|---|---|---|---|
| 1 | 2 | 3 | 4 | 5 | 6 | 7 | 8 | 9 | 10 |
| 0 | 714.153.8 | 0 | 90.30769 | 0 | 99.53846 | 0 | 12.61538 | 0 | |
| 0 | 357.0769 | 0 | 45.15385 | 0 | 49.76923 | 0 | 6.307692 | 0 | 0 |
| 0 | 244.3846 | 0 | 29 | 0 | 32.84615 | 0 | 1.692308 | 0 | 0 |
| 0 | 164.7692 | 0 | 18.61538 | 0 | 19.38462 | 0 | | 0 | 0 |
| 0 | 98.23077 | 0 | 6.692308 | 0 | 35.53846 | 0 | 0 | 0 | 0 |
| 0 | 51.30769 | 0 | 2.846154 | 0 | 1.692308 | 0 | 0 | 0 | 0 |
| 0 | 23.61538 | 0 | 0.923077 | 0 | 0 | 0 | 0 | 0 | 0 |
| 0 | 10.15385 | 0 | 0 | 0 | 0 | 0 | 0 | 0 | 0 |

IFN-α concentration secreted = 10.6 pg/100ul supernatant × 10 = 106 pg/ml

FIG. 6B

PBS
SARS-CoV-2 Delta S6P 1ug
SARS-CoV-2 Delta S6P 5ug
SARS-CoV-2 Delta S6P 10ug

| | Brazil | 614D | UK | Delta | 614G | SA |
|---|---|---|---|---|---|---|
| Bottom | -15.62 | 7.732 | 30.58 | ~ 20.32 | 32.71 | ~ 36.38 |
| Top | 100.2 | 98.64 | 103.4 | 96.09 | 99.09 | 96.21 |
| LogIC50 | 0.1078 | 0.1586 | ~ 0.3087 | ~ 0.3568 | ~ 0.3392 | ~ 0.7679 |
| HillSlope | -0.7194 | -1.103 | ~ -13.53 | ~ -5.223 | ~ -9.990 | ~ -13.08 |
| IC50 | 1.282 | 1.441 | ~ 2.035 | ~ 2.274 | ~ 2.184 | ~ 5.861 |
| Span | 115.8 | 90.91 | 72.81 | ~ 75.77 | 66.38 | ~ 59.83 |

| | Brazil | 614D | UK | Delta | 614G | SA |
|---|---|---|---|---|---|---|
| Bottom | 1.599 | -2.077 | -10.53 | -9.014 | -6.549 | -7.281 |
| Top | 98.14 | 101.5 | 103.9 | 103.3 | 104.7 | 103.3 |
| LogIC50 | -1.687 | -1.268 | -0.7468 | -0.9301 | -1.049 | -0.8520 |
| IC50 | 0.02058 | 0.05393 | 0.1791 | 0.1175 | 0.08928 | 0.1406 |
| Span | 96.54 | 103.6 | 114.5 | 112.3 | 111.2 | 110.6 |

| | G1 | G3 | G2 | G4 | G5 |
|---|---|---|---|---|---|
| Bottom | 27.93 | 19.93 | 12.05 | 8.802 | 5.295 |
| Top | 100.0 | 100.0 | 99.99 | 99.99 | 99.99 |
| LogIC50 | -1.504 | -1.532 | -1.546 | -1.421 | -1.370 |
| HillSlope | -1.644 | -1.818 | -1.390 | -1.329 | -1.905 |
| IC50 | 0.03137 | 0.02934 | 0.02844 | 0.03796 | 0.04269 |
| Span | 72.07 | 80.08 | 87.94 | 91.19 | 94.69 |

| | G1 | G3 | G2 | G4 | G5 |
|---|---|---|---|---|---|
| Bottom | 17.32 | 10.39 | 6.301 | 4.964 | 3.560 |
| Top | 99.99 | 100.0 | 100.0 | 100.0 | 100.0 |
| LogIC50 | -0.6918 | -1.370 | -0.6441 | -1.017 | -1.023 |
| HillSlope | -3.387 | -2.224 | -3.658 | -2.705 | -4.180 |
| IC50 | 0.2034 | 0.04262 | 0.2270 | 0.09613 | 0.09491 |
| Span | 82.67 | 89.61 | 93.61 | 95.04 | 96.45 |

| | G1 | G3 | G2 | G4 | G5 |
|---|---|---|---|---|---|
| Bottom | 50.87 | 36.50 | 25.20 | 14.55 | 0.148 |
| Top | 99.98 | 99.98 | 100.0 | 99.98 | 99.98 |
| LogIC50 | -0.4525 | -1.199 | -0.8310 | -0.6647 | -0.8470 |
| HillSlope | -2.304 | -2.294 | -2.505 | -2.419 | -2.342 |
| IC50 | 0.3528 | 0.06324 | 0.1476 | 0.2164 | 0.1422 |
| Span | 40.12 | 63.48 | 74.82 | 85.43 | 99.84 |

| | G1 | G3 | G2 | G4 | G5 |
|---|---|---|---|---|---|
| Bottom | 13.63 | 7.899 | 5.324 | 3.106 | 1.741 |
| Top | 100.0 | 100.0 | 100.0 | 100.0 | 100.0 |
| LogIC50 | -0.4659 | -0.9044 | -0.4099 | -0.3405 | -0.6234 |
| HillSlope | -2.345 | -3.170 | -3.711 | -3.185 | -3.214 |
| IC50 | 0.3421 | 0.1246 | 0.3891 | 0.4566 | 0.2380 |
| Span | 86.37 | 92.10 | 94.68 | 96.89 | 98.26 |

| Group | G1 | G2 | G3 | G4 | G5 |
|---|---|---|---|---|---|
| 1ST immunization | BNT162b2 | mRNA-1273 | RV-1730 | BNT162b2 | mRNA-1273 |
| 2ND immunization | BNT162b2 | mRNA-1273 | RV-1730 | RV-1730 | RV-1730 |
| WT | 0.031 | 0.028 | 0.029 | 0.038 | 0.043 |
| Delta | 0.203 | 0.0227 | 0.043 | 0.096 | 0.095 |
| Omicron BA.1 | 0.353 | 0.148 | 0.063 | 0.216 | 0.142 |
| Omicron BA.2 | 0.341 | 0.389 | 0.125 | 0.457 | 0.238 |

FIG. 20

COMPOSITIONS AND METHODS OF mRNA VACCINES AGAINST NOVEL CORONAVIRUS INFECTION

CROSS-REFERENCE TO RELATED APPLICATION

This application is a continuation of International Patent Application No. PCT/US2022/039997, filed Aug. 10, 2022, which claims priority to U.S. Provisional application No. 63/232,101, filed Aug. 11, 2021, the contents of which are hereby incorporated by reference in its entirety.

INCORPORATION BY REFERENCE OF SEQUENCE LISTING

The instant application contains a Sequence Listing which has been submitted electronically in XML format and is hereby incorporated by reference in its entirety. Said XML copy, created on Oct. 17, 2022, is named 129774-0185.xml and is 126,559 bytes in size.

TECHNICAL FIELD

Prophylactic and therapeutic agents for vaccination, prevention and treatment of 2019-nCoV infections are provided.

BACKGROUND

Coronaviruses (CoVs) have repeatedly crossed species barriers and some have emerged as important human pathogens. During the past two decades, two coronaviruses infecting animals have evolved and caused outbreaks in humans: severe acute respiratory syndrome-related coronavirus (SARS-CoV, 2002, genus: *Betacoronavirus*, subgenus: *Sarbecovirus*), and Middle East respiratory syndrome-related coronavirus (MERS-CoV, 2012, genus: *Betacoronavirus*, subgenus: *Merbecovirus*). See, for example, Drosten et al., *New Engl J Med.* 2003; 348: 1967-1976; and Zaki et al., *New Engl J Med.* 2012; 367:1814-1820.

The SARS-CoV-2 2019 (COVID-19) is a new strain of coronavirus that causes coronavirus disease. See, for example, Zhu et al., *N Engl J Med.* 2020, 382:727-733. Accordingly to the COVID-19 Weekly Epidemiological Update and Weekly Operational Update dated Jul. 26, 2021 and published by World Health Organization (WHO), there are close to 200 million confirmed cases and more than 4 million confirmed deaths worldwide. No cure is available for COVID-19, while steroid has been used for therapeutic management of hospitalized adults, and the Food and Drug Administration (FDA) has issued Emergency Use Authorizations (EUAs) for anti-SARS-CoV-2 antibodies in treating non-hospitalized individuals with COVID-19, such as sotrovimab, and the combination of casirivimab and imdevimab. See, for example, COVID-19 Treatment Guidelines Panel. Coronavirus Disease 2019 (COVID-19) Treatment Guidelines. National Institutes of Health. available at www.covid19treatmentguidelines.nih.gov and last accessed on Jul. 27, 2021.

Accordingly, there remains an urgent need for effective prevention and treatment of a SARS-CoV-2 infection. This disclosure satisfies this need and provides related advantages as well.

SUMMARY

Provided herein are spike (s) proteins or immunologic fragments thereof as well as a deoxyribonucleic acid (DNA)

or a ribonucleic acid (RNA) encoding a spike (S) protein or an immunogenic fragment thereof of a severe acute respiratory syndrome coronavirus 2 (SARS-CoV-2). The S protein or immunogenic fragment thereof comprises or consists essentially of, or yet further consists of at least one non-naturally occurring amino acid mutation, for example, as compared to an S protein of a SARS-CoV-2 delta variant, such as SEQ ID NO: 1 or a variant thereof. In some embodiments, the at least one non-naturally occurring amino acid mutation comprises, or alternatively consists essentially of, or yet further consists of one or more of: a serine (S) as the amino acid corresponding to R682 of SEQ ID NO: 1 (R682S), a glycine (G) as the amino acid corresponding to R685 of SEQ ID NO: 1 (R685G), a proline (P) as the amino acid corresponding to F817 of SEQ ID NO: 1 (F817P), a P as the amino acid corresponding to A892 of SEQ ID NO: 1 (A892P), a P as the amino acid corresponding to A899 of SEQ ID NO: 1 (A899P), a P as the amino acid corresponding to A942 of SEQ ID NO: 1 (A942P), a P as the amino acid corresponding to K986 of SEQ ID NO: 1 (K986P), or a P as the amino acid corresponding to V987 of SEQ ID NO: 1 (V987P). In some embodiments, the RNA encoding a spike (S) protein or an immunogenic fragment thereof does not comprise SEQ ID NO: 2. In one aspect, the RNA encoding the S protein or an immunogenic fragment thereof comprises SEQ ID NO: 55. In some embodiments, the RNA is a messenger RNA (mRNA).

In some embodiments, the mRNA encodes an S protein that further comprises, or consisting essentially of, or yet further consisting of, one or more of mutations which can be found in a SARS-CoV-2 naturally occurring variant, such as a delta variant. In some embodiments, these mutations comprise, or alternatively consist essentially of, or yet further consist of one or more of: a lysine (K) as the amino acid corresponding to N440 of SEQ ID NO: 1 (N440K), a K as the amino acid corresponding to E484 of SEQ ID NO: 1 (E484K), an arginine (R) as the amino acid corresponding to T19 of SEQ ID NO: 1 (T19R), a phenylalanine (F) as the amino acid corresponding to V70 of SEQ ID NO: 1 (V70F), an isoleucine (I) as the amino acid corresponding to T95 of SEQ ID NO: 1 (T95I), an aspartic acid (D) as the amino acid corresponding to G142 of SEQ ID NO: 1 (G142D), a deletion corresponding to E156 of SEQ ID NO: 1 (E156Δ), a deletion corresponding to F157 of SEQ ID NO: 1 (F157Δ), a G as the amino acid corresponding to R158 of SEQ ID NO: 1 (R158G), a valine (V) as the amino acid corresponding to A222 of SEQ ID NO: 1 (A222V), a leucine (L) as the amino acid corresponding to W258 of SEQ ID NO: 1 (W258L), an asparagine (N) as the amino acid corresponding to K417 of SEQ ID NO: 1 (K417N), an R as the amino acid corresponding to K417 of SEQ ID NO: 1 (L452R), a K as the amino acid corresponding to T478 of SEQ ID NO: 1 (T478K), a G as the amino acid corresponding to D614 of SEQ ID NO: 1 (D614G), an R as the amino acid corresponding to P681 of SEQ ID NO: 1 (P681R), or an N as the amino acid corresponding to D950 of SEQ ID NO: 1 (D950N).

In some embodiments, the S protein or an immunogenic fragment thereof comprises, or alternatively consists essentially of, or yet further consists of the polypeptide of any one of SEQ ID NO: 5, 6, 7, 10, 11, or 14, or an equivalent of each thereof. This disclosure further provides the RNA or DNA encoding these polypeptides and equivalents thereof. In some embodiments, the RNA comprises, or alternatively consists essentially of, or yet further consists of the polynucleotide of SEQ ID NO: 9, 13, or 16, or an equivalent of each thereof. In some embodiments, the RNA further comprises one or more of a three prime untranslated region (3' UTR), a polyadenylation (polyA) tail and a five prime untranslated region (5' UTR). In some embodiments, the RNA comprises, or alternatively consists essentially of, or yet further consists of SEQ ID NO: 32. SEQ ID NOs: 9, 13, 16 encode S polypeptides. SEQ ID NO: 32 is SEQ ID NO: 9, further comprising the 5 and 3' UTRs and a polyA tail.

In one aspect, provided is a polynucleotide, such as a DNA, encoding an RNA as disclosed herein. Also provided are complements of the encoding DNA. In a further aspect, provided is a vector comprising a polynucleotide as disclosed herein. In one embodiment, the vector is a plasmid, optionally comprising, or alternatively consisting essentially of, or yet further consisting of SEQ ID NO: 33 or an equivalent thereof. In yet a further aspect, provided is a cell comprising one or more of: an RNA as disclosed herein, a polynucleotide as disclosed herein, or a vector as disclosed herein. In one aspect, provided is a composition comprising, or alternatively consisting essentially of, or yet further consisting of a carrier, optionally a pharmaceutically acceptable carrier and one or more of: an RNA as disclosed herein, a polynucleotide as disclosed herein, a vector as disclosed herein, or a cell as disclosed herein.

Additionally provided is a method of producing DNA or an RNA as disclosed herein. In some embodiments, the method comprises, or alternatively consists essentially of, or yet further consisting of culturing a cell as disclosed herein under conditions suitable for expressing the DNA and/or the RNA. In other embodiments, the method comprises, or alternatively consists essentially of, or yet further consists of contacting a polynucleotide or a vector as disclosed herein with an RNA polymerase, adenosine triphosphate (ATP), cytidine triphosphate (CTP), guanosine-5'-triphosphate (GTP), and uridine triphosphate (UTP) or a chemically modified UTP (such as N1-methyl pseudouridine trisphosphate) under conditions suitable for expressing the RNA. In further embodiments, a method as disclosed herein further comprises isolating the DNA or the RNA.

In one aspect, provided is a composition comprising, or alternatively consisting essentially of, or yet further consisting of a protein, a polypeptide, an RNA or DNA as disclosed herein and a carrier such as a pharmaceutically acceptable carrier. In some embodiments, the pharmaceutically acceptable carrier comprises, or alternatively consists essentially of, or yet further consists of a polymeric nanoparticle. In further embodiments, the polymeric nanoparticle comprises, or alternatively consists essentially of, or yet further consists of a Histidine-Lysine co-polymer (HKP). In some embodiments, the pharmaceutically acceptable carrier further comprises a lipid, optionally one or more of: a cationic lipid (such as Dlin-MC3-DMA, i.e., MC3), a helper lipid, a cholesterol, or a PEGylated lipid. In some embodiments, the pharmaceutically acceptable carrier comprises, or alternatively consists essentially of, or yet further consists of a lipid nanoparticle (LNP). In some embodiments, the LNP comprises one or more of: 9-Heptadecanyl 8-{(2-hydroxyethyl)[6-oxo-6-(undecyloxy)hexyl]amino}octanoate (SM-102), 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), or an equivalent of each thereof. In further embodiments, the LNP further comprises one or more of: a helper lipid, a cholesterol, or a PEGylated lipid. A further pharmaceutically acceptable carrier can be added to the nanoparticle composition, e.g., phosphate buffered saline and the like.

In further embodiments, the pharmaceutically acceptable carrier further comprises a dilute, an adjuvant, a binder, a stabilizer, a buffer, a salt, a lipophilic solvent, or a preservative. In some embodiments, the nanoparticle is a self-assembled nanoparticle. In a further aspect, provided is a composition comprising, or alternatively consisting essentially of, or yet further consisting of a self-assembled nanoparticle comprising an RNA as disclosed herein. In some embodiments, the nanoparticle encapsulates the RNA. In other embodiments, the nanoparticle is conveniently or non-covalently linked to the RNA.

In a further embodiments, provided is a method of producing the composition. In some embodiments, the method comprises, or alternatively consists essentially of, or yet further consists of contacting an RNA as disclosed herein with an HKP, thereby the RNA and the HKP are self-assembled into nanoparticles. Additionally or alternatively, the method comprises, or alternatively consists essentially of, or yet further consist of contacting an RNA as disclosed herein with a lipid, thereby the RNA and the lipid are self-assembled into nanoparticles. In further embodiment, the contacting step is performed in a microfluidic mixer, such as NanoAssemblr Ignite.

In another aspect, provided is a method of one or more of: (a) preventing a subject from having a symptomatic SARS-CoV-2 infection, (b) inducing an immune response to SARS-CoV-2 in a subject in need thereof, (c) reducing the binding of a SARS-CoV-2 or an S protein thereof with angiotensin converting enzyme 2 (ACE2) in a subject in need thereof, (d) treating a subject infected with SARS-CoV-2, or (c) reducing a SARS-CoV-2 viral load in a subject in need thereof. The method comprises, or alternatively consists essentially of, or yet further consists of administering to the subject one or more of: an RNA or DNA as disclosed herein, a polynucleotide as disclosed herein, a vector as disclosed herein, or a composition as disclosed herein.

In one aspect, provided is an inhalation system comprising, or alternatively consisting essentially of, or yet further consisting of an RNA or DNA as disclosed herein, a polynucleotide as disclosed herein, a vector as disclosed herein, or a composition as disclosed herein, and a nebulizer.

In another aspect, provided is a method of producing a spike (S) protein or an immunogenic fragment thereof of a severe acute respiratory syndrome coronavirus 2 (SARS-CoV-2). The method comprises, or alternatively consists essentially of, or yet further consists of culturing a cell as disclosed herein under conditions suitable for expressing the S protein or immunogenic fragment thereof. In further embodiments, the method herein further comprises isolating the S protein or immunogenic fragment thereof. Alternatively or in addition, the S protein or an immunogenic fragment thereof can be produced by administering a composition comprising the DNA and/or RNA to a subject.

Additionally, provided is a method for screening a candidate agent reducing or inhibiting the binding of SARS-CoV-2 and its receptor, such as ACE2, optionally in a subject or on a cell of the subject or both. The method comprises, or alternatively consist essentially of, or yet further consists of expressing a spike (S) protein or an immunogenic fragment thereof from an RNA as disclosed herein, and measuring the binding between the expressed S protein or immunogenic fragment thereof and the SARS-CoV-2 receptor, such as ACE2, with or without the presence of the candidate agent or with different concentrations of the candidate agent. In some embodiments, less binding between the expressed S protein or immunogenic fragment thereof and the SARS- CoV-2 receptor with the presence of the candidate agent compared to without the candidate agent, indicates that the candidate agent reduces or inhibits the binding of SARS-CoV-2 and its receptor. In some embodiments, decreased binding between the expressed S protein or immunogenic fragment thereof and the SARS-CoV-2 receptor while increasing the concentration of the candidate agent indicates the candidate agent reduces or inhibits the binding of SARS-CoV-2 and its receptor.

In yet a further aspect, provided is a method for selecting an RNA encoding a spike (S) protein or an immunogenic fragment thereof of a severe acute respiratory syndrome coronavirus 2 (SARS-CoV-2). The method comprises, or alternatively consists essentially of, or yet further consists of transducing the RNA into a cell, culturing the cell under conditions suitable for expressing the RNA, and measuring IFN-α or IFN-β or both secreted by the cell. In some embodiments, the method further comprises selecting the RNA if no secretion of IFN-α or IFN-β or both or less secretion of IFN-α or IFN-β or both compared to an RNA encoding a wild type S protein or an immunogenic fragment thereof.

Also provided is a kit for use in a method as described herein. In some embodiments, the kit comprises, or alternatively consists essentially of, or yet further consists of instructions for use and one or more of: an RNA as disclosed herein, a polynucleotide as disclosed herein, a vector as disclosed herein, a composition as disclosed herein, or an inhalation system as disclosed herein.

BRIEF DESCRIPTION OF THE DRAWINGS

FIG. 2B, polyA 60 (SEQ ID NO: 28 or 57)) or no PolyA tail (FIG. 2C).

FIGS. 5A-5B provide a quantitative result of an IFN-α ELISA as demonstrated in Example 9. FIG. 5A is the standard curve while FIG. 5B provides the corresponding calculation.

FIGS. 6A-6B provide a quantitative result of an IFN-β ELISA result as demonstrated in Example 9. FIG. 6A is the standard curve while FIG. 6B provides the corresponding calculation.

FIG. 8A shows group mean body weights of non-immunized and immunized mice. FIG. 8B shows group mean body weights of non-immunized and immunized mice after viral challenge with SARS-CoV-2/human/ITA/INMI1/2020 isolate (NCBI Accession number: MT066156). Body weight in mice of Groups 1 to 4 after immunization at NLS, and after viral challenge with SARS-CoV-2/human/ITA/INMI1/2020 isolate. Body weight of each individual mouse was calculated as a percentage of body weight measured after delivery to NLS, and as a percentage of body weight measured before viral challenging at GMU. The mean and standard error of the mean (SEM) for each group of mice are presented. Group 1—"C" is represents control non-immunized mice. FIG. 8C shows group mean body weights of non-immunized and immunized mice prior to viral challenge with SARS-CoV-2 B.1.1617.2 Delta variant. FIG. 8D shows group mean body weights of non-immunized and immunized mice after viral challenge with SARS-CoV-2 B.1.1617.2 Delta variant. m-Co is a control vaccine delivered at Low Dose (0.50 μg/mouse) and High Dose (5 μg/mouse). Non-control mice were vaccinated with RV-1730 (labeled "RNAImmune in FIG. 8C and FIG. 8D) which uses an RL-007 carrier.

FIG. 11A shows $PRNT_{50}$ of post-prime immunization mouse serum collected on Day 13; FIG. 11B shows $PRNT_{90}$ of post-prime immunization mouse serum collected on Day 13; FIG. 11C shows $PRNT_{50}$ of post-boost immunization mouse serum collected on Day 27; FIG. 11D shows $PRNT_{90}$ of post-boost immunization mouse serum collected on Day 27. Symbols and horizontal lines represent individual titers of each sample and mean titers of each group, respectively. Serum titers were expressed as reciprocals $Log_2$ dilution. Experiments are described in Example 10.

FIG. 15A shows images taken and quantified by using Cytation7. $^{*}P<0.05$, $^{**}P<0.001$. FIG. 15B is a graph quantifying IFN-γ spots per $2\times10^5$ cells re-stimulated ex vivo with Delta Spike protein subunit S1. FIG. 15**C is a graph quantifying IFN-γ spots per $2\times10^5$ cells re-stimulated ex vivo with Delta Spike protein subunit S2. Experiments are described in Example 15.

FIG. 20 is a graph of $IC_{50}$ (serum %) of heterologous vaccination sera in a pseudovirus neutralizing assay across five groups of mice (G1, G2, G3, G4 and G5). Neutralization antibody titers against SARS-CoV-2 pseudovirus particles including wild-type SARS-CoV-2, Delta SARS-CoV-2, Omicron BA.1 SARS-CoV-2, and Omicron BA.2 SARS-CoV-2, were measured following first and second SARS-CoV-2 mRNA vaccine immunization doses. Mice received a combination of first and second vaccine immunization doses of RV-1730, or a SARS-CoV-2 vaccine as known in the art, such as BNT162b2 available from Pfizer-BioNTech, or mRNA-1273 available from Moderna. Experiments are described in Example 13.

DETAILED DESCRIPTION

Definitions

Figure 1:
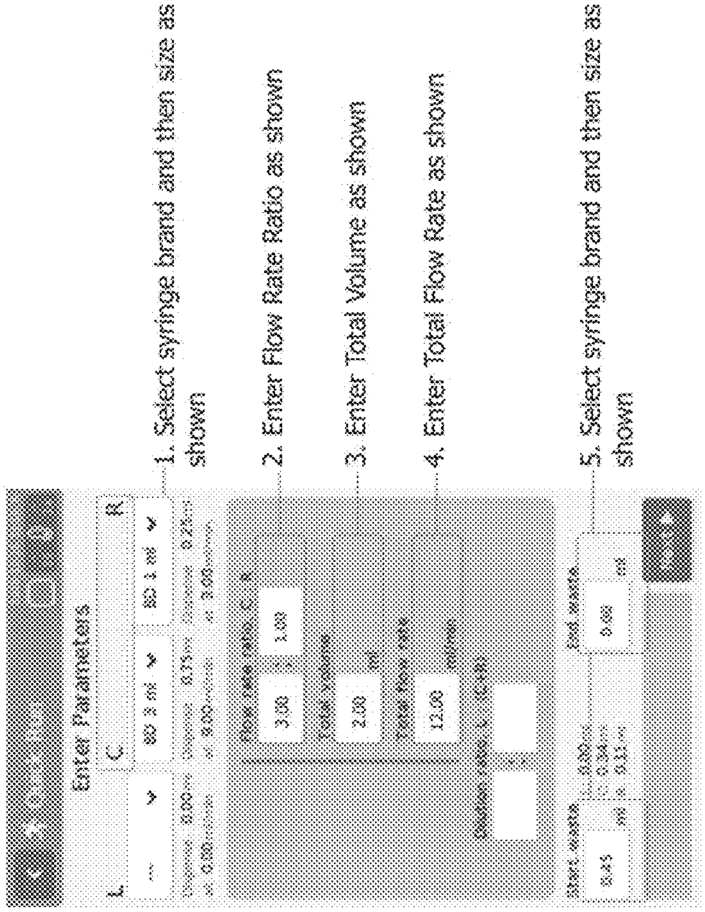
FIG. 1 provides a representative parameter setting of NanoAssemblr Ignite for producing an RNA in a RL-007 lipid. RL-007 is prepared by mixing a final concentration of 6.25 mM of SM-102, 1.25 mM of DSPC, 4.815 mM of Cholesterol, and 0.1875 of mM DMG-PEG2000 (i.e., a 50:10:38:1.5 molar ratio). 0.13 mg/mL of mRNA was mixed in a 3:1 (v/v) ratio with RL-007.

As it would be understood, the section or subsection headings as used herein is for organizational purposes only and are not to be construed as limiting and/or separating the subject matter described.

It is to be understood that this disclosure is not limited to particular embodiments described, as such may, of course, vary. It is also to be understood that the terminology used herein is for the purpose of describing particular embodiments only, and is not intended to be limiting, since the scope of this disclosure will be limited only by the appended claims.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present disclosure, the preferred methods, devices, and materials are now described. All technical and patent publications cited herein are incorporated herein by reference in their entirety. Nothing herein is to be construed as an admission that the disclosure is not entitled to antedate such disclosure by virtue of prior disclosure.

The practice of the present disclosure will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3rd edition (Cold Spring Harbor Laboratory Press (2002)); Sohail (ed.) (2004) Gene Silencing by RNA Interference: Technology and Application (CRC Press); and Plotkin et al., Plotkin; s Human Vaccines, $7^{th}$ edition (Elsevier).

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compounds, compositions and methods include the recited elements, but not exclude others. "Consisting essentially of" when used to define compounds, compositions and methods, shall mean excluding other elements of any essential significance to the combination. Thus, a composition consisting essentially of the elements as defined herein would not exclude trace contaminants, e.g., from the isolation and purification method and pharmaceutically acceptable carriers, preservatives, and the like. "Consisting of" shall mean excluding more than trace elements of other ingredients. Embodiments defined by each of these transition terms are within the scope of this technology.

All numerical designations, e.g., pH, temperature, time, concentration, and molecular weight, including ranges, are approximations which are varied (+) or (−) by increments of 1, 5, or 10%. It is to be understood, although not always explicitly stated that all numerical designations are preceded by the term "about." It also is to be understood, although not always explicitly stated, that the reagents described herein are merely exemplary and that equivalents of such are known in the art.

The term "about," as used herein when referring to a measurable value such as an amount or concentration and the like, is meant to encompass variations of 20%, 10%, 5%, 1%, 0.5%, or even 0.1% of the specified amount.

As used herein, comparative terms as used herein, such as high, low, increase, decrease, reduce, or any grammatical variation thereof, can refer to certain variation from the reference. In some embodiments, such variation can refer to about 10%, or about 20%, or about 30%, or about 40%, or about 50%, or about 60%, or about 70%, or about 80%, or about 90%, or about 1 fold, or about 2 folds, or about 3 folds, or about 4 folds, or about 5 folds, or about 6 folds, or about 7 folds, or about 8 folds, or about 9 folds, or about 10 folds, or about 20 folds, or about 30 folds, or about 40 folds, or about 50 folds, or about 60 folds, or about 70 folds, or about 80 folds, or about 90 folds, or about 100 folds or more higher than the reference. In some embodiments, such variation can refer to about 1%, or about 2%, or about 3%, or about 4%, or about 5%, or about 6%, or about 7%, or about 8%, or about 0%, or about 10%, or about 20%, or about 30%, or about 40%, or about 50%, or about 60%, or about 70%, or about 75%, or about 80%, or about 85%, or about 90%, or about 95%, or about 96%, or about 97%, or about 98%, or about 99% of the reference.

As will be understood by one skilled in the art, for any and all purposes, all ranges disclosed herein also encompass any and all possible subranges and combinations of subranges thereof. Furthermore, as will be understood by one skilled in the art, a range includes each individual member.

"Optional" or "optionally" means that the subsequently described circumstance may or may not occur, so that the description includes instances where the circumstance occurs and instances where it does not.

As used herein, "and/or" refers to and encompasses any and all possible combinations of one or more of the associated listed items, as well as the lack of combinations when interpreted in the alternative ("or").

"Substantially" or "essentially" means nearly totally or completely, for instance, 95% or greater of some given quantity. In some embodiments, "substantially" or "essentially" means 95%, 96%, 97%, 98%, 99%, 99.5%, or 99.9%.

The terms or "acceptable," "effective," or "sufficient" when used to describe the selection of any components, ranges, dose forms, etc. disclosed herein intend that said component, range, dose form, etc. is suitable for the disclosed purpose.

In some embodiments, the terms "first" "second" "third" "fourth" or similar in a component name are used to distinguish and identify more than one components sharing certain identity in their names. For example, "first RNA" and "second RNA" are used to distinguishing two RNAs.

Severe acute respiratory syndrome coronavirus 2 (SARS-CoV-2), also referred to as 2019 novel coronavirus (2019-nCoV) or human coronavirus 2019 (HCoV-19 or hCoV-19), is the virus that causes COVID-19 (coronavirus disease 2019), the respiratory illness responsible for the COVID-19 pandemic.

Each SARS-CoV-2 virion is 50-200 nanometers in diameter, comprising a linear, positive-sense, single-stranded RNA genome (about 30,000 bases long) and four structural proteins, known as the S (spike), E (envelope), M (membrane), and N (nucleocapsid) proteins. The N protein holds the RNA genome, and the S, E, and M proteins together create the viral envelope. Coronavirus S proteins are glycoproteins that are divided into two functional parts (S1 and S2). In SARS-CoV-2, the spike protein is the protein responsible for allowing the virus to attach to and fuse with the membrane of a host cell; specifically, its S1 subunit catalyzes attachment, the S2 subunit fusion. Studies have shown that SARS-CoV-2 has sufficient affinity to the receptor angiotensin converting enzyme 2 (ACE2) on human cells to use them as a mechanism of cell entry. Initial spike protein priming by transmembrane protease, serine 2 (TMPRSS2) is also shown as essential for entry of SARS-CoV-2. The host protein neuropilin 1 (NRP1) may aid the virus in host cell entry using ACE2. After a SARS-CoV-2 virion attaches to a target cell, the cell's TMPRSS2 cuts open the spike protein of the virus, exposing a fusion peptide in the S2 subunit, and the host receptor ACE2. After fusion, an endosome forms around the virion, separating it from the rest of the host cell. The virion escapes when the pH of the endosome drops or when cathepsin, a host cysteine protease, cleaves it. The virion then releases RNA into the cell and forces the cell to produce and disseminate copies of the virus, which infect more cells.

Genetic variants of SARS-CoV-2 have been emerging and circulating around the world throughout the COVID-19 pandemic. The B.1.1.7 (Alpha), B.1.351 (Beta), B.1.617.2 (Delta), and P.1 (Gamma) variants circulating in the United States are classified as variants of concern. Other variants are also present, such as B.1.526 (Iota), B.1.427 (Epsilon), B.1.429 (Epsilon), B.1.617 (Kappa, Delta), B.1.525 (Eta), and P.2 (Zeta). Accordingly, the term "SARS-CoV-2" as used herein can refer to any one or more or all of the variants. In some embodiments, SARS-CoV-2 as used herein refers to a delta variant, which was first identified in India. In further embodiments, SARS-CoV-2 delta variant comprises mutations in the gene encoding the S protein causing one or more of the following amino acid mutations in the S protein: T19R, V70F, T95I, G142D, E156Δ, F157Δ, R158G, A222V, W258L, K417N, L452R, T478K, D614G, P681R, or D950N. In some embodiments, the delta variant is a delta plus variant comprising the amino acid mutation of K417N.

Subjects with a SARS-CoV-2 infection can experience a range of clinical manifestations, from an asymptomatic SARS-CoV-2 infection with no symptoms, to a symptomatic SARS-CoV-2 infection with critical illness. SARS-CoV-2 infection can be grouped into the following severity of illness categories; however, the criteria for each category may overlap or vary across clinical guidelines and clinical trials, and a patient's clinical status may change over time. Asymptomatic or presymptomatic SARS-CoV-2 infection occurs when a subject tests positive for SARS-CoV-2 using a virologic test, but exhibits no symptoms (e.g., fever, cough, sore throat, malaise, headache, muscle pain, nausea, vomiting, diarrhea, loss of taste and smell) consistent with a symptomatic SARS-CoV-2 infection. A symptomatic SARS-CoV-2 infection occurs when a subject exhibits mild, moderate, severe, or critical illness associated with SARS-CoV-2 infection, as defined by the U.S. National Institutes of Health. Subjects with mild illness associated with SARS-CoV-2 infection exhibit symptoms including, but not limited to, fever, cough, sore throat, malaise, headache, muscle pain, nausea, vomiting, diarrhea, loss of taste and smell, but do not have shortness of breath, dyspnea, or abnormal chest imaging. Subjects with moderate illness associated with SARS-CoV-2 infection show evidence of lower respiratory disease during clinical assessment or imaging and have an oxygen saturation ($SpO_2$)≥94% on room air at sea level. Subjects with severe illness associated with SARS-CoV-2 infection have $SpO_2$<94% on room air at sea level, a ratio of arterial partial pressure of oxygen to fraction of inspired oxygen ($PaO_2/FiO_2$)<300 mm Hg, a respiratory rate >30 breaths/min, or lung infiltrates >50%. Subjects with critical illness associated with SARS-CoV-2 infection have respiratory failure, septic shock, and/or multiple organ dysfunction.

Symptoms of a coronavirus infection include, but are not limited to, mild symptoms, such as fatigues, tingling, tingling or numbness in the hands and feet, dizziness, confusion, brain fog, body ache, chills, loss of appetite, nausea, vomiting, abdominal pain or discomfort, loss of smell, inability to taste, muscle weakness, photophobia, adenopathy, headaches, cough, dry cough, shortness of breath, sore throat, lower extremity weakness/numbness, diarrhea, low blood $O_2$, sneezing, runny nose or post-nasal drip; severe symptoms, such as ventilatory use, high fever, severe cough, delirium, seizures, stroke, systematic inflammation, cytokine storm; and other symptoms, such as fever, swollen adenoids, pneumonia, bronchitis, and Dyspnea.

Viral infection of a coronavirus, such as SARS-CoV-2, can be detected via a commercially available test known in the art, for example via polymerase chain reaction (PCR) or immunoassay may be used. In some embodiments, a method as disclosed herein further comprises detecting a coronavirus using a test known in the art. In one embodiment, active viral infection refers to an ongoing infection wherein the virus is replicating and producing new virus. Such active viral infection may be detected using polymerase chain reaction (PCR). Non-limiting examples of primers and probes suitable for use in the PCR include 2019-nCoV CDC Probe and Primer Kit for SARS-CoV-2 (BioSearch Technologies, Catalog No. KIT-nCoV-PP1-1000), 2019-nCoV Kit, 500 rxn (Integrated DNA Technologies (IDT), Catalog No. 10006606) and 2019-nCoV Kit, 1000 rxn (Integrated DNA Technologies (IDT), Catalog No. 10006770). Also see, www.cdc.gov/coronavirus/2019-ncov/lab/rt-pcr-panel-primer-probes.html and www.cdc.gov/coronavirus/2019-ncov/downloads/List-of-Acceptable-Commercial-Primers-Probes.pdf. Suitable protocols for performing such tests can be found at www.cdc.gov/coronavirus/2019-ncov/lab/virus-requests.html, www.fda.gov/media/134922/download, www.cdc.gov/coronavirus/2019-ncov/downloads/processing-sputum-specimens.pdf, www.fda.gov/media/134922/download, www.fda.gov/media/134919/download, www.fda.gov/media/134922/download, last accessed on Aug. 10, 2021. In some embodiments, diagnostic assays for COVID-19 based on detecting antibodies is combined with those disclosed herein, such as those discussed by Lisboa Bastos M et al. (Diagnostic accuracy of serological tests for covid-19: systematic review and meta-analysis. BMJ. 2020 Jul. 1; 370:m2516. doi: 10.1136/bmj.m2516).

Other commercially available tests include, but not limited to those listed in the Table below.

Commercially available tests for SARS-CoV-2 and COVID-19

| Company Name | Test Name |
|---|---|
| 3D Medicines | SARS-CoV-2 and Influenza A & B RT-qPCR Detection Kit |
| Abbott | SARS-CoV-2 IgG test |
| Abbott | ID Now COVID-19 |

-continued

| Commercially available tests for SARS-CoV-2 and COVID-19 | |
|---|---|
| Company Name | Test Name |
| Abbott | Abbott RealTime SARS-CoV-2 EUA test |
| Anatolia Geneworks | Bosphore Novel Coronavirus (2019-nCoV) Detection Kit |
| ARUP Laboratories | COVID-19 |
| A*STAR, Tan Tock Seng Hospital of Singapore | A*STAR Fortitude 2.0 |
| Assure Tech | COVID-19 IgG/IgM Rapid Test Device |
| Atila BioSystems | iAMP COVID-19 Detection Kit |
| AusDiagnostics | AusDiagnostics SARS-CoV-2, influenza, RSV panel |
| Autobio Diagnostics | Anti-SARS-CoV-2 Rapid Test |
| Avellino Lab | Avellino SARS-CoV-2/COVID-19 (AvellinoCoV2) |
| Bako Diagnostics | BakoDx SARS-CoV-2 RNA test |
| Baptist Hospital Miami Pathology/Laboratory Medicine Lab | COVID-19 RT-PCR Test |
| Becton Dickinson | BD SARS-CoV-2 Reagents for BD MAX System |
| Becton Dickinson, BioGx | BioGX SARS-CoV-2 Reagents for the BD MAX System |
| Beijing Decombio Biotechnology | Novel Coronavirus IgM/IgG Combo Rapid Test-Cassette |
| Beijing Diagreat Biotechnologies | 2019-nCoV IgG, IgM Antibody Determination Kits<br>2019-nCoV IgG/IgM Antibody Rapid Test Kit |
| Beijing Kewei Clinical Diagnostic Reagent | Genonto RapidTest10 COVID-19 IgG/IgM Antibody Rapid Test Kit |
| Beijing O&D Biotech | Coronavirus disease (COVID-19) Total Antibody Rapid Test (Colloidal Gold) |
| Beroni Group | SARS-CoV-2 IgG/IgM Antibody Detection Kit |
| BGI | Real-Time Fluorescent RT-PCR kit for detecting SARS-2019-nCoV |
| Biodesix | SARS-CoV-2 Droplet Digital PCR (ddPCR) test |
| Biolidics | 2019-nCoV IgG/IgM Detection Kit (Colloidal Gold) |
| BioMedomics | COVID-19 IgM-IgG Rapid Test |
| BioMérieux | SARS-COV-2 R-GENE test |
| BioMérieux/BioFire Defense | BioFire COVID-19 test |
| Bioneer | AccuPower COVID-19 Real-Time RT-PCR Kit, AccuPower SARS-CoV-2 Real-Time RT-PCR Kit |
| Bio-Rad Laboratories | SARS-CoV-2 Total Ab test |
| BioReference Laboratories | Novel Coronavirus COVID-19 |
| Boston Children's Hospital Infectious Diseases Diagnostic Laboratory (IDDL) | Childrens-Altona-SARS-CoV-2 assay |
| BTNX | Rapid Response COVID-19 IgG/IgM Test Cassette |
| Cellex | qSARS-CoV-2 IgG/IgM Rapid Test |
| Centers for Disease Control and Prevention (performed at qualified high-complexity CLIA laboratories designated by CDC) | CDC 2019-Novel Coronavirus (2019-nCoV) Real-Time RT-PCR Diagnostic Panel (CDC) |
| Cepheid | Xpert Xpress SARS-CoV-2 test |
| CerTest BioTec | ViaSure SARS-CoV-2 Real Time PCR Detection Kit |
| Chembio Diagnostics | DDP COVID-19 IgM/IgG System |
| Children's Hospital of Philadelphia Infectious Disease Diagnostics Laboratory | SARS-CoV-2 RT-PCR test |
| ChromaCode | HDPCR SARS-CoV-2 real-time PCR assay |
| CirrusDx Laboratories | CirrusDx SARS-CoV-2 Assay |
| Co-Diagnostics | Logix Smart Coronavirus Disease 2019 (COVID-19) Kit |
| Core Technology | CoreTest COVID-19 IgM/IgG Ab Test |
| Credo Diagnostics Biomedical | VitaPCR SARS-CoV2 Assay |
| DiaCarta | QuantiVirus SARS-CoV-2 test kit |
| Diagnostic Solutions Laboratory | COVID-19 Assay |
| DiaSorin Molecular | Simplexa COVID-19 Direct |
| Diatherix Eurofins | COVID-19 Panel |
| Diazyme Laboratories | Diazyme DZ-LITE SARS-CoV-2 IgG, IgM CLIA Kits |
| Eachy Biopharmaceuticals | AccuRapid SARS-CoV-2 IgM/IgG Test Kit (Lateral Flow Immunoassay) |
| Euroimmun/PerkinElmer | EuroRealTime SARS-CoV-2 |
| Euroimmun/PerkinElmer | Anti-SARS-CoV-2 ELISAs (IgA and IgG) |
| Exact Sciences | SARS-CoV-2 Test |
| Fosun Pharma USA | Fosun COVID-19 RT-PCR Detection Kit |
| Fulgent Genetics/MedScan Laboratory | COVID-19 |

-continued

| Commercially available tests for SARS-CoV-2 and COVID-19 | |
|---|---|
| Company Name | Test Name |
| Genetic Signatures | EasyScreen SARS-CoV-2 detection kit |
| Genetron | Detection Kit for Novel Coronavirus (SARS-CoV-2) RNA (PCR-Fluorescence Probing) |
| GenMark Diagnostics | ePlex SARS-CoV-2 Test |
| Genomica/PharmMar Group | 2 kits: qCOVID-19, CLART COVID-19 |
| GenoSensor | GS COVID-19 RT-PCR Kit |
| Gnomegen | Gnomegen COVID-19 RT-Digital PCR Detection Kit |
| Gold Standard Diagnostics | SARS-CoV-2 IgG, IgM, IgA assays |
| Guangzhou Wondfo Biotech | SARS-CoV-2 Antibody Test |
| Hackensack University Medical Center (HUMC) Molecular Pathology Laboratory | CDI Enhanced COVID-19 Test |
| Hangzhou AllTest Biotech | AllTest 2019-nCoV IgG/IgM Rapid Test Cassette, AllTest COVID IgG/IgM Rapid Test Dipstick |
| Hangzhou Biotest Biotech | COVID-19 IgG/IgM Rapid Test Cassette |
| Hangzhou Clongene Biotech | Clungene COVID-19 IgM/IgG Rapid Test Cassette |
| Hangzhou Testsealabs Biotechnology | One Step SARS-CoV2 (COVID-19) IgG/IgM Test |
| Healgen Scientific | COVID-19 IgG/IgM Rapid Test Cassette(Whole Blood/Serum/Plasma) |
| Hologic | Panther Fusion SARS-CoV-2 assay |
| InBios International | Smart Detect SARS-CoV-2 rRT-PCR Kit |
| Innovita (Tangshan) Biological Technology | 2019-nCoV Ab Test (Colloidal Gold) |
| Integrated DNA Technologies/Danaher | IDT 2019-novel coronavirus kit |
| Integrity Laboratories | SARS-CoV-2 Assay |
| Ipsum Diagnostics | COV-19 IDx assay |
| Jiangsu Macro & Micro-Test Med-Tech | SARS-CoV-2 IgM/IgG Rapid Assay Kit (Colloidal Gold) |
| JN Medsys | ProTect Covid-19 kit |
| Kogene Biotech | 2019 Novel Coronavirus Real-time PCR Kit |
| KorvaLabs | Curative-Korva SARS-Cov-2 Assay |
| Laboratory Corporation of America | LabCorp 2019 Novel Coronavirus test |
| LGC, Biosearch Technologies | 2019-nCoV CDC-qualified Probe and Primer Kits for SARS-CoV-2 |
| Lifeassay Diagnostics | Test-it COVID-19 IgM/IgG Lateral Flow Assay |
| Luminex | ARIES SARS-CoV-2 Assay |
| Luminex | NxTAGCoV Extended Panel Assay |
| Maccura Biotechnology | SARS-CoV-2 Fluorescent PCR Kit |
| Massachusetts General Hospital | MGH COVID-19 qPCR assay |
| Medical Systems Biotechnology | Coronavirus Disease 2019 Antibody (IgM/IgG) Combined Test Kit |
| Mesa Biotech | Accula SARS-CoV-2 test |
| Mount Sinai Labs | COVID-19 ELISA IgG Antibody Test |
| Nanjing Liming Bio-products | SARS-CoV-2 IgM/IgG Antibody Rapid Test Kit |
| NanoResearch | NanoMedicina SARS-CoV-2 IgM/IgG Antibody Rapid Test |
| Nantong Diagnos Biotechnology | (2019-nCoV) New coronavirus Antibody Test (Colloidal Gold) |
| NeuMoDx Molecular | NeuMoDx SARS-CoV-2 Assay |
| Nirmidas Biotech | COVID-19 (SARS-CoV-2) IgM/IgG Antibody Detection Kit |
| Northwestern Medicine Diagnostic Molecular Laboratory | SARS-Cov-2 Assay |
| Novacyt/Primerdesign | COVID-19 Genesig Real-Time PCR assay |
| NY State Department of Health (performed at Wadsworth Center and New York City Department of Health and Mental Hygiene, Public Health Laboratories) | New York SARS-CoV-2 Real-time Reverse Transcriptase (RT)-PCR Diagnostic Panel |
| Orig3n | Orig3n 2019 Novel Coronavirus (COVID-19) Test |
| Ortho Clinical Diagnostics | Vitros Immunodiagnostic Products Anti-SARS-CoV-2 Total Reagent Pack and Calibrators |
| Osang Healthcare | GeneFinder COVID-19 Plus RealAmp Kit |
| PathoFinder | RealAccurate Quadruplex Corona-plus PCR Kit |
| PCL | COVID19 IgG/IgM Rapid Gold |
| PerkinElmer | PerkinElmer New Coronavirus Nucleic Acid Detection Kit |
| Phamatech | COVID19 IgG/IgM Rapid Test |
| Promedical | COVID-19 Rapid Test, Wondfo SARS-CoV-2 Antibody Test (Lateral Flow Method) |
| Qiagen | QiaStat-Dx Respiratory SARS-CoV-2 Panel |
| Quest Diagnostics | Coronavirus Disease 2019 (COVID-19) Test |

-continued

| Commercially available tests for SARS-CoV-2 and COVID-19 | |
|---|---|
| Company Name | Test Name |
| Quidel | Lyra SARS-CoV-2 Assay |
| Rendu Biotechnology | 2019-nCoV detection kit |
| Roche | Cobas SARS-CoV-2 Test |
| Rutgers University Clinical Genomics Laboratory | ThermoFisher - Applied Biosystems TaqPath COVID-19 Combo Kit |
| ScienCell Research Laboratories | ScienCell SARS-CoV-2 Coronavirus Real-time RT-PCR (RT-qPCR) Detection Kit |
| SD Biosensor | Standard Q COVID-19 IgM/IgG Duo |
| Seegene | Allplex 2019-nCoV Assay |
| Sentinel Diagnostics | STAT-NAT COVID-19 HK kit, B kit |
| Shanghai Fosun Long March Medical Science/Shanghai Fosun Pharmaceutical | novel coronavirus nucleic acid detection kit |
| Shenzhen Landwind Medical | COVID-19 IgG/IgM Rapid Test Device |
| Snibe Diagnostics | Maglumi 2019-nCoV (SARS-CoV-2) IgM/IgG kits |
| SolGent | DiaPlexQ Novel Coronavirus (2019-nCoV) Detection kit |
| Specialty Diagnostic (SDI) Laboratories | SDI SARS-CoV-2 Assay |
| Stanford Health Care Clinical Virology Laboratory | SARS-CoV-2 PCR Assay |
| SureScreen Diagnostics | SureScreen COVID19 IgM/IgG Rapid Test Cassette |
| Suzhou Kangheshun Medical Technology | SARS-CoV-2 IgG/IgM Rapid Test Cassette |
| Systaaq Diagnostic Products | 2019-Novel Coronavirus (COVID-19) Real Time PCR Kit |
| Telepoint Medical Services | SARS-CoV-2 IgG/IgM Rapid Qualitative Test |
| Thermo Fisher Scientific | TaqPath COVID-19 Combo Kit, RT-PCR CE-IVD Kit |
| Tianjin Beroni Biotechnology | SARS-CoV-2 IgG/IgM Antibody Detection Kit |
| TIB Molbiol Syntheselabor | Sarbecovirus E-gene |
| Trax Management Services | Phoenix Dx 2019-CoV |
| United Biomedical | UBI SARS-CoV-2 ELISA |
| University of North Carolina Medical Center | UNC Health SARS-CoV-2 real-time RT-PCR test |
| Vela Diagnostics | ViroKey SARS-CoV-2 RT-PCR Test |
| Viracor Eurofins | Viracor SARS-CoV-2 assay |
| Vision Medicals | SARS-CoV-2 Clinical Sequencing assay |
| VivaChek Biotech (Hangzhou) | VivaDiag COVID-19 IgM/IgG Rapid Test |
| Yale New Haven Hospital Clinical Virology Laboratory | SARS-CoV-2 PCR test |
| YD Diagnostics | MolecuTech Real-Time COVID-19 |
| Zhejiang Orient Gene Biotech | COVID-19 IgG/IgM Rapid Test Cassette |
| Zhengzhou Fortune Bioscience | IgG/IgM Antibody Rapid Test Kits (Colloidal Gold Immunochromatography method) |
| Zhongshan Bio-Tech | SARS-CoV-2 IgM/IgG (GICA) |
| Zhuhai Encode Medical Engineering | Novel Coronavirus (COVID-19) IgG/IgM Rapid Test Device |
| Zhuhai Livzon Diagnostics | Diagnostic Kit for IgM/IgG Antibody to Coronavirus (SARS-CoV-2) (Colloidal Gold) |

The term "protein", "peptide" and "polypeptide" are used interchangeably and in their broadest sense to refer to a compound of two or more subunit amino acids, amino acid analogs or peptidomimetics. The subunits (which are also referred to as residues) may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

As used herein, the terms "spike protein," "spike glycoprotein" or "S protein" are used interchangeably, referring to a glycoprotein projecting from the lipid bilayer of the surface of an enveloped virus, such as SARS-CoV-2. In some embodiments, an S protein refers to an S protein of a SARS-CoV-2. In further embodiments, an S protein or an equivalent thereof as used herein also refers to an S protein variant (for example, an S protein of a naturally occurring SARS-CoV-2 variant, such as a delta variant), an S protein mutant (for example, a mutated S protein as disclosed herein), an S protein fragment (such as an immunogenic fragment), or any combination thereof (such as, a naturally occurring variant engineered with additional mutation(s), or a fragment thereof).

In some embodiments, an S protein as used herein comprises, or consists essentially of, or yet further consists of an S1 polypeptide or an S2 polypeptide or both. In some embodiments, an S protein as used herein is a precursor protein comprising, or consisting essentially of, or yet further consisting of both S1 and S2. Such precursor can be processed into S1 and S2 by Cathepsin L (CTSL), Transmembrane Serine Protease (TMPRSS2) or furin to yield the mature S1 and S2 protein. In some embodiments, the S protein as used herein refers to a protein complex comprising, or consisting essentially of, or yet further consisting of a mature S1 protein and a mature S2 protein. In other embodiments, the S protein as used herein refers to an S1 protein. In yet other embodiments, the S protein as used herein refers to an S2 protein. In some embodiments, the precursor protein comprises, or consists essentially of, or yet further consists of the polypeptide as set forth in SEQ ID NO: 1 or an equivalent thereof. In some embodiments, the S1 protein comprises, or consists essentially or, or yet further consists of the polypeptide as set forth in amino acid (aa) 13 to aa 685 of SEQ ID NO: 1 or an equivalent thereof. In some embodiments, the S2 protein comprises, or consists essentially or, or yet further consists of the polypeptide as set forth in amino acid (aa) 686 to aa 1273 of SEQ ID NO: 1 or an equivalent thereof. In some embodiments, the S2 protein comprises, or consists essentially or, or yet further consists of the polypeptide as set forth in amino acid (aa) 816 to aa 1273 of SEQ ID NO: 1 or an equivalent thereof. Further non-limiting exemplary sequences of an S protein or the underlying gene may be found under Gene ID: 43740568 (retrieved from www.ncbi.nlm.nih.gov/gene/43740568, last accessed on Aug. 1, 2021), NCBI Reference Sequence: NC_045512.2 (retrieved from www.ncbi.nlm.nih.gov/nuccore/NC_045512.2/, last accessed on Aug. 1, 2021) or UniProtKB/Swiss-Prot: PODTC2 (retrieved from www.uniprot.org/uniprot/PODTC2, last accessed on Aug. 1, 2021), which are incorporated by reference herein.

In some embodiments, a fragment (such as an immunogenic fragment) of an S protein comprises, or consists essentially of, or yet further consists of a receptor binding domain (RBD) of the S protein. In some embodiments, a receptor-binding domain (RBD) refers to a short immunogenic fragment from a virus that binds to a specific endogenous receptor sequence to gain entry into target cells. In some embodiments, RBD refer to a part of the 'spike' glycoprotein (S-domain) which is needed to interact with endogenous receptors to facilitate membrane fusion and delivery to the cytoplasm. In some embodiments, the RBD as used herein comprises, or consists essentially of, or yet further consists of the polypeptide as set forth in aa 319 to aa 541 of SEQ ID NO: 1 or an equivalent thereof.

As used herein the term "angiotensin converting enzyme 2" or "ACE2" refers to an enzyme attached to the membrane of cells optionally located in the intestines, kidney, testis, gallbladder, and heart. ACE2 serves as the entry point into cells for some coronaviruses, including HCoV-NL63, SARS-CoV, and SARS-CoV-2. The SARS-CoV-2 spike protein itself is known to damage the epithelium via down-regulation of ACE2. In some embodiments, the term "ACE2" refers to a human ACE2. Non-limiting exemplary sequences of this protein or the underlying gene may be found under Gene Cards ID: GC0XM015494 (retrieved from www.genecards.org/cgi-bin/carddisp.pl?gene=ACE2, last accessed on Aug. 1, 2021), HGNC: 13557 (retrieved from www.genenames.org/data/gene-symbol-report/#!/hgnc_id/13557, last accessed on Aug. 1, 2021), NCBI Entrez Gene: 59272 (retrieved from www.ncbi.nlm.nih.gov/gene/59272, last accessed on Aug. 1, 2021), Ensembl: ENSG00000130234 (retrieved from useast.ensembl.org/Homo_sapiens/Gene/Summary?g=ENSG00000130234; r=X:15494566-15607236, last accessed on Aug. 1, 2021), OMIM®: 300335 (retrieved from omim.org/entry/300335, last accessed on Aug. 1, 2021), or UniProtKB/Swiss-Prot: Q9BYF1 (retrieved from www.uniprot.org/uniprot/Q9BYF1, last accessed on Aug. 1, 2021), which are incorporated by reference herein.

As used herein the term "Transmembrane Serine Protease 2" or "TMPRSS2" refers to protein comprising a type II transmembrane domain, a receptor class A domain, a scavenger receptor cysteine-rich domain and a protease domain. This protein facilitates entry of viruses into host cells by proteolytically cleaving and activating viral envelope glycoproteins. Viruses found to use this protein for cell entry include Influenza virus and the human coronaviruses HCoV-229E, MERS-CoV, SARS-CoV and SARS-CoV-2. In some embodiments, the term "TMPRSS2" refers to a human TMPRSS2. Non-limiting exemplary sequences of this protein or the underlying gene may be found under Gene Cards ID GC21M041464 (retrieved from www.genecards.org/cgi-bin/carddisp.pl?gene=TMPRSS2, last accessed on Aug. 1, 2021), HGNC: 11876 (retrieved from www.genenames.org/data/gene-symbol-report/#!/hgnc_id/11876, last accessed on Aug. 1, 2021), NCBI Entrez Gene: 7113 (retrieved from www.ncbi.nlm.nih.gov/gene/7113, last accessed on Aug. 1, 2021), Ensembl: ENSG00000184012 (retrieved from uscast.ensembl.org/Homo_sapiens/Gene/Summary?g=ENSG00000184012; r=21:41464300-41531116, last accessed on Aug. 1, 2021), OMIM®: 602060 (retrieved from omim.org/entry/602060, last accessed on Aug. 1, 2021), or UniProtKB/Swiss-Prot: 015393 (retrieved from www.uniprot.org/uniprot/015393, last accessed on Aug. 1, 2021), which are incorporated by reference herein.

As used herein the term "Cathepsin L" or "CTSL" refers to a protein, which is a member of the peptidase Cl family, and a dimer composed of disulfide-linked heavy and light chains, both produced from a single protein precursor. Additionally, this protein cleaves the S1 subunit of the SARS-CoV-2 spike protein, which is necessary for entry of the virus into the cell. In some embodiments, the term "CTSL" refers to a human CTSL. Non-limiting exemplary sequences of this protein or the underlying gene may be found under Gene Cards ID GC09P087725 (retrieved from www.genecards.org/cgi-bin/carddisp.pl?gene=CTSL, last accessed on Aug. 1, 2021), HGNC: 2537 (retrieved from www.genenames.org/data/gene-symbol-report/#!/hgnc_id/2537, last accessed on Aug. 1, 2021), NCBI Entrez Gene: 1514 (retrieved from www.ncbi.nlm.nih.gov/gene/1514, last accessed on Aug. 1, 2021), Ensembl: ENSG00000135047 (retrieved from useast.ensembl.org/Homo_sapiens/Gene/Summary?g=ENSG00000135047; r=9:87724051-87731469, last accessed on Aug. 1, 2021), OMIM®: 116880 (retrieved from omim.org/entry/116880, last accessed on Aug. 1, 2021), or UniProtKB/Swiss-Prot: P07711 (retrieved from www.uniprot.org/uniprot/P07711, last accessed on Aug. 1, 2021), which are incorporated by reference herein.

As used herein the term "furin" refers to is a protease enzyme capable of cleavage at the RX(K/R)R (RKR or RRR)) consensus motif. It also facilitates SARS-CoV-2 infections by proteolytically cleaving the spike protein at the monobasic S1/S2 cleavage site, RRAR (SEQ ID NO: 48). This cleavage is essential for spike protein-mediated cell-cell fusion and entry into human lung cells. In some embodiments, the term furin refers to a mammal furin, such as a bovine furin, see for example UniProtKB Q28193 retrieved from www.uniprot.org/uniprot/Q28193 last accessed on Aug. 10, 2021. In some embodiments, the term "furin" refers to a human furin. Non-limiting exemplary sequences of this protein or the underlying gene may be found under Gene Cards ID: GC15P090868 (retrieved from www.genecards.org/cgi-bin/carddisp.pl?gene=FURIN, last accessed on Aug. 1, 2021), HGNC: 8568 (retrieved from www.genenames.org/data/gene-symbol-report/#!/hgnc_id/8568, last accessed on Aug. 1, 2021), NCBI Entrez Gene: 5045 (retrieved from www.ncbi.nlm.nih.gov/gene/5045, last accessed on Aug. 1, 2021), Ensembl: ENSG00000140564 (retrieved from useast.ensembl.org/Homo_sapiens/Gene/Summary?g=ENSG00000140564; r=15:90868588-

90883564, last accessed on Aug. 1, 2021), OMIM®: 136950 (retrieved from omim.org/entry/136950, last accessed on Aug. 1, 2021), or UniProtKB/Swiss-Prot: P09958 (retrieved from www.uniprot.org/uniprot/P09958, last accessed on Aug. 1, 2021), which are incorporated by reference herein.

In some embodiments, a fragment of a protein can be an immunogenic fragment. As used herein, the term "immunogenic fragment" refers to such a polypeptide fragment, which at least partially retains the immunogenicity of the protein from which it is derived. In some embodiments, the immunogenic fragment is at least about 3 amino acid (aa) long, or at least about 4 aa long, or at least about 5 aa long, or at least about 6 aa long, or at least about 7 aa long, or at least about 8 aa long, or at least about 9 aa long, or at least about 10, aa long, or at least about 15, aa long, or at least about 20 aa long, or at least about 25 aa long, or at least about 30 aa long, or at least about 35 aa long, or at least about 40 aa long, or at least about 50 aa long, or at least about 60 aa long, or at least about 70 aa long, or at least about 80 aa long, or at least about 90 aa long, or at least about 100 aa long, or at least about 120 aa long, or at least about 150 aa long, or at least about 200, or longer. In some embodiments, an immunogenic fragment of an S protein comprises, or alternatively consists essentially of, or yet further consists of an RBD of the S protein.

As used herein, an amino acid (aa) or nucleotide (nt) residue position in a sequence of interest "corresponding to" an identified position in a reference sequence refers to that the residue position is aligned to the identified position in a sequence alignment between the sequence of interest and the reference sequence. Various programs are available for performing such sequence alignments, such as Clustal Omega and BLAST. In one aspect, equivalent polynucleotides, proteins and corresponding sequences can be determined using BLAST (accessible at blast.ncbi.nlm.nih.gov/Blast.cgi, last accessed on Aug. 1, 2021).

As used herein, an amino acid mutation is referred to herein as two letters separated by an integer, such as T19R. The first letter provides the one letter code of the original amino acid residue to be mutated; while the last letter provides the mutation, such as A indicating a deletion, or one letter code of the mutated amino acid residue. In some embodiments, the integer is the numbering of the to-be-mutated amino acid residue in the amino acid sequence free of the mutation, optionally counting from the N terminus to the C terminus. In some embodiments, the integer is the numbering of the mutated amino acid residue in the mutated amino acid sequence, optionally counting from the N terminus to the C terminus. In some embodiments, the integer is the numbering of the amino acid residue in SEQ ID NO: 1 that corresponds to (such as aligned to) the to-be-mutated residue or the mutated residue or both.

It is to be inferred without explicit recitation and unless otherwise intended, that when the present disclosure relates to a polypeptide, protein, polynucleotide, an equivalent or a biologically equivalent of such is intended within the scope of this disclosure. As used herein, the term "biological equivalent thereof" is intended to be synonymous with "equivalent thereof" when referring to a reference protein, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or at least 80% homology or identity, or at least about 85% homology or identity, or alternatively at least about 90% homology or identity, or alternatively at least about 95% homology or identity, or alternatively at least about 96% homology or identity, or alternatively at least about 97% homology or identity, or alternatively at least about 98% homology or identity, or alternatively at least about 99% homology or identity (in one aspect, as determined using the Clustal Omega alignment program) and exhibits substantially equivalent biological activity to the reference protein, polypeptide or nucleic acid. Alternatively, when referring to polynucleotides, an equivalent thereof is a polynucleotide that hybridizes under stringent conditions to the reference polynucleotide or its complementary sequence.

An equivalent of a reference polypeptide comprises, consists essentially of, or alternatively consists of an polypeptide having at least 80%, or at least 85%, or at least 90%, or at least 95%, or at least about 96%, or at least 97%, or at least 98%, or at least 99% amino acid identity to the reference polypeptide (as determined, in one aspect using the Clustal Omega alignment program), or a polypeptide that is encoded by a polynucleotide that hybridizes under conditions of high stringency to the complementary sequence of a polynucleotide encoding the reference polypeptide, optionally wherein conditions of high stringency comprises incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water.

In some embodiments, a first sequence (nucleic acid sequence or amino acid) is compared to a second sequence, and the identity percentage between the two sequences can be calculated. In further embodiments, the first sequence can be referred to herein as an equivalent and the second sequence can be referred to herein as a reference sequence. In yet further embodiments, the identity percentage is calculated based on the full-length sequence of the first sequence. In other embodiments, the identity percentage is calculated based on the full-length sequence of the second sequence.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "RNA" as used herein refers to its generally accepted meaning in the art. Generally, the term RNA refers to a polynucleotide comprising at least one ribofuranoside moiety. The term can include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, for example at one or more nucleotides of the RNA. Nucleotides in the nucleic acid molecules can also comprise non-standard nucleotides, such as non-naturally occurring nucleotides or chemically synthesized nucleotides or deoxynucleotides. These altered RNAs can be referred to as analogs or analogs of naturally-occurring RNA. In some embodiments, the RNA is a messenger RNA (mRNA).

"Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo. In some embodiments, an mRNA as disclosed herein comprises, or consists essentially of, or yet further consists of at least one coding region, a 5' untranslated region (UTR), a 3' UTR, a 5' cap and a poly-A tail.

Vaccination is the most successful medical approach to disease prevention and control. The successful development and use of vaccines has saved thousands of lives and large amounts of money. A key advantage of RNA vaccines is that RNA can be produced in the laboratory from a DNA template using readily available materials, less expensively and faster than conventional vaccine production, which can require the use of chicken eggs or other mammalian cells. In addition, mRNA vaccines have the potential to streamline vaccine discovery and development, and facilitate a rapid response to emerging infectious diseases, see, for example, Maruggi et al., *Mol Ther.* 2019; 27(4): 757-772.

Preclinical and clinical trials have shown that mRNA vaccines provide a safe and long-lasting immune response in animal models and humans. mRNA vaccines against infectious diseases may be developed as prophylactic or therapeutic treatments. mRNA vaccines expressing antigens of infectious pathogens have been shown to induce potent T cell and humoral immune responses. See, for example, Pardi et al., *Nat Rev Drug Discov.* 2018; 17:261-279. The production procedure to generate mRNA vaccines is cell-free, simple, and rapid, compared to production of whole microbe, live attenuated, and subunit vaccines. This fast and simple manufacturing process makes mRNA a promising bio-product that can potentially fill the gap between emerging infectious disease and the desperate need for effective vaccines.

The term "isolated" as used herein with respect to nucleic acids, such as DNA or RNA, refers to molecules separated from other DNAs or RNAs, respectively that are present in the natural source of the macromolecule. The term "isolated nucleic acid" is meant to include nucleic acid fragments which are not naturally occurring as fragments and would not be found in the natural state. The term "isolated" is also used herein to refer to polypeptides, proteins and/or host cells that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, or protein, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, or protein, does not require "isolation" to distinguish it from its naturally occurring counterpart.

In some embodiments, the term "engineered" or "recombinant" refers to having at least one modification not normally found in a naturally occurring protein, polypeptide, polynucleotide, strain, wild-type strain or the parental host strain of the referenced species. In some embodiments, the term "engineered" or "recombinant" refers to being synthetized by human intervention. As used herein, the term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, "complementary" sequences refer to two nucleotide sequences which, when aligned anti-parallel to each other, contain multiple individual nucleotide bases which pair with each other. Paring of nucleotide bases forms hydrogen bonds and thus stabilizes the double strand structure formed by the complementary sequences. It is not necessary for every nucleotide base in two sequences to pair with each other for sequences to be considered "complementary". Sequences may be considered complementary, for example, if at least 30%, 40%, 50%, 55%, 60%, 65%, 70%, 75%, 80%, 85%, 90%, 95%, 98%, 99%, or 100% of the nucleotide bases in two sequences pair with each other. In some embodiments, the term complementary refers to 100% of the nucleotide bases in two sequences pair with each other. In addition, sequences may still be considered "complementary" when the total lengths of the two sequences are significantly different from each other. For example, a primer of 15 nucleotides may be considered "complementary" to a longer polynucleotide containing hundreds of nucleotides if multiple individual nucleotide bases of the primer pair with nucleotide bases in the longer polynucleotide when the primer is aligned anti-parallel to a particular region of the longer polynucleotide. Nucleotide bases paring is known in the field, such as in DNA, the purine adenine (A) pairs with the pyrimidine thymine (T) and the pyrimidine cytosine (C) always pairs with the purine guanine (G); while in RNA, adenine (A) pairs with uracil (U) and guanine (G) pairs with cytosine (C). Further, the nucleotide bases aligned anti-parallel to each other in two complementary sequences, but not a pair, are referred to herein as a mismatch.

A "gene" refers to a polynucleotide containing at least one open reading frame (ORF) that is capable of encoding a particular polypeptide or protein after being transcribed and translated.

The term "express" refers to the production of a gene product, such as mRNA, peptides, polypeptides or proteins. As used herein, "expression" refers to the process by which polynucleotides are transcribed into mRNA or the process by which the transcribed mRNA is subsequently being translated into peptides, polypeptides, or proteins. If the polynucleotide is derived from genomic DNA, expression may include splicing of the mRNA in a eukaryotic cell.

A "gene product" or alternatively a "gene expression product" refers to the amino acid (e.g., peptide or polypeptide) generated when a gene is transcribed and translated. In some embodiments, the gene product may refer to an mRNA or other RNA, such as an interfering RNA, generated when a gene is transcribed.

The term "encode" as it is applied to polynucleotides refers to a polynucleotide which is said to "encode" a polypeptide if, in its native state or when manipulated by methods well known to those skilled in the art, it can be transcribed to produce the mRNA for the polypeptide or a fragment thereof, and optionally translated to produce the polypeptide or a fragment thereof. The antisense strand is the complement of such a nucleic acid, and the encoding sequence can be deduced therefrom. Further, as used herein an amino acid sequence coding sequence refers to a nucleotide sequence encoding the amino acid sequence.

The terms "chemical modification" and "chemically modified" refer to modification with respect to adenosine (A), guanosine (G), uridine (U), thymidine (T) or cytidine (C) ribonucleosides or deoxyribnucleosides in at least one of their position, pattern, percent or population. In some embodiments, the term refers to the ribonucleotide modifications in naturally occurring 5'-terminal mRNA cap moieties. In further embodiments, the chemical modification is selected from pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methoxyuridine, or 2'-O-methyl uridine. In some embodiments the extent of incorporation of chemically modified nucleotides has been optimized for improved immune responses to the vaccine formulation. In other embodiments, the term excludes the ribonucleotide modifications in naturally occurring 5'-terminal mRNA cap moieties.

Polynucleotides (e.g., RNA polynucleotides, such as mRNA polynucleotides), in some embodiments, comprise non-natural modified nucleotides that are introduced during synthesis or post-synthesis of the polynucleotides to achieve desired functions or properties. The modifications may be present on an internucleotide linkages, purine or pyrimidine bases, or sugars. The modification may be introduced with chemical synthesis or with a polymerase enzyme at the terminal of a chain or anywhere else in the chain. Any of the regions of a polynucleotide may be chemically modified.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher percentage of residues of the RNA is chemically modified by one or more of modifications as disclosed herein. In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher percentage of uridine residues of the RNA is chemically modified by one or more of modifications as disclosed herein.

In some embodiments, an RNA as disclosed herein is optimized. Optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide.

A "3' untranslated region" (3' UTR) refers to a region of an mRNA that is directly downstream (i.e., 3') from the stop codon (i.e., the codon of an mRNA transcript that signals a termination of translation) that does not encode a polypeptide. In some embodiments, a 3' UTR as used herein comprises, or consists essentially of, or yet further consists of one or more of SEQ ID NOs: 18, 22, or 24.

A "5' untranslated region" (5' UTR) refers to a region of an RNA that is directly upstream (i.e., 5') from the start codon (i.e., the first codon of an mRNA transcript translated by a ribosome) that does not encode a polypeptide. In some embodiments, a 5' UTR as used herein comprises, or consists essentially of, or yet further consists of one or both of SEQ ID NO: 20 or 26.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. Additionally or alternatively, in a relevant biological setting (e.g., in cells, in vivo) the polyA tail functions to protect mRNA from enzymatic degradation, e.g., in the cytoplasm, and aids in transcription termination, export of the mRNA from the nucleus and translation. In some embodiments, a polyA tail as used herein comprises, or consists essentially of, or yet further consists of one or more of: SEQ ID NOs: 27, 28, 30, or 56-57.

In vitro transcription (IVT) methods permit template-directed synthesis of RNA molecules of almost any sequence. The size of the RNA molecules that can be synthesized using IVT methods range from short oligonucleotides to long nucleic acid polymers of several thousand bases. IVT methods permit synthesis of large quantities of RNA transcript (e.g., from microgram to milligram quantities) (Beckert et al., Methods Mol Biol. 703:29-41(2011); Rio et al. RNA: A Laboratory Manual. Cold Spring Harbor: Cold Spring Harbor Laboratory Press, 2011, 205-220; and Cooper, Geoffery M. The Cell: A Molecular Approach. 4th ed. Washington D.C.: ASM Press, 2007, 262-299). Generally, IVT utilizes a DNA template featuring a promoter sequence upstream of a sequence of interest. The promoter sequence is most commonly of bacteriophage origin (ex. the T7, T3 or SP6 promoter sequence) but many other promotor sequences can be tolerated including those designed de novo. Transcription of the DNA template is typically best achieved by using the RNA polymerase corresponding to the specific bacteriophage promoter sequence. Exemplary RNA polymerases include, but are not limited to T7 RNA polymerase, T3 RNA polymerase, or SP6 RNA polymerase, among others. IVT is generally initiated at a dsDNA but can proceed on a single strand.

It will be appreciated that an RNA as disclosed herein can be made using any appropriate synthesis method. For example, in some embodiments, an RNA is made using IVT from a single bottom strand DNA as a template and complementary oligonucleotide that serves as promotor. The single bottom strand DNA may act as a DNA template for in vitro transcription of RNA, and may be obtained from, for example, a plasmid, a PCR product, or chemical synthesis. In some embodiments, the single bottom strand DNA is linearized from a circular template. The single bottom strand DNA template generally includes a promoter sequence, e.g., a bacteriophage promoter sequence, to facilitate IVT. Methods of making RNA using a single bottom strand DNA and a top strand promoter complementary oligonucleotide are known in the art. An exemplary method includes, but is not limited to, annealing the DNA bottom strand template with the top strand promoter complementary oligonucleotide (e.g., T7 promoter complementary oligonucleotide, T3 promoter complementary oligonucleotide, or SP6 promoter complementary oligonucleotide), followed by IVT using an RNA polymerase corresponding to the promoter sequence, e.g., a T7 RNA polymerase, a T3 RNA polymerase, or an SP6 RNA polymerase.

IVT methods can also be performed using a double-stranded DNA template. For example, in some embodiments, the double-stranded DNA template is made by extending a complementary oligonucleotide to generate a complementary DNA strand using strand extension techniques available in the art. In some embodiments, a single bottom strand DNA template containing a promoter sequence and sequence encoding one or more epitopes of interest is annealed to a top strand promoter complementary oligonucleotide and subjected to a PCR-like process to extend the top strand to generate a double-stranded DNA template. Alternatively or additionally, a top strand DNA containing a sequence complementary to the bottom strand promoter sequence and complementary to the sequence encoding one or more epitopes of interest is annealed to a bottom strand promoter oligonucleotide and subjected to a PCR-like process to extend the bottom strand to generate a double-stranded DNA template. In some embodiments, the number of PCR-like cycles ranges from 1 to 20 cycles, e.g., 3 to 10 cycles. In some embodiments, a double-stranded DNA template is synthesized wholly or in part by chemical synthesis methods. The double-stranded DNA template can be subjected to in vitro transcription as described herein.

"Under transcriptional control", which is also used herein as "directing expression of" or any grammatical variation thereof, is a term well understood in the art and indicates that transcription and optionally translation of a polynucleotide sequence, usually a DNA sequence, depends on its being operatively linked to an element which contributes to the initiation of, or promotes, transcription.

"Operatively linked" intends the polynucleotides are arranged in a manner that allows them to function in a cell.

The term "a regulatory sequence", "an expression control element" or "promoter" as used herein, intends a polynucleotide that is operatively linked to a target polynucleotide to be transcribed or replicated, and facilitates the expression or replication of the target polynucleotide.

A promoter is an example of an expression control element or a regulatory sequence. Promoters can be located 5' or upstream of a gene or other polynucleotide, that provides a control point for regulated gene transcription. In some embodiments, a promoter as used herein is corresponding to the RNA polymerase. In further embodiments, a promoter as sued herein comprises, or consists essentially of, or yet further consists of a T7 promoter, or a SP6 promoter, or a T3 promoter. Non-limiting examples of suitable promoters are provided in WO2001009377A1.

An "RNA polymerase" refers to an enzyme that produces a polyribonucleotide sequence, complementary to a pre-existing template polynucleotide (DNA or RNA). In some embodiments, the RNA polymerase is a bacteriophage RNA polymerase, optionally a T7 RNA polymerase, or a SP6 RNA polymerase, or a T3 RNA polymerase. Non-limiting examples of suitable polymerase are further detailed in U.S. Ser. No. 10/526,629B2.

In some embodiments, the term "vector" intends a recombinant vector that retains the ability to infect and transduce non-dividing and/or slowly-dividing cells and optionally integrate into the target cell's genome. Non-limiting examples of vectors include a plasmid, a nanoparticle, a liposome, a virus, a cosmid, a phage, a BAC, a YAC, etc. In some embodiments, plasmid vectors may be prepared from commercially available vectors. In other embodiments, viral vectors may be produced from baculoviruses, retroviruses, adenoviruses, AAVs, etc. according to techniques known in the art. In one embodiment, the viral vector is a lentiviral vector. In one embodiment, the viral vector is a retroviral vector. In one embodiment, the vector is a plasmid. In one embodiment, the vector is a nanoparticle, optionally a polymeric nanoparticle or a lipid nanoparticle.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances. Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene. This is a cheap and easy way of mass-producing a gene or the protein it then codes for.

A "viral vector" is defined as a recombinantly produced virus or viral particle that comprises a polynucleotide to be delivered into a host cell, either in vivo, ex vivo or in vitro. As is known to those of skill in the art, there are 6 classes of viruses. The DNA viruses constitute classes I and II. The RNA viruses and retroviruses make up the remaining classes. Class III viruses have a double-stranded RNA genome. Class IV viruses have a positive single-stranded RNA genome, the genome itself acting as mRNA Class V viruses have a negative single-stranded RNA genome used as a template for mRNA synthesis. Class VI viruses have a positive single-stranded RNA genome but with a DNA intermediate not only in replication but also in mRNA synthesis. Retroviruses carry their genetic information in the form of RNA; however, once the virus infects a cell, the RNA is reverse-transcribed into the DNA form which integrates into the genomic DNA of the infected cell. The integrated DNA form is called a provirus. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. Sec, Schlesinger and Dubensky (1999) Curr. Opin. Biotechnol. 5:434-439 and Ying, et al. (1999) Nat. Med. 5(7):823-827. As used herein, Multiplicity of infection (MOI) refers to the number of viral particles that are added per cell during infection.

A retrovirus such as a gammaretrovirus and/or a lentivirus comprises (a) envelope comprising lipids and glycoprotein, (b) a vector genome, which is a RNA (usually a dimer RNA comprising a cap at the 5' end and a polyA tail at the 3' end flanked by LTRs) derived to the target cell, (c) a capsid, and (d) proteins, such as a protease. U.S. Pat. No. 6,924,123 discloses that certain retroviral sequence facilitate integration into the target cell genome. This patent teaches that each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome. The LTRs themselves are identical sequences that can be divided into three elements, which are called U3, R and U5. U3 is derived from the sequence unique to the 3' end of the RNA. R is derived from a sequence repeated at both ends of the RNA, and U5 is derived from the sequence unique to the 5' end of the RNA. The sizes of the three elements can vary considerably among different retroviruses. For the viral genome. and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

For the production of viral vector particles, the vector RNA genome is expressed from a DNA construct encoding it, in a host cell. The components of the particles not encoded by the vector genome are provided in trans by additional nucleic acid sequences (the "packaging system", which usually includes either or both of the gag/pol and env genes) expressed in the host cell. The set of sequences required for the production of the viral vector particles may be introduced into the host cell by transient transfection, or they may be integrated into the host cell genome, or they may be provided in a mixture of ways. The techniques involved are known to those skilled in the art.

The term "adeno-associated virus" or "AAV" as used herein refers to a member of the class of viruses associated with this name and belonging to the genus dependoparvovirus, family Parvoviridae. Multiple serotypes of this virus are known to be suitable for gene delivery; all known serotypes can infect cells from various tissue types. At least 11 sequentially numbered, AAV serotypes are known in the art. Non-limiting exemplary serotypes useful in the methods disclosed herein include any of the 11 serotypes, e.g., AAV2, AAV8, AAV9, or variant or synthetic serotypes, e.g., AAV-DJ and AAV PHP.B. The AAV particle comprises, alternatively consists essentially of, or yet further consists of three major viral proteins: VP1, VP2 and VP3. In one embodiment, the AAV refers to of the serotype AAV1, AAV2, AAV4, AAV5, AAV6, AAV7, AAV8, AAV9, AAV10, AAV11, AAV12, AAV13, AAV PHP.B, or AAV rh74. These vectors are commercially available or have been described in the patent or technical literature.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

The term "a regulatory sequence" "an expression control element" or "promoter" as used herein, intends a polynucleotide that is operatively linked to a target polynucleotide to be transcribed and/or replicated, and facilitates the expression and/or replication of the target polynucleotide. A promoter is an example of an expression control element or a regulatory sequence. Promoters can be located 5' or upstream of a gene or other polynucleotide, that provides a control point for regulated gene transcription. Polymerase II and III are examples of promoters.

A polymerase II or "pol II" promoter catalyzes the transcription of DNA to synthesize precursors of mRNA, and most shRNA and microRNA. Examples of pol II promoters are known in the art and include without limitation, the phosphoglycerate kinase ("PGK") promoter; EF1-alpha; CMV (minimal cytomegalovirus promoter); and LTRs from retroviral and lentiviral vectors.

An enhancer is a regulatory element that increases the expression of a target sequence. A "promoter/enhancer" is a polynucleotide that contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

When hybridization occurs in an antiparallel configuration between two single-stranded polynucleotides, the reaction is called "annealing" and those polynucleotides are described as "complementary." A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure. In some embodiments, the identity is calculated between two peptides or polynucleotides over their full-length, or over the shorter sequence of the two, or over the longer sequence of the two.

A polynucleotide or polynucleotide region (or a polypeptide or polypeptide region) has a certain percentage (for example, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example, those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: blast.ncbi.nlm.nih.gov/Blast.cgi, last accessed on Aug. 1, 2021.

In some embodiments, the polynucleotide as disclosed herein is a RNA or an analog thereof. In some embodiments, the polynucleotide as disclosed herein is a DNA or an analog thereof. In some embodiments, the polynucleotide as disclosed herein is a hybrid of DNA and RNA or an analog thereof.

In some embodiments, an equivalent to a reference nucleic acid, polynucleotide or oligonucleotide encodes the same sequence encoded by the reference. In some embodiments, an equivalent to a reference nucleic acid, polynucleotide or oligonucleotide hybridizes to the reference, a complement reference, a reverse reference, or a reverse-complement reference, optionally under conditions of high stringency.

Additionally or alternatively, an equivalent nucleic acid, polynucleotide or oligonucleotide is one having at least 70% sequence identity, or at least 75% sequence identity, or at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence, or alternatively at least 99% sequence identity to the reference nucleic acid, polynucleotide, or oligonucleotide, or alternatively an equivalent nucleic acid hybridizes under conditions of high stringency to a reference polynucleotide or its complementary. In one aspect, the equivalent must encode the same protein or a functional equivalent of the protein that optionally can be identified through one or more assays described herein. In addition or alternatively, the equivalent of a polynucleotide would encode a protein or polypeptide of the same or similar function as the reference or parent polynucleotide.

The term "transduce" or "transduction" refers to the process whereby a foreign nucleotide sequence is introduced into a cell. In some embodiments, this transduction is done via a vector, viral or non-viral.

"Detectable label", "label", "detectable marker" or "marker" are used interchangeably, including, but not limited to radioisotopes, fluorochromes, chemiluminescent compounds, dyes, and proteins, including enzymes. Detectable labels can also be attached to a polynucleotide, polypeptide, protein or composition described herein.

As used herein, the term "label" or a detectable label intends a directly or indirectly detectable compound or composition that is conjugated directly or indirectly to the composition to be detected, e.g., N-terminal histidine tags (N-His), magnetically active isotopes, e.g., $^{115}$Sn, $^{117}$Sn and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected, or it may be quantified. A response that is simply detected generally comprises a response whose existence merely is confirmed, whereas a response that is quantified generally comprises a response having a quantifiable (e.g., numerically reportable) value such as an intensity, polarization, or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals (6th ed). Examples of luminescent probes include, but are not limited to, aequorin and luciferases.

As used herein, the term "immunoconjugate" comprises an antibody or an antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multispecific antibody.

Examples of suitable fluorescent labels include, but are not limited to, fluorescein, rhodamine, tetramethylrhodamine, cosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6th ed.).

In some embodiments, the fluorescent label is functionalized to facilitate covalent attachment to a cellular component present in or on the surface of the cell or tissue such as a cell surface marker. Suitable functional groups, include, but are not limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

As used herein, a purification label or maker refers to a label that may be used in purifying the molecule or component that the label is conjugated to, such as an epitope tag (including but not limited to a Myc tag, a human influenza hemagglutinin (HA) tag, a FLAG tag), an affinity tag (including but not limited to a glutathione-S transferase (GST), a poly-Histidine (His) tag, Calmodulin Binding Protein (CBP), or Maltose-binding protein (MBP)), or a fluorescent tag.

A "selection marker" refers to a protein or a gene encoding the protein necessary for survival or growth of a cell grown in a selective culture regimen. Typical selection markers include sequences that encode proteins, which confer resistance to selective agents, such as antibiotics, herbicides, or other toxins. Examples of selection markers include genes for conferring resistance to antibiotics, such as spectinomycin, streptomycin, tetracycline, ampicillin, kanamycin, G 418, neomycin, bleomycin, hygromycin, methotrexate, dicamba, glufosinate, or glyphosate.

The term "culturing" refers to the in vitro or ex vivo propagation of cells or organisms on or in media of various kinds. It is understood that the descendants of a cell grown in culture may not be completely identical (i.e., morphologically, genetically, or phenotypically) to the parent cell.

In some embodiments, the cell as disclosed herein is a eukaryotic cell or a prokaryotic cell. In some embodiments, the cell is a human cell. In some embodiments, the cell is a cell line, such as a human embryonic kidney 293 cell (HEK 293 cell or 293 cell), a 293T cell, or an a549 cell.

"Host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. The host cell can be a prokaryotic or a eukaryotic cell. In some embodiments, the host cell is a cell line, such as a human embryonic kidney 293 cell (HEK 293 cell or 293 cell), a 293T cell, or an a549 cell.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, canine, bovine, porcine, murine, rat, avian, reptilian and human.

"Prokaryotic cells" that usually lack a nucleus or any other membrane-bound organelles and are divided into two domains, bacteria and archaca. Additionally, instead of having chromosomal DNA, these cells' genetic information is in a circular loop called a plasmid. Bacterial cells are very small, roughly the size of an animal mitochondrion (about 1-2 μm in diameter and 10 μm long). Prokaryotic cells feature three major shapes: rod shaped, spherical, and spiral. Instead of going through elaborate replication processes like eukaryotes, bacterial cells divide by binary fission. Examples include but are not limited to *bacillus* bacteria, *E. coli* bacterium, and *Salmonella* bacterium.

A "composition" is intended to mean a combination of active agent and another compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers.

Carriers also include pharmaceutical excipients and additives proteins, peptides, amino acids, lipids, and carbohydrates (e.g., sugars, including monosaccharides, di-, tri, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

A composition as disclosed herein can be a pharmaceutical composition. A "pharmaceutical composition" is intended to include the combination of an active agent with a carrier, inert or active, making the composition suitable for diagnostic or therapeutic use in vitro, in vivo or ex vivo.

"Pharmaceutically acceptable carriers" refers to any diluents, excipients, or carriers that may be used in the compositions disclosed herein. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They may be selected with respect to the intended form of administration, that is, oral tablets, capsules, elixirs, syrups and the like, and consistent with conventional pharmaceutical practices.

As used herein, the term "excipient" refers to a natural or synthetic substance formulated alongside the active ingredient of a medication, included for the purpose of long-term stabilization, bulking up solid formulations, or to confer a therapeutic enhancement on the active ingredient in the final dosage form, such as facilitating drug absorption, reducing viscosity, or enhancing solubility.

The compositions used in accordance with the disclosure can be packaged in dosage unit form for case of administration and uniformity of dosage. The term "unit dose" or "dosage" refers to physically discrete units suitable for use in a subject, each unit containing a predetermined quantity of the composition calculated to produce the desired responses in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions are administered in a manner compatible with the dosage formulation and in such amount as is therapeutically or prophylactically effective. The formulations are easily administered in a variety of dosage forms, such as the type of injectable solutions described herein.

A unit dose, dosage, or regimen can be determined from the IC50 of a given polynucleotide, vector, cell, composition, or kit, for neutralizing activity against a SARS-CoV-2 polypeptide or polynucleotide, preferably a SARS-CoV-2 spike protein. "IC50" means the concentration of polynucleotide, vector, cell, composition, or kit required for 50% inhibition. Alternatively, the effective amount can be determined from the EC50 of a given polynucleotide, vector, cell, composition, or kit. "EC50" means the plasma concentration required to obtain 50% of the maximum neutralizing effect in vivo.

A combination as used herein intends that the individual active ingredients of the compositions are separately formulated for use in combination, and can be separately packaged with or without specific dosages. The active ingredients of the combination can be administered concurrently or sequentially.

The four-branched histidine-lysine (HK) peptide polymer H2K4b has been shown to be a good carrier of large molecular weight DNA plasmids (Leng et al. *Nucleic Acids Res* 2005; 33:e40.), but a poor carrier of relatively low molecular weight siRNA (Leng et al. *J Gene Med* 2005; 7:977-986). Two histidine-rich peptides analogs of H2K4b, namely H3K4b and H3K(+H)4b, were shown to be effective carriers of siRNA (Leng et al. *J Gene Med* 2005; 7: 977-986. Chou et al. *Biomaterials* 2014; 35:846-855), although H3K(+H)4b appeared to be modestly more effective (Leng et al. *Mol Ther* 2012; 20:2282-2290). Moreover, the H3K4b carrier of siRNA induced cytokines to a significantly greater degree in vitro and in vivo than H3K(+H)4b siRNA polyplexes (Leng et al. *Mol Ther* 2012; 20:2282-2290). Suitable HK polypeptides are described in WO/2001/047496, WO/2003/090719, and WO/2006/060182, the contents of each of which are incorporated herein in their entireties. These polypeptides have a lysine backbone (three lysine residues) where the lysine side chain ε-amino groups and the N-terminus are coupled to various HK sequences. HK polypeptide carriers can be synthesized by methods that are well-known in the art including, for example, solid-phase synthesis.

It was found that such histidine-lysine peptide polymers ("HK polymers" or "HKP") were surprisingly effective as mRNA carriers, and that they can be used, alone or in combination with liposomes, to provide effective delivery of mRNA into target cells. Similar to PEI and other carriers, initial results suggested HK polymers differ in their ability to carry and release nucleic acids. However, because HK polymers can be reproducibly made on a peptide synthesizer, their amino acid sequence can be easily varied, thereby allowing fine control of the binding and release of RNAs, as well as the stability of polyplexes containing the HK polymers and RNA (Chou et al. *Biomaterials* 2014; 35:846-855. Midoux et al. *Bioconjug Chem* 1999; 10:406-411. Henig et al. *Journal of American Chemical Society* 1999; 121:5123-5126). When mRNA molecules are admixed with one or more HKP carriers the components self-assemble into nanoparticles.

As described herein, advantageously the HK polymer comprises four short peptide branches linked to a three-lysine amino acid core. The peptide branches consist of histidine and lysine amino acids, in different configurations. The general structure of these histidine-lysine peptide polymers (HK polymers) is shown in Formula I, where R represents the peptide branches and K is the amino acid L-lysine.

Formula I

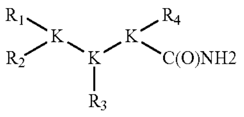

In Formula I where K is L-lysine and each of $R_1$, $R_2$, $R_3$ and $R_4$ is independently a histidine-lysine peptide. The $R_1$-4 branches may be the same or different in the HK polymers of the invention. When a R branch is "different", the amino acid sequence of that branch differs from each of the other R branches in the polymer. Suitable R branches used in the HK polymers of the invention shown in Formula I include, but are not limited to, the following R branches $R_A$-$R_{\_J}$:

$R_A$ = KHKHHKHHKHHKHHKHHKHK- (SEQ ID NO: 38)

$R_B$ = KHHHKHHHKHHHKHHHK- (SEQ ID NO: 39)

$R_C$ = KHHHKHHHKHHHHKHHHK- (SEQ ID NO: 40)

$R_D$ = kHHHkHHHkHHHHkHHHk- (SEQ ID NO: 41)

$R_E$ = HKHHHKHHHKHHHHKHHHK- (SEQ ID NO: 42)

$R_F$ = HHKHHHKHHHKHHHHKHHHK- (SEQ ID NO: 43)

$R_G$ = KHHHHKHHHHKHHHHKHHHHK- (SEQ ID NO: 44)

$R_H$ = KHHHKHHHKHHHKHHHHK- (SEQ ID NO: 45)

$R_I$ = KHHHKHHHHKHHHKHHHK- (SEQ ID NO: 46)

$R_J$ = KHHHKHHHHKHHHKHHHHK- (SEQ ID NO: 47)

Specific HK polymers that may be used in the mRNA compositions include, but are not limited to, HK polymers where each of $R_1$, $R_2$, $R_3$ and $R_4$ is the same and selected from $R_A$-$R_J$ (Table 1). These HK polymers are termed H2K4b, H3K4b, H3K(+H)4b, H3k(+H)4b, H-H3K(+H)4b, HH-H3K(+H)4b, H4K4b, H3K(1+H)4b, H3K(3+H)4b and H3K(1,3+H)4b, respectively. In each of these 10 examples, upper case "K" represents a L-lysine, and lower case "k" represents D-lysine. Extra histidine residues, in comparison to H3K4b, are underlined within the branch sequences. Nomenclature of the HK polymers is as follows:

1) for H3K4b, the dominant repeating sequence in the branches is -HHHK- (SEQ ID NO: 49), thus "H3K" is part of the name; the "4b" refers to the number of branches;
2) there are four -HHHK- (SEQ ID NO: 49) motifs in each branch of H3K4b and analogues; the first -HHHK- motif (SEQ ID NO: 49) ("1") is closest to the lysine core;
3) H3K(+H)4b is an analogue of H3K4b in which one extra histidine is inserted in the second -HHHK- motif (SEQ ID NO: 49) (motif 2) of H3K4b;
4) for H3K(1+H)4b and H3K(3+H)4b peptides, there is an extra histidine in the first (motif 1) and third (motif 3) motifs, respectively;
5) for H3K(1,3+H)4b, there are two extra histidines in both the first and the third motifs of the branches.

TABLE 1

| Polymer | Branch Sequence | Sequence Identifier |
|---|---|---|
| H2K4b | $R_A$ = KHKHHKHHKHHKHHKHHKHK- | (SEQ ID NO: 38) |
| | 4 3 2 1 | |
| H3K4b | $R_B$ = KHHHKHHHKHHHKHHHK - | (SEQ ID NO: 39) |
| H3K(+H)4b | $R_C$ = KHHHKHHHKHHHHKHHHK- | (SEQ ID NO: 40) |
| H3k(+H)4b | $R_D$ = kHHHkHHHkHHHHkHHHk- | (SEQ ID NO: 41) |
| H-H3K(+H)4b | $R_E$ = HKHHHKHHHKHHHHKHHHK- | (SEQ ID NO: 42) |
| HH-H3K(+H)4b | $R_F$ = HHKHHHKHHHKHHHHKHHHK- | (SEQ ID NO: 43) |
| H4K4b | $R_G$ = KHHHHKHHHHKHHHHKHHHHK- | (SEQ ID NO: 44) |
| H3K (1+H)4b | $R_H$ = KHHHKHHHKHHHKHHHHK- | (SEQ ID NO: 45) |
| H3K (3+H)4b | $R_I$ = KHHHKHHHHKHHHKHHHK- | (SEQ ID NO: 46) |
| H3K (1,3+H)4b | $R_J$ = KHHHKHHHHKHHHKHHHHK- | (SEQ ID NO: 47) |

Methods well known in the art, including gel retardation assays, heparin displacement assays and flow cytometry can be performed to assess performance of different formulations containing HK polymer plus liposome in successfully delivering mRNA. Suitable methods are described in, for example, Gujrati et al, *Mol. Pharmaceutics* 11:2734-2744 (2014), and Pärnaste et al., *Mol Ther Nucleic Acids.* 7: 1-10 (2017).

Detection of mRNA uptake into cells can also be achieved using SMARTFLARE® technology (Millipore Sigma). These smart flares are beads that have a sequence attached that, when recognizing the RNA sequence in the cell, produce an increase in fluorescence that can be analyzed with a fluorescent microscope.

Other methods include measuring protein expressions from an mRNA, for example, an mRNA encoding luciferase can be used to measure the efficiency of transfection. See, for example, He et al (*J Gene Med.* 2021 February; 23(2): e3295) demonstrating the efficacy of delivering mRNA using a luciferase model HKP and liposome formulation.

In the luciferase model as described above, the combination of H3K(+H)4b and DOTAP (a cationic lipid) surprisingly was synergistic in its ability to carry mRNA into MDA-MB-231 cells (H3K(+H)4b/liposomes vs liposomes, P<0.0001). The combination was about 3-fold and 8-fold more effective as carriers of mRNA than the polymer alone and the cationic lipid carrier, respectively. Not all HK peptides demonstrated the synergistic activity with DOTAP lipid. For example, the combination of H3K4b and DOTAP was less effective than the DOTAP liposomes as carriers of luciferase mRNA. Besides DOTAP, other cationic lipids that may be used with HK peptides include Lipofectin (ThermoFisher), Lipofectamine (ThermoFisher), and DOSPER.

In the luciferase model as described above, the D-isomer of H3k (+H)4b, in which the L-lysines in the branches are replaced with D-lysines, was the most effective polymeric carrier (H3k(+H)4b vs. H3K(+H)4b, P<0.05). The D-isomer/liposome carrier of mRNA was nearly 4-fold and 10-fold more effective than the H3k(+H)4b alone and liposome carrier, respectively. Although the D-H3k(+H)4b/lipid combination was modestly more effective than the L-H3K (+H)4b/lipidmbination, this comparison was not statistically different.

Both H3K4b and H3K(+H)4b can be used as carriers of nucleic acids in vitro See, for example, Leng et al. *J Gene Med* 2005; 7: 977-986; and Chou et al., *Cancer Gene Ther* 2011; 18: 707-716. Despite these previous findings, H3K(+H)4b was markedly better as a carrier of mRNA compared to other similar analogues in the luciferase model (Table 2).

TABLE 2

| Polymer | Ratio(wt:wt; mRNA:Polymer) | RLU/ug-Protein |
|---|---|---|
| H3K(+H)4b | 1:4 | 1532.9 ± 122.9 |
| | 1:8 | 1656.3 ± 202.5 |
| | 1:12 | 1033.4 ± 197 |
| H3k(+H)4b | 1:4 | 1851.6 ± 138.3 |
| | 1:8 | 1787.2 ± 195.2 |
| | 1:12 | 1982.3 ± 210.7 |
| H3K4b | 1:4 | 156.8 ± 41.8 |
| | 1:8 | 62.1 ± 13.2 |
| | 1:12 | 18.1 ± 4.0 |
| H3K(3 + H)4b | 1:4 | 61.7 ± 5.7 |
| | 1:8 | 68.7 ± 3.1 |
| | 1:12 | 59.0 ± 7.5 |
| H3K(1 + H)4b | 1:4 | 24.3 ± 4.5 |
| | 1:8 | 15.0 ± 3.6 |
| | 1:12 | 7.3 ± 2.5 |
| H-H3K(+H)4b | 1:4 | 1107.5 ± 140.4 |
| | 1:8 | 874.6 ± 65.2 |
| | 1:12 | 676.4 ± 25.7 |
| HH-H3K(+H)4b | 1:4 | 1101.9 ± 106.6 |
| | 1:8 | 832.2 ± 75.3 |
| | 1:12 | 739.8 ± 105.4 |
| H4K4b | 1:4 | 896.4 ± 112.6 |
| | 1:8 | 821.8 ± 115.6 |
| | 1:12 | 522.4 ± 69.2 |
| H3K(1,3 + H)4b | 1:4 | 518.3 ± 134.7 |
| | 1:8 | 427.7 ± 18.1 |
| | 1:12 | 378 ± 5.2 |

TABLE 2-continued

| Polymer | Ratio(wt:wt; mRNA:Polymer) | RLU/ug-Protein |
|---|---|---|
| H2K4b | 1:4 | 546.7 ± 70.1 |
| | 1:8 | 132.3 ± 58.5 |
| | 1:12 | 194.7 ± 18.4 |

Especially, it has higher mRNA transfection efficiency than H3K4b in various weight:weight (HK:mRNA) ratios. At a 4:1 ratio, luciferase expression was 10-fold higher with H3K(+H)4b than H3K4b in MDA-MB-231 cells without significant cytotoxicity. Moreover, the buffering capacity does not seem to be an essential factor in their transfection differences since the percent of histidines (by weight) in H3K4b and H3K(+H)4b is 68.9 and 70.6%, respectively.

Gel retardation assays show that the electrophoretic mobility of mRNA was delayed by the HK polymers. The retardation effect increased with higher peptide to mRNA weight ratios. However, mRNA was completely retarded in 2:1 ratio of H3K(+H)4b, whereas it was not completely retarded by H3K4b. This suggested that H3K(+H)4b could form a more stable polyplex, which was advantageous for its ability to be a suitable carrier for mRNA delivery.

Further confirmation that the H3K(+H)4b peptide binds more tightly to mRNA was demonstrated with a heparin-displacement assay. Various concentrations of heparin was added into the polyplexes formed with mRNA and HK and it was observed that, particularly at the lower concentrations of heparin, mRNA was released by the H3K4b polymer more readily than the H3K(+H)4b polymer. These data suggest H3K(+H)4b could bind to mRNA and form a more stable polyplex than H3K4b.

With the luciferase mRNA labeled with cyanine-5, the uptake of H3K4b and H3K(+H)4b polyplexes into MDA-MB-231 cells was compared using flow cytometry. At different time points (1, 2, and 4 h), the H3K(+H)4b polyplexes were imported into the cells more efficiently than H3K4b polyplexes. Similar to these results, fluorescent microscopy indicated that H3K(+H)4b polyplexes localized within the acidic endosomal vesicles significantly more than H3K4b polyplexes (H3K4b vs. H3K(+H)4b, P<0.001). Interestingly, irregularly-shaped H3K4b polyplexes, which did not overlap endocytic vesicles, were likely extracellular and were not observed with H3K(+H)4b polyplexes.

It is known both that HK polymers and cationic lipids (i.e., DOTAP) significantly and independently increase transfection with plasmids. See, for example, Chen et al. *Gene Ther* 2000; 7: 1698-1705. Consequently, whether these lipids together with HK polymers enhanced mRNA transfection was investigated. Notably, the H3K(+H)4b and H3k (+H)4b carriers were significantly better carriers of mRNA than the DOTAP liposomes. The combination of H3K(+H)4b and DOTAP lipid was synergistic in the ability to carry mRNA into MDA-MB-231 cells. The combination was about 3-fold and 8-fold more effective as carriers of mRNA than the polymer alone and the liposome carrier, respectively (H3K(+H)4b/lipid vs. liposomes or H3K(+H)4b). Notably, not all HK peptides demonstrated improved activity with DOTAP lipid. The combination of H3K4b and DOTAP carriers was less effective than the DOTAP liposomes as carriers of luciferase mRNA. The combination of DOTAP and H3K(+H)4b carriers were found to be synergistic in their ability to carry mRNA into cells. Sec, for example, He et al. *J Gene Med.* 2020 Nov. 10:03295.

In some embodiments, the carrier, such as the NKP nanoparticle, further comprises a cationic lipid, a PEG-modified lipid, a sterol and a non-cationic lipid. In some embodiments, a cationic lipid is an ionizable cationic lipid and the non-cationic lipid is a neutral lipid, and the sterol is a cholesterol. In some embodiments, a cationic lipid is selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA, or MC3), and di((Z)-non-2-en-1-yl) 9-((4-(dimethylamino)butanoyl)oxy) heptadecanedioate (L319).

In some embodiments, the carrier is a lipid nanoparticle (LNP). In some embodiments, the LNP has a mean diameter of about 50 nm to about 200 nm. In some embodiments, Lipid nanoparticle carriers/formulations typically comprise, or alternatively consist essentially of, or yet further consist of a lipid, in particular, an ionizable cationic lipid, for example, SM-102 as disclosed herein, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino) butanoyl)oxy)heptadecanedioate (L319). In some embodiments, the LNP carriers/formulations further comprise a neutral lipid, a sterol (such as a cholesterol) and a molecule capable of reducing particle aggregation, for example a PEG or PEG-modified lipid (also referred to herein as PEGylated lipid). Additional exemplary lipid nanoparticle compositions and methods of making same are described, for example, in Semple et al. (2010) Nat. Biotechnol. 28:172-176; Jayarama et al. (2012), Angew. Chem. Int. Ed., 51:8529-8533; and Maier et al. (2013) Molecular Therapy 21:1570-1578, the contents of each of which are incorporated herein by reference in their entirety.

In one embodiment, the term "disease" or "disorder" as used herein refers to a SARS-CoV-2 infection, a status of being diagnosed with a SARS-CoV-2 infection, a status of being suspect of having a SARS-CoV-2 infection, or a status of at high risk of having a SARS-CoV-2 infection. In one embodiment, the term "disease" or "disorder" as used herein refers to a symptomatic SARS-CoV-2 infection, a status of being diagnosed with a symptomatic SARS-CoV-2 infection, a status of being suspect of having a symptomatic SARS-CoV-2 infection, or a status of at high risk of having a symptomatic SARS-CoV-2 infection.

In one embodiment, the term "disease" or "disorder" as used herein refers to COVID-19, a status of being diagnosed with COVID-19, a status of being suspect of having COVID-19, or a status of at high risk of having COVID-19. In one embodiment, the term "disease" or "disorder" as used herein refers to a symptomatic COVID-19, a status of being diagnosed with a symptomatic COVID-19, a status of being suspect of having a symptomatic COVID-19, or a status of at high risk of having a symptomatic COVID-19.

As used herein, the term "animal" refers to living multicellular vertebrate organisms, a category that includes, for example, mammals and birds. The term "mammal" includes both human and non-human mammals such as non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, bat, rat, rabbit, guinea pig).

The term "subject," "host," "individual," and "patient" are as used interchangeably herein to refer to animals, typically mammalian animals. Any suitable mammal can be treated by a method described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, bat, rabbit, guinea pig). In some embodiments, a mammal is a human. A mammal can be any age or at any stage of development (e.g., an adult, teen, child, infant, or a mammal in utero). A mammal can be male or female. In some embodiments, a subject is a human. In some embodiments, a subject has or is diagnosed of having or is suspected of having a disease.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. In one aspect, treatment excludes prophylaxis.

In some embodiments, the terms "treating," "treatment," and the like, as used herein, mean ameliorating a disease, so as to reduce, ameliorate, or eliminate its cause, its progression, its severity, or one or more of its symptoms, or otherwise beneficially alter the disease in a subject. Reference to "treating," or "treatment" of a patient is intended to include prophylaxis. Treatment may also be preemptive in nature, i.e., it may include prevention of disease in a subject exposed to or at risk for the disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

"Immune response" broadly refers to the antigen-specific responses of lymphocytes to foreign substances. The terms "immunogen" and "immunogenic" refer to molecules with the capacity to elicit an immune response. All immunogens are antigens, however, not all antigens are immunogenic. An immune response disclosed herein can be humoral (via antibody activity) or cell-mediated (via T cell activation). The response may occur in vivo or in vitro. The skilled artisan will understand that a variety of macromolecules, including proteins, nucleic acids, fatty acids, lipids, lipopolysaccharides and polysaccharides have the potential to be immunogenic. The skilled artisan will further understand that nucleic acids encoding a molecule capable of eliciting an immune response necessarily encode an immunogen. The artisan will further understand that immunogens are not limited to full-length molecules, but may include partial molecules.

As used herein, "viral load", also known as "viral burden," "viral titer", "viral level" or "viral expression" in some embodiments, is a measure of the severity of a viral infection, and can be calculated by estimating the amount of virus in an infected organism, an involved body fluid, or a biological sample.

As used herein, a biological sample, or a sample, is obtained from a subject. Exemplary samples include, but are not limited to, cell sample, tissue sample, biopsy, liquid samples such as blood and other liquid samples of biological origin, including, but not limited to, anterior nasal swab, ocular fluids (aqueous and vitreous humor), peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood.

In some embodiments, the sample may be an upper respiratory specimen, such as a nasopharyngeal (NP) specimen, an oropharyngeal (OP) specimen, a nasal mid-turbinate swab, an anterior nares (nasal swab) specimen, or nasopharyngeal wash/aspirate or nasal wash/aspirate (NW) specimen.

In some embodiments, the samples include fluid from a subject, including, without limitation, blood or a blood product (e.g., serum, plasma, or the like), umbilical cord blood, amniotic fluid, cerebrospinal fluid, spinal fluid, lavage fluid (e.g., bronchoalveolar, gastric, peritoneal, ductal, car, arthroscopic), washings of female reproductive tract, urine, feces, sputum, saliva, nasal mucous, prostate fluid, lavage, semen, lymphatic fluid, bile, tears, sweat, breast milk, breast fluid, the like or combinations thereof. In some embodiments, a liquid biological sample is a blood plasma or serum sample. The term "blood" as used herein refers to a blood sample or preparation from a subject. The term encompasses whole blood, blood product or any fraction of blood, such as serum, plasma, buffy coat, or the like as conventionally defined. In some embodiments, the term "blood" refers to peripheral blood. Blood plasma refers to the fraction of whole blood resulting from centrifugation of blood treated with anticoagulants. Blood serum refers to the watery portion of fluid remaining after a blood sample has coagulated. Fluid samples often are collected in accordance with standard protocols hospitals or clinics generally follow. For blood, an appropriate amount of peripheral blood (e.g., between 3-40 milliliters) often is collected and can be stored according to standard procedures prior to or after preparation.

The term "adjuvant" refers to a substance or mixture that enhances the immune response to an antigen. As non-limiting example, the adjuvant can comprise dimethyldioctadecylammonium-bromide, dimethyldioctadecylammonium-chloride, dimethyldioctadecylammonium-phosphate or dimethyldioctadecylammonium-acetate (DDA) and an apolar fraction or part of said apolar fraction of a total lipid extract of a *mycobacterium* (See e.g., U.S. Pat. No. 8,241,610). In another embodiment, the synthetic nanocarrier may comprise at least one polynucleotide and an adjuvant. As a non-limiting example, the synthetic nanocarrier comprising and adjuvant can be formulated by the methods described in WO2011150240 and US20110293700, each of which is herein incorporated by reference in its entirety.

The term "contacting" means direct or indirect binding or interaction between two or more. A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration.

"Administration" or "delivery" of a polynucleotide, vector, cell or vector or other agent and compositions containing same can be performed in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician or in the case of animals, by the treating veterinarian. In some embodiments, administering or a grammatical variation thereof also refers to more than one doses with certain interval. In some embodiments, the interval is 1 day, 2 days, 3 days, 4 days, 5 days, 6 days, 1 week, 10 days, 2 weeks, 3 weeks, 1 month, 2 months, 3 months, 4 months, 5 months, 6 months, 1 year or longer. In some embodiments, one dose is repeated for once, twice, three times, four times, five times, six times, seven times, eight times, nine times, ten times or more. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include inhalation, intramuscular administration, nasal administration, oral administration, intraperitoneal, infusion, injection, and topical application. In preferred embodiments, the route of administration is inhalation or intramuscular administration. In some embodiments, the administration is an infusion (for example to peripheral blood of a subject) over a certain period of time, such as about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 24 hours or longer.

The term administration shall include without limitation, administration by oral, parenteral (e.g., intramuscular, intraperitoneal, intravenous, intracerebroventricular (ICV), intrathecal, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. The disclosure is not limited by the route of administration, the formulation or dosing schedule.

In some embodiments, an RNA, polynucleotide, vector, cell or composition as disclosed herein is administered in an effective amount. An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents disclosed herein for any particular subject depends upon a variety of factors including the activity of the specific agent employed, bioavailability of the agent, the route of administration, the age of the animal and its body weight, general health, sex, the diet of the animal, the time of administration, the rate of excretion, the drug combination, and the severity of the particular disorder being treated and form of administration. In general, one will desire to administer an amount of the agent that is effective to achieve a serum level commensurate with the concentrations found to be effective in vivo. These considerations, as well as effective formulations and administration procedures are well known in the art and are described in standard textbooks.

As used herein, the term "RL-007" and RL007" refers to an lipid nanoparticle formulation or mix that is prepared by mixing a final concentration of 6.25 mM of SM-102, 1.25 mM of DSPC, 4.815 mM of Cholesterol, and 0.1875 of mM DMG-PEG2000 (i.e., a 50:10:38:1.5 molar ratio). The Terms "RL-007 vaccine", "RL007 vaccine", "RL-007 mRNA vaccine", or "RL007 mRNA vaccine" refer to a vaccine which comprises, or alternatively consists essentially of, or yet further consists of an RL-007 carrier. In some embodiments, the pharmaceutically acceptable carrier comprises, or alternatively consists essentially of, or yet further consists of RL-007.

Modes for Carrying Out the Disclosure

RNA

The disclosure herein provides a ribonucleic acid (RNA) or DNA encoding a spike (S) protein or a fragment thereof (such as an immunogenic fragment) of a severe acute respiratory syndrome coronavirus 2 (SARS-CoV-2). The S protein or fragment comprises, or consists essentially of, or yet further consists of, at least one non-naturally occurring amino acid mutation.

In some embodiments, the fragment or immunogenic fragment comprises, or alternatively consists essentially of, or yet further consists of a receptor binding domain (RBD) of the S protein or an equivalent thereof, such as a fragment corresponding (such as aligning) to aa 319 to aa 541 of SEQ ID NO: 1. In some embodiments, a receptor-binding domain (RBD) refers to a short immunogenic fragment from a virus that binds to a specific endogenous receptor sequence to gain entry into target cells. In some embodiments, RBD refer to a part of the 'spike' glycoprotein which is needed to interact with endogenous receptors to facilitate membrane fusion and delivery to the cytoplasm. In some embodiments, the RBD as used herein comprises, or consists essentially of, or yet further consists of the polypeptide as set forth in aa 319 to aa 541 of SEQ ID NO: 1 or an equivalent thereof. In some embodiments, the fragment or immunogenic fragment is at least about 5 amino acids long, or at least about 8 amino acids long, or at least about 10 amino acids long, or at least about 15 amino acids long, or at least about 20 amino acids long, or at least about 25 amino acids long, or at least about 30 amino acids long, or at least about 40 amino acids long, or at least about 50 amino acids long, or at least about 60 amino acids long, or at least about 70 amino acids long, or at least about 80 amino acids long, or at least about 100 amino acids long, or at least about 125 amino acids long, or at least about 150 amino acids long, or at least about 160 amino acids long, or at least about 170 amino acids long, or at least about 180 amino acids long, or at least about 190 amino acids long, or at least about 200 amino acids long, or at least about 250 amino acids long, or at least about 300, or longer; and optionally comprises, consists essentially of, or yet further consists of a RBD of the S protein or an equivalent thereof. The immunogenic fragment is useful for inducing an immune response to the SARS-CoV-2, or reducing or inhibiting the binding of SARS-CoV-2 to its receptor, such as ACE2, or both and a fragment that is non-immunogenic is useful as a control in the assays as provided herein.

In some embodiments, the at least one non-naturally occurring amino acid mutation comprises, or alternatively consists essentially of, or yet further consists of a mutation in a furin-like cleavage site. In further embodiments, the furin-like cleavage site comprises, or alternatively consists of, or yet further consists of RRAR (SEQ ID NO: 48). In yet further embodiments, a furin-like cleavage site in an S protein or a fragment thereof as disclosed herein corresponds to (e.g., aligns to) amino acid (aa) 682 to aa 685 of SEQ ID NO: 1. In some embodiments, the at least one non-naturally occurring amino acid mutation comprises, or alternatively consists essentially of, or yet further consists of one or more of: a serine (S) as the amino acid corresponding to R682 of SEQ ID NO: 1 (R682S), an S as the amino acid corresponding to R683 of SEQ ID NO: 1 (R683S), a glycine (G) as the amino acid corresponding to R685 of SEQ ID NO: 1 (R685G), or a G as the amino acid corresponding to R682 of SEQ ID NO: 1 (R682G). In some embodiments, the at least one non-naturally occurring amino acid mutation comprises, or alternatively consists essentially of, or yet further consists R682S and R685G. In some embodiments, a mutated furin-like cleavage site stabilize the S protein or fragment thereof as disclosed herein.

Additionally or alternatively, the at least one non-naturally occurring amino acid mutation comprises, or alternatively consists essentially of, or yet further consists of a proline (P) as the amino acid corresponding to any one or more (such as any two, or any three, or any four, or any five, or all six) of F817 of SEQ ID NO: 1 (F817P), A892 of SEQ ID NO: 1 (A892P), A899 of SEQ ID NO: 1 (A899P), A942 of SEQ ID NO: 1 (A942P), K986 of SEQ ID NO: 1 (K986P), or V987 of SEQ ID NO: 1 (V987P). In some embodiments, the at least one non-naturally occurring amino acid mutation comprises, or alternatively consists essentially of, yet further consists of K986P and V987P. These two mutations are referred to herein as S2P. In some embodiments, the at least one non-naturally occurring amino acid mutation comprises, or alternatively consists essentially of, yet further consists of F817P, A892P, A899P, A942P, K986P, and V987P. These six mutations are referred to herein as "S-HexaPro" or "S6P". In some embodiments, an S protein or a fragment (such as an immunogenic fragment thereof) comprising the S2P or S6P mutations has one or more of the following properties compared to those without the S2P or S6P mutations: increased expression level in vivo or in vitro or both; higher stability, such as room temperature, under heat, or after freeze-thaws; or maintaining the protein conformation.

In some embodiments, the at least one non-naturally occurring amino acid mutation comprises, or alternatively consists essentially of, or yet further consists of one or more of: a serine (S) as the amino acid corresponding to R682 of SEQ ID NO: 1 (R682S), a glycine (G) as the amino acid corresponding to R685 of SEQ ID NO: 1 (R685G), a proline (P) as the amino acid corresponding to F817 of SEQ ID NO: 1 (F817P), a P as the amino acid corresponding to A892 of SEQ ID NO: 1 (A892P), a P as the amino acid corresponding to A899 of SEQ ID NO: 1 (A899P), a P as the amino acid corresponding to A942 of SEQ ID NO: 1 (A942P), a P as the amino acid corresponding to K986 of SEQ ID NO: 1 (K986P), or a P as the amino acid corresponding to V987 of SEQ ID NO: 1 (V987P).

Without wishing to be bound by the theory, an S protein or a fragment thereof comprises a mutated furin-like cleavage site and S2P or S6P mutations shows an advantage (such as an higher expression level in vivo and in vitro, or a better stability, or both) over those free of these mutations, or comprising a mutated furin-like cleavage site alone, or comprising S2P or S6P alone. In some embodiments, the advantage of comprising both mutation sets is synergistic.

In some embodiments, the S protein or fragment thereof is derived from a naturally occurring SARS-CoV-2 variant, such as an alpha variant, a beta variant, a delta variant, or a gamma variant. For example, the at least one non-naturally occurring amino acid mutations as disclosed herein can be engineered to a S protein variant or a fragment thereof, such as an alpha variant, a beta variant, a delta variant, or a gamma variant, thus arriving at a mutated S protein or a fragment thereof.

In further embodiments, the S protein or fragment thereof is derived from a chimeric SARS-CoV-2 S protein. The chimeric S protein comprises, or alternatively consists essentially of, or yet further consists of a first naturally occurring S variant having one or more of its amino acids or continuous segments substituted with the corresponding amino acids or continuous segments of a second naturally occurring S variant.

In some embodiments, the S protein or fragment thereof further comprises one or more mutations, which was found in a naturally occurring SARS-CoV-2 variant, such as a delta variant. In some embodiments, the one or more mutations comprises, or alternatively consists essentially of, or yet further consists of one or both of: a lysine (K) as the amino acid corresponding to N440 of SEQ ID NO: 1 (N440K), or a K as the amino acid corresponding to E484 of SEQ ID NO: 1 (E484K). Additionally or alternatively, the one or more mutations comprises, or alternatively consists essentially of, or yet further consists of an arginine (R) as the amino acid corresponding to T19 of SEQ ID NO: 1 (T19R), a phenylalanine (F) as the amino acid corresponding to V70 of SEQ ID NO: 1 (V70F), an isoleucine (I) as the amino acid corresponding to T95 of SEQ ID NO: 1 (T95I), an aspartic acid (D) as the amino acid corresponding to G142 of SEQ ID NO: 1 (G142D), a deletion corresponding to E156 of SEQ ID NO: 1 (E156Δ), a deletion corresponding to F157 of SEQ ID NO: 1 (F157Δ), a G as the amino acid corresponding to R158 of SEQ ID NO:1 (R158G), a valine (V) as the amino acid corresponding to A222 of SEQ ID NO: 1 (A222V), a leucine (L) as the amino acid corresponding to W258 of SEQ ID NO: 1 (W258L), an asparagine (N) as the amino acid corresponding to K417 of SEQ ID NO: 1 (K417N), an R as the amino acid corresponding to K417 of SEQ ID NO: 1 (L452R), a K as the amino acid corresponding to T478 of SEQ ID NO: 1 (T478K), a G as the amino acid corresponding to D614 of SEQ ID NO: 1 (D614G), an R as the amino acid corresponding to P681 of SEQ ID NO: 1 (P681R), or an N as the amino acid corresponding to D950 of SEQ ID NO: 1 (D950N). In some embodiments, the one or more mutations comprises, or alternatively consists essentially of, or yet further consists of T19R, T95I, G142D, E156Δ, F157Δ, R158G, L452R, T478K, D614G, P681R and D950N. In some embodiments, the one or more mutations comprises, or alternatively consists essentially of, or yet further consists of T19R, T95I, G142D, E156Δ, F157Δ, R158G, L452R, T478K, D614G and D950N. In some embodiments, the one or more mutations comprises, or alternatively consists essentially of, or yet further consists of T19R, V70F, T95I, G142D, E156Δ, F157Δ, R158G, A222V, W258L, K417N, L452R, T478K, D614G, P681R and D950N. In some embodiments, the one or more mutations comprises, or alternatively consists essentially of, or yet further consists of T19R, V70F, T95I, G142D, E156Δ, F157Δ, R158G, A222V, W258L, K417N, N440K, LA52R, T478K, E484K, D614G, P681R and D950N.

In some embodiments, the S protein comprises, or alternatively consists essentially of, or yet further consists of the polypeptide of SEQ ID NO: 5 or an equivalent thereof. In some embodiments, the equivalent of SEQ ID NO: 5 retains the mutations of SEQ ID NO: 5, i.e., T19R, T95I, G142D, E156Δ, F157Δ, R158G, L452R, T478K, D614G, P681R, R682S, R685G, D950N, K986P, and V987P. In further embodiments, the RNA or DNA comprises, or alternatively consists essentially of, or yet further consists of a polynucleotide encoding SEQ ID NO: 5 or an equivalent thereof.

In some embodiments, the S protein comprises, or alternatively consists essentially of, or yet further consists of the polypeptide of SEQ ID NO: 6 or an equivalent thereof. In some embodiments, the equivalent of SEQ ID NO: 6 retains the mutations of SEQ ID NO: 6, i.e., T19R, T95I, G142D, E156Δ, F157Δ, R158G, L452R, T478K, D614G, R682S, R685G, D950N, K986P, and V987P. In further embodiments, the RNA or DNA comprises, or alternatively consists essentially of, or yet further consists of a polynucleotide encoding SEQ ID NO: 6 or an equivalent thereof.

In some embodiments, the S protein comprises, or alternatively consists essentially of, or yet further consists of the polypeptide of SEQ ID NO: 7 or an equivalent thereof. In some embodiments, the equivalent of SEQ ID NO: 7 retains the mutations of SEQ ID NO: 7, i.e., T19R, T95I, G142D, E156Δ, F157Δ, R158G, L452R, T478K, D614G, P681R, D950N, F817P, A892P, A899P, A942P, K986P, V987P, R682S and R685G. In further embodiments, the RNA comprises, or alternatively consists essentially of, or yet further consists of the polynucleotide of SEQ ID NO: 9 or an equivalent thereof. In some embodiments, the equivalent of SEQ ID NO: 9 still encodes SEQ ID NO: 7 or an equivalent thereof.

In some embodiments, the S protein comprises, or alternatively consists essentially of, or yet further consists of the polypeptide of SEQ ID NO: 10 or an equivalent thereof. In some embodiments, the equivalent of SEQ ID NO: 10 retains the mutations of SEQ ID NO: 10, i.e., T19R, T95I, G142D, E156Δ, F157Δ, R158G, L452R, T478K, D614G, D950N, F817P, A892P, A899P, A942P, K986P, V987P, R682S and R685G. In further embodiments, the RNA or DNA comprises, or alternatively consists essentially of, or yet further consists of a polynucleotide encoding SEQ ID NO: 10 or an equivalent thereof.

In some embodiments, the S protein comprises, or alternatively consists essentially of, or yet further consists of the polypeptide of SEQ ID NO: 11 or an equivalent thereof. In some embodiments, the equivalent of SEQ ID NO: 11 retains the mutations of SEQ ID NO: 11, i.e., T19R, V70F, T95I, G142D, E156Δ, F157Δ, R158G, A222V, W258L, K417N, L452R, T478K, D614G, P681R, D950N, F817P, A892P, A899P, A942P, K986P, V987P, R682S and R685G. In further embodiments, the RNA comprises, or alternatively consists essentially of, or yet further consists of the polynucleotide of SEQ ID NO: 13 or an equivalent thereof. In some embodiments, the equivalent of SEQ ID NO: 13 still encodes SEQ ID NO: 11 or an equivalent thereof.

In some embodiments, the S protein comprises, or alternatively consists essentially of, or yet further consists of the polypeptide of SEQ ID NO: 14 or an equivalent thereof. In some embodiments, the equivalent of SEQ ID NO: 14 retains the mutations of SEQ ID NO: 14, i.e., T19R, V70F, T95I, G142D, E156Δ, F157Δ, R158G, A222V, W258L, K417N, L452R, T478K, D614G, P681R, D950N, E484K, N440K, F817P, A892P, A899P, A942P, K986P, V987P, R682S and R685G. In further embodiments, the RNA comprises, or alternatively consists essentially of, or yet further consists of the polynucleotide of SEQ ID NO: 16 or an equivalent thereof. In some embodiments, the equivalent of SEQ ID NO: 16 still encodes SEQ ID NO: 14 or an equivalent thereof. In one aspect, the RNA comprises, or consists essentially of, or yet further consists of a sequence disclosed in SEQ ID NO: 55, or an equivalent thereof.

In some embodiments, the equivalent of any one of SEQ ID NOs: 9, 13, or 16 consists of an GC content of about 35% to about 70% across the full length of the equivalent.

In some embodiments, the equivalent is at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99%, or more identical to the full-length reference sequence.

In some embodiments, the RNA further comprises a 3' UTR. In further embodiments, the 3'UTR comprises, or alternatively consists essentially of, or consists of any one of SEQ ID NOs: 18, 22, or 24.

In some embodiments, the RNA further comprises a 5' UTR. In further embodiments, the 5' UTR comprises, or alternatively consists essentially of, or consists of SEQ ID NO: 20 or 26.

In some embodiments, the RNA further comprises a polyA tail. In further embodiments, the poly A tail comprises any one of SEQ ID NOs: 27, 28, or 30.

In some embodiments, the RNA further comprises a 5' cap. In further embodiments, the 5' cap comprises, or alternatively consists of, or yet further consists of a 5' CleanCap. This structure uses an initiating capped trimer to yield a naturally occurring 5' cap structure.

In some embodiments, the RNA comprises, or alternatively consists essentially of, or consist of, optionally from 5' to 3', a 5'UTR, a coding sequence encoding an S protein or a fragment as disclosed herein, a 3'UTR and a polyA. In further embodiments, the RNA comprises, or alternatively consists essentially of, or consists of SEQ ID NO: 32 or 52.

In some embodiments, the RNA is a messenger RNA (mRNA). Further provided are DNA molecules encoding these RNA as well as the complements thereof.

In some embodiments, the RNA is chemically modified. In further embodiments, the modification comprises, or alternatively consists essentially of, or consists of modifying a uridine (U) residue to an N1-methyl-pseudouridine residue. Additionally or alternatively, the modification comprises, or alternatively consists essentially of, or consist of modifying a U residue to a pseudouridine residue.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher percentage of residues of the RNA is chemically modified.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or higher percentage of uridine residues of the RNA is chemically modified, optionally to N1-methyl pseudouridine or pseudouridine. In further embodiments, at least about 50%, or at least about 70%, or about 100% of the uridine residues in the RNA are N1-methyl pseudouridine or pseudouridine.

In some embodiments, all or some of uridine residues are replaced by pseudouridines during in vitro transcription. This modification stabilizes the mRNA against enzymatic degradation in the cell, leading to enhanced translation efficiency of the mRNA. The pseudouridines used can be N1-methyl-pseudouridine, or other modifications that are well known in the art such as N6m-ethyladenosine (m6A), inosine, pseudouridine, 5-methylcytidine (m5C), 5-hydroxymethylcytidine (hm5C), and N1-methyladenosine (m1A). The modification optionally is made throughout the entire mRNA. The skilled artisan will recognize that other modified RNA residues can be used to stabilize the protein's 3 dimensional structure and increase protein translation.

Without wishing to be bound by the theory, an RNA encoding a naturally occurring S protein activates an endosomal RNA sensing pathway such as TLR3, TLR7, and TLR8 (Toll-like receptor), thereby induces innate immunity which in turn inhibits spike protein translation. In addition, a secreted IFN-β provokes tumor cell death upon binding of cognate receptor expressed on the cell surface by activation of the downstream apoptotic pathway. However, an optimized RNA expressing a mutated S protein as disclosed herein avoids this disadvantage, and thus presents an improved translation efficiency (innate immunity) which in turn inhibits spike protein translation. In some embodiments, the optimized RNA can be administered to a subject in need thereof, expressing the mutated S protein in vivo. In further embodiments, the expressed S protein can induce an immune response in the subject, which in turns preventing or treating a SARS-CoV-2 infection as disclosed herein. Additionally or alternatively, the optimized RNA expresses the mutated S protein in vitro and optionally such expressed S protein can activate an immune cell in vitro. The activated immune cells can then be used to treat a subject in need thereof.

In another aspect, provided is a method of producing a spike (S) protein or an immunogenic fragment thereof of a severe acute respiratory syndrome coronavirus 2 (SARS-CoV-2). In some embodiments, the method is an in vitro method. The method comprises, or alternatively consists essentially of, or yet further consists of culturing a cell as disclosed herein under conditions suitable for expressing the S protein or immunogenic fragment thereof. In further embodiments, the method herein further comprises isolating the S protein or immunogenic fragment thereof. In some embodiments, the cell is a host cell as disclosed herein.

Additionally, provided is a method for screening a candidate agent reducing or inhibiting the binding of SARS-CoV-2 and its receptor, such as ACE2, optionally in a subject or on a cell of the subject or both. The method comprises, or alternatively consist essentially of, or yet further consists of expressing a spike (S) protein or an immunogenic fragment thereof from an RNA as disclosed herein, and measuring the binding between the expressed S protein or immunogenic fragment thereof and the SARS-CoV-2 receptor, such as ACE2, with or without the presence of the candidate agent or with different concentrations of the candidate agent. In some embodiments, less binding between the expressed S protein or immunogenic fragment thereof and the SARS-CoV-2 receptor with the presence of the candidate agent compared to without the candidate agent, indicates that the candidate agent reduces or inhibits the binding of SARS-CoV-2 and its receptor. In some embodiments, decreased binding between the expressed S protein or immunogenic fragment thereof and the SARS-CoV-2 receptor while increasing the concentration of the candidate agent indicates the candidate agent reduces or inhibits the binding of SARS-CoV-2 and its receptor. In some embodiments, the S protein or immunogenic fragment thereof is expressed in a host cell in the measuring step. Additionally or alternatively, the receptor, such as ACE2, is expressed in a host cell in the measuring step. In some embodiments, the receptor, such as ACE2, is isolated from a host cell in the measuring step, In other embodiments, the S protein or immunogenic fragment thereof is isolated from a host cell in the measuring step. In some embodiments, the isolated S protein or immunogenic fragment thereof or the isolated receptor further comprises a detectable label, such as a fluorescent protein. In further embodiments, the binding between the S protein or immunogenic fragment thereof and the receptor is performed using a fluorescence-based assay, such as fluorescent microscopy or Fluorescence-Activated Cell Sorting (FACS)

In yet a further aspect, provided is a method for selecting an RNA encoding a spike (S) protein or an immunogenic fragment thereof of a severe acute respiratory syndrome coronavirus 2 (SARS-CoV-2). The method comprises, or alternatively consists essentially of, or yet further consists of transducing the RNA into a cell, culturing the cell under conditions suitable for expressing the RNA, and measuring IFN-α or IFN-β or both secreted by the cell. In some embodiments, the method further comprises selecting the RNA if no secretion of IFN-α or IFN-β or both or less secretion of IFN-α or IFN-β or both compared to an RNA encoding a wild type S protein or an immunogenic fragment thereof. In some embodiments, the IFN-α or IFN-β or both is measured using enzyme-linked immunosorbent assay.

Polynucleotides, Vectors, Cells and Related Methods

In one aspect, provided is a polynucleotide encoding an RNA as disclosed herein, or a polynucleotide complementary thereto. In some embodiments, the polynucleotide is selected from the group of: a deoxyribonucleic acid (DNA), an RNA, a hybrid of DNA and RNA, or an analog of each thereof.

In some embodiments, the disclosure provides a polynucleotide encoding a spike (S) protein or an immunogenic fragment thereof of a severe acute respiratory syndrome coronavirus 2 (SARS-CoV-2) the S protein or immunogenic fragment thereof comprising at least one non-naturally occurring amino acid mutation. A non-limiting example of such polynucleotide comprises, or alternatively consists essentially of, or consists of a the sequence of SEQ ID NO: 55. In some embodiments, the disclosure provides a polynucleotide encoding a spike (S) protein or an immunogenic fragment thereof of a severe acute respiratory syndrome coronavirus 2 (SARS-CoV-2) comprising at least one non-naturally occurring amino acid mutation, wherein the polynucleotide comprises, or alternatively consists essentially of, or consists of a the sequence of SEQ ID NO: 52.

In a further aspect, provided is a vector comprising, or alternatively consisting essentially of, or consisting of a polynucleotide as disclosed herein. In some embodiments, the polynucleotide is a vector comprising, or alternatively consisting essentially of, or consisting of the sequence of SEQ ID NO: 53.

In some embodiments, the vector further comprises a regulatory sequence operatively linked to the polynucleotide to direct the transcription thereof. In some embodiments, the regulatory sequence is suitable for use in an in vitro transcription system. In further embodiments, the regulatory sequence comprises, or alternatively consists essentially of, or consists of a promotor. In yet further embodiments, the promoter is an RNA polymerase promoter, optionally a bacteriophage RNA polymerase promoter. In some embodiment, the promoter comprises, or consists essentially of, or further consists of a T7 promoter, or a SP6 promoter, or a T3 promoter. In some embodiments, the T7 promoter comprises, or consists essentially of, or yet further consists of TAATACGACTCACTATAA (SEQ ID NO: 51). In some embodiments, the regulatory sequence is suitable for use in a cell to expressing an RNA as disclosed herein. In further embodiments, the regulatory sequence comprises, or alternatively consists essentially of, or yet further consists of a promotor, or an enhancer or both.

In some embodiments, the vector further comprises a regulatory sequence operatively linked to the polynucleotide to direct the replication thereof. In further embodiments, the regulatory sequence comprises, or alternatively consists essentially of, or yet further consists of one or more of the following: an origin of replication or a primer annealing site, a promoter, or an enhancer.

In some embodiments, an RNA, or a polynucleotide, or a vector further comprises a marker selected from a detectable marker, a purification marker, or a selection marker.

In some embodiments, the vector is a non-viral vector, optionally a plasmid, or a liposome, or a micelle. In some embodiments, the plasmid comprises, or alternatively consists essentially of, or consists of SEQ ID NO: 33 or an equivalent thereof. In some embodiments, the vector is a viral vector, optionally an adenoviral vector, or an adeno-associated viral vector, or a retroviral vector, or a lentiviral vector, or a plant viral vector.

In some embodiments, a polynucleotide or a vector as disclosed herein is suitable for producing (such as transcribing or expressing or replicating) an RNA as disclosed herein. Such production can be in vivo or in vitro. For example, the polynucleotide or vector can be used to produce or replicate the RNA in vitro. Such RNA is then administrated to a subject in need thereof optionally with a suitable pharmaceutical acceptable carrier. Alternatively, the polynucleotide or vector can be used as a gene therapy and directly administrated to a subject in need thereof optionally with a suitable pharmaceutical acceptable carrier. In further embodiments, the gene therapy can additionally deliver other prophylactic or therapeutic agent to the subject.

In another aspect, a cell comprising one or more of: an RNA as disclosed herein, a polynucleotide as disclosed herein, or a vector as disclosed herein. In some embodiments, the cell is a prokaryotic cell, optionally an *Escherichia coli* cell. In some embodiments, the cell is a eukaryotic cell, optionally a mammal cell, an insect cell, or a yeast cell. In some embodiments, the cell is a human embryonic kidney 293 cell (HEK 293 cell or 293 cell) or a 293T cell.

In some embodiments, a cell as disclosed herein is suitable for producing (such as transcribing or expressing) an RNA as disclosed herein. Such production can be in vivo or in vitro. For example, the cell can be used to produce the RNA in vitro. Such RNA is then administrated to a subject in need thereof optionally with a suitable pharmaceutical acceptable carrier. Alternatively, the cell can be used as a cell therapy and directly administrated to a subject in need thereof optionally with a suitable pharmaceutical acceptable carrier. In further embodiments, the cell therapy can additionally deliver other prophylactic or therapeutic agent to the subject.

In yet another aspect, provided is a composition comprising, or alternatively consisting essentially of, or yet further consisting of a carrier, optionally a pharmaceutically acceptable carrier, and one or more of: an RNA as disclosed herein, a polynucleotide as disclosed herein, a vector as disclosed herein, or a cell as disclosed herein.

In some embodiments, the composition further comprises an additional prophylactic or therapeutic agent.

In some embodiments, the additional prophylactic or therapeutic agent is suitable for preventing or treating a SARS-CoV-2 related disease as disclosed herein. In further embodiments, the additional prophylactic or therapeutic agent comprises, or alternatively consists essentially of, or yet further consists of an anti-viral agent, optionally remdesivir, lopinavir, ritonavir, ivermectin, tamiflu, or favipiravir; an anti-inflammatory agent, optionally dexamethasone, tocilizumab, kevzara, colcrys, hydroxychloroquine, chloroquine, or a kinase inhibitor; a covalescent plasma from a subject recovered from a SARS-CoV-2 infection; an antibody binding to SARS-CoV-2, optionally bamlanivimab, etesevimab, casirivimab, or imdevimab; or an antibiotic agent, optionally azithromycin.

In some embodiments, the additional prophylactic agent is suitable for preventing a disease that is not related to SARS-CoV-2. For example, the additional prophylactic agent comprises, or alternatively consists essentially of, or yet further consists of a vaccine for another coronavirus, such as SARS-CoV or MERS-CoV. Additionally or alternatively, the additional prophylactic agent comprises, or alternatively consists essentially of, or yet further consists of a vaccine for another virus, such as an influenza (flu) vaccine, a papillomavirus vaccine, an Hepatitis A vaccine, an Hepatitis B vaccine, an Hepatitis c vaccine, a polio vaccine, a chickenpox varicella vaccine, a measles vaccine, a mumps vaccine, a rubella vaccine, a rotavirus vaccine. In some embodiments, the additional prophylactic agent comprises, or alternatively consists essentially of, or yet further consists of a vaccine for a bacterium or other pathogen, such as a diphtheria vaccine, a *Haemophilus influenzae* type b vaccine, a Pertussis vaccine, a pneumococcus vaccine, a Tetanus vaccine, or a Meningococcal vaccine. In some embodiments, the additional prophylactic agent comprises, or alternatively consists essentially of, or yet further consists of a vaccine for a non-infectious disease, such as a cancer.

In some embodiments, the composition further comprises an adjuvant.

In one aspect, provided is a method of producing an RNA as disclosed herein. In some embodiments, the method comprises, or alternatively consists essentially of, or yet further consists of culturing a cell as disclosure herein under conditions suitable for expressing and/or replicating the RNA. In further embodiments, the RNA is produced by a plasmid DNA (pDNA) vector delivery system. In yet further embodiments, the plasmid vectors can be adapted for mRNA vaccine production. Commonly used plasmids include pSFV1, pcDNA3 and pTK126, which are all commercially available. One unique mRNA expression system is pEVL (see, Grier et al. *Mol Ther Nucleic Acids.* 19; 5:e306 (2016)).

In some embodiments, the method comprises, or alternatively consists essentially of, or yet further consists of contacting a polynucleotide as disclosed herein or a vector as disclosed herein with an RNA polymerase, adenosine triphosphate (ATP), cytidine triphosphate (CTP), guanosine-5'-triphosphate (GTP), and uridine triphosphate (UTP) or a chemically modified UTP under conditions suitable for expressing the RNA. In some embodiments, the RNA is produced in a linear in vitro transcription (IVT) system from a linear DNA template comprising a bacteriophage promoter, UTRs and a coding sequence, by using a RNA polymerase (T7, T3 or SP6) and a mix of the different nucleosides. In some embodiments, the method further comprises isolating the RNA. In further embodiments, the method further comprises storing the RNA.

Formulation and Related Methods

In one aspect, provided is a composition comprising, or alternatively consisting essentially of, or yet further consisting of an RNA as disclosed herein and a pharmaceutically acceptable carrier.

In some embodiments, the pharmaceutically acceptable carrier comprises, or alternatively consists essentially of, or yet further consists of a polymeric nanoparticle. In some embodiments, the polymeric nanoparticle comprises, or alternatively consists essentially of, or yet further consists of a Histidine-Lysine co-polymer (HKP). In some embodiments, the HKP comprises a side chain selected from SEQ ID NOs: 34-47. Without wishing to be bound by the theory, RNA in the composition has a higher stability compared to the RNA free of a nanoparticle.

In some embodiments, the pharmaceutically acceptable carrier further comprises a lipid. In further embodiments, the lipid comprises a cationic lipid, optionally ionizable. In yet further embodiments, the cationic lipid comprises Dlin-MC3-DMA (MC3) or dioleoyloxy-3-(trimethylammonio) propane (DOTAP) or both. In some embodiments, the lipid further comprises one or more of: a helper lipid, a cholesterol, or a PEGylated lipid.

In some embodiments, the pharmaceutically acceptable carrier comprises, or alternatively consists essentially of, or yet further consists of a lipid nanoparticle (LNP). In further embodiments, the LNP comprises, or alternatively consists essentially of, or yet further consists of one or more of: 9-Heptadecanyl 8-{(2-hydroxyethyl)[6-oxo-6-(undecyloxy) hexyl]amino}octanoate (SM-102), 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy) heptadecanedioate (L319), or an equivalent of each thereof. In yet further embodiments, the LNP further comprises one or more of: a helper lipid, a cholesterol, or a PEGylated lipid.

In some embodiments, the helper lipid comprises, or alternatively consists essentially of, or yet further consists of one or more of: disteroylphosphatidyl choline (DSPC), Dipalmitoylphosphatidylcholine (DPPC), (2R)-3-(Hexadecanoyloxy)-2-{[(9Z)-octadec-9-enoyl]oxy}propyl 2-(trimethylazaniumyl)ethyl phosphate (POPC), or dioleoyl phosphatidylethanolamine (DOPE).

As used herein, the term “RL-007” and RL007" refers to an ionizable lipid equivalent that is prepared by mixing a final concentration of 6.25 mM of SM-102, 1.25 mM of DSPC, 4.815 mM of Cholesterol, and 0.1875 of mM DMG-PEG2000 (i.e., a 50:10:38:1.5 molar ratio). The Terms “RL-007 vaccine”, “RL007 vaccine”, “RL-007 mRNA vaccine”, or “RL007 mRNA vaccine” refer to a vaccine which comprises, or alternatively consists essentially of, or yet further consists of an RL-007 carrier. In some embodiments, the pharmaceutically acceptable carrier comprises, or alternatively consists essentially of, or yet further consists of RL-007.

In some embodiments, wherein the cholesterol comprises, or alternatively consists essentially of, or yet further consists of a plant cholesterol or an animal cholesterol or both.

In some embodiments, the PEGylated lipid comprises, or alternatively consists essentially of, or yet further consists of one or more of: PEG-c-DOMG (R-3-[(ω-methoxy-poly(ethyleneglycol)2000)carbamoyl)]-1,2-dimyristyloxypropyl-3-amine), PEG-DSG (1,2-Distearoyl-sn-glycerol, methoxypolyethylene glycol), PEG-DMG (1,2-Dimyristoyl-sn-glycerol) optionally PEG2000-DMG ((1,2-dimyristoyl-sn-glycero-3-phophoethanolamine-N-[methoxy(polyethylene glycol)-2000)], or PEG-DPG (1,2-Dipalmitoyl-sn-glycerol, methoxypolyethylene glycol).

In a further aspect, provided is a method of producing a composition comprising, or alternatively consisting essentially of, or yet further consisting of an RNA as disclosed herein and an HKP. The method comprises, or alternatively consists essentially of, or yet further consists of contacting the RNA with an HKP, thereby the RNA and the HKP are self-assembled into nanoparticles.

In some embodiments, the mass ratio of HKP and the RNA in the contacting step is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of HKP and the RNA in the contacting step is about 2.5:1. In another embodiment, the mass ratio of HKP and the RNA in the contacting step is about 4:1.

In some embodiments, the method further comprises contacting the HKP and RNA with a cationic lipid. In further embodiments, the cationic lipid comprises, or consists essentially of, or yet further consists of Dlin-MC3-DMA (MC3) or DOTAP (dioleoyloxy-3-(trimethylammonio)propane) or both. In yet further embodiments, the mass ratio of the cationic lipid and the RNA in the contacting step is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of the RNA and the cationic lipid in the contacting step is about 1:1. Accordingly, the mass ratio of the HKP, the RNA and the cationic lipid in the contacting step can be calculated based on the ratio between the HKP and the RNA and the ratio between the RNA and the cationic lipid. For example, if the ratio of the HKP to the RNA is about 4:1 and the ratio of the RNA to the cationic lipid is about 1:1, the ratio of the HKP to the RNA to the cationic lipid is about 4:1:1.

In one embodiments, HKP(+H) stock solution (10 mg/mL) was prepared in nuclease free water. A concentrated stock solution was diluted to 2.5 mg/mL in water. mRNA working solution (1 mg/mL) was prepared in 1 mM citrate buffer (pH 6.0). The mRNA/HKP(+H) polyplex was formed by mixing equal volumes of 2.5 mg/mL HKP(+H) and 1 mg/mL mRNA using microfluidics. The mass ratio of HKP (+H) to mRNA is 2.5:1. The mRNA/HKP(+H) polyplex was incubated for 30 min at room temperature before use. For preparation of all peptide based polyplexes, the size was determined with the Zetasizer (Malvern Panalytical) prior to its transfection or injection.

In some embodiments, the pharmaceutical comprises, or consists essentially of or yet further consists of a polymeric nanoparticle or a lipid nanoparticle both of which comprises a cationic lipid (such as one or more of those as disclosed herein), a helper lipid (such as one or more of those as disclosed herein), a cholesterol (such as one or more of those as disclosed herein) and a PEGylated lipid (such as one or more of those as disclosed herein). In further embodiments, a polymeric nanoparticle further comprises HKP. In some embodiments, the mass ratio of the cationic lipid, helper lipid, cholesterol and PEGylated lipid is about 1:1:1:1:1.

In some embodiments, the mass ratio of the cationic lipid and the helper lipid is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of the cationic lipid and the helper lipid is about 1:1.

In some embodiments, the mass ratio of the cationic lipid and cholesterol is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of the cationic lipid and cholesterol is about 1:1.

In some embodiments, the mass ratio of the cationic lipid and PEGylated lipid is about 10:1 to about 1:10, including any range or ratio there between, for example, about 5:1 to 1:5, about 5:1 to 1:1, about 10:1, about 9.5:1, about 9:1, about 8.5:1, about 8:1, about 7.5:1, about 7:1, about 6.5:1, about 6:1, about 5.5:1, about 5:1, about 4.5:1, about 4:1, about 3.5:1, about 3:1, about 2:5:1, about 2:1, about 1.5:1, about 1:1, about 1:1.5, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. In one embodiment, the mass ratio of the cationic lipid and PEGylated lipid is about 1:1.

The mass ratio of the cationic lipid, helper lipid, cholesterol and PEGylated lipid can be calculated by one of skill in the art based on the ratios of the cationic lipid and the helper lipid, the cationic lipid and the cholesterol and the cationic lipid and the PEGylated lipid as disclosed herein.

In some embodiments, the LNPs comprise, or consists essentially of, or yet further consists of SM-102, DSPC, cholesterol and PEG2000-DMG. In one embodiment, the mass ratio of the SM-102, DSPC, cholesterol and PEG200-

DMG is about 1:1:1:1 and/or wherein the molar ratio of the SM-102, DSPC, cholesterol and PEG2000-DMG is about 50:10:38.5:1.5.

In some embodiments, a mass ratio as provided here can be substituted with another parameter, such as a molar ratio, a weight percentage over the total weight, a component's weight over the total volume, or a molar percentage over the total molar amount. Knowing the component and its molecular weight, one of skill in the art would have no difficulty in converting a mass ratio to a molar ratio or other equivalent parameters.

In a further aspect, provided is a method of producing a composition comprising, or alternatively consisting essentially of, or yet further consisting of an RNA as disclosed herein and an LNP. The method comprises, or alternatively consists essentially of, or yet further consists of contacting the RNA with the LNP, thereby the RNA and the LNP are self-assembled into nanoparticles.

In some embodiments, the contacting step is performed in a microfluidic mixer, optionally selected from a slit interdigitial micromixer, or a staggered herringbone micromixer (SHM). In one embodiment, the microfluidic mixer is NanoAssemblr Ignite.

In some embodiments, the composition further comprises an additional prophylactic or therapeutic agent, such as those as disclosed herein. As used herein, the term "prophylactic or therapeutic agent" comprises, consists essentially of, or further consists of a nucleic acid (e.g., an mRNA), compound, polypeptide, antibody, antigen-binding portion thereof, composition, vector, antigen, host cell, and/or any pharmaceutically acceptable compositions comprising antigens, host cells, and/or additional therapeutic agents (e.g., formulations). In some embodiments, the additional prophylactic or therapeutic agent is suitable for preventing or treating a SARS-CoV-2 related disease as disclosed herein. In some embodiments, the additional prophylactic or therapeutic agent comprises, or alternatively consists essentially of, or yet further consists of an anti-viral agent, vaccine, or effective dose of a nucleic acid for vaccination, prevention, and treatment against SARS-CoV-2. In some embodiments, the additional prophylactic or therapeutic agent is suitable for preventing or treating a SARS-CoV-2 naturally occurring variant, such as a Alpha, Beta, Gamma, Delta, and/or Omicron variant. In some further embodiments, the additional prophylactic or therapeutic agent is suitable for preventing or treating a SARS-CoV-2 naturally occurring variant and its descendent lineages. As used herein, a descendent lineage of a SARS-CoV-2 naturally occurring variant is a group of closely related viruses with a common ancestor, all of which cause COVID-19. Descendent lineages of a SARS-CoV-2 naturally occurring variant include, but are not limited to Alpha B.1.1.7 and Q lineages; Beta B.1.351; Gamma P.1; Delta B.1.617.2 and AY lineages; Epsilon B.1.427 and B.1.429; Eta B.1.525; Iota B.1.526; Kappa B.1.617.1; Mu B.1.621, B.1.621.1; Zeta P.2; and/or Omicron B.1.1.529, BA.1, BA.1.1, BA.2, BA.3, BA.4 and BA.5 lineages.

In further embodiments, the additional prophylactic or therapeutic agent comprises, or alternatively consists essentially of, or yet further consists of an anti-viral agent, optionally remdesivir, lopinavir, ritonavir, ivermectin, tamiflu, or favipiravir; an anti-inflammatory agent, optionally dexamethasone, tocilizumab, kevzara, colcrys, hydroxychloroquine, chloroquine, or a kinase inhibitor; a covalescent plasma from a subject recovered from a SARS-CoV-2 infection; an antibody binding to SARS-CoV-2, optionally bamlanivimab, etesevimab, casirivimab, or imdevimab; or an antibiotic agent, optionally azithromycin.

In some embodiments, the additional prophylactic or therapeutic agent is suitable for preventing a disease that is not related to SARS-CoV-2. For example, the additional prophylactic or therapeutic agent comprises, or alternatively consists essentially of, or yet further consists of a vaccine for another coronavirus, such as SARS-CoV or MERS-CoV. Additionally or alternatively, the additional prophylactic or therapeutic agent comprises, or alternatively consists essentially of, or yet further consists of a vaccine for another virus, such as an influenza (flu) vaccine, a papillomavirus vaccine, an Hepatitis A vaccine, an Hepatitis B vaccine, an Hepatitis c vaccine, a polio vaccine, a chickenpox varicella vaccine, a measles vaccine, a mumps vaccine, a rubella vaccine, a rotavirus vaccine. In some embodiments, the additional prophylactic or therapeutic agent comprises, or alternatively consists essentially of, or yet further consists of a vaccine for a bacterium or other pathogen, such as a diphtheria vaccine, a *Haemophilus influenzae* type b vaccine, a Pertussis vaccine, a pneumococcus vaccine, a Tetanus vaccine, or a Meningococcal vaccine. In some embodiments, the additional prophylactic or therapeutic agent comprises, or alternatively consists essentially of, or yet further consists of a vaccine for a non-infectious disease, such as a cancer.

Methods of Treatment

In one aspect, provided is a method for preventing or treating a disease as disclosed herein. Additionally or alternatively, provided is a method of one or more of: (a) preventing a subject from having a symptomatic SARS-CoV-2 infection; (b) preventing a subject from hospitalization after infection by SARS-CoV-2; (c) preventing a subject from requiring intensive care (such as in an intensive care unit (ICU)) or a ventilator or both after infection by a SARS-CoV; (d) inducing an immune response to SARS-CoV-2 in a subject in need thereof; (c) reducing the binding of a SARS-CoV-2 or an S protein thereof with its receptor, such as angiotensin converting enzyme 2 (ACE2), in a subject in need thereof; (f) treating a subject infected with SARS-CoV-2; or (g) reducing a SARS-CoV-2 viral load in a subject in need thereof.

Host neutralizing antibodies block the binding of a SARS-CoV-2 or an S protein thereof with its receptors, such as ACE2, resulting in neutralized virus and decreased SARS-CoV-2 viral loads. Viral load is a measure of the severity of a viral infection, and can be calculated directly by estimating the amount of virus in an infected organism, an involved body fluid, or a biological sample. Quantification of viral load can generally be performed by utilizing a Plaque Reduction Neutralization Assay (PRNT). PRNT is a serological test which utilizes the ability of a specific antibody to neutralize a virus, in turn, preventing the virus from causing the formation of plaques in a cell monolayer. The assay involves mixing a constant amount of virus with dilutions of the serum specimen being tested, followed by plating of the mixture onto cells of an appropriate cell line for the individual virus. The concentration of plaque forming units can be determined by the number of plaques formed after a few days. A dye is added for visualization of the plaques, and the number of plaques in an individual plate is divided by the original number of virons to calculate the percentage neutralization. Depending on the virus, the plaque forming units (p.f.u.) are measured by microscopic observations, fluorescent antibodies, or specific dyes that react with the infected cell. Neutralizing titers can be calculated as the reciprocal of the lowest dilution that resulted in a greater than 50% reduction ($PRNT_{50}$) or 90% reduction ($PRNT_{90}$) in p.f.u. (plaque forming units) relative to negative control sera. Sera collected from two fully vaccinated subjects and serum from unvaccinated subjects can be used as a positive and negative controls, respectively.

An induced immune response in a subject therefore comprises inducing increased neutralizing antibody titers, increased splenocyte Th1-cytokine levels (IFN-γ, IL-2, TNF-α) and Th2-cytokines levels (IL-4, IL-5, IL-13), and/or inducing decreased viral loads. The present disclosure provides a method of inducing an immune response in a subject against SARS-CoV-2. In some embodiments, the method comprises administering to the subject an effective dose of an RNA, or polynucleotide, or vector, or cell or composition as disclosed herein, thereby inducing in the subject an immune response specific to a SARS-CoV-2 antigen, wherein neutralizing antibody titers in the subject are increased following vaccination relative to neutralizing antibody titers in an unvaccinated subject. In some embodiments, the neutralizing antibody titers in the subject are increased 1 log to 10 log following vaccination relative to neutralizing antibody titers in an unvaccinated subject. In some embodiments, the neutralizing antibody titers in the subject are increased 1 log, 2 log, 3 log, 4 log, 5 log, or 10 log following vaccination relative to neutralizing antibody titers in an unvaccinated subject.

In other embodiments, the immune response is assessed by measuring splenocytes Th1-cytokine levels (IFN-γ, IL-2, TNF-α) and Th2-cytokine levels (IL-4, IL-5, IL-13) in the subject. In some embodiments, the method comprises administering to the subject an effective dose of an RNA, or polynucleotide, or vector, or cell or composition as disclosed herein, thereby inducing in the subject an immune response specific to a SARS-CoV-2 antigen, wherein splenocytes Th1-cytokine levels (IFN-γ, IL-2, TNF-α) and/or Th2-cytokine levels (IL-4, IL-5, IL-13) in the subject are increased following vaccination relative to neutralizing antibody titers in an unvaccinated subject.

The method comprises, or alternatively consists essentially of, or yet further consists of administering to the subject, optionally an effective amount of, one or more of: an RNA as disclosed herein, a polynucleotide as disclosed herein, a vector as disclosed herein, a cell as disclosed herein, or a composition as disclosed herein.

In some embodiments, the method further comprises treating the subject in need thereof, such as administering to the subject, an additional prophylactic or therapeutic agent.

In some embodiments, the additional prophylactic or therapeutic agent is suitable for preventing or treating a SARS-CoV-2 related disease as disclosed herein. In further embodiments, the additional prophylactic or therapeutic agent comprises, or alternatively consists essentially of, or yet further consists of an anti-viral agent, optionally remdesivir, lopinavir, ritonavir, ivermectin, tamiflu, or favipiravir; an anti-inflammatory agent, optionally dexamethasone, tocilizumab, kevzara, colcrys, hydroxychloroquine, chloroquine, or a kinase inhibitor; a covalescent plasma from a subject recovered from a SARS-CoV-2 infection; an antibody binding to SARS-CoV-2, optionally bamlanivimab, etesevimab, casirivimab, or imdevimab; or an antibiotic agent, optionally azithromycin.

In some embodiments, the additional prophylactic agent is suitable for preventing a disease that is not related to SARS-CoV-2. For example, the additional prophylactic agent comprises, or alternatively consists essentially of, or yet further consists of a vaccine for another coronavirus, such as SARS-CoV or MERS-CoV. Additionally or alternatively, the additional prophylactic agent comprises, or alternatively consists essentially of, or yet further consists of a vaccine for another virus, such as an influenza (flu) vaccine, a papillomavirus vaccine, an Hepatitis A vaccine, an Hepatitis B vaccine, an Hepatitis c vaccine, a polio vaccine, a chickenpox varicella vaccine, a measles vaccine, a mumps vaccine, a rubella vaccine, a rotavirus vaccine. In some embodiments, the additional prophylactic agent comprises, or alternatively consists essentially of, or yet further consists of a vaccine for a bacterium or other pathogen, such as a diphtheria vaccine, a *Haemophilus influenzae* type b vaccine, a Pertussis vaccine, a pneumococcus vaccine, a Tetanus vaccine, or a Meningococcal vaccine. In some embodiments, the additional prophylactic agent comprises, or alternatively consists essentially of, or yet further consists of a vaccine for a non-infectious disease, such as a cancer.

In some embodiments, the subject does not have a SARS-CoV-2 infection when administrated with the RNA or the composition. In some embodiments, a SARS-CoV-2 infection can be diagnosed using a conventional method, such as a nucleic acid amplification test (NAATs), an antigen test, or an antibody test. NAATs for SARS-CoV-2 specifically identify the RNA (ribonucleic acid) sequences that comprise the genetic material of the virus, including but not limited to reverse transcription polymerase chain reaction (RT-PCR), or an isothermal amplification (such as nicking endonuclease amplification reaction (NEAR), transcription mediated amplification (TMA), loop-mediated isothermal amplification (LAMP), helicase-dependent amplification (HDA), clustered regularly interspaced short palindromic repeats (CRISPR) or strand displacement amplification (SDA)). Antigen tests are immunoassays that detect the presence of a specific viral antigen, which implies current viral infection. More details are available at www.cdc.gov/coronavirus/2019-ncov/lab/resources/antigen-tests-guidelines.html assessed on Aug. 1, 2021. Antibody or serology tests look for antibodies in blood that fight SARS-CoV-2, and are commonly used to indicate a past infection or a successful vaccination. However, IgM antibody can persist for weeks to months following infection, though its persistence appears to be shorter than IgG; therefore, detection of IgM may suggest relatively recent infection. More details are available at www.cdc.gov/coronavirus/2019-ncov/lab/resources/antibody-tests-guidelines.html assessed on Aug. 1, 2021.

In some embodiments, the subject is at risk of having a disease as disclosed herein, such as SARS-CoV-2 infection. In some embodiments, the subject has not been exposed to SARS-CoV-2. In some embodiments, the subject is at risk of exposing to SARS-CoV-2.

In some embodiments, the subject is more likely than others to become severely ill after being infected by SARS-CoV-2. For example, they can require hospitalization, intensive care, or a ventilator, or die, after the infection. In some embodiments, the subject is over age 65. In some embodiments, the subject is over age 45. In some embodiments, the subject has one or more of the following medical conditions: a cancer, a chronic kidney disease, a chronic lung diseases (such as chronic obstructive pulmonary disease (COPD), asthma (moderate-to-severe), interstitial lung disease, cystic fibrosis, or pulmonary hypertension), dementia or other neurological conditions, diabetes (type 1 or type 2), Down syndrome, a heart condition (such as heart failure, coronary artery disease, cardiomyopathies or hypertension), an HIV infection, an immunocompromised state (weakened immune system), a liver disease, overweight, obesity, pregnancy, a sickle cell disease, thalassemia, smoking (current or former), a solid organ or blood stem cell transplant, stroke or cerebrovascular disease (such as those affecting blood flow to the brain), or a substance use disorder.

In some embodiments, the administrations is by inhalation. In further embodiments, the RNA or the composition is atomized by a nebulizer inhalation system prior to or during administration. In yet further embodiments, the nebulizer system is a portable nebulizer for whole respiratory tract drug delivery.

In some embodiments, the administration is by subcutaneous injection. In some embodiments, the administration is by intramuscular injection. In some embodiments, the administration is by intraperitoneal injection (i.p).

In some embodiment, a composition as disclosed herein can be in the form of an aerosol, dispersion, solution, or suspension and can be formulated for inhalation, intramuscular, oral, sublingual, buccal, parenteral, nasal, subcutaneous, intradermal, or topical administration. The term parenteral as used herein includes percutaneous, subcutaneous, intravascular (e.g., intravenous), intramuscular, or intrathecal injection or infusion techniques and the like.

As used herein, an effective dose of an RNA, or polynucleotide, or vector, or cell or composition as disclosed herein is the dose required to produce a protective immune response in the subject to be administered. A protective immune response in the present context is one that prevents or ameliorates disease in a subject challenged with SARS-CoV-2 or a pseudovirus thereof. The RNA, or polynucleotide, or vector, or cell or composition as disclosed herein can be administered one or more times. An initial measurement of an immune response to the vaccine may be made by measuring production of antibodies in the subject receiving the RNA, or polynucleotide, or vector, or cell, or composition. Methods of measuring antibody production in this manner are also well known in the art, is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the formulated composition. In some embodiments, an effective dose of an RNA, or polynucleotide, or vector, or cell or composition as disclosed herein is administered twice. In some embodiments, an effective dose of an RNA, or polynucleotide, or vector, or cell or composition as disclosed herein is administered twice at an interval of at least 21 days, at least 28 days, at least 35 days, at least 42 days, at least 49 days, at least 56 days, or at least 64 days In a further aspect, provided is an inhalation system comprising, or alternatively consisting essentially of, or yet further consisting of an RNA as disclosed herein, a polynucleotide as disclosed herein, a vector as disclosed herein, or a composition as disclosed herein and a nebulizer. In further embodiments, the nebulizer is a portable nebulizer for whole respiratory tract drug delivery.

In some embodiments, the RNA compositions can be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic or prophylactic effect. The desired dosage can be delivered three times a day, two times a day, once a day, every other day, every third day, every week, every two weeks, every three weeks, every four weeks, every 2 months, every three months, every 6 months, etc. In certain embodiments, the desired dosage can be delivered using multiple administrations (e.g., two, three, four, five, six, seven, eight, nine, ten, eleven, twelve, thirteen, fourteen, or more administrations). When multiple administrations are employed, split dosing regimens such as those described herein can be used. In some embodiments, the RNA compositions can be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg. In some embodiments, the RNA compositions can be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, the RNA compositions can be administered at an effective dosage level. The effective dose of the RNA, as provided herein, may range from about 10 μg-500 pg, administered as a single dose or as multiple (e.g., booster) doses. In some embodiments, a single dose of a vaccine composition (e.g., administered once, twice, three times, or more) comprises about 10 μg RNA. In some embodiments, a single dose of a vaccine composition (e.g., administered once, twice, three times, or more) comprises about 20 μg RNA. In some embodiments, a single dose of a vaccine composition (e.g., administered once, twice, three times, or more) comprises about 30 μg RNA. In some embodiments, a single dose of a vaccine composition (e.g., administered once, twice, three times, or more) comprises about 40 μg RNA. In some embodiments, a single dose of a vaccine composition (e.g., administered once, twice, three times, or more) comprises about 50 μg RNA. In some embodiments, a single dose of a vaccine composition (e.g., administered once, twice, three times, or more) comprises about 100 μg RNA. In some embodiments, a single dose of a vaccine composition (e.g., administered once, twice, three times, or more) comprises at least 25 pg RNA. In some embodiments, a single dose of a vaccine composition (e.g., administered once, twice, three times, or more) comprises less than 100 μg RNA. In some embodiments, a single dose of a vaccine composition (e.g., administered once, twice, three times, or more) comprises 100 μg or less RNA. In some embodiments, a single dose of a vaccine composition (e.g., administered once, twice, three times, or more) comprises about 250 μg RNA.

In some embodiments, a total amount of RNA administered to a subject is about 10 μg, about 20 μg, about 30 μg, about 40 μg, about 50 μg, about 100 μg, about 200 μg, about 250 μg, or about 500 μg mRNA. In some embodiments, a total amount of RNA administered to a subject is about 50 μg. In some embodiments, a total amount of RNA administered to a subject is about 100 μg. In some embodiments, a total amount of RNA administered to a subject is about 250 μg. In some embodiments, a total amount of RNA administered to a subject is about 500 μg.

In some embodiments, the RNA compositions can be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a the RNA composition can be administered three or four times.

Kits

In one aspect, provided is a kit for use in a method as disclosed herein.

In some embodiments, the kit comprises, or alternatively consists essentially of, or yet further consist of instructions for use and one or more of: a RNA as disclosed herein, a polynucleotide as disclosed herein, a vector as disclosed herein, a composition as disclosed herein, or an inhalation system as disclosed herein. In further embodiments, the kit is suitable for use in a method of treatment as disclosed herein.

In some embodiments, the kit comprises, or alternatively consists essentially of, or yet further consist of instructions for use and one or more of: an RNA as disclosed herein, a polynucleotide as disclosed herein, a vector as disclosed herein, a cell as disclosed herein, a composition as disclosed herein, an HKP, or a lipid optionally a cationic lipid. In further embodiments, the kit is suitable for use in a method producing an RNA or a composition as disclosed herein.

In some embodiments, the kit comprises, or alternatively consists essentially of, or yet further consist of instructions of use, a polynucleotide or a vector as disclosed herein, an RNA polymerase, ATP, CTP, GTP, and UTP or a chemically modified UTP. In further embodiments, the kit is suitable for use in an in vitro method producing an RNA or a composition as disclosed herein.

The following examples are included to demonstrate some embodiments of the disclosure. However, those of skill in the art should, in light of the present disclosure, appreciate that many changes can be made in the specific embodiments which are disclosed and still obtain a like or similar result without departing from the spirit and scope of the invention.

EXAMPLES

Example 1: RNA Synthesis

A tested RNA as disclosed herein was synthesized, for example by in vitro transcription (IVT) using a vector as disclosed herein and an IVT kit available to one of skill in the art (such as MAXIscript™ T7 Transcription Kit from ThermoFisher Scientific), and then purified by selective binding of dsRNA to cellulose in an ethanol-containing chromatography buffer containing 10 mM HEPES (pH 7.2), 0.1 mM EDTA, 125 mM NaCl, 16% ethanol and cellulose fibers and centrifugation. Almost 90% of dsRNA could be removed after this procedure. See, for example, Baiersdorfer et. al, 2019, Mol Ther Nucleic Acids. 2019 Apr. 15; 15:26-35. Contaminants could be also eliminated using FPLC and HPLC, see, for example, Kariko et. al, 2011, Nucleic Acids Res. 2011 November; 39(21):e142.

Example 2: Peptides (HK Polymers) Preparation

The HK peptide polymers were synthesized on a Rainin Voyager synthesizer (Tucson, AZ) by the biopolymer core facility at the University of Maryland.

Example 3: In Vitro Formulation Preparation

PNI-Genvoy lipid nanoparticle (LNP) formulation: Lipid nanoparticles were formulated using the GenVoy Platform with PNI NanoAssemblr (Precision NanoSystems, Vancouver, British Columbia, Canada) as the positive control in both in vitro and in vivo assays.

HKP(+H) formulation version 1: HKP(+H) stock solution (10 mg/mL) was prepared in nuclease free water. A concentrated stock solution was diluted to 2.5 mg/mL in water. mRNA working solution (1 mg/mL) was prepared in 1 mM citrate buffer (pH 6.0). The mRNA/HKP(+H) polyplex was formed by mixing equal volumes of 2.5 mg/mL HKP(+H) and 1 mg/mL mRNA using microfluidics. The mass ratio of HKP(+H) to mRNA is 2.5:1. The mRNA/HKP(+H) polyplex was incubated for 30 min at room temperature before use. For preparation of all peptide based polyplexes, the size was determined with the Zetasizer (Malvern Panalytical) prior to its transfection or injection.

HKP(+H) formulation version 2: HKP(+H) stock solution (10 mg/mL) was prepared in nuclease free water. A concentrated stock solution was diluted to 4 mg/mL in water. mRNA working solution (1 mg/mL) was prepared in 1 mM citrate buffer (pH 6.0). The mRNA/HKP(+H) polyplex was formed by mixing equal volumes of 4 mg/mL HKP(+H) and 1 mg/mL mRNA. The mass ratio of HKP(+H) to mRNA is 4:1. The mRNA/HKP(+H) polyplex was incubated for 30 min at room temperature before use. The size of each peptide-based polyplex was determined with the Zetasizer (Malvern Panalytical) prior to transfection or injection.

HKP(+H)/DOTAP formulation (post-mixed DOTAP): HKP(+H) stock solution (10 mg/mL) was prepared in nuclease free water. A concentrated stock solution was diluted to 4 mg/mL in water. DOTAP (Sigma-Aldrich) is 1 mg/mL in aqueous buffered solution. mRNA working solution (1 mg/mL) was prepared in 1 mM citrate buffer (pH 6.0). First the mRNA/HKP(+H) polyplex was formed by mixing equal volumes of 4 mg/mL HKP(+H) and 1 mg/mL mRNA. The mRNA/HKP(+H) polyplex was incubated for 30 min at room temperature. Next, the same volume of DOTAP to HKP(+H) solution was added to the mRNA/HKP(+H) polyplex. The mass ratio of HKP(+H)/DOTAP to mRNA was 4:1:1. The mRNA/HKP(+H)/DOTAP nanoparticle was incubated for 30 min at room temperature before use.

HKP(+H)/MC3 or HKP(+H)/DOTAP formulations (pre-mixed MC3 or DOTAP): HKP(+H) stock solution (10 mg/mL) was prepared in nuclease-free water. A concentrated stock solution was diluted to 4 mg/mL in water. DOTAP or MC3 is 1 mg/mL in aqueous buffered solution. mRNA working solution (1 mg/mL) was prepared in 1 mM citrate buffer (pH 6.0). Equal volumes of HKP(+H) and MC3 were pre-mixed at a 4:1 mass ratio and the same volume of mRNA to HKP(+H) solution was added to a pre-mixed HKP(+H)/MC3. The mRNA/HKP(+H)/MC3 nanoparticle was formed by mixing pre-mixed 4 mg/mL HKP(+H)/1 mg/mL MC3 and 1 mg/mL mRNA. The mass ratio of HKP(+H)/MC3 to mRNA is 4:1:1. The mRNA/HKP(+H)/MC3 nanoparticle was incubated for 30 min at room temperature before use.

HKP(+H)/PLA NP formulation: HKP(+H) stock solution (10 mg/mL) was prepared in nuclease free water. A concentrated stock solution was diluted to 4 mg/mL in water. A poly-L-Lactic Acid (PLA) nanoparticle (5 mg/mL) was prepared in water. mRNA working solution (1 mg/mL) was prepared in 1 mM citrate buffer (pH 6.0). Equal volumes of HKP(+H) and mRNA were mixed at a 4:1 mass ratio. The mRNA/HKP(+H) polyplex was incubated for 30 min at room temperature, and then the same volume of PLA nanoparticle to HKP(+H) solution was added to the mRNA/HKP(+H) nanoparticle so that the mRNA/HKP(+H) polyplex was adsorbed on the surface of the PLA nanoparticle. The mass ratio of HKP(+H)/PLA to mRNA was 4:5:1. The mRNA/HKP(+H)/PLA nanoparticle was incubated for 30 min at room temperature before use.

TABLE 6

Lipids and RNA working solutions were prepared according to the Table below.

| | Molar ratio | M.W. | Final working solution(12.5 mM lipid) | 4x Stock(mM each) in 100% Ethanol | Supplier and Product Information |
|---|---|---|---|---|---|
| Ionizable lipid equivalent (e.g., SM-102) | 50 | | 6.25 | 25.00 | |
| DSPC | 10 | 790.145 | 1.25 | 5.00 | avantilipids.com/product/850365 (last accessed on Aug. 9th, 2021) |
| Cholesterol | 38.5 | 386.654 | 4.8125 | 19.25 | avantilipids.com/product/700100 (last accessed on Aug. 9th, 2021) |
| PEG2000-DMG | 1.5 | 2509.2 | 0.1875 | 0.75 | broadpharm.com/web/product.php?catalog=BP-25496 (last accessed on Aug. 9th, 2021) |
| mRNA | TriLink Clean Cap mRNA | | in 50 mM Sodium Citrate | | www.trilinkbiotech.com/custom-mrna-synthesis (last accessed on Aug. 9th, 2021) |

Briefly, the working area was cleaned thoroughly with 70% ethanol. A 4× stock solution of each lipids was made in 100% Ethanol and stored at −20° C. until use. Lipid working solution was prepared by combining each of the following components in a ratio of 1:1:1:1 (final concentration 12.5 mM): Ionizable cationic lipid ((heptadecan-9-yl 8-((2-hydroxyethyl) (6-oxo-6-(undecyloxy) hexyl) amino) octanoate}) SM-102 equivalent, a helper lipid (such as 1,2-Distearoyl-sn-glycero-3 phosphocholine (DSPC)), a cholesterol, and PEG2000-DMG (i.e., 1-monomethoxypolyethyleneglycol-2,3-dimyristylglycerol with polyethylene glycol of average molecular weight 2000). The RNA working solution was prepared in Formulation Buffer (50 mM Sodium Citrate pH4.0). RNA concentration depends on Lipid concentrations, the Flow Rate Ratio and the N/P ratio.

The RNA and lipid nanoparticle was prepared: The NanoAssemblr Ignite was turned on and "Quick Run" was selected from the Main Menu. The parameters were set as shown in FIG. 1 by selecting a field, selecting a value from the drop-down menu or entering the number with the on-screen keyboard and then tapping the check mark. The lid of the Ignite was open and the Cartridge Adaptor was ensured as installed over the "L" inlet of the cartridge slot with the arrow facing upwards, then a NxGen™ cartridge was removed from the package and inserted in the cartridge slot. The rotating block was raised until the cartridge luers were visible. At least 1.5 mL prepared RNA working solution was drawn into a 3 mL syringe. A blunt needle was used if necessary. The needle was removed, air bubbles were cleared from the syringe and the plunger was used to advance the liquid to the tip. Drips from the syringe tip were avoided. The syringe was inserted into the "C" inlet of the Ignite Cartridge and twisted clockwise to engage the Luer Lock. At least 0.5 mL prepared Lipid Working solution was drawn into a 1 mL syringe using a blunt needle if necessary. The needle was removed, air bubbles were cleared from the syringe and the plunger was used to advance the liquid to the tip. Drips from the syringe tip were avoided. The syringe was inserted into the "R" inlet of the Ignite Cartridge. The rotating block was returned to the downwards position. The sample switch arm for two 15 mL conical tubes was ensured as installed. A 15 mL conical collection tube was marked with "RNA-LNP" and pushed into the clip labeled "Sample". Another tube was marked with "waste" and pushed into the clip labeled "Waste". The Ignite lid was closed and "Next" on the screen was tapped. The parameters and the information in the dialog box were confirmed. The "Start" button was pressed. The pushers of the Ignite™ were then injecting the fluids into the microfluidic cartridge. The formulation was collected in the tube labeled "RNA-LNP". After the motors were positioned themselves back in the home position, the screen indicated when it was safe to open the lid. The lid was open once it was safe and the conical collection tube labeled "RNA-LNP" was removed and set aside for characterization and further processing immediately. The rotating block was raised and the syringes were removed from Ignite™ and discarded. The rotating block was returned to the downward position and the NxGen cartridge was removed and discarded. To make additional samples, the back "<" button was tapped to return to the Quick Run Screen and the steps described in this paragraph were repeated except the initial quick run setting step.

For the characterization of formulated lipid nanoparticles (LNPs), following preparation, 25-50 μL of the sample fraction was mixed with 650 μL of ultra pure water (Invitrogen) and the intensity-averaged particle size (Z-average) was measured on ZetaSizer (Malvern Instruments Inc.).

The sample fraction was transferred immediately to a Slide-a-lyzer G2 dialysis cassette (10000 MWCO, Thermo Fischer Scientific Inc.) and dialyzed over night at 4° C. against PBS (pH7.4).

The LNP formulations were concentrated using Amicon ultra-centrifugal filters (EMD Millipore, Billerica, MA, USA), passed through a 0.22-μm filter (Acrodisc) and stored at 4° C. (PBS).

The sample fraction was also collected and measured for the particle size (post dialysis particle size).

The final mRNA concentration and encapsulation efficiency (EE) were measured using Quant-it Ribogreen Assay Kit (Thermo Fischer Scientific).

Example 4: In-Vitro Transfection of mRNA

To verify the proper protein expression of RNAs, an EGFP mRNA or a tested RNA as disclosed herein is transiently transfected into human embryonic kidney 293T cells (293T cells). Briefly, $4.8\times10^5$ cells are plated into a 6 well plate containing 2 ml of DMEM (10% fetal bovine serum and 1% Penicillin-Streptomycin (ThermoFisher Scientific)). After 24 hr, when the cells are 70-90% confluent, the EGFR mRNA or the tested RNA is transfected into 293T cells using Lipofectamine MessengerMAX Transfection Reagent (ThermoFisher Scientific) according to the manual protocol. The transfected 293T cells are cultured for two day and then measured for in vitro protein expression.

Various formulations/carriers as disclosed herein are also examined for their ability to carry the EGFP mRNA or the tested RNA into a target host cell, such as human embryonic kidney 293 cells (HEK 293 cells). Briefly, $4.8\times10^5$ cells are plated into a 6 well plate containing 2 ml of DMEM (10% fetal bovine serum and Penicillin-Streptomycin (ThermoFisher Scientific)). After 24 hr, when the cells are 70-90% confluent, a formulation/carrier with the EGFP mRNA or the tested RNA as disclosed herein is added into each well. 293T cells are cultured for two day and then measured for in vitro protein expression.

Example 5: In Vitro Protein Expression Measurement

Immunofluorescence analysis: Two days post transfection, protein expression is measured by immunofluorescence imaging using a Cytation5 Cell Imaging Multi-Mode Reader (Biotek, Winooski, VT).

Cell lysate preparation: Two days post transfection, culture media is aspirated and cells are washed on ice with ice-cold PBS. Ice-cold lysis buffer (RIPA, ThermoFisher Scientific) with protease inhibitor (ThermoFisher Scientific) is added and the cells are incubated for 30 minutes at 4□C. Cells are then harvested using a cell scraper and lysed by sonication. Centrifugation at 10,000 g for 20 minutes at 4° C. pellets cell debris, and the supernatant is transferred to a fresh microcentrifuge tube. The protein concentration of the lysate is determined by Bradford or BCA protein assay for Western blot.

Western blot: Briefly, in each well of a gel, 20-50 μg of protein is mixed with 4×SDS sample buffer (ThermoFisher Scientific), 10× Reducing buffer (ThermoFisher Scientific), and additional dd$H_2$O (ThermoFisher Scientific) with a total loading volume of 25 μl/well. The mixture is denatured by heating at 95° C. for 5 minutes and cooled to room temperature and centrifuged before loading onto a NUPAGE™ 4 to 12%, Bis-Tris gel (ThermoFisher Scientific). After electrophoretic separation, the gel is removed from the cassette and transferred using an IBLOT™ 2 Dry Blotting System (ThermoFisher Scientific). The transferred membrane is blocked with 5% fat-free milk powder in TBST for 1 hr at room temperature (RT), incubated with primary antibody for overnight at 4° C., washed three times with TBST (0.05% Tween20 in TBS) buffer, and incubated with secondary antibody, which is HRP conjugated Mouse IgG (H+L) Secondary Antibody (ThermoFisher Scientific, A24512) for 1 hr at RT. Transferred membrane is then developed by Pierce ECL Western Blotting Substrate (ThermoFisher Scientific) and is imaged using chemiluminescent imaging system.

In some embodiments, the primary antibody specifically recognizes and binds to an S protein of SARS-CoV-2 or a fragment thereof, such as an S2 protein or a RBD of the S protein or both. Accordingly, expression of a tested RNA to its protein product is assessed. In further embodiments, a loading control for the Western blot was performed. For example, the same sample was tested using Western blot as described above, except the primary antibody specifically recognizes and binds to β-actin. A substantially similar protein levels among groups are found in the loading control.

Figure 2A:
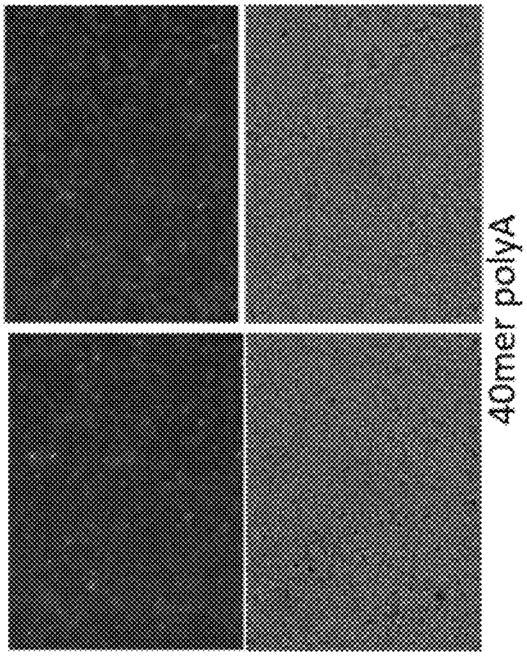
FIGS. 2A-2C provide representative images showing expression of a Blue Fluorescent Protein in cells transfected with RNAs encoding the Blue Fluorescent Protein and comprising various polyA tails (FIG. 2A, polyA 40 (SEQ ID NO: 27 or 56)
Figure 2B:
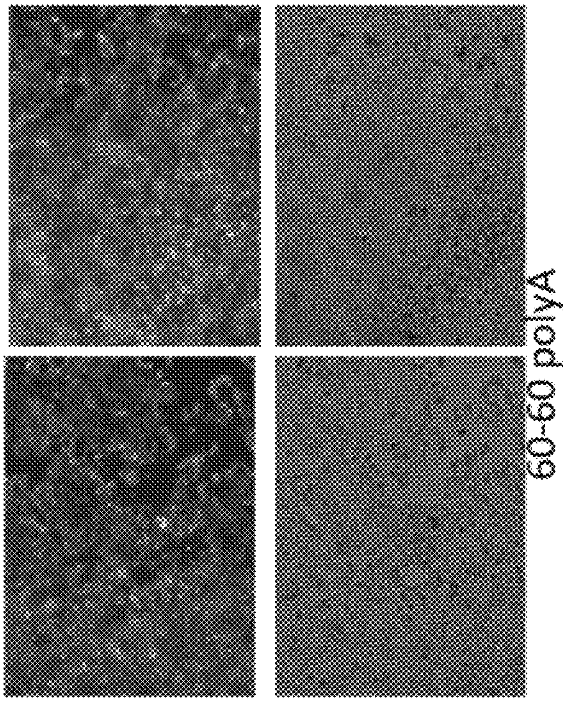
Figure 2C:
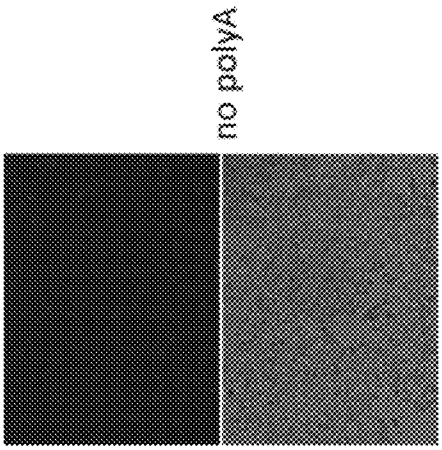

RNAs with different polyA tails, such as a 40 mer polyA (referred to herein as "polyA 40") (SEQ ID NO: 27) or a 60-60 polyA (see "polyA 60") (SEQ ID NO: 28), were synthesized, purified, transfected to cells, and tested for protein expression. Briefly, DNA constructs comprising β-globulin 5' and 3' UTRs, Blue Fluorescent Protein 2 (BFP2) coding sequence, and different synthetic polyA tails were synthesized by Twist Bioscience. In further embodiments, the DNA constructs further comprise a plasmid backbone comprising, or consisting essentially of, or yet further consisting of a kanamycin selection marker, the pUC57 backbone, and a T7 promoter to make the plasmid in vitro transcription (IVT) competent. IVT was performed as described previously. RNA was transfected into HEK293T cells and Blue Fluorescent Protein (BFP) florescence intensity was observed using a Citation 5 microscope from BioTek. The results are shown in FIG. 2. A top panel of each of FIGS. 2A-2C provides a representative image showing the BFP fluorescence, while a bottom panel of each of FIGS. 2A-2C provides the corresponding bright filed image.

Figure 3:
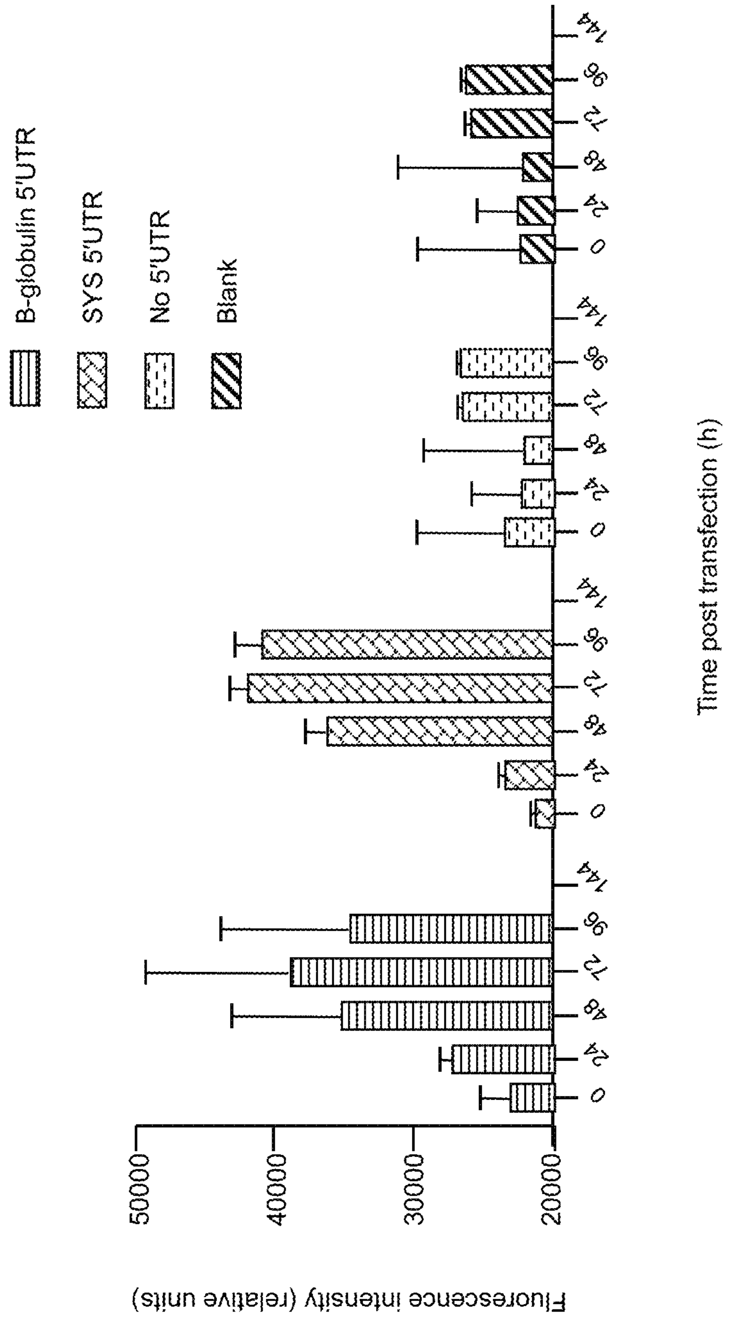
FIG. 3 provides a bar graph showing expression of a Blue Fluorescent Protein indicated by fluorescence intensity measured at various time points (0 hour, 24 hours, 48 hours, 72 hours, 96 hours and 144 hours) post transfection of RNAs encoding the Blue Fluorescent Protein and comprising different UTRs. The first set of bars from the left represents data acquired using β-globulin 5' UTR. The second set of bars from the left represents data acquired using SYS 5' UTR as disclosed herein. The third set of bars from the left represents data acquired using no 5' UTR. The fourth set of bars from the left represents data acquired from the blank control group. Error bars indicate the standard deviation of 3 replicates.

Additionally, RNAs with various UTRs, such as a β-globulin UTR or a SYS UTR as disclosed herein, were synthesized, purified, transfected to cells, and tested for protein expression. Briefly, DNA constructs comprising different 5'UTRs and BFP2 were synthesized by Twist Bioscience. The constructs further comprise a plasmid backbone comprising, or consisting essentially of, or yet further consisting of a kanamycin selection marker, the pUC57 backbone, and a T7 promoter to make the plasmid in vitro transcription (IVT) competent. Once plasmids were prepared and purified, IVT was performed as described previously. RNA was transfected into HEK293T cells using MessengerMax transfection reagent (Thermofisher) and BFP florescent intensity was measured using a Citation 5 microscope from BioTek. Different 5'UTRs were compared at various time points. Sec, FIG. 3. Error bars indicate the standard deviation of 3 replicates.

Example 6: Binding with Human ACE2

Further investigated is binding between an S protein, a variant and/or a mutant thereof expressed by a tested RNA as disclosed herein and its receptor on a human cell, such as human ACE2. For example, cells (such as HEK293T (Cat #CRL-3216, ATCC) or a549 (Cat #CCL-185, ATCC)) transfected with the tested RNA and expressing the S protein, variant and/or mutant thereof are incubated with a human ACE2 directly or indirectly labeled with a fluorescent protein, such as FITC. The incubated cells are optionally washed to remove the unbound ACE2. Flow cytometry is performed and the mean fluorescence intensity (MFI) of each cell was measured qualitatively. The higher the MFI is, the more ACE2 binds to the cell, indicating a stronger binding (such as showing a higher binding affinity) between ACE2 and the S protein, variant and/or mutant thereof expressed by the cell.

Example 7: In Vivo Animal Model and Injection

An in vivo study was performed. Briefly, 6-8 week old female BALB/C are randomized into each group, 4 mice per each group and injected intramuscularly into the right flank with 30 μg of an EGFP mRNA with different formulations. With the same formulations mentioned above, a tested RNA is also prepared for in vivo analysis and antibody titer measurement and binding.

On day 28, a second injection for boosting is made and on day 35 serum is collected and analyzed by immunoassay (ELISA) for measurement of antibody titer.

Example 8: In Vivo Animal Models

Other suitable animal models can be used to investigate a tested RNA in a formulation/carrier as disclosed herein and assess its efficiency for use in a method as disclosed herein and for therapy alone or in combination with other possible therapies, such as anti-inflammatory therapies.

In one example, used herein is a genetically modified animal model expressing human ACE2 optionally under a tissue-specific promoter (for example, the Krt 18 promoter for epithelial cells; K18-hACE2 mice), or a universal promoter (cytomegalovirus enhancer followed by the chicken β-actin promoter) or the endogenous mouse Ace2 promoter. All of these mice are susceptible to infection by SARS-CoV-2, but differences in their expression of human ACE2 result in a pathogenic range of mild to lethal disease. In some embodiments, the animal is mouse. Alternative animal models include syrian hamsters, whose ACE2 is significantly similar to human ones and considered as susceptible to infection with SARS-CoV-2; ferrets; and non-human primates.

A RNA composition, such as a tested RNA in a formulation/carrier as disclosed herein, was administered to the animal prior to or concurrently with a challenge with SARS-CoV-2 or a pseudovirus thereof. The administration of the RNA composition was repeated at least once or twice. A second administration of the RNA composition occurred about two or about three weeks apart. Animals not challenged with the SARS-CoV-2 or pseudovirus served as a negative control while those challenged with the SARS-CoV-2 or pseudovirus but not treated served as a positive control. Additional controls were used, such as animals treated with a SARS-CoV-2 vaccine as known in the art, such as BNT162b2 available from Pfizer-BioNTech, mRNA-1273 available from Moderna, or JNJ-78436735 from Johnson & Johnson's Janssen, and challenged with the SARS-CoV-2 or pseudovirus.

Viral load, lung pathology, immune cell infiltration to the lung, cytokine release, body weight, fur, posture, respiratory distress (such as laboured breathing), lethargy or not, nasal discharge, wheezing, oropharyngeal build-up of mucus, sneezing, loose stools and etc. were monitored after the administration of the RNA composition in order to assess the effects.

Example 9: Confirmation of Type-I Interferon Secretion (IFN-α and IFN-β) from the A549 Cells Transfected with a Modified or Unmodified SARS-CoV-2 Spike mRNA Vaccine Candidates Experiments were performed to test whether the viral RNA sensing pathway activates the innate immunity in A549 cells transfected with SARS-CoV-2 spike mRNA (SBI), results in generation of IFN-β and subsequently repression of SARS-CoV-2 S protein translation. The same experimental setting was applied to an RNA expressing a SARS-CoV-2 S protein (wild type or comprising S2P or S6P mutations)s, such as an RNA encoding a wild-type SARS-CoV-2 S protein (labeled as "SARS-CoV-2 Spike WT(SBI) "), an RNA encoding a wild-type SARS-CoV-2 S protein with all uridine residues of the RNA chemically modified, optionally to pseudouridine, further optionally to N1-methyl pseudouridine (labeled as "SARS-CoV-2 Spike WT(100% modified)"), an RNA encoding a SARS-CoV-2 S protein which is a wild type mutated at K986P and V987P with at least one uridine residues of the RNA chemically modified, optionally to pseudouridine, further optionally to N1-methyl pseudouridine (labeled as "SARS-CoV-2 Spike S2P WT"), an RNA encoding a SARS-CoV-2 S protein which is a wild type mutated at D614G, K986P and V987P with at least one uridine residues of the RNA chemically modified, optionally to pseudouridine, further optionally to N1-methyl pseudouridine (labeled as "SARS-CoV-2 Spike S2P D614G"), an RNA encoding a SARS-CoV-2 S protein which is a wild type mutated at D614G with at least one uridine residues of the RNA chemically modified, optionally to pseudouridine, further optionally to N1-methyl pseudouridine (labeled as "SARS-CoV-2 Spike D614G WT"), a sequence optimized RNA encoding a SARS-CoV-2 S protein which is a wild type mutated at F817P, A892P, A899P, A942P, K986P, and V987P with at least one uridine residues of the RNA chemically modified, optionally to pseudouridine, further optionally to N1-methyl pseudouridine (labeled as "SARS-CoV-2 Spike S6P (RNAimmune)"), an RNA encoding a beta variant of SARS-CoV-2 S protein firstly identified in South Africa and further mutated at F817P, A892P, A899P, A942P, K986P, and V987P with at least one uridine residues of the RNA chemically modified, optionally to pseudouridine, further optionally to N1-methyl pseudouridine (labeled as "SARS-CoV-2 Spike S6P_SA"), a sequence optimized RNA encoding a beta variant of SARS-CoV-2 S protein firstly identified in South Africa and further mutated at F817P, A892P, A899P, A942P, K986P, and V987P with at least one uridine residues of the RNA chemically modified, optionally to pseudouridine, further optionally to N1-methyl pseudouridine (labeled as "SARS-CoV-2 Spike S6P_SA_GS"), or an RNA encoding a RBD of a SARS-CoV-2 S protein with at least one uridine residues of the RNA chemically modified, optionally to pseudouridine, further optionally to N1-methyl pseudouridine (labeled as "RBD"). See more details in the table below. In further embodiments, the wild type SARS-CoV-2 S protein comprises, or consists essentially of, or yet further consists of a polypeptide as set forth in SEQ ID NO: 1.

TABLE 7

| Sequence | Description | Sequence Optimized? | Modified Uridine? |
|---|---|---|---|
| SARS-CoV-2 Spike WT(SBI) | wild type spike protein | No | No |
| SARS-CoV-2 Spike WT(100% modified) | wild type spike protein with 100% uridine modification | No | Yes |
| SARS-CoV-2 Spike S2P WT | wild type spike with S2P mutation | No | Yes |
| SARS-CoV-2 Spike S2P D614G | wild type spike with S2P mutation and D614G mutation | No | Yes |
| SARS-CoV-2 Spike | wild type spike with | No | Yes |

TABLE 7-continued

| Sequence | Description | Sequence Optimized? | Modified Uridine? |
|---|---|---|---|
| D614G WT | D614G mutation | | |
| SARS-CoV-2 Spike S6P (RNAimmune) | Spike with S6P mutation | Yes | Yes |
| SARS-CoV-2 Spike S6P_SA | Spike with S6P and South Africa mutation | No | Yes |
| SARS-CoV-2 Spike S6P_SA_GS | | Yes | Yes |
| RBD | RBD region only | No | Yes |

Additionally, the same experimental setting is applied to a tested RNA in a formulation/carrier as disclosed herein.

Materials and Methods 293T cells were transiently transfected with RNAs encoding one of the following and formulated at an about 1:3 ratio of RNA to lipid:SARS-CoV-2 Spike WT(SBI), SARS-CoV-2 Spike WT(100% modified), SARS-CoV-2 Spike S2P WT, SARS-CoV-2 Spike S2P D614G, SARS-CoV-2 Spike D614G WT, SARS-CoV-2 Spike S6P (RNAimmune), SARS-CoV-2 Spike S6P_SA, SARS-CoV-2 Spike S6P_SA_GS, or RBD.

2 ml of A549 cells were plated at a density of $2.5\times10^5$ cells in 12 well plates. The cells were incubated for 24 hours at 37° C. in a 5% $CO_2$ incubator. RNA(1 μg) was diluted in 50 μl of Opti-MEM-I. 7.5 μl of Lipofectamine MessengerMAX (Invitrogen, Cat #LMRNA008) was also diluted and incubated for 10 minutes at RT. The diluted mRNA mixture was added to the diluted lipid. Incubation was performed for 5 minutes at RT. mRNA-lipid complex was added to the cells and incubated for 24 hours at 37° C. in a 5% $CO_2$ incubator.

ELISA detecting IFN-α was performed using VeriKine Human IFN-α ELISA Kit (Cat 41100, pbl assay science). 1 ml of the culture supernatant was transferred to a new tube and centrifuged for 5 minutes at 3000 rpm. The culture supernatant was then transferred to a new tube and stored at −80° C. until use.

Figure 4:
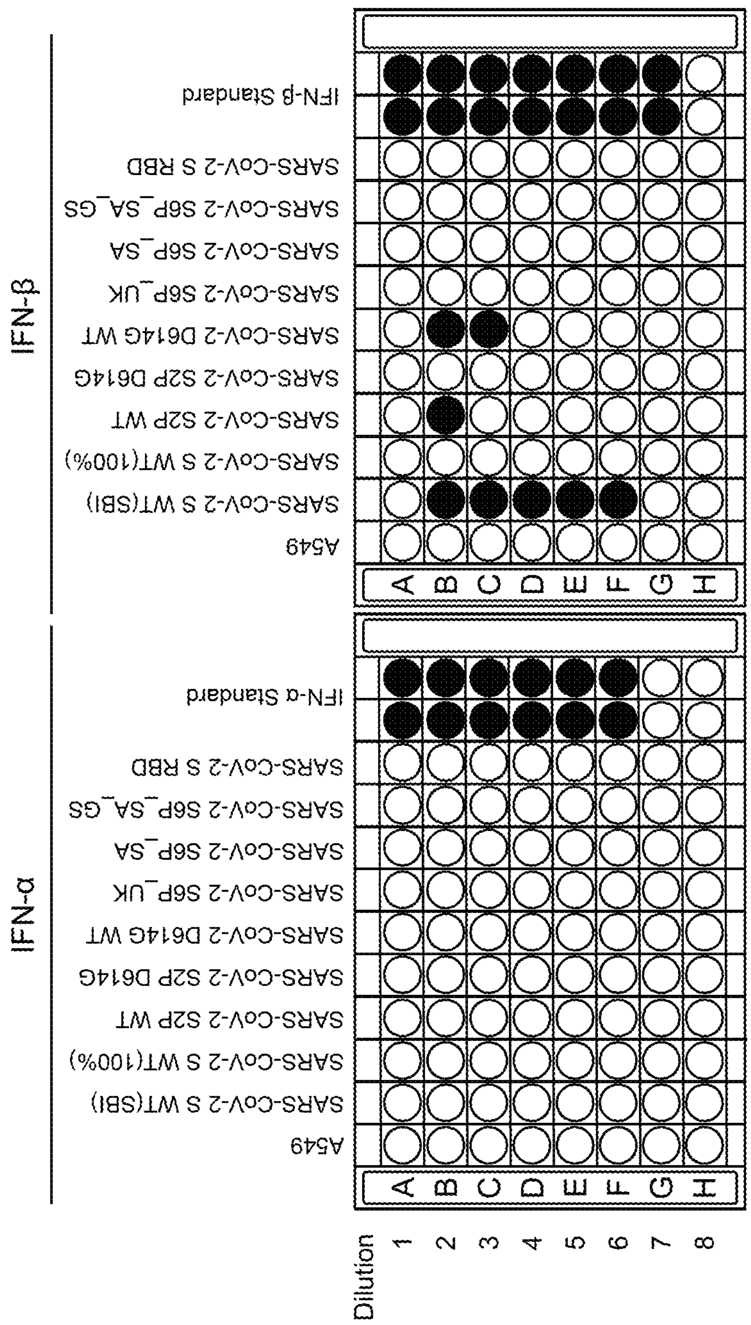
FIG. 4 shows representative IFN-α and IFN-β ELISA results as detailed in Example 9. S WT stands for spike protein wild type. S RBD stands for spike receptor binding protein. S2P stands for comprising the K986P and V987P mutations. S6P stands for comprising the mutations of F817P, A892P, A899P, A942P, K986P, and V987P. UK stands for the alpha variant firstly identified in United Kingdom. SA stands for the beta variant firstly identified in South Africa. GS stands for a sequence-optimized RNA (SEQ ID NO: 54). A549 indicates negative control A549 lung carcinoma epithelial cells.

A standard curve was generated: a high sensitivity standard curve 12.5-500 pg/ml or extended range standard curve 156-5000 pg/ml was constructed. Six polypropylene tubes (S1-S6) were labeled and filled with 250 μl Dilution Buffer. Polypropylene tips were used to add the Human IFN-α Standard to S6 and mix gently. Tips were changed between each dilution. 250 μl was removed from S6 and added to S5. The same series dilution was performed for S4-S1. All dilutions were refrigerated until use (FIG. 4).

ELISA detecting IFN-β was performed using VeriKine Human IFN-β ELISA Kit (Cat 41410, pbl assay science). 1 ml of the culture supernatant was transferred to a new tube and centrifuged for 5 minutes at 3000 rpm. The culture supernatant was then transferred to a new tube and stored at −80° C. until use.

A standard curve was generated: Seven polypropylene tubes were labeled (S1-S7). Using polypropylene tips, 250 μl Standard Diluent was added to each tube, except S7 where 492.5 μl Standard Diluent was added. 10 μl of the Human IFN-β Standard was added to 90 μl of Standard Diluent. 7.5 μl of prediluted standard was added to S7 and mixed thoroughly. 250 μl of S7 was transferred to S6 and mixed thoroughly. The same series dilution was performed for the reset S5-S1. All dilutions were set aside until use.

The number of microplate strips required to test the desired number of samples were determined plus the appropriate number of wells needed to run blanks and standards. 100 μl of the interferon standard, blank or sample were added to each well, covered with a plate sealer and incubated for 1 hour. After 1 hour, the contents of the plate were emptied and the wells were washed for one time only with diluted Wash Buffer. 100 μl of diluted Antibody Solution was added to each well, covered with a plate sealer and incubated for 1 hour. After 1 hour, the contents of the plate were emptied and the wells were washed for three times with diluted Wash Buffer. 100 μl of diluted HRP Solution was added to each well, covered with a plate sealer and incubated for 1 hour. During this incubation period, the TMB Substrate Solution was warmed to RT (22-25° C.). After 1 hour, the contents of the plate were emptied and the wells were washed for four times with diluted Wash Buffer. 100 μl of the TMB Substrate Solution was added to each well and incubate, in the dark, at RT (22-25° C.), for 15 minutes. A plate sealer was not used during the incubation. After the 15 minutes incubation of TMB, 100 μl of Stop Solution was added to each well. Using a microplate reader, the absorbance at 450 nm was determined within 5 minutes after the addition of the Stop Solution.

In some embodiments, 293T cells are transiently transfected with a tested RNA in a formulation/carrier as disclosed herein, for example using the transfection method as described above. IFN-α and IFN-β release of the transfected cells are measured, for example, using a method as described above.

Results

Figure 5A:
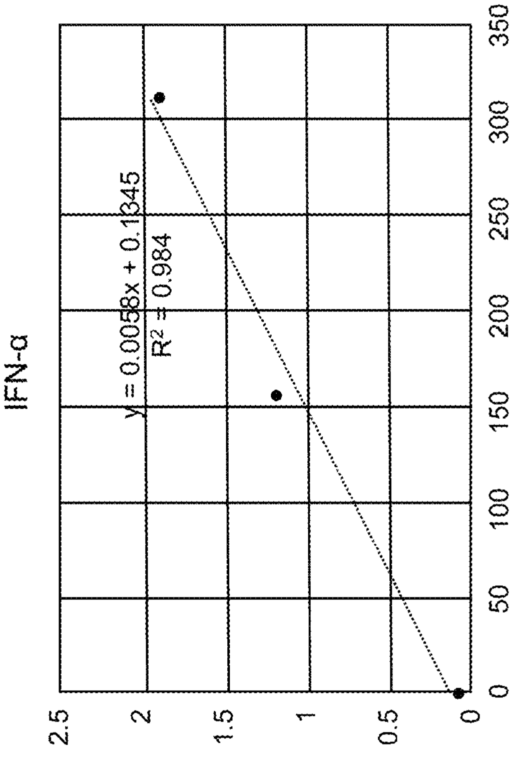
Figure 6A:
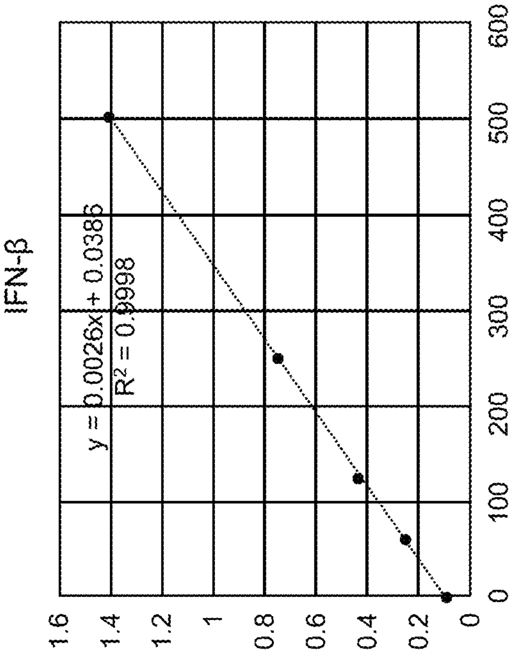

To assess IFN-α and IFN-β secretion from A549 cells, ELISA was performed as described herein. A representative resultant ELISA plate was photographed and is shown in FIG. 4, while the results were further quantified as show in FIGS. 5-6. The data demonstrated that interferon-α (IFN-α or IFN-Alpha) only secreted from the A549 cells transfected a unmodified SARS-CoV-2 Spike mRNA(SBI) and interferon-β (IFN-β or IFN-Beta) secreted from the A549 cells transfected an unmodified SARS-CoV-2 Spike mRNA(SBI), S2P WT, D614G WT and S6P_SA.

Conclusions

Interferon-α only secreted from the A549 cells transfected an unmodified SARS-CoV-2 Spike mRNA(SBI). Interferon-β secreted from the A549 cells transfected an unmodified RNA encoding the SARS-CoV-2 Spike WT(SBI), or SARS-CoV-2 Spike S2P WT, or SARS-CoV-2 Spike D614G WT, or SARS-CoV-2 Spike S6P_SA. Accordingly, without wishing to be bound by the theory, the observed lack of spike protein expression in A549 cell transfected with an unmodified RNA encoding the SARS-CoV-2 Spike WT(SBI) (data not shown) may be caused by the activation of strong cGAS-STING pathway (innate immunity) which inhibits spike protein translation.

Figure 8A:
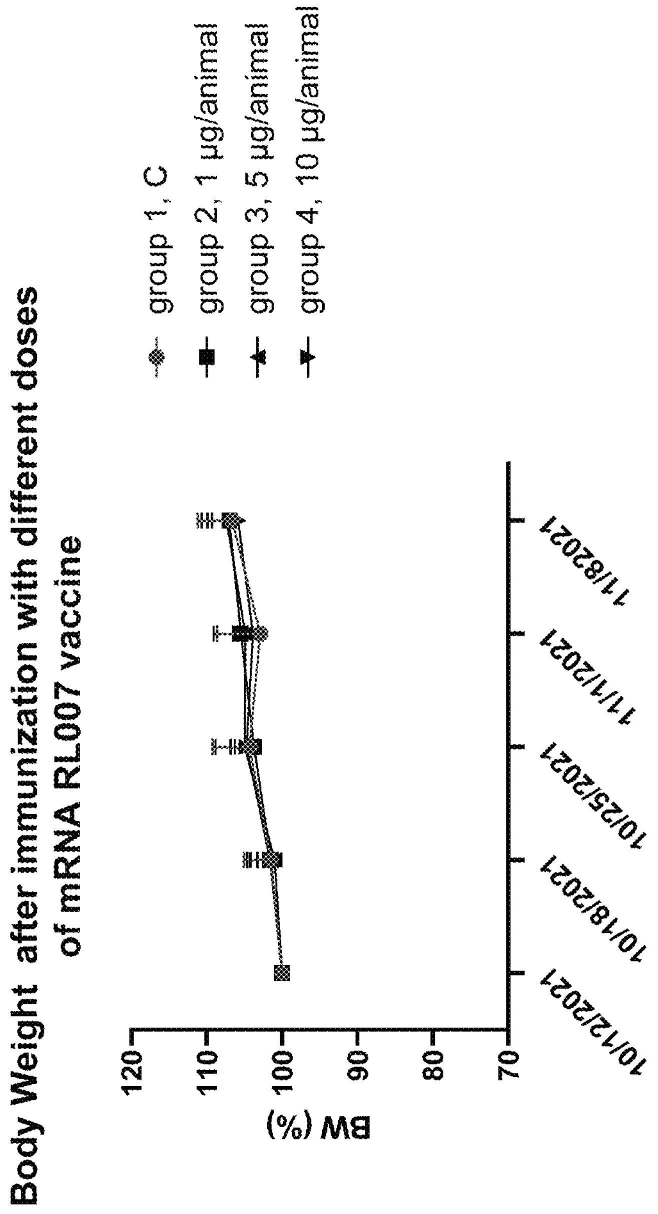
FIGS. 8A-8D show body weights of treated mice.
Figure 8B:
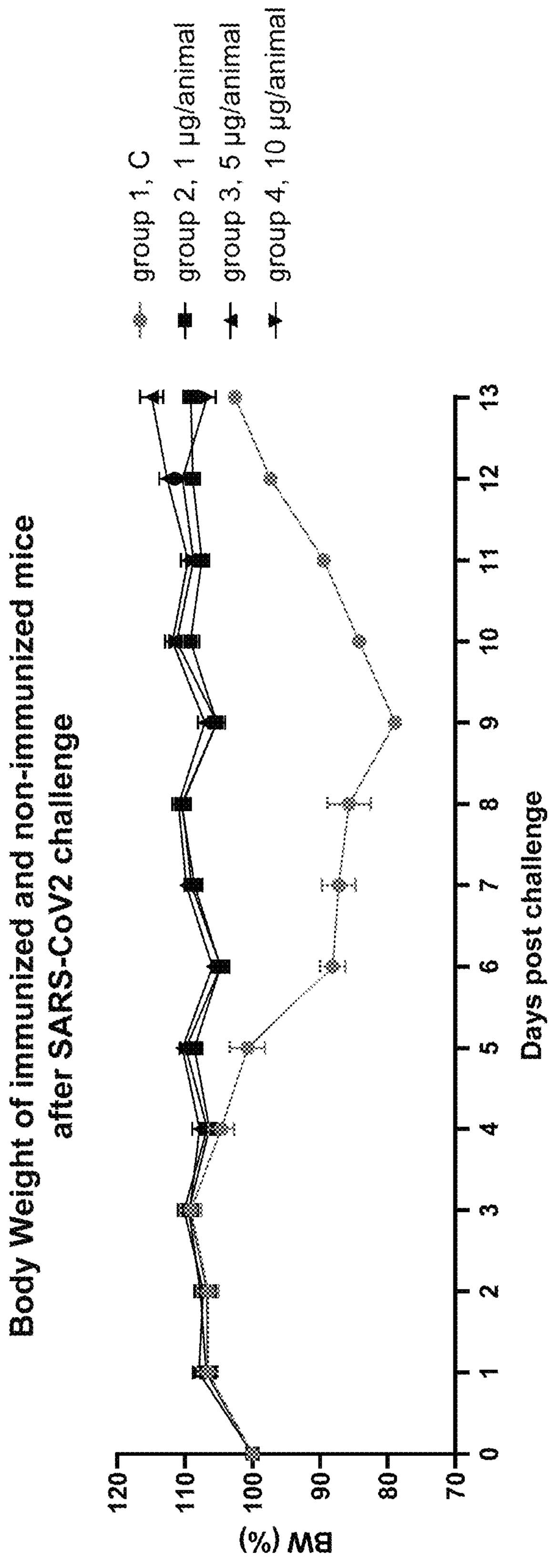
Figure 8C:
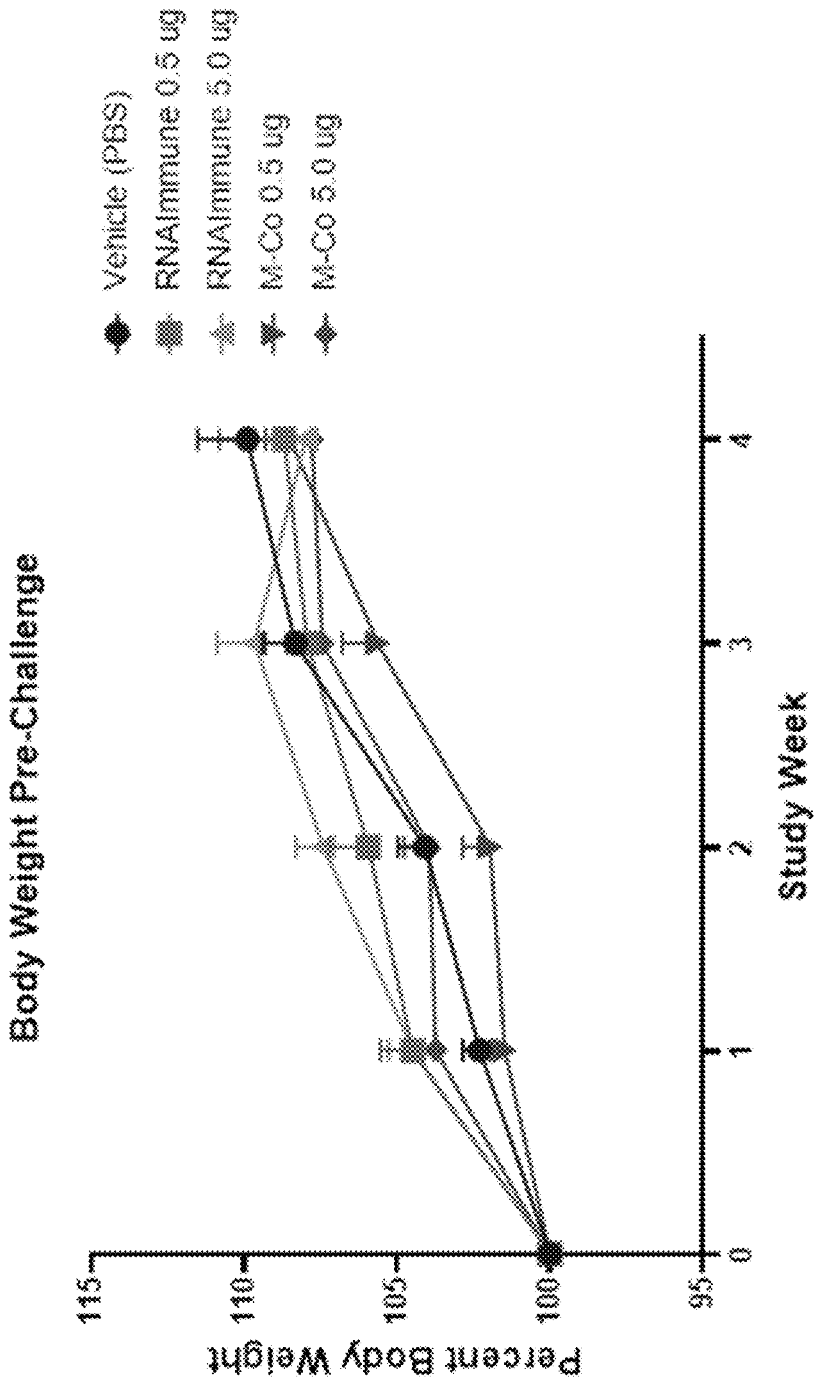
Figure 8D:
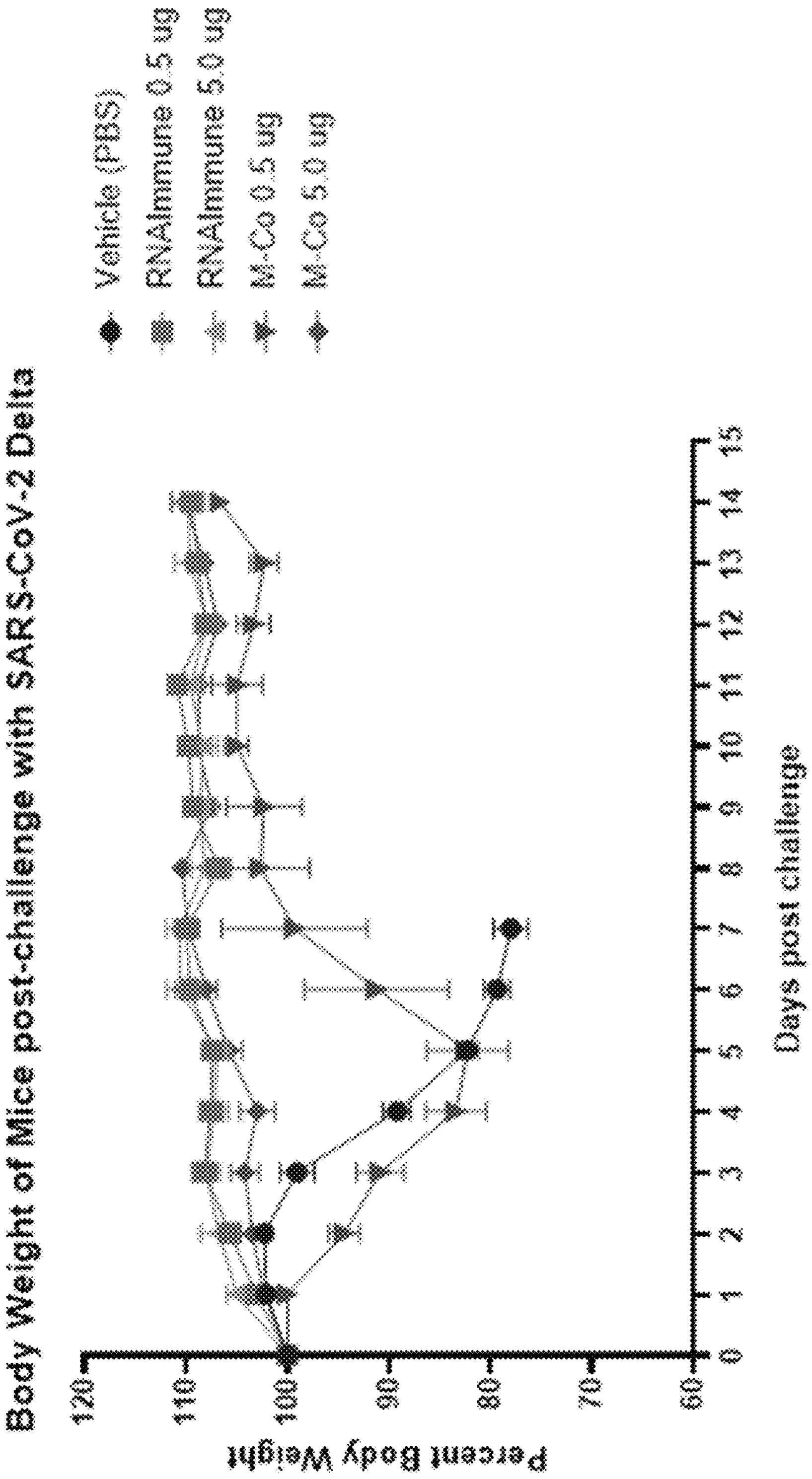

Example 10: Evaluation of Immunogenicity and Efficacy of a SARS-CoV-2 Spike mRNA Vaccine Against SARS-CoV-2 in K18-hACE2 Mice A total of forty (40) six- to eight-week-old (6-8) female K18-hACE2 mice were purchased from Jackson Laboratory. All animal experiments were conducted at the Noble Life Science in collaboration with George Mason University (GMU). The study was conducted without direct involvement of Quality Assurance but adhered to applicable NLS SOPs and following the guidelines and approval of the Institutional of Animal Care and Use Committee (IACUC), GMU Biomedical Research Laboratories. Mice were assigned to four (4) groups consisting of ten (10) mice each following an acclimation period. Table 3 shows dosing groups for SARS-CoV-2/human/ITA/INMI1/2020 challenge. Table 4 shows dose groups for ARS-CoV-2 B.1.1617.2 delta variant. On Day 0 and Day 14, animals in group one (1) and were inoculated intramuscularly with vehicle and mice in groups two (2), three (3), and four (4) were inoculated intramuscularly with escalating doses of a representative RL-007 mRNA vaccine formulation, prepared according to Example 3, comprising SEQ ID NO: 52. This vaccine formulation is designated "RV-1730" and uses an RL-007 carrier. Blood was collected from the mice on Days −1, 13, and 27 and serum samples were used for plaque-reduction neutralization test (PRNT). On Day 28, animals were challenged intranasally with $5.5\times10^4$ PFU/mouse SARS-CoV-2/human/ITA/INMI1/2020 wild type variant (NLS-GMU-WB2-042121) (FIG. 8A and FIG. 8B) or $1.5\times10^4$ PFU/mouse SARS-CoV-2 B.1.1617.2 Delta variant (FIG. 8C and FIG. 8D). All mice were monitored daily for mortality, body weight, body temperature and scored for clinical signs of distress for thirteen (13) days after challenge. Mice that had a clinical severity score of >10 or lost >20% of their pre-challenge body weight were humanely euthanized and recorded as non-survivors. All surviving mice were euthanized thirteen (13) days after challenge. A portion of lung tissue was harvested from euthanized mice, placed into 10% formalin and shipped to Histoserv for histopathological assays by H&E staining.

TABLE 3

Dosing Groups for SARS-CoV-2/human/ITA/INMI1/2020 challenge study

| Group | Mouse Strain | Animal Number/ Sex | Test Article | Injection Volume (mL) | Route | Frequency | Transfer mice to GMU | Serum Samples for PRNT | Challenge Virus (D 28) | Post-SARS-CoV-2 challenge monitoring |
|---|---|---|---|---|---|---|---|---|---|---|
| 1 | K18-hACE2 Mice | 10/ Female | 1xPBS | 50 | I.M. | D 0, D 14 | D 21 | D −1, D 13, D 27 | SARS-CoV-2/ human/ ITA/ INMI1/ 2020 | D 28 to D41 |
| 2 | | | RL007 mRNA vaccine 20 mg/mL (1 mg/mouse) | | | | | | | |
| 3 | | | RL007 mRNA vaccine 100 mg/mL (5 mg/mouse | | | | | | | |
| 4 | | | RL007 mRNA vaccine 200 mg/mL (10 mg/mouse) | | | | | | | |

TABLE 4

Dose Groups for ARS-CoV-2 B.1.1617.2 Delta variant

| Group | Mouse Strain | Animal Number/ Sex | Test Article | Route | Frequency | Transfer mice to GMU | Serum Samples for PRNT | Challenge Virus (D 27, D 28) | Post- SARS-CoV-2 challenge monitoring |
|---|---|---|---|---|---|---|---|---|---|
| 1 | K18-hACE2 Mice | 15/ Female | 1xPBS | I.M. | D 0, D 14 | D 21 | D −1, D 13, D 27 | SARS-CoV-2 B.1.1617.2 Delta variant | D 28 to D 42 |
| 2 | | | RNAImmune mRNA vaccine Low Dose (0.50 µg/mouse) | | | | | | |
| 3 | | | RNAImmune mRNA vaccine High Dose (5 µg/mouse) | | | | | | |
| 4 | | | m-Co control vaccine Low Dose (0.50 µg/mouse) | | | | | | |
| 5 | | | M-Co control vaccine High Dose (5 µg/mouse) | | | | | | |

Mice were monitored daily for up to fourteen (14) days post challenge for mortality, clinical signs of distress, body weight, and body temperature. A severity score for clinical distress was recorded daily for each mouse based on a GMU-IACUC approved Animal Study Clinical Monitoring Chart (Table 5). Briefly, a score from 0 (normal) to 3 (severely sick) in four (4) observable phenotypic categories 1) Appearance, 2) Mobility, 3) Attitude, 4) Respiratory Distress, and body weight were recorded daily for each individual mouse. Mice that had a cumulative score of 10 or greater were humanely euthanized.

TABLE 5

Clinical Severity Scoring Matrix

| Appearance | Mobility | Attitude | Respiratory Distress | Body Weight | Total Score |
|---|---|---|---|---|---|
| 0 - Smooth coat, bright eyes | 0 - Active/ Scurrying | 0 - Alert | 0 - Normal | 0 = Normal | 0-5 and all categories ≤1 = Normal 1X daily monitoring |
| 1 - Slightly scruffy and/or hunched at rest | 1 - Walking | 1 - Alert, playful when stimulated | 1 - Ocular and nasal discharge, Sneezing | 1 = 0 to 10% weight loss | 6-9 or any single score >1 = 2X daily monitoring |
| 2 - Scruffy and/or hunched at rest, watery eyes | 2 - Slow movement | 2 - Alert, not playful when stimulated | 2 - Heavy ocular and nasal discharge, cough and wheezing | 2 = 10-20% weight loss | ≥10 or any single score = 3 = Euthanize |
| 3 - Very scruffy and/or hunched, | 3 - No movement/ Unresponsive when touched/ stimulated | 3 - Not alert, not playful | 3. Severe respiratory distress, Open mouth breathing | 3 = Greater than 20% weight loss | FD = Found Dead |

The neutralizing titers of serum specimens collected on Study Day −1, Day 13, and Day 27 were assessed using plaque reduction neutralization titration (PRNT). All sera were heat inactivated by incubation at 56° C. for 30 minutes prior to testing. Six serial two-fold dilutions of each serum were prepared in EMEM. Dilutions ranged from 1:4 to 1:3200 and were adjusted to account for increased neutralizing activity at different time points and treatment groups. Twenty-five microliters (25 μL) of each dilution was combined with 25 μL of SARS-CoV-2 B.1.1617.2 Delta variant BEI: NR-55672 viral stock, mixed and incubated at 37° C. for one (1) hour. Supernatant was removed from Vero-E6 cells seeded the night before in 12 well plates and replaced with 300 μL of Eagle Minimum Essential Medium (EMEM) in each well. The incubated virus+diluted serum mixtures were added on top of Vero E6 monolayer and plates were incubated at 37° C./5% $CO_2$ for 1 hour. Plates were shaken every 10-15 minutes during incubation. After one-hour incubation, 1.5 ml overlayer containing 2×EMEM and 0.6% agarose at a ratio of 1:1 was added to the plates. Plates were incubated for 72 hours at 37° C./5% $CO_2$ after solidification of agarose at room temperature. Following incubation, cells were fixed by adding 0.5 ml of 10% formaldehyde into each well on top of the agarose and incubating at room temperature overnight. The palettes of agarose were gently removed, and the cellular monolayers were stained for 10 to 15 minutes with the addition of 0.5 ml of 1% crystal violet. After staining, the plates were washed with water to remove excess stain solution and plaques were manually enumerated for each viral dilution. The neutralizing titers were calculated as the reciprocal of the lowest dilution that resulted in a greater than 50% reduction ($PRNT_{50}$) or 90% reduction ($PRNT_{90}$) in p.f.u. (plaque forming units) relative to negative control sera. Human sera collected from two fully vaccinated males and serum from naïve mice were used as a positive and negative controls, respectively.

Figure 7:
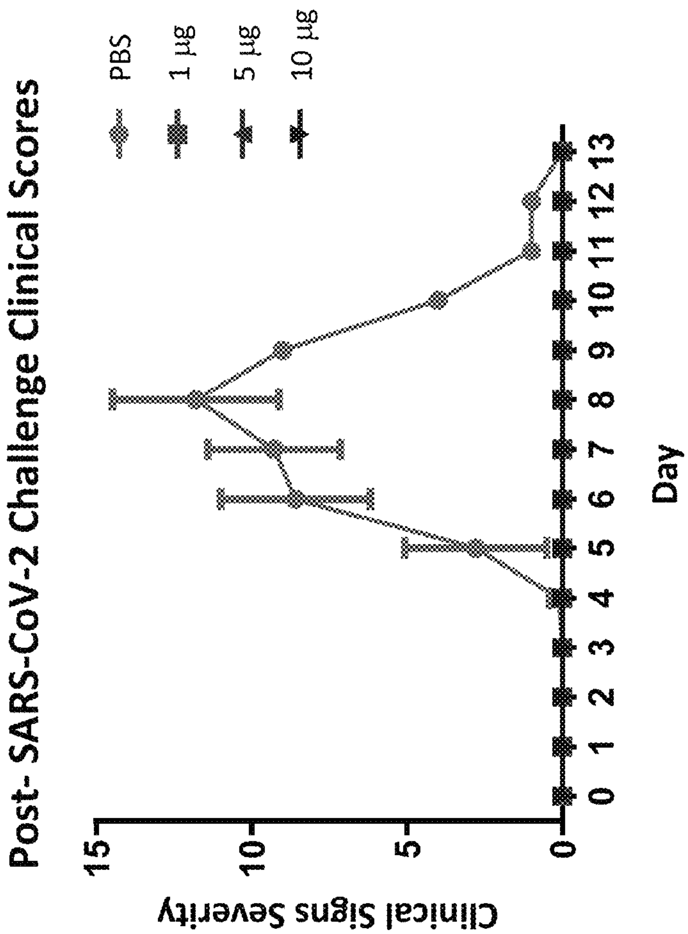
FIG. 7 shows a clinical severity score curve in immunized and non-immunized mice after challenge with SARS-CoV-2/human/ITA/INMI1/2020 virus. Mice in Group 1 were administered PBS, Group 2 mice were immunized with mRNA RL-007 1 μg/animal, Group 3 mice were immunized with mRNA RL007 5 μg/animal, Group 4 mice were immunized with mRNA RL007 10 μg/animal before viral challenge.
Figure 9:
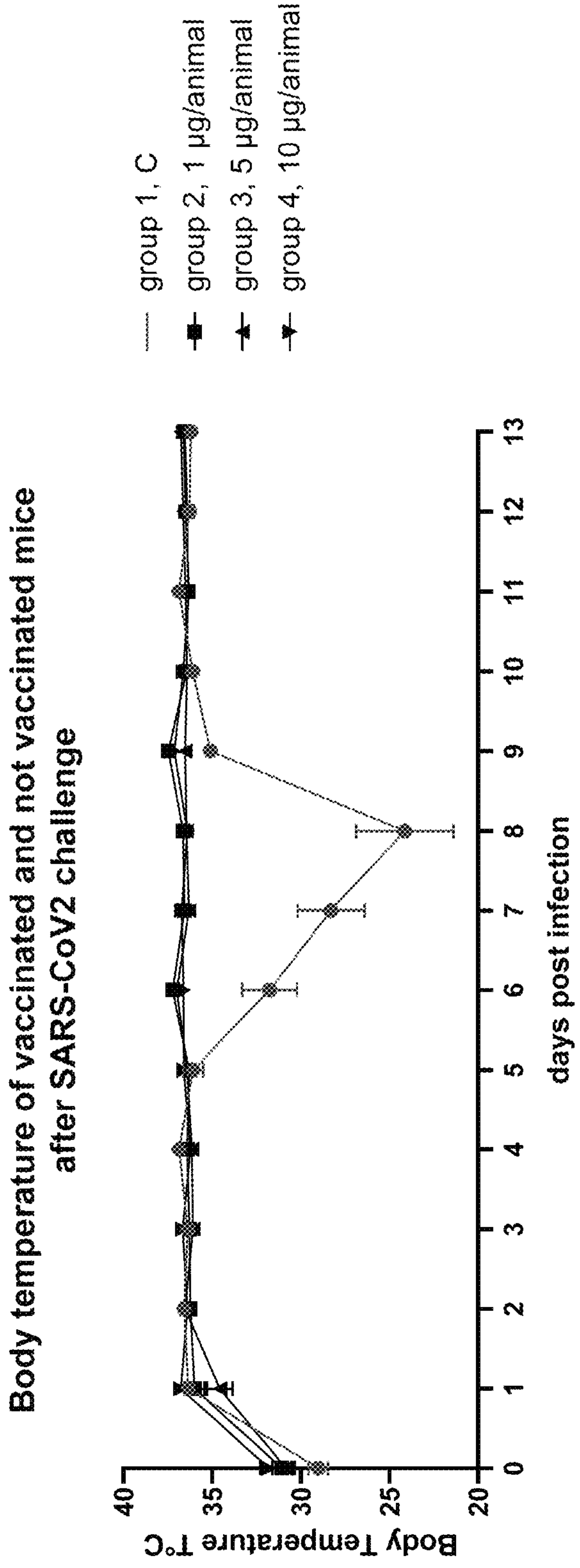
FIG. 9 shows body temperature curves in mice of Groups 1 to 4 after viral challenge with SARS-CoV-2/human/ITA/INMI1/2020 (NCBI Accession number: MT066156). The mean and standard error of the mean (SEM) for each group of mice are represented. Mice in Group 1 were administered PBS, Group 2 mice were immunized with mRNA RL-007 1 μg/animal, Group 3 mice were immunized with mRNA RL007 5 μg/animal, Group 4 mice were immunized with mRNA RL007 10 μg/animal before viral challenge. Experiments are described in Example 10.
Figure 10:
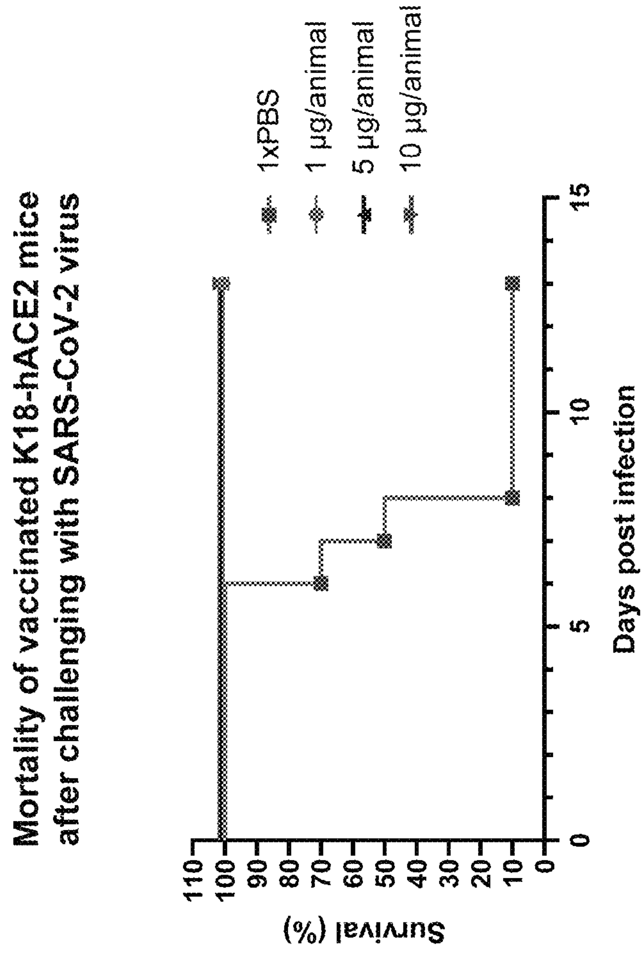
FIG. 10 is a Kaplan Meier curve showing the survival rate for mice challenged with SARS-CoV-2. Mice in Group 1 were administered PBS, Group 2 mice were immunized with mRNA RL-007 1 μg/animal, Group 3 mice were immunized with mRNA RL007 5 μg/animal, Group 4 mice were immunized with mRNA RL007 10 μg/animal before viral challenge. Experiments are described in Example 10.
Figure 11A:
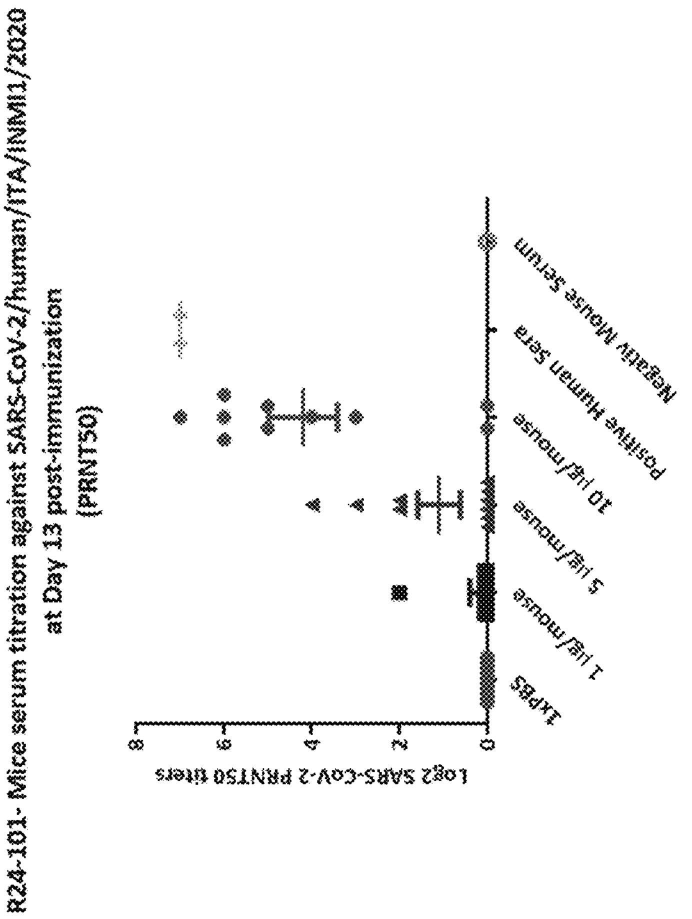
FIG. 11A, FIG. 11B, FIG. 11C, and FIG. 11D show mouse serum titration data against SARS-CoV-2/human/ITA/INMI1/2020 assessed using plaque reduction neutralization titration (PRNT). The neutralizing titers were calculated as the reciprocal of the lowest dilution that resulted in a greater than 50% reduction ($PRNT_{50}$) or 90% reduction ($PRNT_{90}$) in plaque forming units (p.f.u.) relative to negative control sera.
Figure 11B:
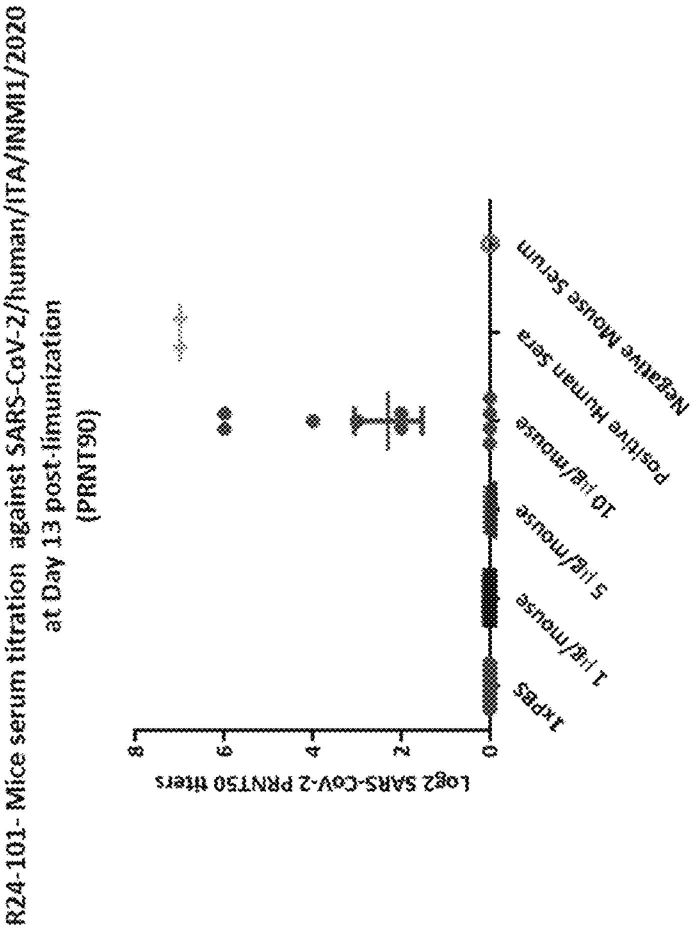
Figure 11C:
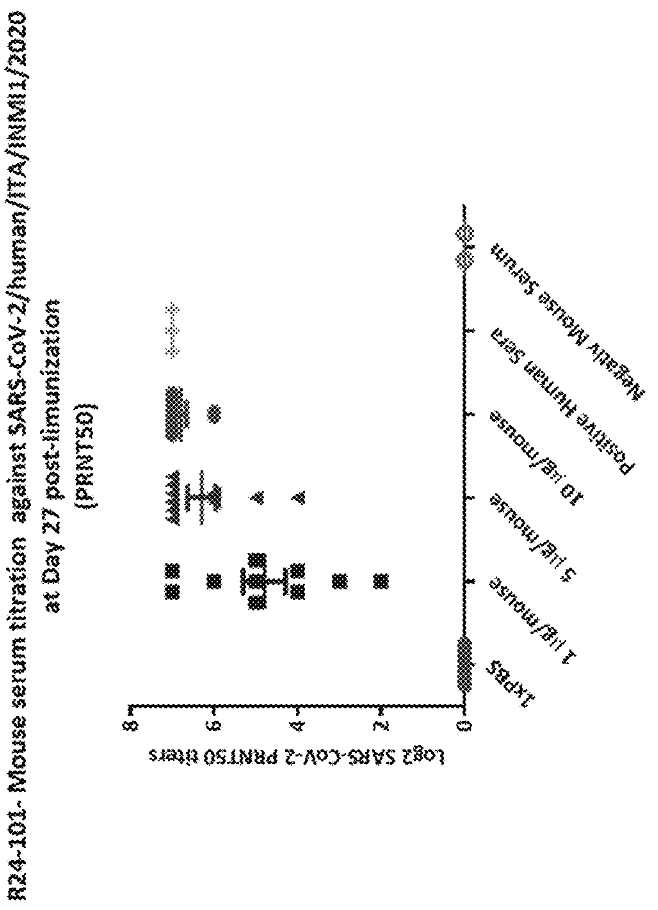
Figure 11D:
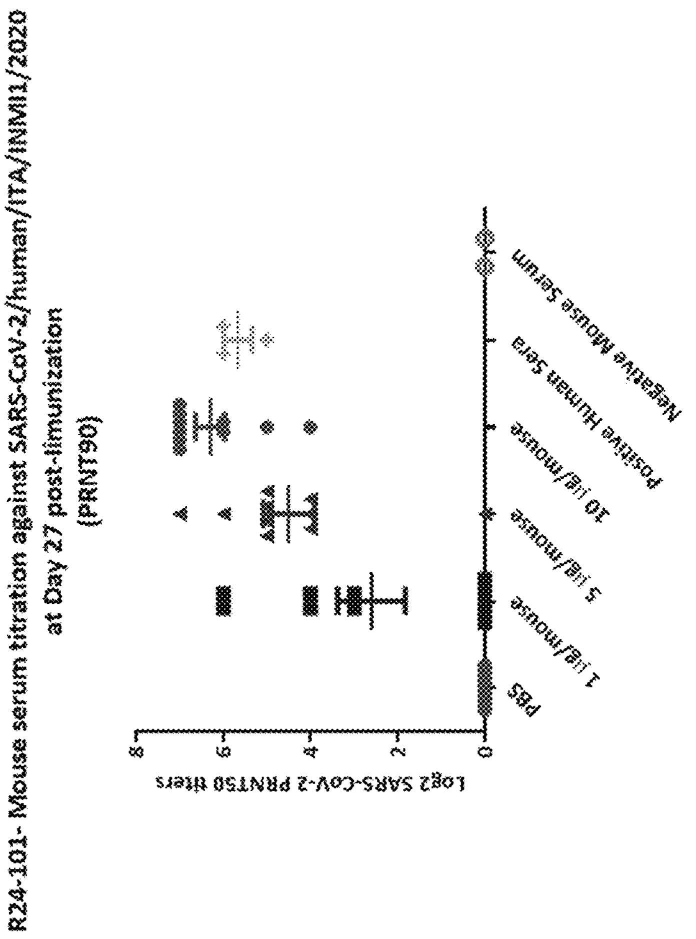

Results: All mice immunized with RL-007 (Group 2, 3, and 4 mice) exhibited no increase in clinical sign severity following challenge with SARS-CoV-2. In contrast, Group 1 mice exhibited sharp increases in clinical sign severity following SARS-CoV-2 challenge (FIG. 7). The SARS-CoV-2 spike mRNA vaccine was shown to have no effect on group 2, 3, or 4 mouse bodyweight (FIG. 8A). Following SARS-CoV-2 challenge, mice administered all mice immunized with SARS-CoV-2 spike mRNA vaccine (Group 2, 3, and 4 mice) exhibited no change in bodyweight as compared to the control (group 1) mice, which exhibited declining bodyweight at least four days after SARS-CoV-2 challenge (FIG. 8B). A similar trend was observed following viral challenge with SARS-CoV-2 B.1.1617.2 Delta variant (FIG. 8C and FIG. 8D). Mouse body temperatures followed similar trends, where SARS-CoV-2 spike mRNA vaccine-immunized mice showed stable body temperatures over the days following SARS-CoV-2 challenge, whereas the control mice experienced decreased body temperatures at least five days following virus challenge (FIG. 9). All SARS-CoV-2 spike mRNA vaccinated mice survived at least up to 13 days following SARS-CoV-2 challenge (FIG. 10). 10% of control mice survived at least 8 days post challenge (FIG. 10). High neutralizing antibody titers were observed at least 13 (FIG. 11A and FIG. 11B) and 27 (FIG. 11C and FIG. 11D) days post-immunization.

Conclusions: These data suggest that the SARS-CoV-2 spike mRNA vaccines provided herein are capable of preventing a subject from having symptoms (e.g., clinical sign severity, changes in body temperature, and/or changes in body weight) of or symptomatic SARS-CoV-2 infection. As demonstrated herein, immunization with the SARS-CoV-2 spike mRNA vaccine is capable inducing an immune response to SARS-CoV-2 in a subject by, e.g., increasing neutralizing antibody titers against SARS-CoV-2 following immunization for a period of at least 13 or at least 27 days. The provided SARS-CoV-2 spike mRNA vaccines can therefore treat subjects infected with SARS-CoV2, and reduce a subject's SARS-CoV-2 viral load.

Example 11: Viral Titers in Nasal Passages and Lung Tissues

A portion of right lung tissue of each mouse euthanized was collected and placed into 10% formalin. Lung tissue samples fixed with formalin were removed from ABSL3 and shipped to Histoserv (19526 Amaranth Dr, Germantown, MD 20874) for histopathological assays. A portion of lung tissue for each of the mice designated for euthanasia on Day 3 post challenge was placed into cell culture medium for analysis of viral titers in lung tissues. Viral titers in nasal passages and lung tissues were determined in five mice (5) from each group three (3) days post viral challenge. Mice were anesthetized by inhalation of isoflurane and nasal washes were collected from each mouse in a total volume of 100 mL of sterile nasal wash buffer for determination of viral replication and shedding in the upper respiratory tract (pfu/mL). Mice were humanely euthanized under a heavy plane of anesthesia and lung tissues were collected. Tissue from the right lung lobe was placed into tissue culture medium, homogenized and used for determination of viral titer in the lower respiratory tract. Serial ten-fold dilutions of each nasal wash or lung homogenate were prepared in EMEM. Supernatant was removed from Vero-E6 cells seeded the night before in 12 well plates and replaced with 300 μL of diluted nasal wash or lung homogenate in each well. The plates were incubated at 37° C./5% $CO_2$ for 1 hour. Plates were shaken every 10-15 minutes during incubation. After one-hour incubation, 1.5 mL overlayer containing 2×EMEM and 0.6% agarose at a ratio of 1:1 was added to the plates. Plates were incubated for 72 hours at 37° C./5% $CO_2$ after solidification of agarose at room temperature. Following incubation, cells were fixed by adding 0.5 mL of 10% formaldehyde into each well on top of the agarose and incubating at room temperature overnight. The palettes of agarose were gently removed, and the cellular monolayers were stained for 10 to 15 minutes with the addition of 0.5 ml of 1% crystal violet. After staining, the plates were washed with water to remove excess stain solution and plaques were manually enumerated for each viral dilution. Viral titers were calculated as pfu/mL.

Figure 12:
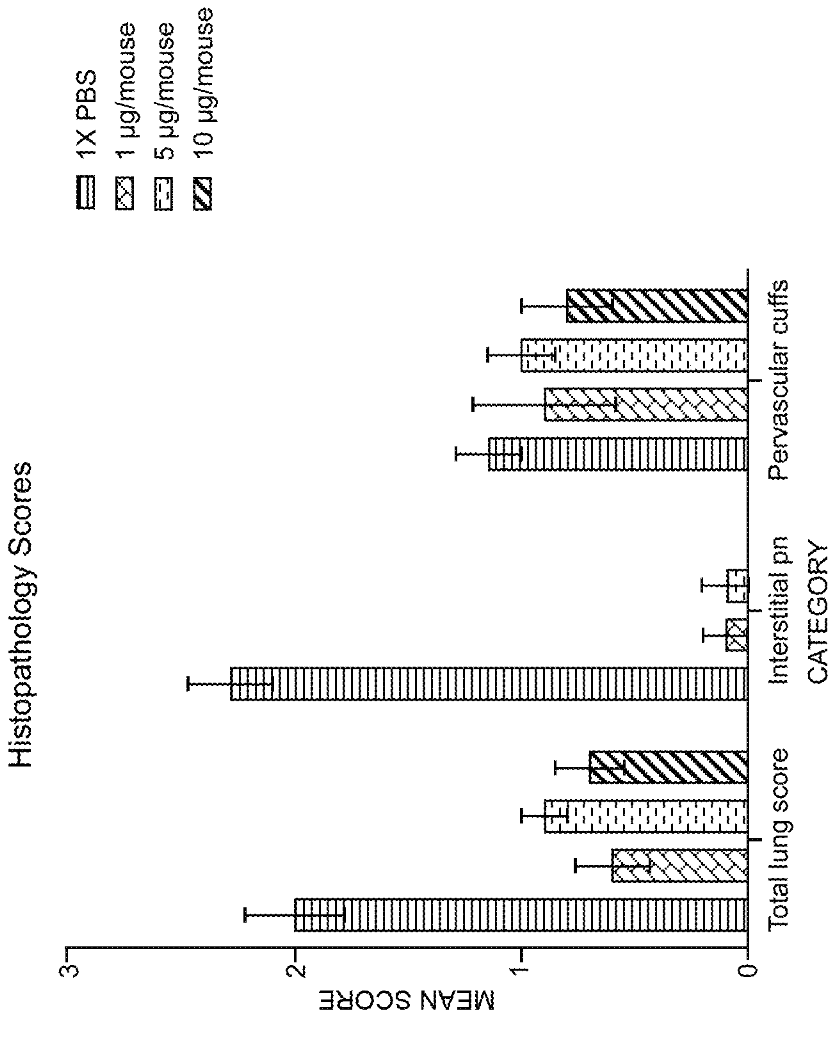
FIG. 12 shows histopathology score for lung tissues harvested at euthanasia. The histopathology score is graphical representation of the Total lung score, Interstitial pneumonia (pn), and Pervascular cuffs scored on a scale based on percentage of lung involved (0=none; 1=0-25%; 2=26-50%; 3=51-75%; and 4=76-100%) and (specific lung lesions: 0=none; 1=minimal; 2=mild; 3=moderate; and 4=severe) for each group. A portion of lung tissue for mice designated for euthanasia on Day 3 post SARS-CoV-2/human/ITA/INMI1/2020 challenge was analyzed for viral titers in lung tissues. Viral titers in lung tissues were determined in five mice (5) from each group three (3) days post viral challenge. Group 1 mice were administered PBS control (identified as "C" in FIG. 7). Groups 2, 3, and 4 mice were immunized with and RL007 mRNA vaccine with dose 1 μg/animal, 5 μg/animal, 10 μg/animal, respectively. Viral titers were calculated as p.f.u./mL. Experiments are described in Example 11
Figure 13:
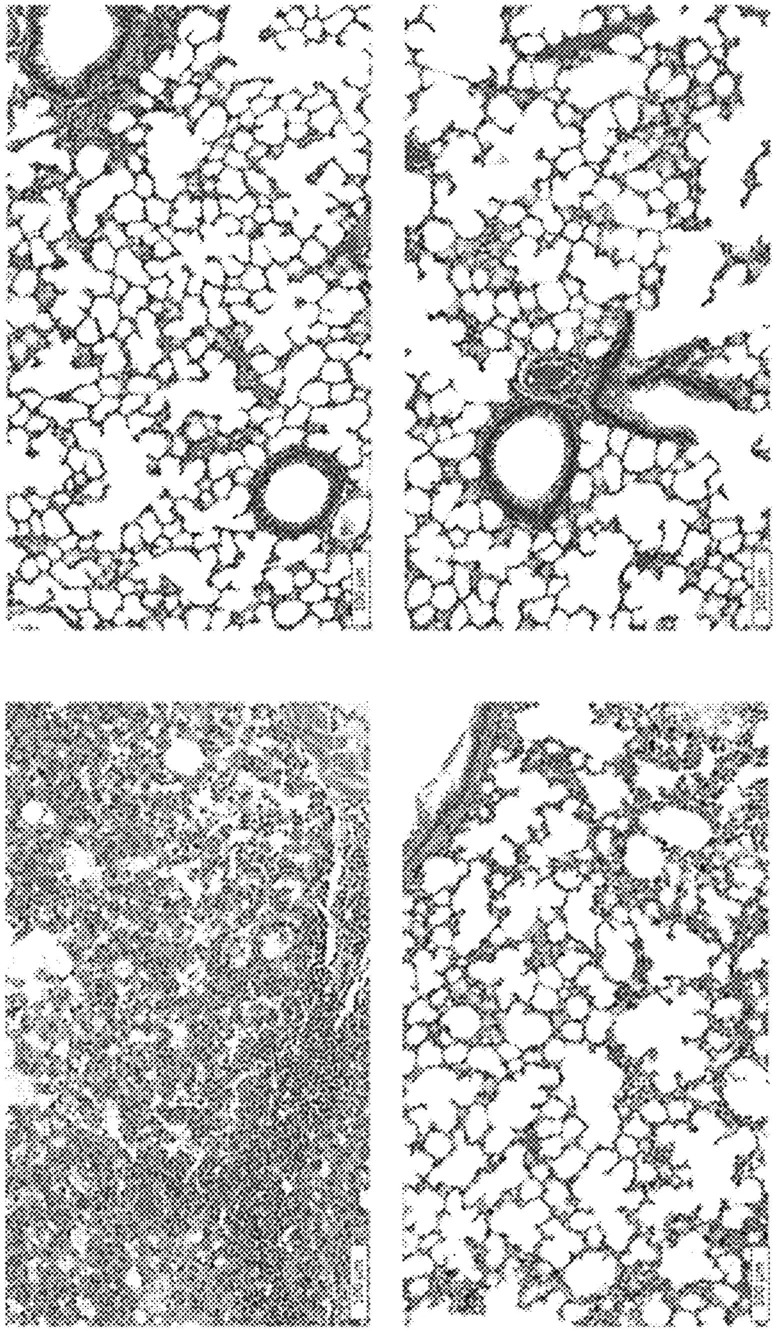
FIG. 13 shows histopathology images for representative lung tissues of mice treated as disclosed in FIG. 7, harvested 13 days post-challenge with SARS-CoV-2. H&E stained tissue slides from representative mice for each group were scanned at 20× magnification. Group 1 mice were administered PBS control. Groups 2, 3, and 4 mice were immunized with mRNA vaccine RL007 with dose 1 μg/animal, 5 μg/animal, 10 μg/animal, respectively. Top left: Group 1, mouse R24-101-010; Top Right: Group 2, mouse R24-101-013; Bottom Left: Group 3, mouse R24-101-023; Bottom Right: Group 4, mouse R24-101-034. Experiments are described in Example 11.

Results and Conclusions: Histopathology images for representative lung tissues harvested 13 days post-challenge with SARS-CoV-2 are shown in FIG. 13. Histopathology scores were determined based upon total lung score, interstitial pneumonia, and perivascular cuffs (FIG. 12). Mice immunized with SARS-CoV-2 spike mRNA vaccine had low mean histopathology scores for each of the three measures when compared to wild type mice, indicating that SARS-CoV-2 spike mRNA vaccine provides protection against tissue level symptoms and damage onset by SARS-CoV-2 infection.

Example 12: Immunogenicity of Serum Immunized with RL007

To assess immunogenicity of SARS-CoV-2 delta variant, RV-1730, in mice, naïve 6- to 8-week-old female BALB/c mice were randomly divided into groups of five-eight mice and vaccinated via intradermal injection with RL007 (1, 5, 10 and 20 μg per mouse). All mice were immunized twice at 21-day intervals. Blood was taken before each immunization at 14 and 35 days after the first immunization via tail bleed or cardiac puncture. The blood was allowed to clot overnight at 4° C. before the serum was harvested by centrifugation at 10,000×g for 10 min at 4° C. Samples were stored at 4° C. until further analysis. To determine S1- and RBD-specific serum IgG titers, MaxiSorp plates (BioLegend) were coated with 100 μl of recombinant S1 or RBD (1 μg/ml) in sodium carbonate buffer overnight at 4° C. The wells were washed 3 times with PBS-T and incubated the plates with 200 μl of blocking buffer for 2 hours at RT. After washing 3 times with PBS-T, the plate was incubated with 100 μl of sera for 2 hours at RT. And the plate washed 5 times with PBS-T and incubated with HRP-conjugated secondary antibody for 1 hour at RT. Finally, the plate was washed 5 times with PBS-T and incubated the plates with 100 μl of 1×TMB substrate for 10 minutes. The reaction was stopped by adding 100 μl of 1N—HCl and read at 450 nm using the Cytation7. For reciprocal endpoint IgG titers, 2-fold serial diluted sera were added to the wells immobilized with different spike proteins. All procedures were the same as described above.

Figure 17:
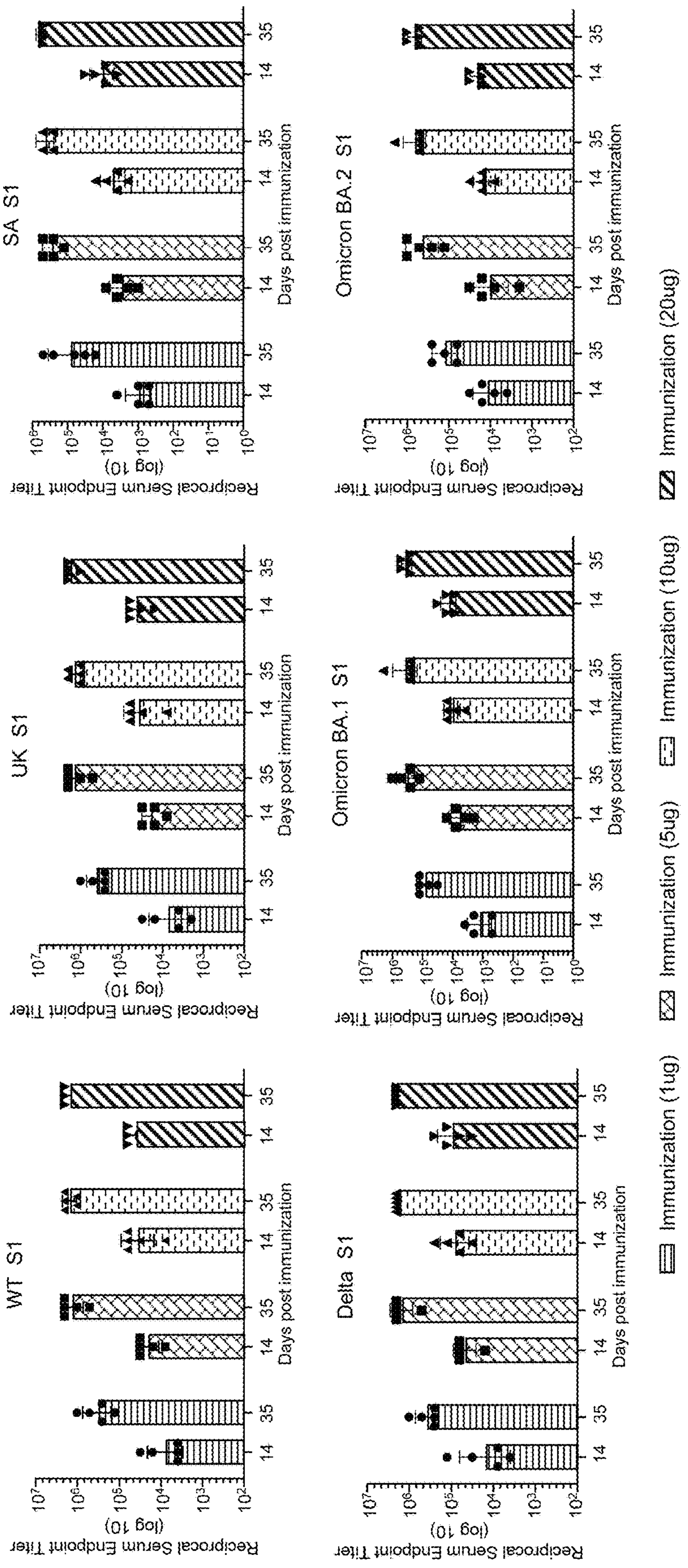
FIG. 17 shows endpoint IgG titers of RV-1730 immunized sera against different variant spike proteins. RV-1730 is a representative RL-007 mRNA vaccine formulation, prepared according to Example 3, comprising SEQ ID NO: 52. SEQ ID NO: 52 comprises the open reading frame depicted in SEQ ID NO: 55. RV-1730 uses a RL-007 carrier prepared according to Example 3. Experiments are described in Example 12.
Figure 18A:
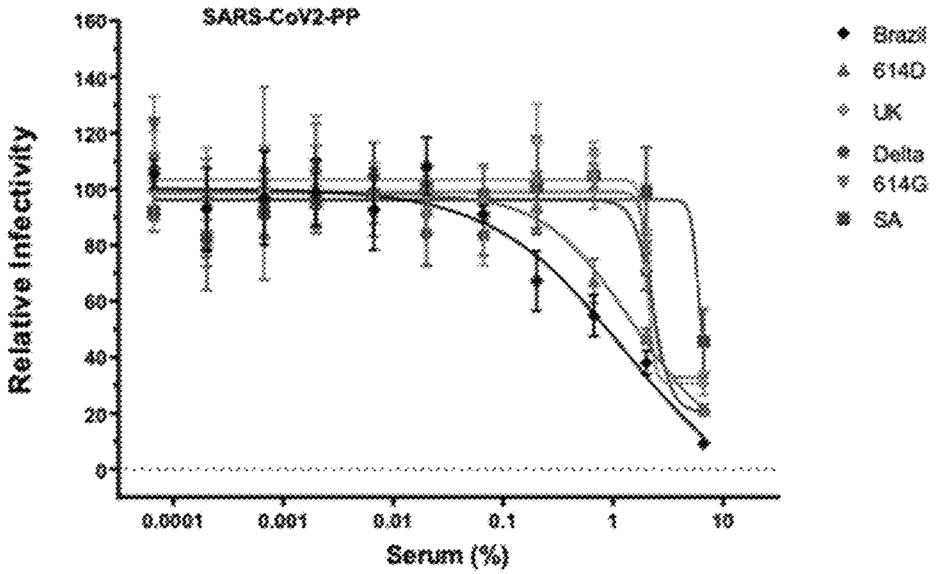
FIG. 18A and FIG. 18B show neutralization antibody titers against SARS-CoV-2 Pseudovirus particles (PP) after RV-1730 immunization at day 14 (FIG. 18A) and day 35 (FIG. 18B) as demonstrated in Example 13. Data are shown for Brazil: Gamma variant, 614D: wild-type, UK: Alpha variant, Delta: Delta variant, 614G: D614G variant, SA: Beta variant pseudovirus particles. Experiments are described in Example 13.
Figure 18B:
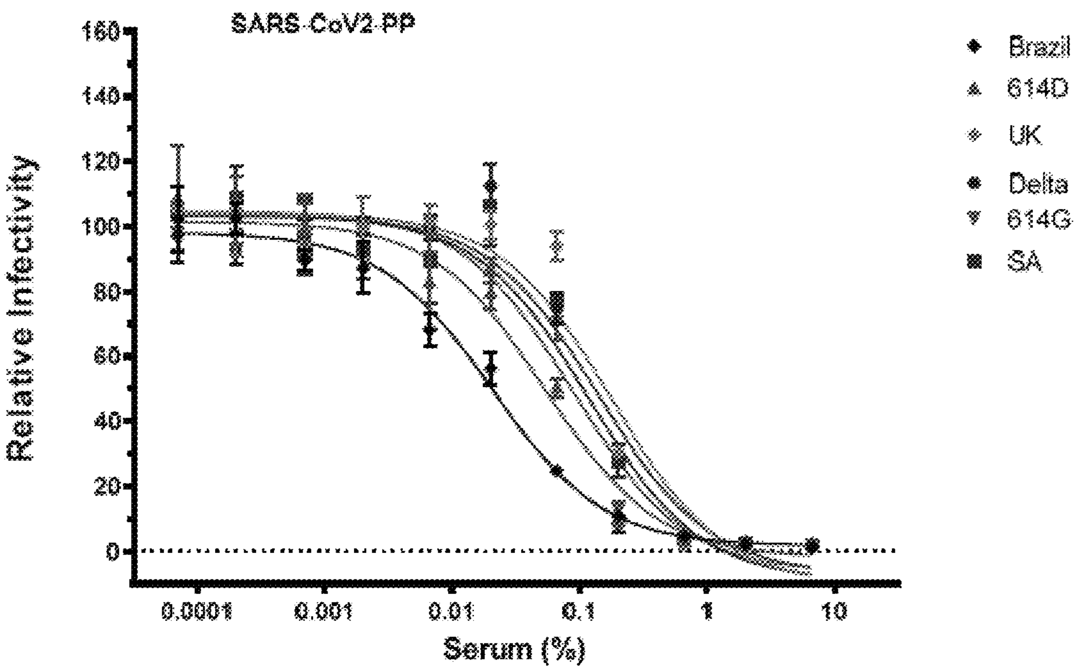
Figure 19A:
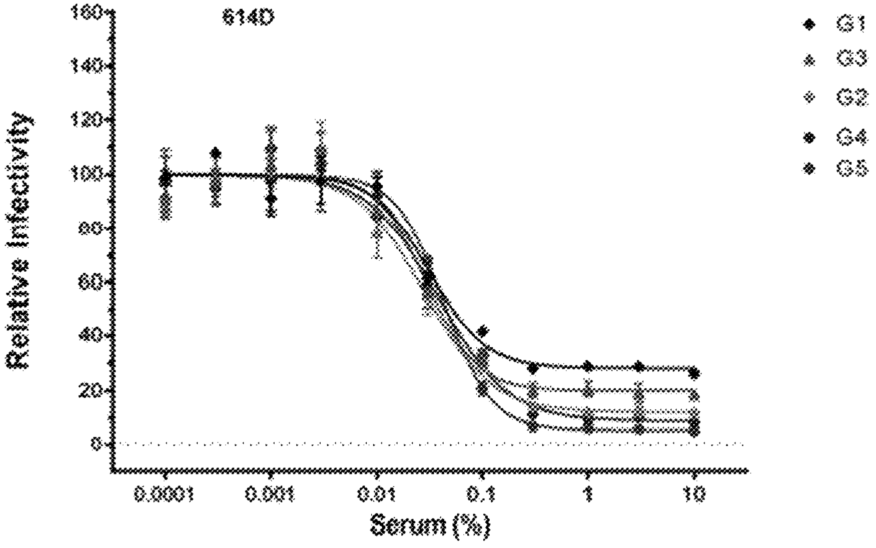
FIGS. 19A-19D show the effect of immunized mouse sera on different SARS-CoV-2-PPs infection across five groups of mice (G1, G2, G3, G4 and G5). The x-axis shows compound concentration and the Y-axis shows relative PP infectivity. Data are shown for 614D-PP (FIG. 19A), Delta-PP (FIG. 19B), Omicron-PP (FIG. 19C), BA.2-PP (FIG. 19D). Experiments are described in Example 13.
Figure 19B:
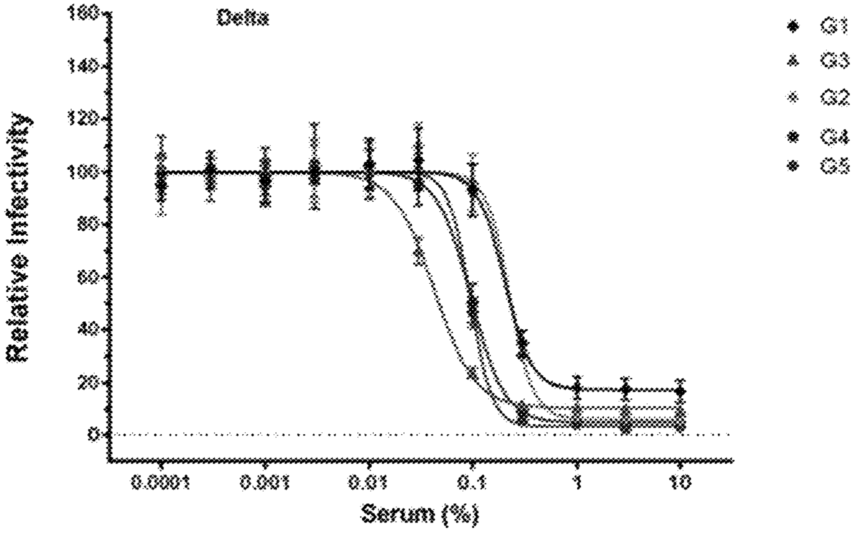
Figure 19C:
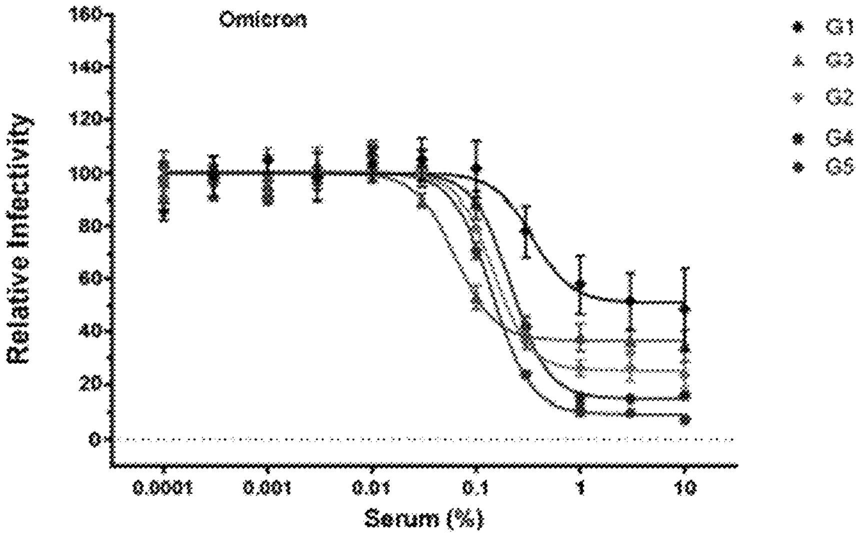
Figure 19D:
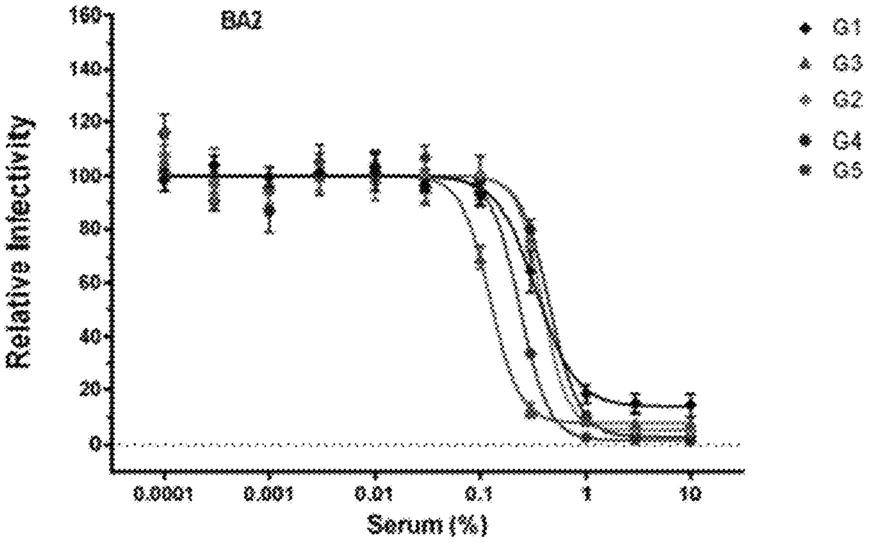

Results and Conclusions: Increased endpoint IgG titers of RL007 immunized sera against different variant spike proteins was observed after first and second immunization doses (FIG. 17). The SARS-CoV-2 spike mRNA vaccine is therefore capable inducing an immune response against different SARS-CoV-2 variant spike proteins in a subject by, e.g., increasing IgG titers against SARS-CoV-2 following first and second immunization doses for a period of at least 14 or at least 35 days.

Example 13: Determination of Neutralizing Antibody Titers of Serum Immunized with RL007

To determine the titers of neutralizing antibodies, we first generated SARS-CoV-2-Psudovirus Particles. In brief, murine Leukemia Virus (MLV) particles pseudotyped with a SARS-CoV-2 Spike protein construct were generated in HEK293T (Cat #CRL-3216, ATCC) cells, following a protocol described previously for SARS-CoV1,2 with some modification. All the plasmid DNAs were purified with ZymoPURE II Plasmid Midiprep Kit (Cat #D4201, Zymo Rescarch). In brief, 8 million HEK293T cells were plate into a 10-cm tissue culture dish (Cat #sc-251460, Santa Cruz) in 16 ml DMEM (Cat #25-500, Genesee Scientific)+10% FBS (Cat #35-010-CV, Corning Life Sciences) without any antibiotics. On the 2nd day, the cells were transfected with 8 μg pTG-Luc, 6 μg pCMV-MLVgag-pol and 6 μg pcDNA3.1-SARS-CoV-2-Spike-□C19 of different variants using Lipofectamine 3000 reagent (Cat #L3000015, ThermoFisher). The cells were cultured for an additional 48 hr. The supernatant was collected into a 50-ml Falcon tube and spun at 290×g for 7 min. The supernatant (pseudotyped virus solution) was then passed through a 0.45 μm filter (Cat #sc-358814, Santa Cruz) using appropriate syringe. The pseudotyped virus solution was then aliquoted into cryovials and stored at −80° C. Each 10-cm cell culture dish produces about 16 ml SARS-CoV-2-PP. The SARS-CoV-2-PP was tested for the quality control with HEK293-ACE2 cell line (created at Codex BioSolutions). For neutralizing assay with pseudovirus, the serum was heat inactivated by incubate the serum at 56° C. for 30 min. The day before the infection, $7.5\times10^3$ HEK293-ACE2 cells were plated into a 384-well white clear plate (Cat #353963, Corning Life Sciences) precoated with Poly D Lysine (Cat #3439-100-1, Trevigen, Inc) in 15 µl culture medium (DMEM+10% FetalClone II Serum, Cat #SH3006603, Fisher Scientific). The cell plate was placed in a $CO_2$ incubator)(37° C. On the 2nd day, the serum to be tested was diluted in the culture medium on a 96-well compound plate. 65 µl of SARS-CoV-2 MLV pseudovirus particles (pp) were mixed with 26 µl of the testing sample prepared above and incubated at 37° C. for 1 hr. After the medium in each well of 384-well cell plate was removed, 17.5 µl of each serum-pp mixture was added into each well. The plate was centrifuged at 54×g for 15 min at 4° C. and additional 7.5 ml of the culture medium was then added into each well. Luciferase activities were measured with Firefly Luciferase Assay Kit (CB-80552-010, Codex BioSolutions Inc). $IC_{50}$ values were calculated based on curve fitting in GraphPad Prism (data was normalized as the percentage of infectivity).

Results and Conclusions: Neutralization antibody titers against SARS-CoV-2 pseudovirus particles were measured following first and second immunization doses. $IC_{50}$ values were calculated based on curve fitting. Strain-specific neutralization was observed. Curves and $IC_{50}$ values are shown in FIG. 18A, FIG. 18B, FIG. 19A, and FIG. 19B. $IC_{50}$ values are tabulated in FIG. 20 for each of the neutralization assay conditions provided. These data demonstrate that the SARS-CoV-2 spike mRNA vaccine provided herein is capable of inducing an immune response against different SARS-CoV-2 variant spike proteins in a subject infected with SARS-CoV-2 by, e.g., increasing neutralizing antibody titers against SARS-CoV-2 following at least 14 or 35 days after first and second immunization doses.

Example 14: Intracellular Cytokine Staining

Spleens from mice were collected and processed into single-cell suspensions in RPMI1640 media supplemented with 10% heat-inactivated fetal calf serum and penicillin/streptomycin (R10 media). Red blood cells were lysed using RBC lysis buffer (KD Medical) and resuspended in R10 media to stop the lysis. Splenocytes were counted and 200,000 cells per well were added to 96 well plates. Cells were then stimulated for 72 hours at 37° C. with 2 µg of PepMix™ SARS-CoV-2 (Spike B.1.617.2/Delta) (JPT Peptide Technologies GmbH) or media alone as a negative control. The plates were centrifuged, and supernatant was collected and frozen at −80° C. for cytokine detection. Measurements and analyses of secreted cytokines from a murine 11-plex kit were performed using a multiplex bead-based technology (Luminex) assay with a Luminex 100/200 instrument (Luminex) after 2-fold dilution of supernatants.

Figure 14:
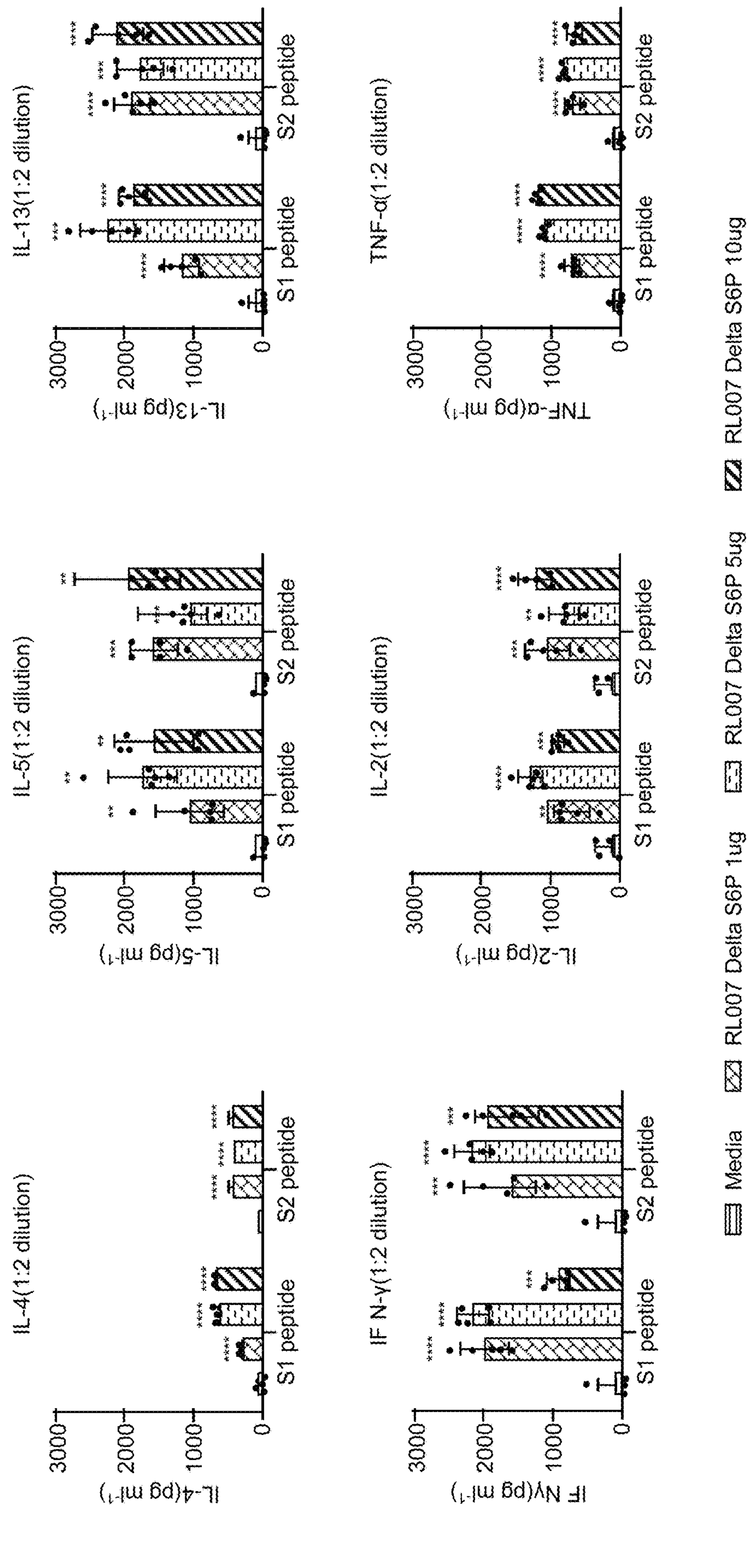
FIG. 14 shows Th-1 and Th-2 cytokine measurements of mice treated as disclosed in FIG. 7 nine weeks post-boost. Splenocytes were isolated from 5 mice per group and re-stimulated with no peptides or pools of overlapping peptides from SARS-CoV-2 S protein. After 72 hours, the culture supernatants were harvested by centrifugation and the secreted Th1-cytokines (IFN-γ, IL-2, TNF-α) and Th2-cytokines (IL-4, IL-5, IL-13) were measured using the bead-based, 11-plex TH1/TH2 mouse ProcartaPlex multiplex immunoassay (Thermo Fisher Scientific). Fluorescence was measured with a Luminex 100/200 system and analyzed with ProcartaPlex Analyst 1.0 software (Thermo Fisher Scientific). Below the lower limit of quantification were set to zero. $^{}P<0.01$, $^{*}P<0.001$, and $^{****}P<0.0001$ (unpaired Student's t-test, compared to PBS control). Experiments are described in Example 14.

Results and Conclusions: After 72 hours, the culture supernatants were harvested by centrifugation and the secreted Th1-cytokines (IFN-γ, IL-2, TNF-α) and Th2-cytokines (IL-4, IL-5, IL-13) were measured. Stimulation with SARS-CoV-2 S proteins increased the secretion of Th1-cytokines (IFN-γ, IL-2, TNF-α) and Th2-cytokines (IL-4, IL-5, IL-13 in all SARS-CoV-2 spike mRNA vaccine-treated mice (FIG. 14). These data indicate that SARS-CoV-2 spike mRNA vaccines of the present disclosure induce a balanced Th1/Th2 immune response against SARS-CoV-2 in a subject infected with SARS-CoV-2 by, e.g., inducing cytokine release against SARS-CoV-2 infection.

Example 15: IFN-γ ELISPOT Analysis on Splenocytes

Figure 15A:
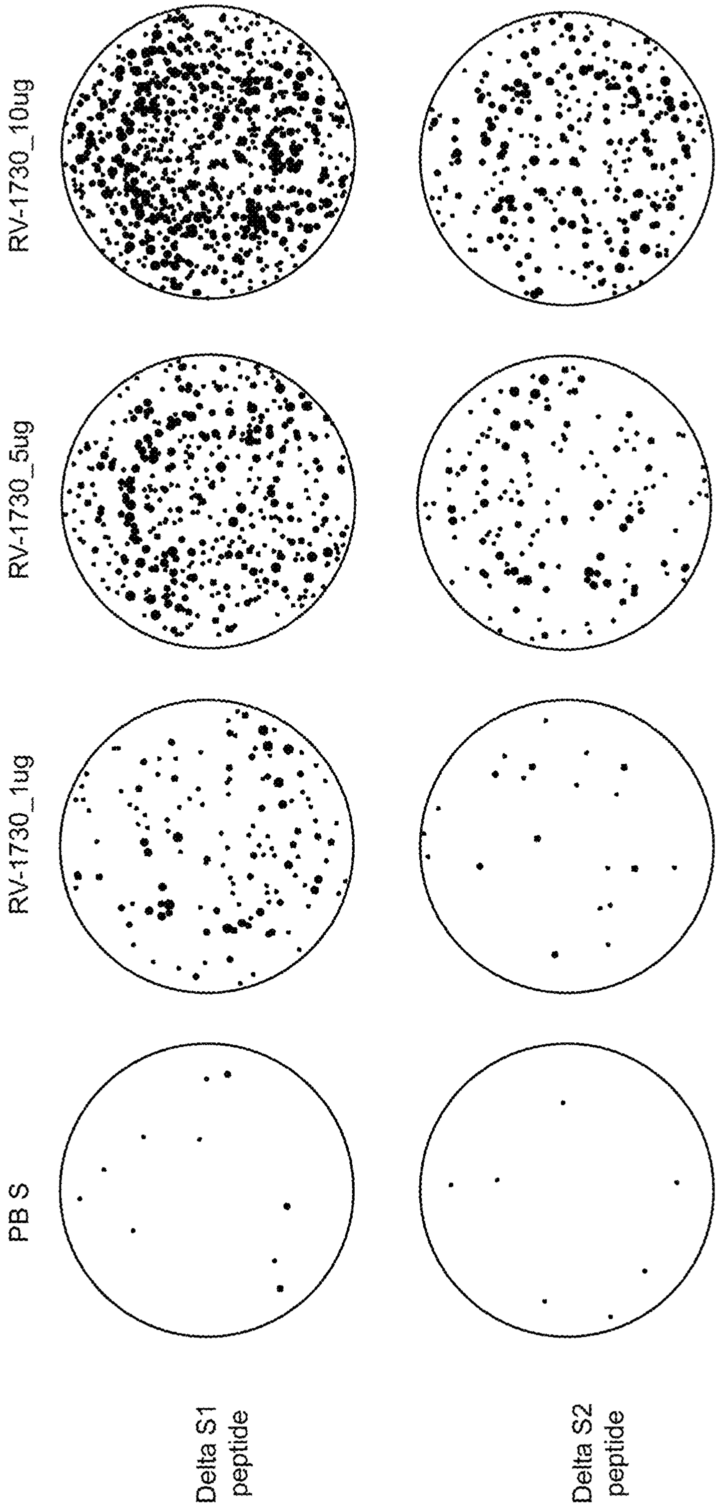
FIG. 15A, FIG. 15B, and FIG. 15C show IFN-γ ELISPOT analysis on splenocytes. 9 weeks post-boost, splenocytes were isolated from 5 mice per group, then splenocytes ($2\times10^5$ cells per 96 well) were plated onto mouse IFN-γ ELISpot plates (Mabtech) and re-stimulated ex vivo with pools of overlapping peptides from SARS-CoV-2 Delta Spike protein subunits S1 and S2 for 16 hours.

Spleens from mice were collected and processed into single-cell suspensions in RPMI1640 media supplemented with 10% heat-inactivated fetal calf serum and penicillin/streptomycin (R10 media). Red blood cells were lysed using RBC lysis buffer (KD Medical) and resuspended in R10 media to stop the lysis. Splenocytes were counted and 200,000 cells per well in a 6-well plate and were added to the plates of the Mouse IFN-g ELISpotPLUS (HRP) kit (Mabtech). Cells were then stimulated for 16 hours at 37° C. with 2 µg of PepMix™ SARS-CoV-2 (Spike B.1.617.2/Delta) (JPT Peptide Technologies GmbH) or media alone as a negative control. Spots were developed as per the manufacturer's instructions. Spots were quantified by Cytation7 and are shown in FIG. 15A.

Figure 15B:
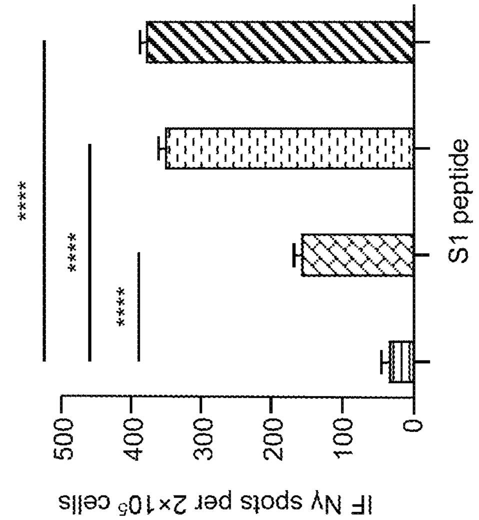
Figure 15C:
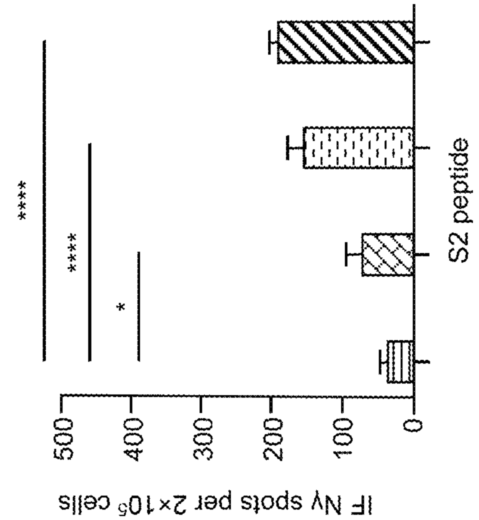

Results and Conclusions: Increased amounts of IFN-γ spots were present in cells from SARS-CoV-2 spike mRNA vaccinated mice compared to unvaccinated control mice (FIG. 15B and FIG. 15C). These data indicate that the SARS-CoV-2 spike mRNA vaccines of the present disclosure can induce an immune response against SARS-CoV-2 in a subject, by, e.g., increasing IFN-γ levels in the subject.

Example 16: Th1/Th2 Cytokine Analysis of Memory T Cells

Following re-stimulation with peptide pools (S1 and S2) corresponding to the S protein, the culture supernatants of splenocytes from RV-1730-immunized mice was assessed the secreted cytokines using Th1/Th2 Cytokine 11-plex mouse procartaplex panel. In brief, nine weeks post-boost, splenocytes were isolated from 5 mice per group and re-stimulated with no peptides or pools of overlapping peptides from SARS-CoV-2 S protein in the presence of a protein transport inhibitor cocktail. After 16 hours, intracellular cytokine staining (ICS) was performed to quantify $CD4^+$ and $CD8^+$ T cell responses. Cytokine expression in the presence of no peptides was considered background and subtracted from the responses measured from the S1 and S2 peptide pools for each individual mouse.

Figure 16:
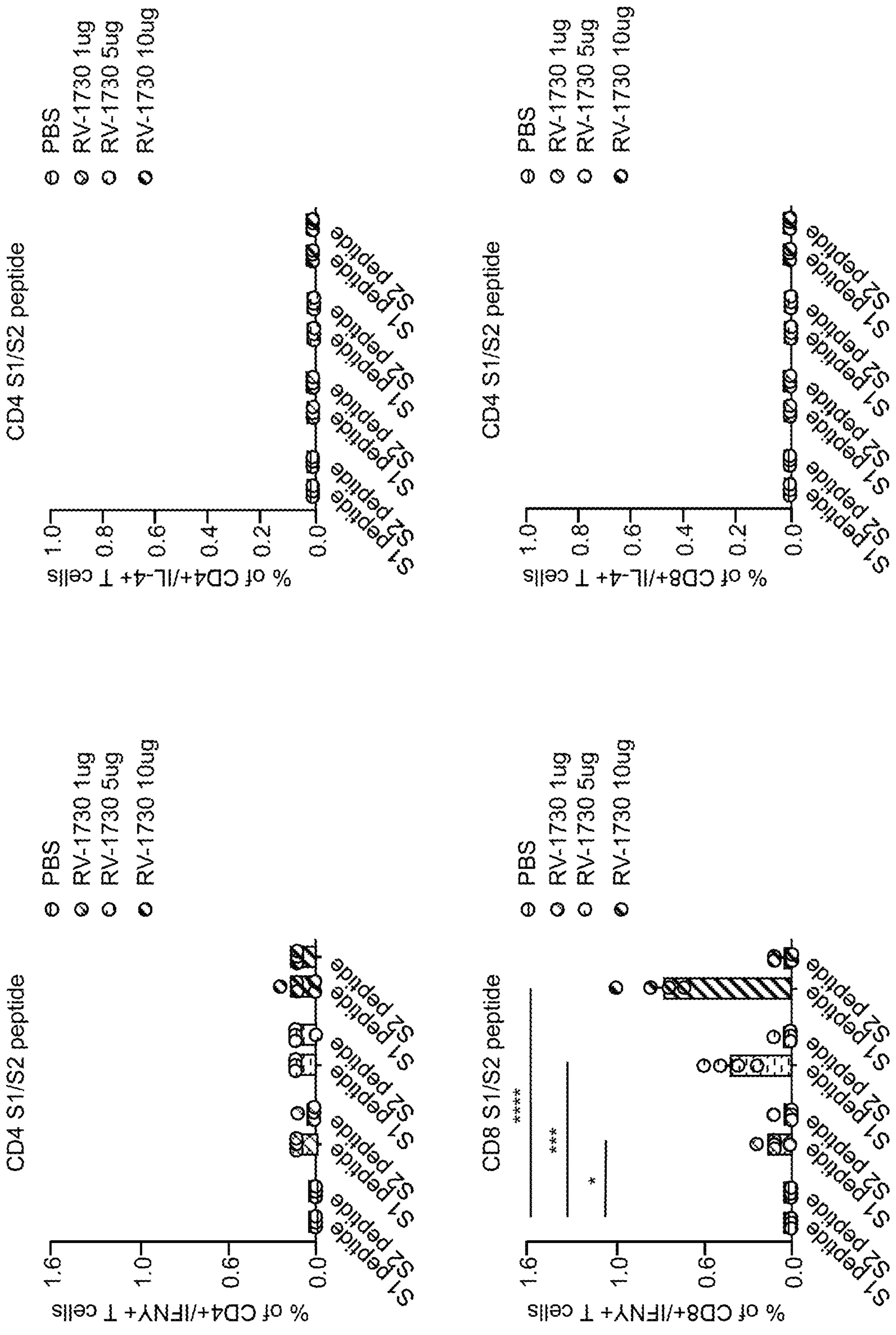
FIG. 16 shows cytokine analysis of memory T cells using a flow cytometry. Nine weeks post-boost, splenocytes were isolated from 5 mice per group and re-stimulated with no peptides or pools of overlapping peptides from SARS-CoV-2 S protein in the presence of a protein transport inhibitor cocktail. Mice were treated as demonstrated in Example 16. After 16 hours, intracellular cytokine staining (ICS) was performed to quantify $CD4^+$ and $CD8^+$ T cell responses. Cytokine expression in the presence of no peptides was considered background and subtracted from the responses measured from the S1 and S2 peptide pools for each individual mouse. Experiments are described in Example 16.

Results and Conclusions: $CD4^+$/IFN-γ and $CD8^+$/IFN-γ T cell responses were increased in culture supernatants of splenocytes from SARS-CoV-2 spike mRNA vaccinated mice compared to unvaccinated control mice (FIG. 16). The SARS-CoV-2 spike mRNA vaccines of the present disclosure can induce an immune response against SARS-CoV-2 in a subject, by, e.g., increasing $CD4^+$/IFN-γ and $CD8^+$/IFN-γ T cell responses in the subject. RV-1730 induces robust neutralizing activity and CD8 T cell responses, balanced Th1/Th2 antibody isotype responses, as well as cytokine release from T cells by ex vivo stimulation with SARS-CoV-2 spike protein peptides. This broad spectrum effectiveness in inducing a strong cellular immune response provides the unique capability to not only use RV-1730 against current/existing SARS-CoV-2 variants and descendent lineages therein, but also to implement RV-1730 against any new SARS-CoV-2 variants of concern that may arise in the future.

TABLE 8

| SEQUENCES | | | |
|---|---|---|---|
| Designation | Amino Acid Sequence | DNA Sequence | RNA Sequence |
| S protein | SEQ ID NO: 1 | — | — |
| S protein D614G and S6P | SEQ ID NO: 2 | SEQ ID NO: 3 (non-optimized) | SEQ ID NO: 4 (non-optimized) |
| deltaC S2P | SEQ ID NO: 5 | | |
| deltaC S2P WC | SEQ ID NO: 6 | | |
| deltaC S6P | SEQ ID NO: 7 | SEQ ID NO: 8 | SEQ ID NO: 9 |
| deltaC S6P WC | SEQ ID NO: 10 | | |
| deltaC S6P plus | SEQ ID NO: 11 | SEQ ID NO: 12 | SEQ ID NO: 13 |
| DPCh | SEQ ID NO: 14 | SEQ ID NO: 15 | SEQ ID NO: 16 |
| 3'UTR | — | SEQ ID NO: 17 | SEQ ID NO: 18 |
| β-globulin 5'UTR | — | SEQ ID NO: 19 | SEQ ID NO: 20 |
| SYS UTR 2.0 | — | SEQ ID NO: 21 | SEQ ID NO: 22 |
| SYS UTR 1.0 | — | SEQ ID NO: 23 | SEQ ID NO: 24 |
| SYS4 5'UTR | — | SEQ ID NO: 25 | SEQ ID NO: 26 |
| polyA 40 | — | SEQ ID NO: 56 | SEQ ID NO: 27 |
| polyA 60 | — | SEQ ID NO: 57 | SEQ ID NO: 28 |
| polyA signal HSV | — | SEQ ID NO: 29 | SEQ ID NO: 30 |
| 5'UTR-deltaC S6P-3' UTR-polyA | | SEQ ID NO: 31 | SEQ ID NO: 32 |
| Plasmid | — | SEQ ID NO: 33 | — |
| Side chains of HKP | SEQ ID NO: 34 to 47 | — | — |

SEQ ID NO: 1, amino acid sequence of S protein:
MFVFLVLLPLVSSQCVNLTTRTQLPPAYTNSFTRGVYYPDKVFRSSVLHSTQDLFLPFFS

NVTWFHAIHVSGTNGTKRFDNPVLPFNDGVYFASTEKSNIIRGWIFGTTLDSKTQSLLIV

NNATNVVIKVCEFQFCNDPFLGVYYHKNNKSWMESEFRVYSSANNCTFEYVSQPFLMD

LEGKQGNFKNLREFVFKNIDGYFKIYSKHTPINLVRDLPQGFSALEPLVDLPIGINITRFQT

LLALHRSYLTPGDSSSGWTAGAAAYYVGYLQPRTFLLKYNENGTITDAVDCALDPLSET

KCTLKSFTVEKGIYQTSNFRVQPTESIVRFPNITNLCPFGEVFNATRFASVYAWNRKRISN

CVADYSVLYNSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDISTEIYQAGSTPC

NGVEGFNCYFPLQSYGFQPTNGVGYQPYRVVVLSFELLHAPATVCGPKKSTNLVKNKC

VN

FNFNGLTGTGVLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCLIGAEHVNN

SYECDIPIGAGICASYQTQTNSPRRARSVASQSIIAYTMSLGAENSVAYSNNSIAIPTNFTI

SVTTEILPVSMTKTSVDCTMYICGDSTECSNLLLQYGSFCTQLNRALTGIAVEQDKNTQE

VFAQVKQIYKTPPIKDFGGFNFSQILPDPSKPSKRSFIEDLLFNKVTLADAGFIKQYGDC

LGDIAARDLICAQKFNGLTVLPPLLTDEMIAQYTSALLAGTITSGWTFGAGAALQIPFAM

QMAYRFNGIGVTQNVLYENQKLIANQFNSAIGKIQDSLSSTASALGKLQDVVNQNAQAL

NTLVKQLSSNFGAISSVLNDILSRLDKVEAEVQIDRLITGRLQSLQTYVTQQLIRAAEIRA

SANLAATKMSECVLGQSKRVDFCGKGYHLMSFPQSAPHGVVFLHVTYVPAQEKNFTTA

PAICHDGKAHFPREGVFVSNGTHWFVTQRNFYEPQIITTDNTFVSGNCDVVIGIVNNTVY

DP

LQPELDSFKEELDKYFKNHTSPDVDLGDISGINASVVNIQKEIDRLNEVAKNLNESLIDL

QELGKYEQYIKWPWYIWLGFIAGLIAIVMVTIMLCCMTSCCSCLKGCCSCGSCCKFDED

DSEPVLKGVKLHYT

-continued

SEQ ID NO: 2, amino acid sequence of S protein comprising D614G (marked in bold font with underlines) and S6P mutations (F817P, A892P, A899P, A942P, K986P, and V987P, marked in bold and italic font with underlines):

MFVFLVLLPLVSSQCVNLTTRTQLPPAYTNSFTRGVYYPDKVFRSSVLHSTQDLFLPFFS

NVTWFHAIHVSGTNGTKRFDNPVLPFNDGVYFASTEKSNIIRGWIFGTTLDSKTQSLLIV

NNATNVVIKVCEFQFCNDPFLGVYYHKNNKSWMESEFRVYSSANNCTFEYVSQPFLMD

LEGKQGNFKNLREFVFKNIDGYFKIYSKHTPINLVRDLPQGFSALEPLVDLPIGINITRFQT

LLALHRSYLTPGDSSSGWTAGAAAYYVGYLQPRTFLLKYNENGTITDAVDCALDPLSET

KCTLKSFTVEKGIYQTSNFRVQPTESIVRFPNITNLCPFGEVFNATRFASVYAWNRKRISN

CVADYSVLYNSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDISTEIYQAGSTPC

NGVEGFNCYFPLQSYGFQPTNGVGYQPYRVVVLSFELLHAPATVCGPKKSTNLVKNKC

VNFNFNGLTGTGVLTESNKKFLPFQQFGRDIADTTDAVRDPQTLEILDITPCSFGGVSVITP

GTNTSNQVAVLYQGVNCTEVPVAIHADQLTPTWRVYSTGSNVFQTRAGCLIGAEHVNN

SYECDIPIGAGICASYQTQTNSPSRAGSVASQSIIAYTMSLGAENSVAYSNNSIAIPTNFTI

SVTTEILPVSMTKTSVDCTMYICGDSTECSNLLLQYGSFCTQLNRALTGIAVEQDKNTQE

VFAQVKQIYKTPPIKDFGGFNFSQILPDPSKPSKRS*P*IEDLLFNKVTLADAGFIKQYGDC

LGDIAARDLICAQKFNGLTVLPPLLTDEMIAQYTSALLAGTITSGWTFGAG*P*ALQIPF*P*M

QMAYRFNGIGVTQNVLYENQKLIANQFNSAIGKIQDSLSST*P*SALGKLQDVVNQNAQAL

NTLVKQLSSNFGAISSVLNDILSRLD*PP*EAEVQIDRLITGRLQSLQTYVTQQLIRAAEIRA

SANLAATKMSECVLGQSKRVDFCGKGYHLMSFPQSAPHGVVFLHVTYVPAQEKNFTTA

PAICHDGKAHFPREGVFVSNGTHWFVTQRNFYEPQIITTDNTFVSGNCDVVIGIVNNTVY

DPLQPELDSFKEELDKYFKNHTSPDVDLGDISGINASVVNIQKEIDRLNEVAKNLNESLID

L

QELGKYEQYIKWPWYIWLGFIAGLIAIVMVTIMLCCMTSCCSCLKGCCSCGSCCKFDED

DSEPVLKGVKLHYT

SEQ ID NO: 3, non-optimized DNA sequence encoding SEQ ID NO: 2:

ATGTTTGTTTTTCTTGTTTTATTGCCACTAGTCTCTAGTCAGTGTGTTAATCTTACAAC

CAGAACTCAATTACCCCCTGCATACACTAATTCTTTCACACGTGGTGTTTATTACCCT

GACAAAGTTTTCAGATCCTCAGTTTTACATTCAACTCAGGACTTGTTCTTACCTTTCTT

TTCCAATGTTACTTGGTTCCATGCTATACATGTCTCTGGGACCAATGGTACTAAGAGG

TTTGATAACCCTGTCCTACCATTTAATGATGGTGTTTATTTTGCTTCCACTGAGAAGT

CTAACATAATAAGAGGCTGGATTTTTGGTACTACTTTAGATTCGAAGACCCAGTCCCT

ACTTATTGTTAATAACGCTACTAATGTTGTTATTAAAGTCTGTGAATTTCAATTTTGT

AATGATCCATTTTTGGGTGTTTATTACCACAAAAACAACAAAAGTTGGATGGAAAGT

GAGTTCAGAGTTTATTCTAGTGCGAATAATTGCACTTTTGAATATGTCTCTCAGCCTT

TTCTTATGGACCTTGAAGGAAAACAGGGTAATTTCAAAAATCTTAGGGAATTTGTGT

TTAAGAATATTGATGGTTATTTTAAAATATATTCTAAGCACACGCCTATTAATTTAGT

GCGTGATCTCCCTCAGGGTTTTTCGGCTTTAGAACCATTGGTAGATTTGCCAATAGGT

ATTAACATCACTAGGTTTCAAACTTTACTTGCTTTACATAGAAGTTATTTGACTCCTG

GTGATTCTTCTTCAGGTTGGACAGCTGGTGCTGCAGCTTATTATGTGGGTTATCTTCA

ACCTAGGACTTTTCTATTAAAATATAATGAAAATGGAACCATTACAGATGCTGTAGA

-continued

CTGTGCACTTGACCCTCTCTCAGAAACAAAGTGTACGTTGAAATCCTTCACTGTAGA
AAAAGGAATCTATCAAACTTCTAACTTTAGAGTCCAACCAACAGAATCTATTGTTAG
ATTTCCTAATATTACAAACTTGTGCCCTTTTGGTGAAGTTTTTAACGCCACCAGATTT
GCATCTGTTTATGCTTGGAACAGGAAGAGAATCAGCAACTGTGTTGCTGATTATTCT
GTCCTATATAATTCCGCATCATTTTCCACTTTTAAGTGTTATGGAGTGTCTCCTACTAA
ATTAAATGATCTCTGCTTTACTAATGTCTATGCAGATTCATTTGTAATTAGAGGTGAT
GAAGTCAGACAAATCGCTCCAGGGCAAACTGGAAAGATTGCTGATTATAATTATAAA
TTACCAGATGATTTTACAGGCTGCGTTATAGCTTGGAATTCTAACAATCTTGATTCTA
AGGTTGGTGGTAATTATAATTACCTGTATAGATTGTTTAGGAAGTCTAATCTCAAACC
TTTTGAGAGAGATATTTCAACTGAAATCTATCAGGCCGGTAGCACACCTTGTAATGG
TGTTGAAGGTTTTAATTGTTACTTTCCTTTACAATCATATGGTTTCCAACCCACTAATG
GTGTTGGTTACCAACCATACAGAGTAGTAGTACTTTCTTTTGAACTTCTACATGCACC
AGCAACTGTTTGTGGACCTAAAAAGTCTACTAATTTGGTTAAAAACAAATGTGTCAA
TTTCAACTTCAATGGTTTAACAGGCACAGGTGTTCTTACTGAGTCTAACAAAAAGTTT
CTGCCTTTCCAACAATTTGGCAGAGACATTGCTGACACTACTGATGCTGTCCGTGATC
CACAGACACTTGAGATTCTTGACATTACACCATGTTCTTTTGGTGGTGTCAGTGTTAT
AACACCAGGAACAAATACTTCTAACCAGGTTGCTGTTCTTTATCAGGGTGTTAACTG
CACAGAAGTCCCTGTTGCTATTCATGCAGATCAACTTACTCCTACTTGGCGTGTTTAT
TCTACAGGTTCTAATGTTTTTCAAACACGTGCAGGCTGTTTAATAGGGGCTGAACATG
TCAACAACTCATATGAGTGTGACATACCCATTGGTGCAGGTATATGCGCTAGTTATC
AGACTCAGACTAATTCTCCTTCGCGGGCAGGTAGTGTAGCTAGTCAATCCATCATTG
CCTACACTATGTCACTTGGTGCAGAAAATTCAGTTGCTTACTCTAATAACTCTATTGC
CATACCCACAAATTTTACTATTAGTGTTACCACAGAAATTCTACCAGTGTCTATGACC
AAGACATCAGTAGATTGTACAATGTACATTTGTGGTGATTCAACTGAATGCAGCAAT
CTTTTGTTGCAATATGGCAGTTTTTGTACACAATTAAACCGTGCTTTAACTGGAATAG
CTGTTGAACAAGACAAAAACACCCAAGAAGTTTTTGCACAAGTCAAACAAATTTACA
AAACACCACCAATTAAAGATTTTGGTGGTTTTAATTTTTCACAAATATTACCAGATCC
ATCAAAACCAAGCAAGAGGTCACCTATTGAAGATCTACTTTTCAACAAAGTGACACT
TGCAGATGCTGGCTTCATCAAACAATATGGTGATTGCCTTGGTGATATTGCTGCTAGA
GACCTCATTTGTGCACAAAAGTTTAACGGCCTTACTGTTTTGCCACCTTTGCTCACAG
ATGAAATGATTGCTCAATACACTTCTGCACTGTTAGCGGGTACAATCACTTCTGGTTG
GACCTTTGGTGCAGGTCCTGCATTACAAATACCATTTCCTATGCAAATGGCTTATAGG
TTTAATGGTATTGGAGTTACACAGAATGTTCTCTATGAGAACCAAAAATTGATTGCC
AACCAATTTAATAGTGCTATTGGCAAAATTCAAGACTCACTTTCTTCCACACCAAGTG
CACTTGGAAAACTTCAAGATGTGGTCAACCAAAATGCACAAGCTTTAAACACGCTTG
TTAAACAACTTAGCTCCAATTTTGGTGCAATTTCAAGTGTTTTAAATGATATCCTTTC
ACGTCTTGACCCACCTGAGGCTGAAGTGCAAATTGATAGGTTGATCACAGGCAGACT
TCAAAGTTTGCAGACATATGTGACTCAACAATTAATTAGAGCTGCAGAAATCAGAGC
TTCTGCTAATCTTGCTGCTACTAAAATGTCAGAGTGTGTACTTGGACAATCAAAAAG
AGTTGATTTTTGTGGAAAGGGCTATCATCTTATGTCCTTCCCTCAGTCAGCACCTCAT

-continued

GGTGTAGTCTTCTTGCATGTGACTTATGTCCCTGCACAAGAAAAGAACTTCACAACT

GCTCCTGCCATTTGTCATGATGGAAAAGCACACTTTCCTCGTGAAGGTGTCTTTGTTT

CAAATGGCACACACTGGTTTGTAACACAAAGGAATTTTTATGAACCACAAATCATTA

CTACAGACAACACATTTGTGTCTGGTAACTGTGATGTTGTAATAGGAATTGTCAACA

ACACAGTTTATGATCCTTTGCAACCTGAATTAGACTCATTCAAGGAGGAGTTAGATA

AATATTTTAAGAATCATACATCACCAGATGTTGATTTAGGTGACATCTCTGGCATTAA

TGCTTCAGTTGTAAACATTCAAAAAGAAATTGACCGCCTCAATGAGGTTGCCAAGAA

TTTAAATGAATCTCTCATCGATCTCCAAGAACTTGGAAAGTATGAGCAGTATATAAA

ATGGCCATGGTACATTTGGCTAGGTTTTATAGCTGGCTTGATTGCCATAGTAATGGTG

ACAATTATGCTTTGCTGTATGACCAGTTGCTGTAGTTGTCTCAAGGGCTGTTGTTCTT

GTGGATCCTGCTGCAAATTTGATGAAGACGACTCTGAGCCAGTGCTCAAAGGAGTCA

AATTACATTACACATAA

SEQ ID NO: 4, non-optimized RNA sequence encoding
SEQ ID NO: 2:
AUGUUUGUUUUUCUUGUUUUAUUGCCACUAGUCUCUAGUCAGUGUGUUAAUCUU

ACAACCAGAACUCAAUUACCCCCUGCAUACACUAAUUCUUUCACACGUGGUGUUU

AUUACCCUGACAAAGUUUUCAGAUCCUCAGUUUUACAUUCAACUCAGGACUUGUU

CUUACCUUUCUUUUCCAAUGUUACUUGGUUCCAUGCUAUACAUGUCUCUGGGACC

AAUGGUACUAAGAGGUUUGAUAACCCUGUCCUACCAUUUAAUGAUGGUGUUUAU

UUUGCUUCCACUGAGAAGUCUAACAUAAUAAGAGGCUGGAUUUUUGGUACUACUU

UAGAUUCGAAGACCCAGUCCCUACUUAUUGUUAAUAACGCUACUAAUGUUGUUAU

UAAAGUCUGUGAAUUUCAAUUUUGUAAUGAUCCAUUUUUGGGUGUUUAUUACCA

CAAAAACAACAAAAGUUGGAUGGAAAGUGAGUUCAGAGUUUAUUCUAGUGCGAA

UAAUUGCACUUUUGAAUAUGUCUCUCAGCCUUUUCUUAUGGACCUUGAAGGAAAA

CAGGGUAAUUUCAAAAAUCUUAGGGAAUUUGUGUUUAAGAAUAUUGAUGGUUAU

UUUAAAAUAUAUUCUAAGCACACGCCUAUUAAUUUAGUGCGUGAUCUCCCUCAGG

GUUUUUCGGCUUUAGAACCAUUGGUAGAUUUGCCAAUAGGUAUUAACAUCACUAG

GUUUCAAACUUUACUUGCUUUACAUAGAAGUUAUUUGACUCCUGGUGAUUCUUCU

UCAGGUUGGACAGCUGGUGCUGCAGCUUAUUAUGUGGGUUAUCUUCAACCUAGGA

CUUUUCUAUUAAAAUAUAAUGAAAAUGGAACCAUUACAGAUGCUGUAGACUGUG

CACUUGACCCUCUCUCAGAAACAAAGUGUACGUUGAAAUCCUUCACUGUAGAAAA

AGGAAUCUAUCAAACUUCUAACUUUAGAGUCCAACCAACAGAAUCUAUUGUUAGA

UUUCCUAAUAUUACAAACUUGUGCCCUUUUGGUGAAGUUUUUAACGCCACCAGAU

UUGCAUCUGUUUAUGCUUGGAACAGGAAGAGAAUCAGCAACUGUGUUGCUGAUU

AUUCUGUCCUAUAUAAUUCCGCAUCAUUUUCCACUUUUAAGUGUUAUGGAGUGUC

UCCUACUAAAUUAAAUGAUCUCUGCUUUACUAAUGUCUAUGCAGAUUCAUUUGUA

AUUAGAGGUGAUGAAGUCAGACAAAUCGCUCCAGGGCAAACUGGAAAGAUUGCUG

AUUAUAAUUAUAAAUUACCAGAUGAUUUUACAGGCUGCGUUAUAGCUUGGAAUU

CUAACAAUCUUGAUUCUAAGGUUGGUGGUAAUUAUAAUUACCUGUAUAGAUUGU

UUAGGAAGUCUAAUCUCAAACCUUUUGAGAGAGAUAUUUCAACUGAAAUCUAUCA

GGCCGGUAGCACACCUUGUAAUGGUGUUGAAGGUUUUAAUUGUUACUUUCCUUUA

CAAUCAUAUGGUUUCCAACCCACUAAUGGUGUUGGUUACCAACCAUACAGAGUAG

-continued

UAGUACUUUCUUUUGAACUUCUACAUGCACCAGCAACUGUUUGUGGACCUAAAAA

GUCUACUAAUUUGGUUAAAAACAAAUGUGUCAAUUUCAACUUCAAUGGUUUAAC

AGGCACAGGUGUUCUUACUGAGUCUAACAAAAAGUUUCUGCCUUUCCAACAAUUU

GGCAGAGACAUUGCUGACACUACUGAUGCUGUCCGUGAUCCACAGACACUUGAGA

UUCUUGACAUUACACCAUGUUCUUUUGGUGGUGUCAGUGUUAUAACACCAGGAAC

AAAUACUUCUAACCAGGUUGCUGUUCUUUAUCAGGGUGUUAACUGCACAGAAGUC

CCUGUUGCUAUUCAUGCAGAUCAACUUACUCCUACUUGGCGUGUUUAUUCUACAG

GUUCUAAUGUUUUUCAAACACGUGCAGGCUGUUUAAUAGGGGCUGAACAUGUCAA

CAACUCAUAUGAGUGUGACAUACCCAUUGGUGCAGGUAUAUGCGCUAGUUAUCAG

ACUCAGACUAAUUCUCCUUCGCGGGCAGGUAGUGUAGCUAGUCAAUCCAUCAUUG

CCUACACUAUGUCACUUGGUGCAGAAAAUUCAGUUGCUUACUCUAAUAACUCUAU

UGCCAUACCCACAAAUUUUACUAUUAGUGUUACCACAGAAAUUCUACCAGUGUCU

AUGACCAAGACAUCAGUAGAUUGUACAAUGUACAUUUGUGGUGAUUCAACUGAA

UGCAGCAAUCUUUUGUUGCAAUAUGGCAGUUUUUGUACACAAUUAAACCGUGCUU

UAACUGGAAUAGCUGUUGAACAAGACAAAAACACCCAAGAAGUUUUUGCACAAGU

CAAACAAAUUUACAAAACACCACCAAUUAAAGAUUUUGGUGGUUUUAAUUUUUCA

CAAAUAUUACCAGAUCCAUCAAAACCAAGCAAGAGGUCACCUAUUGAAGAUCUAC

UUUUCAACAAAGUGACACUUGCAGAUGCUGGCUUCAUCAAACAAUAUGGUGAUUG

CCUUGGUGAUAUUGCUGCUAGAGACCUCAUUUGUGCACAAAAGUUUAACGGCCUU

ACUGUUUUGCCACCUUUGCUCACAGAUGAAAUGAUUGCUCAAUACACUUCUGCAC

UGUUAGCGGGUACAAUCACUUCUGGUUGGACCUUUGGUGCAGGUCCUGCAUUACA

AAUACCAUUUCCUAUGCAAAUGGCUUAUAGGUUUAAUGGUAUUGGAGUUACACA

GAAUGUUCUCUAUGAGAACCAAAAAUUGAUUGCCAACCAAUUUAAUAGUGCUAUU

GGCAAAAUUCAAGACUCACUUUCUUCCACACCAAGUGCACUUGGAAAACUUCAAG

AUGUGGUCAACCAAAAUGCACAAGCUUUAAACACGCUUGUUAAACAACUUAGCUC

CAAUUUUGGUGCAAUUUCAAGUGUUUUAAAUGAUAUCCUUUCACGUCUUGACCCA

CCUGAGGCUGAAGUGCAAAUUGAUAGGUUGAUCACAGGCAGACUUCAAAGUUUGC

AGACAUAUGUGACUCAACAAUUAAUUAGAGCUGCAGAAAUCAGAGCUUCUGCUAA

UCUUGCUGCUACUAAAAUGUCAGAGUGUGUACUUGGACAAUCAAAAAGAGUUGA

UUUUUGUGGAAAGGGCUAUCAUCUUAUGUCCUUCCCUCAGUCAGCACCUCAUGGU

GUAGUCUUCUUGCAUGUGACUUAUGUCCCUGCACAAGAAAAGAACUUCACAACUG

CUCCUGCCAUUUGUCAUGAUGGAAAAGCACACUUUCCUCGUGAAGGUGUCUUUGU

UUCAAAUGGCACACACUGGUUUGUAACACAAAGGAAUUUUUAUGAACCACAAAUC

AUUACUACAGACAACACAUUUGUGUCUGGUAACUGUGAUGUUGUAAUAGGAAUU

GUCAACAACACAGUUUAUGAUCCUUUGCAACCUGAAUUAGACUCAUUCAAGGAGG

AGUUAGAUAAAUAUUUUAAGAAUCAUACAUCACCAGAUGUUGAUUUAGGUGACA

UCUCUGGCAUUAAUGCUUCAGUUGUAAACAUUCAAAAAGAAAUUGACCGCCUCAA

UGAGGUUGCCAAGAAUUUAAAUGAAUCUCUCAUCGAUCUCCAAGAACUUGGAAAG

UAUGAGCAGUAUAUAAAAUGGCCAUGGUACAUUUGGCUAGGUUUUAUAGCUGGC

UUGAUUGCCAUAGUAAUGGUGACAAUUAUGCUUUGCUGUAUGACCAGUUGCUGU

-continued

AGUUGUCUCAAGGGCUGUUGUUCUUGUGGAUCCUGCUGCAAAUUUGAUGAAGACG

ACUCUGAGCCAGUGCUCAAAGGAGUCAAAUUACAUUACACAUAA

SEQ ID NO: 5, amino acid sequence of S protein comprising the following mutations: delta variant mutations of T19R, T95I, G142D, E156Δ, F157Δ, R158G, L452R, T478K, D614G, P681R, and D950N; S2P (K986P and V987P); and furin-like cleavage site mutations (R682S and R685G):
MFVFLVLLPLVSSQCVNLRTRTQLPPAYTNSFTRGVYYPDKVFRSSVLHSTQDLFLPFFSN

VTWFHAIHVSGTNGTKRFDNPVLPFNDGVYFASIEKSNIIRGWIFGTTLDSKTQSLLIVNN

ATNVVIKVCEFQFCNDPFLDVYYHKNNKSWMESGVYSSANNCTFEYVSQPFLMDLEGK

QGNFKNLREFVFKNIDGYFKIYSKHTPINLVRDLPQGFSALEPLVDLPIGINITRFQTLLAL

HRSYLTPGDSSSGWTAGAAAYYVGYLQPRTFLLKYNENGTITDAVDCALDPLSETKCTL

KSFTVEKGIYQTSNFRVQPTESIVRFPNITNLCPFGEVFNATRFASVYAWNRKRISNCVAD

YSVLYNSASFSTFKCYGVSPTKLNDLCFTNVYADSFVIRGDEVRQIAPGQTGKIADYNYK

LPDDFTGCVIAWNSNNLDSKVGGNYNYRYRLFRKSNLKPFERDISTEIYQAGSKPCNGVE

GFNCYFPLQSYGFQPTNGVGYQPYRVVVLSFELLHAPATVCGPKKSTNLVKNKCVNFNF

NGLTGTGVLTESNKKFLPFQQFGRDIADTTDAVRDPQTLEILDITPCSFGGVSVITPGTNTS

NQVAVLYQGVNCTEVPVAIHADQLTPTWRVYSTGSNVFQTRAGCLIGAEHVNNSYECDI

PIGAGICASYQTQTNSRSRAGSVASQSIIAYTMSLGAENSVAYSNNSIAIPTNFTISVTTEIL

PVSMTKTSVDCTMYICGDSTECSNLLLQYGSFCTQLNRALTGIAVEQDKNTQEVFAQVK

QIYKTPPIKDFGGFNFSQILPDPSKPSKRSFIEDLLFNKVTLADAGFIKQYGDCLGDIAARD

LICAQKFNGLTVLPPLLTDEMIAQYTSALLAGTITSGWTFGAGAALQIPFAMQMAYRFNG

IGVTQNVLYENQKLIANQFNSAIGKIQDSLSSTASALGKLQNVVNQNAQALNTLVKQLSS

NFGAISSVLNDILSRLDPPEAEVQIDRLITGRLQSLQTYVTQQLIRAAEIRASANLAATKMS

ECVLGQSKRVDFCGKGYHLMSFPQSAPHGVVFLHVTYVPAQEKNFTTAPAICHDGKAH

FPREGVFVSNGTHWFVTQRNFYEPQIITTDNTFVSGNCDVVIGIVNNTVYDPLQPELDSFK

EELDKYFKNHTSPDVDLGDISGINASVVNIQKEIDRLNEVAKNLNESLIDLQELGKYEQYI

KWPWYIWLGFIAGLIAIVMVTIMLCCMTSCCSCLKGCCSCGSCCKFDEDDSEPVLKGVK

LHYT.

SEQ ID NO: 6, amino acid sequence of S protein comprising the following mutations: delta variant mutations of T19R, T95I, G142D, E156Δ, F157Δ, R158G, L452R, T478K, D614G, D950N; S2P (K986P and V987P); and furin-like cleavage site mutations (R682S and R685G). It lacks the P681R mutation compared to SEQ ID NO: 5:
MFVFLVLLPLVSSQCVNLRTRTQLPPAYTNSFTRGVYYPDKVFRSSVLHSTQDLFLPFFSN

VTWFHAIHVSGTNGTKRFDNPVLPFNDGVYFASIEKSNIIRGWIFGTTLDSKTQSLLIVNN

ATNVVIKVCEFQFCNDPFLDVYYHKNNKSWMESGVYSSANNCTFEYVSQPFLMDLEGK

QGNFKNLREFVFKNIDGYFKIYSKHTPINLVRDLPQGFSALEPLVDLPIGINITRFQTLLAL

HRSYLTPGDSSSGWTAGAAAYYVGYLQPRTFLLKYNENGTITDAVDCALDPLSETKCTL

KSFTVEKGIYQTSNFRVQPTESIVRFPNITNLCPFGEVFNATRFASVYAWNRKRISNCVAD

YSVLYNSASFSTFKCYGVSPTKLNDLCFTNVYADSFVIRGDEVRQIAPGQTGKIADYNYK

LPDDFTGCVIAWNSNNLDSKVGGNYNYRYRLFRKSNLKPFERDISTEIYQAGSKPCNGVE

GFNCYFPLQSYGFQPTNGVGYQPYRVVVLSFELLHAPATVCGPKKSTNLVKNKCVNFNF

NGLTGTGVLTESNKKFLPFQQFGRDIADTTDAVRDPQTLEILDITPCSFGGVSVITPGTNTS

NQVAVLYQGVNCTEVPVAIHADQLTPTWRVYSTGSNVFQTRAGCLIGAEHVNNSYECDI

-continued

PIGAGICASYQTQTNSPSRAGSVASQSIIAYTMSLGAENSVAYSNNSIAIPTNFTISVTTEIL

PVSMTKTSVDCTMYICGDSTECSNLLLQYGSFCTQLNRALTGIAVEQDKNTQEVFAQVK

QIYKTPPIKDFGGFNFSQILPDPSKPSKRSFIEDLLFNKVTLADAGFIKQYGDCLGDIAARD

LICAQKFNGLTVLPPLLTDEMIAQYTSALLAGTITSGWTFGAGAALQIPFAMQMAYRFNG

IGVTQNVLYENQKLIANQFNSAIGKIQDSLSSTASALGKLQNVVNQNAQALNTLVKQLSS

NFGAISSVLNDILSRLDPPEAEVQIDRLITGRLQSLQTYVTQQLIRAAEIRASANLAATKMS

ECVLGQSKRVDFCGKGYHLMSFPQSAPHGVVFLHVTYVPAQEKNFTTAPAICHDGKAH

FPREGVFVSNGTHWFVTQRNFYEPQIITTDNTFVSGNCDVVIGIVNNTVYDPLQPELDSFK

EELDKYFKNHTSPDVDLGDISGINASVVNIQKEIDRLNEVAKNLNESLIDLQELGKYEQYI

KWPWYIWLGFIAGLIAIVMVTIMLCCMTSCCSCLKGCCSCGSCCKFDEDDSEPVLKGVK

LHYT.

SEQ ID NO: 7, amino acid sequence of S protein comprising the following mutations: delta variant mutations of T19R, T95I, G142D, E156Δ, F157Δ, R158G, L452R, T478K, D614G, P681R, and D950N; S6P (F817P, A892P, A899P, A942P, K986P, and V987P); and furin-like cleavage site mutations (R682S and R685G). It further comprises the mutations of F817P, A892P, A899P, and A942P, compared to SEQ ID NO: 5:

MFVFLVLLPLVSSQCVNLRTRTQLPPAYTNSFTRGVYYPDKVFRSSVLHSTQDLFLPFFSN

VTWFHAIHVSGTNGTKRFDNPVLPFNDGVYFASIEKSNIIRGWIFGTTLDSKTQSLLIVNN

ATNVVIKVCEFQFCNDPFLDVYYHKNNKSWMESGVYSSANNCTFEYVSQPFLMDLEGK

QGNFKNLREFVFKNIDGYFKIYSKHTPINLVRDLPQGFSALEPLVDLPIGINITRFQTLLAL

HRSYLTPGDSSSGWTAGAAAYYVGYLQPRTFLLKYNENGTITDAVDCALDPLSETKCTL

KSFTVEKGIYQTSNFRVQPTESIVRFPNITNLCPFGEVFNATRFASVYAWNRKRISNCVAD

YSVLYNSASFSTFKCYGVSPTKLNDLCFTNVYADSFVIRGDEVRQIAPGQTGKIADYNYK

LPDDFTGCVIAWNSNNLDSKVGGNYNYRYRLFRKSNLKPFERDISTEIYQAGSKPCNGVE

GFNCYFPLQSYGFQPTNGVGYQPYRVVVLSFELLHAPATVCGPKKSTNLVKNKCVNFNF

NGLTGTGVLTESNKKFLPFQQFGRDIADTTDAVRDPQTLEILDITPCSFGGVSVITPGTNTS

NQVAVLYQGVNCTEVPVAIHADQLTPTWRVYSTGSNVFQTRAGCLIGAEHVNNSYECDI

PIGAGICASYQTQTNSRSRAGSVASQSIIAYTMSLGAENSVAYSNNSIAIPTNFTISVTTEIL

PVSMTKTSVDCTMYICGDSTECSNLLLQYGSFCTQLNRALTGIAVEQDKNTQEVFAQVK

QIYKTPPIKDFGGFNFSQILPDPSKPSKRSPIEDLLFNKVTLADAGFIKQYGDCLGDIAARD

LICAQKFNGLTVLPPLLTDEMIAQYTSALLAGTITSGWTFGAGPALQIPFPMQMAYRFNGI

GVTQNVLYENQKLIANQFNSAIGKIQDSLSSTPSALGKLQNVVNQNAQALNTLVKQLSS

NFGAISSVLNDILSRLDPPEAEVQIDRLITGRLQSLQTYVTQQLIRAAEIRASANLAATKMS

ECVLGQSKRVDFCGKGYHLMSFPQSAPHGVVFLHVTYVPAQEKNFTTAPAICHDGKAH

FPREGVFVSNGTHWFVTQRNFYEPQIITTDNTFVSGNCDVVIGIVNNTVYDPLQPELDSFK

EELDKYFKNHTSPDVDLGDISGINASVVNIQKEIDRLNEVAKNLNESLIDLQELGKYEQYI

KWPWYIWLGFIAGLIAIVMVTIMLCCMTSCCSCLKGCCSCGSCCKFDEDDSEPVLKGVK

LHYT.

SEQ ID NO: 8, optimized DNA sequence encoding SEQ ID NO: 7:

ATGTTCGTGTTCCTGGTGCTGCTGCCTCTGGTCAGCAGCCAGTGCGTGAACCTGAGA

ACAAGAACACAGCTTCCTCCAGCCTACACAAACTCTTTTACACGGGGCGTGTACTAT

CCTGACAAGGTGTTCCGGTCCAGCGTGCTGCACTCAACCCAAGACCTGTTCCTGCCCT

-continued

TCTTCAGCAACGTCACCTGGTTCCACGCCATCCACGTGTCTGGCACCAATGGCACAA

AGCGATTCGATAACCCCGTGCTGCCTTTCAACGACGGCGTGTACTTTGCCTCCATCGA

GAAGTCCAACATCATCCGGGGCTGGATCTTCGGGACCACACTGGATAGCAAGACCCA

GTCTCTGCTGATCGTAAACAACGCCACCAACGTGGTCATCAAGGTGTGCGAGTTCCA

GTTCTGCAACGACCCTTTCCTCGATGTGTACTACCACAAGAACAACAAGTCTTGGAT

GGAATCGGGCGTGTATAGCAGCGCCAACAACTGCACCTTCGAATACGTGAGCCAGCC

TTTCCTGATGGACCTGGAAGGCAAACAAGGCAATTTTAAGAACCTGAGAGAATTCGT

GTTCAAAAATATAGACGGCTATTTCAAGATCTACAGCAAGCACACCCCTATTAATCT

GGTGCGGGATCTGCCTCAGGGCTTCAGCGCCCTCGAACCTCTGGTGGACCTGCCAAT

CGGCATCAACATTACAAGATTCCAGACGCTGCTCGCTCTGCACAGATCTTACCTGAC

CCCTGGCGACAGCAGCAGCGGCTGGACCGCCGGCGCCGCCGCTTACTACGTGGGCTA

CCTGCAGCCTAGAACCTTTCTGCTGAAGTACAACGAGAACGGCACCATCACTGATGC

CGTGGATTGCGCCCTGGACCCTCTGTCCGAAACCAAATGTACACTGAAGTCTTTTACC

GTGGAAAAAGGAATCTACCAGACTTCCAACTTCCGGGTGCAGCCGACCGAGAGCAT

CGTGCGGTTCCCTAACATCACAAACCTGTGCCCCTTTGGCGAGGTGTTCAACGCCAC

AAGATTTGCTAGCGTGTACGCCTGGAATAGAAAGAGAATCAGCAACTGCGTGGCCG

ATTACAGCGTGCTGTACAATAGCGCCTCTTTCAGCACCTTCAAATGCTACGGCGTGA

GCCCCACCAAGCTGAACGATCTGTGTTTTACAAACGTGTATGCCGACTCATTCGTAAT

CAGGGGCGATGAGGTGAGACAGATCGCTCCTGGACAGACAGGCAAAATCGCGGACT

ACAACTATAAGCTGCCTGATGACTTCACAGGATGTGTGATCGCATGGAACTCCAATA

ACCTCGACAGCAAGGTGGGCGGAAATTACAATTACCGCTACAGACTGTTTAGAAAG

AGCAATCTGAAACCTTTCGAGAGAGACATCAGCACAGAGATCTACCAGGCCGGCAG

CAAGCCCTGTAACGGCGTCGAGGGCTTCAACTGCTACTTCCCCCTGCAGAGCTACGG

CTTCCAGCCTACCAACGGCGTGGGATACCAGCCTTACAGAGTGGTGGTGCTGAGCTT

CGAGCTGCTGCATGCTCCTGCTACAGTGTGTGGTCCTAAGAAGAGCACCAACCTGGT

TAAGAACAAGTGCGTGAATTTTAACTTCAATGGACTGACCGGAACCGGCGTGCTGAC

CGAAAGCAACAAGAAATTCCTGCCTTTTCAGCAGTTTGGCAGAGACATCGCCGACAC

CACCGACGCCGTGAGAGATCCACAAACCCTGGAAATCCTGGACATCACACCTTGCTC

ATTTGGAGGGGTGTCGGTGATCACACCTGGCACCAACACCAGCAACCAGGTGGCCGT

GCTGTACCAGGGAGTGAATTGTACCGAGGTCCCCGTGGCCATTCACGCCGACCAGCT

GACCCCTACCTGGCGGGTGTACTCCACCGGCTCTAACGTATTCCAGACCAGAGCCGG

CTGTCTGATCGGCGCAGAACACGTGAACAATAGCTACGAGTGCGACATCCCTATCGG

AGCCGGGATCTGCGCTAGCTACCAGACCCAGACAAACTCCAGAAGCAGAGCCGGAA

GCGTGGCCAGCCAGTCTATCATCGCCTACACCATGAGCCTGGGCGCCGAAAACAGCG

TTGCCTACAGCAACAATTCTATCGCCATCCCTACAAACTTCACCATCTCCGTGACCAC

CGAGATCCTGCCTGTCAGCATGACAAAGACCAGCGTAGACTGCACAATGTACATCTG

CGGAGATTCCACCGAGTGTAGTAACCTCCTGCTGCAATACGGATCTTTCTGTACTCAG

CTGAACAGAGCCCTGACCGGCATCGCCGTTGAACAGGACAAGAACACCCAGGAGGT

TTTCGCCCAGGTTAAGCAGATCTACAAAACCCCTCCTATCAAGGACTTCGGAGGCTT

TAACTTCTCCCAGATCCTGCCCGACCCCAGCAAGCCCAGCAAGCGGAGCCCCATCGA

GGACCTGCTGTTCAACAAGGTGACCCTGGCCGACGCCGGCTTCATCAAACAGTACGG

-continued

CGATTGCCTGGGAGACATCGCCGCTAGAGATCTAATTTGCGCCCAAAAGTTTAACGG

CCTGACAGTGCTGCCTCCACTGCTGACAGACGAGATGATCGCCCAGTACACATCTGC

CCTGCTGGCTGGTACCATCACATCTGGCTGGACCTTTGGCGCCGGCCCCGCCCTCCAG

ATCCCTTTCCCCATGCAGATGGCCTACCGGTTCAACGGCATCGGCGTGACCCAGAAC

GTGCTGTACGAAAACCAGAAACTGATCGCCAACCAGTTCAATAGCGCGATCGGCAA

AATCCAGGATAGCCTCAGCTCTACACCCAGCGCTCTTGGCAAGCTGCAAAACGTGGT

GAACCAGAATGCCCAGGCCCTTAACACCCTGGTGAAGCAGCTATCCTCTAATTTCGG

TGCCATCAGCAGCGTGCTGAATGATATCCTGAGCAGACTGGACCCCCCTGAGGCCGA

AGTGCAGATCGACAGACTGATCACCGGAAGACTGCAGAGCCTGCAAACCTACGTGA

CCCAGCAACTGATCCGGGCCGCAGAAATCCGGGCCTCCGCTAACCTGGCCGCTACCA

AGATGAGCGAGTGCGTGCTGGGTCAAAGCAAGCGCGTGGACTTCTGTGGAAAAGGC

TACCACCTGATGAGCTTCCCTCAGAGCGCTCCACACGGCGTGGTGTTCCTGCATGTG

ACTTACGTGCCTGCCCAGGAAAAGAACTTCACCACCGCCCCTGCCATTTGTCACGAC

GGCAAGGCCCACTTCCCCCGGGAAGGCGTGTTTGTGTCTAACGGAACACACTGGTTT

GTGACTCAAAGAAACTTCTACGAGCCACAGATCATCACCACAGATAACACCTTCGTC

AGCGGCAACTGCGACGTGGTGATCGGCATCGTGAACAATACTGTGTACGACCCCCTG

CAGCCAGAGCTCGATTCTTTCAAAGAGGAACTGGATAAGTACTTCAAGAACCACACA

TCCCCCGACGTCGACCTGGGCGATATCAGCGGCATTAACGCCAGCGTGGTGAACATC

CAGAAGGAAATCGATAGACTGAACGAGGTGGCAAAGAACCTGAATGAGTCCCTGAT

TGACCTGCAAGAGCTCGGGAAGTACGAGCAGTATATCAAGTGGCCTTGGTACATCTG

GCTGGGCTTCATCGCGGGCCTGATCGCCATCGTTATGGTGACGATCATGCTGTGCTGC

ATGACCAGTTGCTGTAGCTGCCTGAAGGGCTGCTGCAGCTGCGGCAGCTGTTGCAAG

TTCGACGAGGACGACAGCGAGCCTGTGCTGAAGGGCGTTAAGCTGCACTACACCTGA

SEQ ID NO: 9, optimized RNA sequence encoding
SEQ ID NO: 7:
AUGUUCGUGUUCCUGGUGCUGCUGCCUCUGGUCAGCAGCCAGUGCGUGAACCUGA

GAACAAGAACACAGCUUCCUCCAGCCUACACAAACUCUUUUACACGGGGCGUGUA

CUAUCCUGACAAGGUGUUCCGGUCCAGCGUGCUGCACUCAACCCAAGACCUGUUC

CUGCCCUUCUUCAGCAACGUCACCUGGUUCCACGCCAUCCACGUGUCUGGCACCAA

UGGCACAAAGCGAUUCGAUAACCCCGUGCUGCCUUUCAACGACGGCGUGUACUUU

GCCUCCAUCGAGAAGUCCAACAUCAUCCGGGGCUGGAUCUUCGGGACCACACUGG

AUAGCAAGACCCAGUCUCUGCUGAUCGUAAACAACGCCACCAACGUGGUCAUCAA

GGUGUGCGAGUUCCAGUUCUGCAACGACCCUUUCCUCGAUGUGUACUACCACAAG

AACAACAAGUCUUGGAUGGAAUCGGGCGUGUAUAGCAGCGCCAACAACUGCACCU

UCGAAUACGUGAGCCAGCCUUUCCUGAUGGACCUGGAAGGCAAACAAGGCAAUUU

UAAGAACCUGAGAGAAUUCGUGUUCAAAAAUAUAGACGGCUAUUUCAAGAUCUAC

AGCAAGCACACCCCUAUUAAUCUGGUGCGGGAUCUGCCUCAGGGCUUCAGCGCCC

UCGAACCUCUGGUGGACCUGCCAAUCGGCAUCAACAUUACAAGAUUCCAGACGCU

GCUCGCUCUGCACAGAUCUUACCUGACCCCUGGCGACAGCAGCAGCGGCUGGACC

GCCGGCGCCGCCGCUUACUACGUGGGCUACCUGCAGCCUAGAACCUUUCUGCUGA

AGUACAACGAGAACGGCACCAUCACUGAUGCCGUGGAUUGCGCCCUGGACCCUCU

-continued

GUCCGAAACCAAAUGUACACUGAAGUCUUUUACCGUGGAAAAAGGAAUCUACCAG

ACUUCCAACUUCCGGGUGCAGCCGACCGAGAGCAUCGUGCGGUUCCCUAACAUCA

CAAACCUGUGCCCCUUUGGCGAGGUGUUCAACGCCACAAGAUUUGCUAGCGUGUA

CGCCUGGAAUAGAAAGAGAAUCAGCAACUGCGUGGCCGAUUACAGCGUGCUGUAC

AAUAGCGCCUCUUUCAGCACCUUCAAAUGCUACGGCGUGAGCCCCACCAAGCUGA

ACGAUCUGUGUUUUACAAACGUGUAUGCCGACUCAUUCGUAAUCAGGGGCGAUGA

GGUGAGACAGAUCGCUCCUGGACAGACAGGCAAAAUCGCGGACUACAACUAUAAG

CUGCCUGAUGACUUCACAGGAUGUGUGAUCGCAUGGAACUCCAAUAACCUCGACA

GCAAGGUGGGCGGAAAUUACAAUUACCGCUACAGACUGUUUAGAAAGAGCAAUCU

GAAACCUUUCGAGAGAGACAUCAGCACAGAGAUCUACCAGGCCGGCAGCAAGCCC

UGUAACGGCGUCGAGGGCUUCAACUGCUACUUCCCCCUGCAGAGCUACGGCUUCC

AGCCUACCAACGGCGUGGGAUACCAGCCUUACAGAGUGGUGGUGCUGAGCUUCGA

GCUGCUGCAUGCUCCUGCUACAGUGUGUGGUCCUAAGAAGAGCACCAACCUGGUU

AAGAACAAGUGCGUGAAUUUUAACUUCAAUGGACUGACCGGAACCGGCGUGCUGA

CCGAAAGCAACAAGAAAUUCCUGCCUUUUCAGCAGUUUGGCAGAGACAUCGCCGA

CACCACCGACGCCGUGAGAGAUCCACAAACCCUGGAAAUCCUGGACAUCACACCU

UGCUCAUUUGGAGGGGUGUCGGUGAUCACACCUGGCACCAACACCAGCAACCAGG

UGGCCGUGCUGUACCAGGGAGUGAAUUGUACCGAGGUCCCCGUGGCCAUUCACGC

CGACCAGCUGACCCCUACCUGGCGGGUGUACUCCACCGGCUCUAACGUAUUCCAG

ACCAGAGCCGGCUGUCUGAUCGGCGCAGAACACGUGAACAAUAGCUACGAGUGCG

ACAUCCCUAUCGGAGCCGGGAUCUGCGCUAGCUACCAGACCCAGACAAACUCCAG

AAGCAGAGCCGGAAGCGUGGCCAGCCAGUCUAUCAUCGCCUACACCAUGAGCCUG

GGCGCCGAAAACAGCGUUGCCUACAGCAACAAUUCUAUCGCCAUCCCUACAAACU

UCACCAUCUCCGUGACCACCGAGAUCCUGCCUGUCAGCAUGACAAAGACCAGCGU

AGACUGCACAAUGUACAUCUGCGGAGAUUCCACCGAGUGUAGUAACCUCCUGCUG

CAAUACGGAUCUUUCUGUACUCAGCUGAACAGAGCCCUGACCGGCAUCGCCGUUG

AACAGGACAAGAACACCCAGGAGGUUUUCGCCCAGGUUAAGCAGAUCUACAAAAC

CCCUCCUAUCAAGGACUUCGGAGGCUUUAACUUCUCCCAGAUCCUGCCCGACCCCA

GCAAGCCCAGCAAGCGGAGCCCCAUCGAGGACCUGCUGUUCAACAAGGUGACCCU

GGCCGACGCCGGCUUCAUCAAACAGUACGGCGAUUGCCUGGGAGACAUCGCCGCU

AGAGAUCUAAUUUGCGCCCAAAAGUUUAACGGCCUGACAGUGCUGCCUCCACUGC

UGACAGACGAGAUGAUCGCCCAGUACACAUCUGCCCUGCUGGCUGGUACCAUCAC

AUCUGGCUGGACCUUUGGCGCCGGCCCCGCCCUCCAGAUCCCUUUCCCCAUGCAGA

UGGCCUACCGGUUCAACGGCAUCGGCGUGACCCAGAACGUGCUGUACGAAAACCA

GAAACUGAUCGCCAACCAGUUCAAUAGCGCGAUCGGCAAAAUCCAGGAUAGCCUC

AGCUCUACACCCAGCGCUCUUGGCAAGCUGCAAAACGUGGUGAACCAGAAUGCCC

AGGCCCUUAACACCCUGGUGAAGCAGCUAUCCUCUAAUUUCGGUGCCAUCAGCAG

CGUGCUGAAUGAUAUCCUGAGCAGACUGGACCCCCCUGAGGCCGAAGUGCAGAUC

GACAGACUGAUCACCGGAAGACUGCAGAGCCUGCAAACCUACGUGACCCAGCAAC

UGAUCCGGGCCGCAGAAAUCCGGGCCUCCGCUAACCUGGCCGCUACCAAGAUGAG

CGAGUGCGUGCUGGGUCAAAGCAAGCGCGUGGACUUCUGUGGAAAAGGCUACCAC

-continued

CUGAUGAGCUUCCCUCAGAGCGCUCCACACGGCGUGGUGUUCCUGCAUGUGACUU

ACGUGCCUGCCCAGGAAAAGAACUUCACCACCGCCCCUGCCAUUUGUCACGACGGC

AAGGCCCACUUCCCCCGGGAAGGCGUGUUUGUGUCUAACGGAACACACUGGUUUG

UGACUCAAAGAAACUUCUACGAGCCACAGAUCAUCACCACAGAUAACACCUUCGU

CAGCGGCAACUGCGACGUGGUGAUCGGCAUCGUGAACAAUACUGUGUACGACCCC

CUGCAGCCAGAGCUCGAUUCUUUCAAAGAGGAACUGGAUAAGUACUUCAAGAACC

ACACAUCCCCCGACGUCGACCUGGGCGAUAUCAGCGGCAUUAACGCCAGCGUGGU

GAACAUCCAGAAGGAAAUCGAUAGACUGAACGAGGUGGCAAAGAACCUGAAUGAG

UCCCUGAUUGACCUGCAAGAGCUCGGGAAGUACGAGCAGUAUAUCAAGUGGCCUU

GGUACAUCUGGCUGGGCUUCAUCGCGGGCCUGAUCGCCAUCGUUAUGGUGACGAU

CAUGCUGUGCUGCAUGACCAGUUGCUGUAGCUGCCUGAAGGGCUGCUGCAGCUGC

GGCAGCUGUUGCAAGUUCGACGAGGACGACAGCGAGCCUGUGCUGAAGGGCGUUA

AGCUGCACUACACCUGA

SEQ ID NO: 10, amino acid sequence of S protein comprising the following mutations: delta variant mutations of T19R, T95I, G142D, E156Δ, F157Δ, R158G, L452R, T478K, D614G, and D950N; S6P (F817P, A892P, A899P, A942P, K986P, and V987P); and furin-like cleavage site mutations (R682S and R685G). It lacks the P681R mutation compared to SEQ ID NO: 7:
MFVFLVLLPLVSSQCVNLRTRTQLPPAYTNSFTRGVYYPDKVFRSSVLHSTQDLFLPFFSN

VTWFHAIHVSGTNGTKRFDNPVLPFNDGVYFASIEKSNIIRGWIFGTTLDSKTQSLLIVNN

ATNVVIKVCEFQFCNDPFLDVYYHKNNKSWMESGVYSSANNCTFEYVSQPFLMDLEGK

QGNFKNLREFVFKNIDGYFKIYSKHTPINLVRDLPQGFSALEPLVDLPIGINITRFQTLLAL

HRSYLTPGDSSSGWTAGAAAYYVGYLQPRTFLLKYNENGTITDAVDCALDPLSETKCTL

KSFTVEKGIYQTSNFRVQPTESIVRFPNITNLCPFGEVFNATRFASVYAWNRKRISNCVAD

YSVLYNSASFSTFKCYGVSPTKLNDLCFTNVYADSFVIRGDEVRQIAPGQTGKIADYNYK

LPDDFTGCVIAWNSNNLDSKVGGNYNYRYRLFRKSNLKPFERDISTEIYQAGSKPCNGVE

GFNCYFPLQSYGFQPTNGVGYQPYRVVVLSFELLHAPATVCGPKKSTNLVKNKCVNFNF

NGLTGTGVLTESNKKFLPFQQFGRDIADTTDAVRDPQTLEILDITPCSFGGVSVITPGTNTS

NQVAVLYQGVNCTEVPVAIHADQLTPTWRVYSTGSNVFQTRAGCLIGAEHVNNSYECDI

PIGAGICASYQTQTNS*P*SRAGSVASQSIIAYTMSLGAENSVAYSNNSIAIPTNFTISVTTEIL

PVSMTKTSVDCTMYICGDSTECSNLLLQYGSFCTQLNRALTGIAVEQDKNTQEVFAQVK

QIYKTPPIKDFGGFNFSQILPDPSKPSKRSPIEDLLFNKVTLADAGFIKQYGDCLGDIAARD

LICAQKFNGLTVLPPLLTDEMIAQYTSALLAGTITSGWTFGAGPALQIPFPMQMAYRFNGI

GVTQNVLYENQKLIANQFNSAIGKIQDSLSSTPSALGKLQNVVNQNAQALNTLVKQLSS

NFGAISSVLNDILSRLDPPEAEVQIDRLITGRLQSLQTYVTQQLIRAAEIRASANLAATKMS

ECVLGQSKRVDFCGKGYHLMSFPQSAPHGVVFLHVTYVPAQEKNFTTAPAICHDGKAH

FPREGVFVSNGTHWFVTQRNFYEPQIITTDNTFVSGNCDVVIGIVNNTVYDPLQPELDSFK

EELDKYFKNHTSPDVDLGDISGINASVVNIQKEIDRLNEVAKNLNESLIDLQELGKYEQYI

KWPWYIWLGFIAGLIAIVMVTIMLCCMTSCCSCLKGCCSCGSCCKFDEDDSEPVLKGVK

LHYT.

-continued

SEQ ID NO: 11, amino acid sequence of S protein comprising the following mutations: delta variant mutations of T19R, V70F, T95I, G142D, E156Δ, F157Δ, R158G, A222V, W258L, K417N, L452R, T478K, D614G, P681R, and D950N; S6P (F817P, A892P, A899P, A942P, K986P, and V987P); and furin-like cleavage site mutations (R682S and R685G):

MFVFLVLLPLVSSQCVNLRTRTQLPPAYTNSFTRGVYYPDKVFRSSVLHSTQDLFLPFFSN

VTWFHAIHFSGTNGTKRFDNPVLPFNDGVYFASIEKSNIIRGWIFGTTLDSKTQSLLIVNN

ATNVVIKVCEFQFCNDPFLDVYYHKNNKSWMESGVYSSANNCTFEYVSQPFLMDLEGK

QGNFKNLREFVFKNIDGYFKIYSKHTPINLVRDLPQGFSVLEPLVDLPIGINITRFQTLLAL

HRSYLTPGDSSSGLTAGAAAYYVGYLQPRTFLLKYNENGTITDAVDCALDPLSETKCTL

KSFTVEKGIYQTSNFRVQPTESIVRFPNITNLCPFGEVFNATRFASVYAWNRKRISNCVAD

YSVLYNSASFSTFKCYGVSPTKLNDLCFTNVYADSFVIRGDEVRQIAPGQTGNIADYNYK

LPDDFTGCVIAWNSNNLDSKVGGNYNYRYRLFRKSNLKPFERDISTEIYQAGSKPCNGVE

GFNCYFPLQSYGFQPTNGVGYQPYRVVVLSFELLHAPATVCGPKKSTNLVKNKCVNFNF

NGLTGTGVLTESNKKFLPFQQFGRDIADTTDAVRDPQTLEILDITPCSFGGVSVITPGTNTS

NQVAVLYQGVNCTEVPVAIHADQLTPTWRVYSTGSNVFQTRAGCLIGAEHVNNSYECDI

PIGAGICASYQTQTNSRSRAGSVASQSIIAYTMSLGAENSVAYSNNSIAIPTNFTISVTTEIL

PVSMTKTSVDCTMYICGDSTECSNLLLQYGSFCTQLNRALTGIAVEQDKNTQEVFAQVK

QIYKTPPIKDFGGFNFSQILPDPSKPSKRSPIEDLLFNKVTLADAGFIKQYGDCLGDIAARD

LICAQKFNGLTVLPPLLTDEMIAQYTSALLAGTITSGWTFGAGPALQIPFPMQMAYRFNGI

GVTQNVLYENQKLIANQFNSAIGKIQDSLSSTPSALGKLQNVVNQNAQALNTLVKQLSS

NFGAISSVLNDILSRLDPPEAEVQIDRLITGRLQSLQTYVTQQLIRAAEIRASANLAATKMS

ECVLGQSKRVDFCGKGYHLMSFPQSAPHGVVFLHVTYVPAQEKNFTTAPAICHDGKAH

FPREGVFVSNGTHWFVTQRNFYEPQIITTDNTFVSGNCDVVIGIVNNTVYDPLQPELDSFK

EELDKYFKNHTSPDVDLGDISGINASVVNIQKEIDRLNEVAKNLNESLIDLQELGKYEQYI

KWPWYIWLGFIAGLIAIVMVTIMLCCMTSCCSCLKGCCSCGSCCKFDEDDSEPVLKGVK

LHYT.

SEQ ID NO: 12, optimized DNA sequence encoding SEQ ID NO: 11:

ATGTTCGTGTTCCTGGTGCTGCTGCCTCTGGTCAGCAGCCAGTGCGTGAACCTGAGA

ACAAGAACACAGCTTCCTCCAGCCTACACAAACTCTTTTACACGGGGCGTGTACTAT

CCTGACAAGGTGTTCCGGTCCAGCGTGCTGCACTCAACCCAAGACCTGTTCCTGCCCT

TCTTCAGCAACGTCACCTGGTTCCACGCCATCCACTTCTCTGGCACCAATGGCACAAA

GCGATTCGATAACCCCGTGCTGCCTTTCAACGACGGCGTGTACTTTGCCTCCATCGAG

AAGTCCAACATCATCCGGGGCTGGATCTTCGGGACCACACTGGATAGCAAGACCCAG

TCTCTGCTGATCGTAAACAACGCCACCAACGTGGTCATCAAGGTGTGCGAGTTCCAG

TTCTGCAACGACCCTTTCCTCGATGTGTACTACCACAAGAACAACAAGTCTTGGATG

GAATCGGGCGTGTATAGCAGCGCCAACAACTGCACCTTCGAATACGTGAGCCAGCCT

TTCCTGATGGACCTGGAAGGCAAACAAGGCAATTTTAAGAACCTGAGAGAATTCGTG

TTCAAAAATATAGACGGCTATTTCAAGATCTACAGCAAGCACACCCCTATTAATCTG

GTGCGGGATCTGCCTCAGGGCTTCAGCGTCCTCGAACCTCTGGTGGACCTGCCAATC

GGCATCAACATTACAAGATTCCAGACGCTGCTCGCTCTGCACAGATCTTACCTGACC

CCTGGCGACAGCAGCAGCGGCCTGACCGCCGGCGCCGCCGCTTACTACGTGGGCTAC

-continued

CTGCAGCCTAGAACCTTTCTGCTGAAGTACAACGAGAACGGCACCATCACTGATGCC

GTGGATTGCGCCCTGGACCCTCTGTCCGAAACCAAATGTACACTGAAGTCTTTTACC

GTGGAAAAAGGAATCTACCAGACTTCCAACTTCCGGGTGCAGCCGACCGAGAGCAT

CGTGCGGTTCCCTAACATCACAAACCTGTGCCCCTTTGGCGAGGTGTTCAACGCCAC

AAGATTTGCTAGCGTGTACGCCTGGAATAGAAAGAGAATCAGCAACTGCGTGGCCG

ATTACAGCGTGCTGTACAATAGCGCCTCTTTCAGCACCTTCAAATGCTACGGCGTGA

GCCCCACCAAGCTGAACGATCTGTGTTTTACAAACGTGTATGCCGACTCATTCGTAAT

CAGGGGCGATGAGGTGAGACAGATCGCTCCTGGACAGACAGGCAAcATCGCGGACT

ACAACTATAAGCTGCCTGATGACTTCACAGGATGTGTGATCGCATGGAACTCCAATA

ACCTCGACAGCAAGGTGGGCGGAAATTACAATTACCGCTACAGACTGTTTAGAAAG

AGCAATCTGAAACCTTTCGAGAGAGACATCAGCACAGAGATCTACCAGGCCGGCAG

CAAGCCCTGTAACGGCGTCGAGGGCTTCAACTGCTACTTCCCCCTGCAGAGCTACGG

CTTCCAGCCTACCAACGGCGTGGGATACCAGCCTTACAGAGTGGTGGTGCTGAGCTT

CGAGCTGCTGCATGCTCCTGCTACAGTGTGTGGTCCTAAGAAGAGCACCAACCTGGT

TAAGAACAAGTGCGTGAATTTTAACTTCAATGGACTGACCGGAACCGGCGTGCTGAC

CGAAAGCAACAAGAAATTCCTGCCTTTTCAGCAGTTTGGCAGAGACATCGCCGACAC

CACCGACGCCGTGAGAGATCCACAAACCCTGGAAATCCTGGACATCACACCTTGCTC

ATTTGGAGGGGTGTCGGTGATCACACCTGGCACCAACACCAGCAACCAGGTGGCCGT

GCTGTACCAGGGAGTGAATTGTACCGAGGTCCCCGTGGCCATTCACGCCGACCAGCT

GACCCCTACCTGGCGGGTGTACTCCACCGGCTCTAACGTATTCCAGACCAGAGCCGG

CTGTCTGATCGGCGCAGAACACGTGAACAATAGCTACGAGTGCGACATCCCTATCGG

AGCCGGGATCTGCGCTAGCTACCAGACCCAGACAAACTCCAGAAGCAGAGCCGGAA

GCGTGGCCAGCCAGTCTATCATCGCCTACACCATGAGCCTGGGCGCCGAAAACAGCG

TTGCCTACAGCAACAATTCTATCGCCATCCCTACAAACTTCACCATCTCCGTGACCAC

CGAGATCCTGCCTGTCAGCATGACAAAGACCAGCGTAGACTGCACAATGTACATCTG

CGGAGATTCCACCGAGTGTAGTAACCTCCTGCTGCAATACGGATCTTTCTGTACTCAG

CTGAACAGAGCCCTGACCGGCATCGCCGTTGAACAGGACAAGAACACCCAGGAGGT

TTTCGCCCAGGTTAAGCAGATCTACAAAACCCCTCCTATCAAGGACTTCGGAGGCTT

TAACTTCTCCCAGATCCTGCCCGACCCCAGCAAGCCCAGCAAGCGGAGCCCCATCGA

GGACCTGCTGTTCAACAAGGTGACCCTGGCCGACGCCGGCTTCATCAAACAGTACGG

CGATTGCCTGGGAGACATCGCCGCTAGAGATCTAATTTGCGCCCAAAAGTTTAACGG

CCTGACAGTGCTGCCTCCACTGCTGACAGACGAGATGATCGCCCAGTACACATCTGC

CCTGCTGGCTGGTACCATCACATCTGGCTGGACCTTTGGCGCCGGCCCCGCCCTCCAG

ATCCCTTTCCCCATGCAGATGGCCTACCGGTTCAACGGCATCGGCGTGACCCAGAAC

GTGCTGTACGAAAACCAGAAACTGATCGCCAACCAGTTCAATAGCGCGATCGGCAA

AATCCAGGATAGCCTCAGCTCTACACCCAGCGCTCTTGGCAAGCTGCAAAACGTGGT

GAACCAGAATGCCCAGGCCCTTAACACCCTGGTGAAGCAGCTATCCTCTAATTTCGG

TGCCATCAGCAGCGTGCTGAATGATATCCTGAGCAGACTGGACCCCCCTGAGGCCGA

AGTGCAGATCGACAGACTGATCACCGGAAGACTGCAGAGCCTGCAAACCTACGTGA

CCCAGCAACTGATCCGGGCCGCAGAAATCCGGGCCTCCGCTAACCTGGCCGCTACCA

AGATGAGCGAGTGCGTGCTGGGTCAAAGCAAGCGCGTGGACTTCTGTGGAAAAGGC

-continued

TACCACCTGATGAGCTTCCCTCAGAGCGCTCCACACGGCGTGGTGTTCCTGCATGTG

ACTTACGTGCCTGCCCAGGAAAAGAACTTCACCACCGCCCCTGCCATTTGTCACGAC

GGCAAGGCCCACTTCCCCCGGGAAGGCGTGTTTGTGTCTAACGGAACACACTGGTTT

GTGACTCAAAGAAACTTCTACGAGCCACAGATCATCACCACAGATAACACCTTCGTC

AGCGGCAACTGCGACGTGGTGATCGGCATCGTGAACAATACTGTGTACGACCCCCTG

CAGCCAGAGCTCGATTCTTTCAAAGAGGAACTGGATAAGTACTTCAAGAACCACACA

TCCCCCGACGTCGACCTGGGCGATATCAGCGGCATTAACGCCAGCGTGGTGAACATC

CAGAAGGAAATCGATAGACTGAACGAGGTGGCAAAGAACCTGAATGAGTCCCTGAT

TGACCTGCAAGAGCTCGGGAAGTACGAGCAGTATATCAAGTGGCCTTGGTACATCTG

GCTGGGCTTCATCGCGGGCCTGATCGCCATCGTTATGGTGACGATCATGCTGTGCTGC

ATGACCAGTTGCTGTAGCTGCCTGAAGGGCTGCTGCAGCTGCGGCAGCTGTTGCAAG

TTCGACGAGGACGACAGCGAGCCTGTGCTGAAGGGCGTTAAGCTGCACTACACCTGA

SEQ ID NO: 13, optimized RNA sequence encoding
SEQ ID NO: 11:
AUGUUCGUGUUCCUGGUGCUGCUGCCUCUGGUCAGCAGCCAGUGCGUGAACCUGA

GAACAAGAACACAGCUUCCUCCAGCCUACACAAACUCUUUUACACGGGGCGUGUA

CUAUCCUGACAAGGUGUUCCGGUCCAGCGUGCUGCACUCAACCCAAGACCUGUUC

CUGCCCUUCUUCAGCAACGUCACCUGGUUCCACGCCAUCCACUUCUCUGGCACCAA

UGGCACAAAGCGAUUCGAUAACCCCGUGCUGCCUUUCAACGACGGCGUGUACUUU

GCCUCCAUCGAGAAGUCCAACAUCAUCCGGGGCUGGAUCUUCGGGACCACACUGG

AUAGCAAGACCCAGUCUCUGCUGAUCGUAAACAACGCCACCAACGUGGUCAUCAA

GGUGUGCGAGUUCCAGUUCUGCAACGACCCUUUCCUCGAUGUGUACUACCACAAG

AACAACAAGUCUUGGAUGGAAUCGGGCGUGUAUAGCAGCGCCAACAACUGCACCU

UCGAAUACGUGAGCCAGCCUUUCCUGAUGGACCUGGAAGGCAAACAAGGCAAUUU

UAAGAACCUGAGAGAAUUCGUGUUCAAAAAUAUAGACGGCUAUUUCAAGAUCUAC

AGCAAGCACACCCCUAUUAAUCUGGUGCGGGAUCUGCCUCAGGGCUUCAGCGUCC

UCGAACCUCUGGUGGACCUGCCAAUCGGCAUCAACAUUACAAGAUUCCAGACGCU

GCUCGCUCUGCACAGAUCUUACCUGACCCCUGGCGACAGCAGCAGCGGCCUGACCG

CCGGCGCCGCCGCUUACUACGUGGGCUACCUGCAGCCUAGAACCUUUCUGCUGAA

GUACAACGAGAACGGCACCAUCACUGAUGCCGUGGAUUGCGCCCUGGACCCUCUG

UCCGAAACCAAAUGUACACUGAAGUCUUUUACCGUGGAAAAAGGAAUCUACCAGA

CUUCCAACUUCCGGGUGCAGCCGACCGAGAGCAUCGUGCGGUUCCCUAACAUCAC

AAACCUGUGCCCCUUUGGCGAGGUGUUCAACGCCACAAGAUUUGCUAGCGUGUAC

GCCUGGAAUAGAAAGAGAAUCAGCAACUGCGUGGCCGAUUACAGCGUGCUGUACA

AUAGCGCCUCUUUCAGCACCUUCAAAUGCUACGGCGUGAGCCCCACCAAGCUGAA

CGAUCUGUGUUUUACAAACGUGUAUGCCGACUCAUUCGUAAUCAGGGGCGAUGAG

GUGAGACAGAUCGCUCCUGGACAGACAGGCAACAUCGCGGACUACAACUAUAAGC

UGCCUGAUGACUUCACAGGAUGUGUGAUCGCAUGGAACUCCAAUAACCUCGACAG

CAAGGUGGGCGGAAAUUACAAUUACCGCUACAGACUGUUUAGAAAGAGCAAUCUG

AAACCUUUCGAGAGAGACAUCAGCACAGAGAUCUACCAGGCCGGCAGCAAGCCCU

GUAACGGCGUCGAGGGCUUCAACUGCUACUUCCCCCUGCAGAGCUACGGCUUCCA

-continued

GCCUACCAACGGCGUGGGAUACCAGCCUUACAGAGUGGUGGUGCUGAGCUUCGAG

CUGCUGCAUGCUCCUGCUACAGUGUGUGGUCCUAAGAAGAGCACCAACCUGGUUA

AGAACAAGUGCGUGAAUUUUAACUUCAAUGGACUGACCGGAACCGGCGUGCUGAC

CGAAAGCAACAAGAAAUUCCUGCCUUUUCAGCAGUUUGGCAGAGACAUCGCCGAC

ACCACCGACGCCGUGAGAGAUCCACAAACCCUGGAAAUCCUGGACAUCACACCUU

GCUCAUUUGGAGGGGUGUCGGUGAUCACACCUGGCACCAACACCAGCAACCAGGU

GGCCGUGCUGUACCAGGGAGUGAAUUGUACCGAGGUCCCCGUGGCCAUUCACGCC

GACCAGCUGACCCCUACCUGGCGGGUGUACUCCACCGGCUCUAACGUAUUCCAGA

CCAGAGCCGGCUGUCUGAUCGGCGCAGAACACGUGAACAAUAGCUACGAGUGCGA

CAUCCCUAUCGGAGCCGGGAUCUGCGCUAGCUACCAGACCCAGACAAACUCCAGA

AGCAGAGCCGGAAGCGUGGCCAGCCAGUCUAUCAUCGCCUACACCAUGAGCCUGG

GCGCCGAAAACAGCGUUGCCUACAGCAACAAUUCUAUCGCCAUCCCUACAAACUU

CACCAUCUCCGUGACCACCGAGAUCCUGCCUGUCAGCAUGACAAAGACCAGCGUA

GACUGCACAAUGUACAUCUGCGGAGAUUCCACCGAGUGUAGUAACCUCCUGCUGC

AAUACGGAUCUUUCUGUACUCAGCUGAACAGAGCCCUGACCGGCAUCGCCGUUGA

ACAGGACAAGAACACCCAGGAGGUUUUCGCCCAGGUUAAGCAGAUCUACAAAACC

CCUCCUAUCAAGGACUUCGGAGGCUUUAACUUCUCCCAGAUCCUGCCCGACCCCAG

CAAGCCCAGCAAGCGGAGCCCCAUCGAGGACCUGCUGUUCAACAAGGUGACCCUG

GCCGACGCCGGCUUCAUCAAACAGUACGGCGAUUGCCUGGGAGACAUCGCCGCUA

GAGAUCUAAUUUGCGCCCAAAAGUUUAACGGCCUGACAGUGCUGCCUCCACUGCU

GACAGACGAGAUGAUCGCCCAGUACACAUCUGCCCUGCUGGCUGGUACCAUCACA

UCUGGCUGGACCUUUGGCGCCGGCCCCGCCCUCCAGAUCCCUUUCCCCAUGCAGAU

GGCCUACCGGUUCAACGGCAUCGGCGUGACCCAGAACGUGCUGUACGAAAACCAG

AAACUGAUCGCCAACCAGUUCAAUAGCGCGAUCGGCAAAAUCCAGGAUAGCCUCA

GCUCUACACCCAGCGCUCUUGGCAAGCUGCAAAACGUGGUGAACCAGAAUGCCCA

GGCCCUUAACACCCUGGUGAAGCAGCUAUCCUCUAAUUUCGGUGCCAUCAGCAGC

GUGCUGAAUGAUAUCCUGAGCAGACUGGACCCCCCUGAGGCCGAAGUGCAGAUCG

ACAGACUGAUCACCGGAAGACUGCAGAGCCUGCAAACCUACGUGACCCAGCAACU

GAUCCGGGCCGCAGAAAUCCGGGCCUCCGCUAACCUGGCCGCUACCAAGAUGAGC

GAGUGCGUGCUGGGUCAAAGCAAGCGCGUGGACUUCUGUGGAAAAGGCUACCACC

UGAUGAGCUUCCCUCAGAGCGCUCCACACGGCGUGGUGUUCCUGCAUGUGACUUA

CGUGCCUGCCCAGGAAAAGAACUUCACCACCGCCCCUGCCAUUUGUCACGACGGCA

AGGCCCACUUCCCCCGGGAAGGCGUGUUUGUGUCUAACGGAACACACUGGUUUGU

GACUCAAAGAAACUUCUACGAGCCACAGAUCAUCACCACAGAUAACACCUUCGUC

AGCGGCAACUGCGACGUGGUGAUCGGCAUCGUGAACAAUACUGUGUACGACCCCC

UGCAGCCAGAGCUCGAUUCUUUCAAAGAGGAACUGGAUAAGUACUUCAAGAACCA

CACAUCCCCCGACGUCGACCUGGGCGAUAUCAGCGGCAUUAACGCCAGCGUGGUG

AACAUCCAGAAGGAAAUCGAUAGACUGAACGAGGUGGCAAAGAACCUGAAUGAGU

CCCUGAUUGACCUGCAAGAGCUCGGGAAGUACGAGCAGUAUAUCAAGUGGCCUUG

GUACAUCUGGCUGGGCUUCAUCGCGGGCCUGAUCGCCAUCGUUAUGGUGACGAUC

AUGCUGUGCUGCAUGACCAGUUGCUGUAGCUGCCUGAAGGGCUGCUGCAGCUGCG

-continued

GCAGCUGUUGCAAGUUCGACGAGGACGACAGCGAGCCUGUGCUGAAGGGCGUUAA

GCUGCACUACACCUGA

SEQ ID NO: 14, amino acid sequence of S protein comprising the following mutations: delta variant mutations of T19R, V70F, T95I, G142D, E156Δ, F157Δ, R158G, A222V, W258L, K417N, L452R, T478K, D614G, P681R, and D950N; a beta variant mutation of E484K; a variant mutation of N440K; S6P (F817P, A892P, A899P, A942P, K986P, and V987P); and furin-like cleavage site mutations (R682S and R685G):
MFVFLVLLPLVSSQCVNLRTRTQLPPAYTNSFTRGVYYPDKVFRSSVLHSTQDLFLPFFSN

VTWFHAIHFSGTNGTKRFDNPVLPFNDGVYFASIEKSNIIRGWIFGTTLDSKTQSLLIVNN

ATNVVIKVCEFQFCNDPFLDVYYHKNNKSWMESGVYSSANNCTFEYVSQPFLMDLEGK

QGNFKNLREFVFKNIDGYFKIYSKHTPINLVRDLPQGFSVLEPLVDLPIGINITRFQTLLAL

HRSYLTPGDSSSGLTAGAAAYYVGYLQPRTFLLKYNENGTITDAVDCALDPLSETKCTL

KSFTVEKGIYQTSNFRVQPTESIVRFPNITNLCPFGEVFNATRFASVYAWNRKRISNCVAD

YSVLYNSASFSTFKCYGVSPTKLNDLCFTNVYADSFVIRGDEVRQIAPGQTGNIADYNYK

LPDDFTGCVIAWNSNKLDSKVGGNYNYRYRLFRKSNLKPFERDISTEIYQAGSKPCNGV

KGFNCYFPLQSYGFQPTNGVGYQPYRVVVLSFELLHAPATVCGPKKSTNLVKNKCVNFN

FNGLTGTGVLTESNKKFLPFQQFGRDIADTTDAVRDPQTLEILDITPCSFGGVSVITPGTNT

SNQVAVLYQGVNCTEVPVAIHADQLTPTWRVYSTGSNVFQTRAGCLIGAEHVNNSYEC

DIPIGAGICASYQTQTNSRSRAGSVASQSIIAYTMSLGAENSVAYSNNSIAIPTNFTISVTTE

ILPVSMTKTSVDCTMYICGDSTECSNLLLQYGSFCTQLNRALTGIAVEQDKNTQEVFAQV

KQIYKTPPIKDFGGFNFSQILPDPSKPSKRSPIEDLLFNKVTLADAGFIKQYGDCLGDIAAR

DLICAQKFNGLTVLPPLLTDEMIAQYTSALLAGTITSGWTFGAGPALQIPFPMQMAYRFN

GIGVTQNVLYENQKLIANQFNSAIGKIQDSLSSTPSALGKLQNVVNQNAQALNTLVKQLS

SNFGAISSVLNDILSRLDPPEAEVQIDRLITGRLQSLQTYVTQQLIRAAEIRASANLAATKM

SECVLGQSKRVDFCGKGYHLMSFPQSAPHGVVFLHVTYVPAQEKNFTTAPAICHDGKA

HFPREGVFVSNGTHWFVTQRNFYEPQIITTDNTFVSGNCDVVIGIVNNTVYDPLQPELDSF

KEELDKYFKNHTSPDVDLGDISGINASVVNIQKEIDRLNEVAKNLNESLIDLQELGKYEQ

YIKWPWYIWLGFIAGLIAIVMVTIMLCCMTSCCSCLKGCCSCGSCCKFDEDDSEPVLKGV

KLHYT.

SEQ ID NO: 15, optimized DNA sequence encoding
SEQ ID NO: 14:
ATGTTCGTGTTCCTGGTGCTGCTGCCTCTGGTCAGCAGCCAGTGCGTGAACCTGAGA

ACAAGAACACAGCTTCCTCCAGCCTACACAAACTCTTTTACACGGGGCGTGTACTAT

CCTGACAAGGTGTTCCGGTCCAGCGTGCTGCACTCAACCCAAGACCTGTTCCTGCCCT

TCTTCAGCAACGTCACCTGGTTCCACGCCATCCACTTCTCTGGCACCAATGGCACAAA

GCGATTCGATAACCCCGTGCTGCCTTTCAACGACGGCGTGTACTTTGCCTCCATCGAG

AAGTCCAACATCATCCGGGGCTGGATCTTCGGGACCACACTGGATAGCAAGACCCAG

TCTCTGCTGATCGTAAACAACGCCACCAACGTGGTCATCAAGGTGTGCGAGTTCCAG

TTCTGCAACGACCCTTTCCTCGATGTGTACTACCACAAGAACAACAAGTCTTGGATG

GAATCGGGCGTGTATAGCAGCGCCAACAACTGCACCTTCGAATACGTGAGCCAGCCT

TTCCTGATGGACCTGGAAGGCAAACAAGGCAATTTTAAGAACCTGAGAGAATTCGTG

TTCAAAAATATAGACGGCTATTTCAAGATCTACAGCAAGCACACCCCTATTAATCTG

GTGCGGGATCTGCCTCAGGGCTTCAGCGTCCTCGAACCTCTGGTGGACCTGCCAATC

-continued

GGCATCAACATTACAAGATTCCAGACGCTGCTCGCTCTGCACAGATCTTACCTGACC

CCTGGCGACAGCAGCAGCGGCCTGACCGCCGGCGCCGCCGCTTACTACGTGGGCTAC

CTGCAGCCTAGAACCTTTCTGCTGAAGTACAACGAGAACGGCACCATCACTGATGCC

GTGGATTGCGCCCTGGACCCTCTGTCCGAAACCAAATGTACACTGAAGTCTTTTACC

GTGGAAAAAGGAATCTACCAGACTTCCAACTTCCGGGTGCAGCCGACCGAGAGCAT

CGTGCGGTTCCCTAACATCACAAACCTGTGCCCCTTTGGCGAGGTGTTCAACGCCAC

AAGATTTGCTAGCGTGTACGCCTGGAATAGAAAGAGAATCAGCAACTGCGTGGCCG

ATTACAGCGTGCTGTACAATAGCGCCTCTTTCAGCACCTTCAAATGCTACGGCGTGA

GCCCCACCAAGCTGAACGATCTGTGTTTTACAAACGTGTATGCCGACTCATTCGTAAT

CAGGGGCGATGAGGTGAGACAGATCGCTCCTGGACAGACAGGCAAcATCGCGGACT

ACAACTATAAGCTGCCTGATGACTTCACAGGATGTGTGATCGCATGGAACTCCAATA

AGCTCGACAGCAAGGTGGGCGGAAATTACAATTACCGCTACAGACTGTTTAGAAAG

AGCAATCTGAAACCTTTCGAGAGAGACATCAGCACAGAGATCTACCAGGCCGGCAG

CAAGCCCTGTAACGGCGTCAAGGGCTTCAACTGCTACTTCCCCCTGCAGAGCTACGG

CTTCCAGCCTACCAACGGCGTGGGATACCAGCCTTACAGAGTGGTGGTGCTGAGCTT

CGAGCTGCTGCATGCTCCTGCTACAGTGTGTGGTCCTAAGAAGAGCACCAACCTGGT

TAAGAACAAGTGCGTGAATTTTAACTTCAATGGACTGACCGGAACCGGCGTGCTGAC

CGAAAGCAACAAGAAATTCCTGCCTTTTCAGCAGTTTGGCAGAGACATCGCCGACAC

CACCGACGCCGTGAGAGATCCACAAACCCTGGAAATCCTGGACATCACACCTTGCTC

ATTTGGAGGGGTGTCGGTGATCACACCTGGCACCAACACCAGCAACCAGGTGGCCGT

GCTGTACCAGGGAGTGAATTGTACCGAGGTCCCCGTGGCCATTCACGCCGACCAGCT

GACCCCTACCTGGCGGGTGTACTCCACCGGCTCTAACGTATTCCAGACCAGAGCCGG

CTGTCTGATCGGCGCAGAACACGTGAACAATAGCTACGAGTGCGACATCCCTATCGG

AGCCGGGATCTGCGCTAGCTACCAGACCCAGACAAACTCCAGAAGCAGAGCCGGAA

GCGTGGCCAGCCAGTCTATCATCGCCTACACCATGAGCCTGGGCGCCGAAAACAGCG

TTGCCTACAGCAACAATTCTATCGCCATCCCTACAAACTTCACCATCTCCGTGACCAC

CGAGATCCTGCCTGTCAGCATGACAAAGACCAGCGTAGACTGCACAATGTACATCTG

CGGAGATTCCACCGAGTGTAGTAACCTCCTGCTGCAATACGGATCTTTCTGTACTCAG

CTGAACAGAGCCCTGACCGGCATCGCCGTTGAACAGGACAAGAACACCCAGGAGGT

TTTCGCCCAGGTTAAGCAGATCTACAAAACCCCTCCTATCAAGGACTTCGGAGGCTT

TAACTTCTCCCAGATCCTGCCCGACCCCAGCAAGCCCAGCAAGCGGAGCCCCATCGA

GGACCTGCTGTTCAACAAGGTGACCCTGGCCGACGCCGGCTTCATCAAACAGTACGG

CGATTGCCTGGGAGACATCGCCGCTAGAGATCTAATTTGCGCCCAAAAGTTTAACGG

CCTGACAGTGCTGCCTCCACTGCTGACAGACGAGATGATCGCCCAGTACACATCTGC

CCTGCTGGCTGGTACCATCACATCTGGCTGGACCTTTGGCGCCGGCCCCGCCCTCCAG

ATCCCTTTCCCCATGCAGATGGCCTACCGGTTCAACGGCATCGGCGTGACCCAGAAC

GTGCTGTACGAAAACCAGAAACTGATCGCCAACCAGTTCAATAGCGCGATCGGCAA

AATCCAGGATAGCCTCAGCTCTACACCCAGCGCTCTTGGCAAGCTGCAAAACGTGGT

GAACCAGAATGCCCAGGCCCTTAACACCCTGGTGAAGCAGCTATCCTCTAATTTCGG

TGCCATCAGCAGCGTGCTGAATGATATCCTGAGCAGACTGGACCCCCCTGAGGCCGA

-continued

AGTGCAGATCGACAGACTGATCACCGGAAGACTGCAGAGCCTGCAAACCTACGTGA

CCCAGCAACTGATCCGGGCCGCAGAAATCCGGGCCTCCGCTAACCTGGCCGCTACCA

AGATGAGCGAGTGCGTGCTGGGTCAAAGCAAGCGCGTGGACTTCTGTGGAAAAGGC

TACCACCTGATGAGCTTCCCTCAGAGCGCTCCACACGGCGTGGTGTTCCTGCATGTG

ACTTACGTGCCTGCCCAGGAAAAGAACTTCACCACCGCCCCTGCCATTTGTCACGAC

GGCAAGGCCCACTTCCCCCGGGAAGGCGTGTTTGTGTCTAACGGAACACACTGGTTT

GTGACTCAAAGAAACTTCTACGAGCCACAGATCATCACCACAGATAACACCTTCGTC

AGCGGCAACTGCGACGTGGTGATCGGCATCGTGAACAATACTGTGTACGACCCCCTG

CAGCCAGAGCTCGATTCTTTCAAAGAGGAACTGGATAAGTACTTCAAGAACCACACA

TCCCCCGACGTCGACCTGGGCGATATCAGCGGCATTAACGCCAGCGTGGTGAACATC

CAGAAGGAAATCGATAGACTGAACGAGGTGGCAAAGAACCTGAATGAGTCCCTGAT

TGACCTGCAAGAGCTCGGGAAGTACGAGCAGTATATCAAGTGGCCTTGGTACATCTG

GCTGGGCTTCATCGCGGGCCTGATCGCCATCGTTATGGTGACGATCATGCTGTGCTGC

ATGACCAGTTGCTGTAGCTGCCTGAAGGGCTGCTGCAGCTGCGGCAGCTGTTGCAAG

TTCGACGAGGACGACAGCGAGCCTGTGCTGAAGGGCGTTAAGCTGCACTACACCTGA

SEQ ID NO: 16, optimized RNA sequence encoding
SEQ ID NO: 14:

AUGUUCGUGUUCCUGGUGCUGCUGCCUCUGGUCAGCAGCCAGUGCGUGAACCUGA

GAACAAGAACACAGCUUCCUCCAGCCUACACAAACUCUUUUACACGGGGCGUGUA

CUAUCCUGACAAGGUGUUCCGGUCCAGCGUGCUGCACUCAACCCAAGACCUGUUC

CUGCCCUUCUUCAGCAACGUCACCUGGUUCCACGCCAUCCACUUCUCUGGCACCAA

UGGCACAAAGCGAUUCGAUAACCCCGUGCUGCCUUUCAACGACGGCGUGUACUUU

GCCUCCAUCGAGAAGUCCAACAUCAUCCGGGGCUGGAUCUUCGGGACCACACUGG

AUAGCAAGACCCAGUCUCUGCUGAUCGUAAACAACGCCACCAACGUGGUCAUCAA

GGUGUGCGAGUUCCAGUUCUGCAACGACCCUUUCCUCGAUGUGUACUACCACAAG

AACAACAAGUCUUGGAUGGAAUCGGGCGUGUAUAGCAGCGCCAACAACUGCACCU

UCGAAUACGUGAGCCAGCCUUUCCUGAUGGACCUGGAAGGCAAACAAGGCAAUUU

UAAGAACCUGAGAGAAUUCGUGUUCAAAAAUAUAGACGGCUAUUUCAAGAUCUAC

AGCAAGCACACCCCUAUUAAUCUGGUGCGGGAUCUGCCUCAGGGCUUCAGCGUCC

UCGAACCUCUGGUGGACCUGCCAAUCGGCAUCAACAUUACAAGAUUCCAGACGCU

GCUCGCUCUGCACAGAUCUUACCUGACCCCUGGCGACAGCAGCAGCGGCCUGACCG

CCGGCGCCGCCGCUUACUACGUGGGCUACCUGCAGCCUAGAACCUUUCUGCUGAA

GUACAACGAGAACGGCACCAUCACUGAUGCCGUGGAUUGCGCCCUGGACCCUCUG

UCCGAAACCAAAUGUACACUGAAGUCUUUUACCGUGGAAAAAGGAAUCUACCAGA

CUUCCAACUUCCGGGUGCAGCCGACCGAGAGCAUCGUGCGGUUCCCUAACAUCAC

AAACCUGUGCCCCUUUGGCGAGGUGUUCAACGCCACAAGAUUUGCUAGCGUGUAC

GCCUGGAAUAGAAAGAGAAUCAGCAACUGCGUGGCCGAUUACAGCGUGCUGUACA

AUAGCGCCUCUUUCAGCACCUUCAAAUGCUACGGCGUGAGCCCCACCAAGCUGAA

CGAUCUGUGUUUUACAAACGUGUAUGCCGACUCAUUCGUAAUCAGGGGCGAUGAG

GUGAGACAGAUCGCUCCUGGACAGACAGGCAACAUCGCGGACUACAACUAUAAGC

UGCCUGAUGACUUCACAGGAUGUGUGAUCGCAUGGAACUCCAAUAAGCUCGACAG

CAAGGUGGGCGGAAAUUACAAUUACCGCUACAGACUGUUUAGAAAGAGCAAUCUG

-continued

AAACCUUUCGAGAGAGACAUCAGCACAGAGAUCUACCAGGCCGGCAGCAAGCCCU

GUAACGGCGUCAAGGGCUUCAACUGCUACUUCCCCCUGCAGAGCUACGGCUUCCA

GCCUACCAACGGCGUGGGAUACCAGCCUUACAGAGUGGUGGUGCUGAGCUUCGAG

CUGCUGCAUGCUCCUGCUACAGUGUGUGGUCCUAAGAAGAGCACCAACCUGGUUA

AGAACAAGUGCGUGAAUUUUAACUUCAAUGGACUGACCGGAACCGGCGUGCUGAC

CGAAAGCAACAAGAAAUUCCUGCCUUUUCAGCAGUUUGGCAGAGACAUCGCCGAC

ACCACCGACGCCGUGAGAGAUCCACAAACCCUGGAAAUCCUGGACAUCACACCUU

GCUCAUUUGGAGGGGUGUCGGUGAUCACACCUGGCACCAACACCAGCAACCAGGU

GGCCGUGCUGUACCAGGGAGUGAAUUGUACCGAGGUCCCCGUGGCCAUUCACGCC

GACCAGCUGACCCCUACCUGGCGGGUGUACUCCACCGGCUCUAACGUAUUCCAGA

CCAGAGCCGGCUGUCUGAUCGGCGCAGAACACGUGAACAAUAGCUACGAGUGCGA

CAUCCCUAUCGGAGCCGGGAUCUGCGCUAGCUACCAGACCCAGACAAACUCCAGA

AGCAGAGCCGGAAGCGUGGCCAGCCAGUCUAUCAUCGCCUACACCAUGAGCCUGG

GCGCCGAAAACAGCGUUGCCUACAGCAACAAUUCUAUCGCCAUCCCUACAAACUU

CACCAUCUCCGUGACCACCGAGAUCCUGCCUGUCAGCAUGACAAAGACCAGCGUA

GACUGCACAAUGUACAUCUGCGGAGAUUCCACCGAGUGUAGUAACCUCCUGCUGC

AAUACGGAUCUUUCUGUACUCAGCUGAACAGAGCCCUGACCGGCAUCGCCGUUGA

ACAGGACAAGAACACCCAGGAGGUUUUCGCCCAGGUUAAGCAGAUCUACAAAACC

CCUCCUAUCAAGGACUUCGGAGGCUUUAACUUCUCCCAGAUCCUGCCCGACCCCAG

CAAGCCCAGCAAGCGGAGCCCCAUCGAGGACCUGCUGUUCAACAAGGUGACCCUG

GCCGACGCCGGCUUCAUCAAACAGUACGGCGAUUGCCUGGGAGACAUCGCCGCUA

GAGAUCUAAUUUGCGCCCAAAAGUUUAACGGCCUGACAGUGCUGCCUCCACUGCU

GACAGACGAGAUGAUCGCCCAGUACACAUCUGCCCUGCUGGCUGGUACCAUCACA

UCUGGCUGGACCUUUGGCGCCGGCCCCGCCCUCCAGAUCCCUUUCCCCAUGCAGAU

GGCCUACCGGUUCAACGGCAUCGGCGUGACCCAGAACGUGCUGUACGAAAACCAG

AAACUGAUCGCCAACCAGUUCAAUAGCGCGAUCGGCAAAAUCCAGGAUAGCCUCA

GCUCUACACCCAGCGCUCUUGGCAAGCUGCAAAACGUGGUGAACCAGAAUGCCCA

GGCCCUUAACACCCUGGUGAAGCAGCUAUCCUCUAAUUUCGGUGCCAUCAGCAGC

GUGCUGAAUGAUAUCCUGAGCAGACUGGACCCCCCUGAGGCCGAAGUGCAGAUCG

ACAGACUGAUCACCGGAAGACUGCAGAGCCUGCAAACCUACGUGACCCAGCAACU

GAUCCGGGCCGCAGAAAUCCGGGCCUCCGCUAACCUGGCCGCUACCAAGAUGAGC

GAGUGCGUGCUGGGUCAAAGCAAGCGCGUGGACUUCUGUGGAAAAGGCUACCACC

UGAUGAGCUUCCCUCAGAGCGCUCCACACGGCGUGGUGUUCCUGCAUGUGACUUA

CGUGCCUGCCCAGGAAAAGAACUUCACCACCGCCCCUGCCAUUUGUCACGACGGCA

AGGCCCACUUCCCCCGGGAAGGCGUGUUUGUGUCUAACGGAACACACUGGUUUGU

GACUCAAAGAAACUUCUACGAGCCACAGAUCAUCACCACAGAUAACACCUUCGUC

AGCGGCAACUGCGACGUGGUGAUCGGCAUCGUGAACAAUACUGUGUACGACCCCC

UGCAGCCAGAGCUCGAUUCUUUCAAAGAGGAACUGGAUAAGUACUUCAAGAACCA

CACAUCCCCCGACGUCGACCUGGGCGAUAUCAGCGGCAUUAACGCCAGCGUGGUG

AACAUCCAGAAGGAAAUCGAUAGACUGAACGAGGUGGCAAAGAACCUGAAUGAGU

-continued

CCCUGAUUGACCUGCAAGAGCUCGGGAAGUACGAGCAGUAUAUCAAGUGGCCUUG

GUACAUCUGGCUGGGCUUCAUCGCGGGCCUGAUCGCCAUCGUUAUGGUGACGAUC

AUGCUGUGCUGCAUGACCAGUUGCUGUAGCUGCCUGAAGGGCUGCUGCAGCUGCG

GCAGCUGUUGCAAGUUCGACGAGGACGACAGCGAGCCUGUGCUGAAGGGCGUUAA

GCUGCACUACACCUGA

SEQ ID NO: 17, DNA sequence of 3' UTR:
GCTCGCTTTCTTGCTGTCCAATTTCTATTAAAGGTTCCTTTGTTCCCTAAGTCCAACTA

CTAAACTGGGGGATATTATGAAGGGCCTTGAGCATCTGGATTCTGCCTAATAAAAAA

CATTTATTTTCATTGC

SEQ ID NO: 18, RNA sequence of 3' UTR:
GCUCGCUUUCUUGCUGUCCAAUUUCUAUUAAAGGUUCCUUUGUUCCCUAAGUCCA

ACUACUAAACUGGGGGAUAUUAUGAAGGGCCUUGAGCAUCUGGAUUCUGCCUAAU

AAAAAACAUUUAUUUUCAUUGC

SEQ ID NO: 19, DNA sequence of β-globulin 5'UTR:
ACATTTGCTTCTGACACAACTGTGTTCACTAGCAACCTCAAACAGACACC SEQ ID NO: 20, RNA sequence of β-globulin 5'UTR:
ACAUUUGCUUCUGACACAACUGUGUUCACUAGCAACCUCAAACAGACACC SEQ ID NO: 21, DNA sequence of SYS UTR 2.0:
GGCGCTCGAGCAGGTTCAGAAGGAGATCAAAAACCCCCAAGGATCAAACGCCACC SEQ ID NO: 22, RNA sequence of SYS UTR 2.0:
GGCGCUCGAGCAGGUUCAGAAGGAGAUCAAAAACCCCCAAGGAUCAAACGCCACC SEQ ID NO: 23, DNA sequence of SYS UTR 1.0:
GGGCGCTCGAGCAGGTTCAGAAGGAGATCAAAAACCCCCAAGGATCAAAC SEQ ID NO: 24, RNA sequence of SYS UTR 1.0:
GGGCGCUCGAGCAGGUUCAGAAGGAGAUCAAAAACCCCCAAGGAUCAAAC SEQ ID NO: 25, DNA sequence of SYS4 5'UTR:
GGCGCACGAGCAGGGAGAGAAGGAGATCAAAAACCCCCAAGGATCAAACGCCACC SEQ ID NO: 26, RNA sequence of SYS4 5'UTR:
GGCGCACGAGCAGGGAGAGAAGGAGAUCAAAAACCCCCAAGGAUCAAACGCCACC SEQ ID NO: 56 (DNA) and SEQ ID NO: 27
(RNA) sequence of polyA 40:
AAAAAAAAAAAAAAAAAAAAAAAAAAAAAAAAAAAAAAAA SEQ ID NO: 57 (DNA) and SEQ ID NO: 28
(RNA) sequence of polyA 60:
AAAAAAAAAAAAAAAAAAAAAAAAAAAAAAAAAAAAAAAAAAAAAAAAAAAAAA

AAAAAAGAAAAAAAAAAAAAAAAAAAAAAAAAAAAAAAAAAAAAAAAAAAAAA

AAAAAAAAAAAAA

SEQ ID NO: 29, DNA sequence of polyA signal HSV:
CGGCAATAAAAAGACAGAATAAAACGCACGGTGTTGGGTCGTTTGTTC SEQ ID NO: 30, RNA sequence of polyA signal HSV:
CGGCAAUAAAAAGACAGAAUAAAACGCACGGUGUUGGGUCGUUUGUUC SEQ ID NO: 31, DNA sequence of an exemplified
5'UTR-deltaC S6P-3' UTR-polyA:
GGACATTTGCTTCTGACACAACTGTGTTCACTAGCAACCTCAAACAGACACCGCCAC

CATGTTCGTGTTCCTGGTGCTGCTGCCTCTGGTCAGCAGCCAGTGCGTGAACCTGAGA

ACAAGAACACAGCTTCCTCCAGCCTACACAAACTCTTTTACACGGGGCGTGTACTAT

CCTGACAAGGTGTTCCGGTCCAGCGTGCTGCACTCAACCCAAGACCTGTTCCTGCCCT

TCTTCAGCAACGTCACCTGGTTCCACGCCATCCACGTGTCTGGCACCAATGGCACAA

AGCGATTCGATAACCCCGTGCTGCCTTTCAACGACGGCGTGTACTTTGCCTCCATCGA

GAAGTCCAACATCATCCGGGGCTGGATCTTCGGGACCACACTGGATAGCAAGACCCA

-continued

GTCTCTGCTGATCGTAAACAACGCCACCAACGTGGTCATCAAGGTGTGCGAGTTCCA

GTTCTGCAACGACCCTTTCCTCGATGTGTACTACCACAAGAACAACAAGTCTTGGAT

GGAATCGGGCGTGTATAGCAGCGCCAACAACTGCACCTTCGAATACGTGAGCCAGCC

TTTCCTGATGGACCTGGAAGGCAAACAAGGCAATTTTAAGAACCTGAGAGAATTCGT

GTTCAAAAATATAGACGGCTATTTCAAGATCTACAGCAAGCACACCCCTATTAATCT

GGTGCGGGATCTGCCTCAGGGCTTCAGCGCCCTCGAACCTCTGGTGGACCTGCCAAT

CGGCATCAACATTACAAGATTCCAGACGCTGCTCGCTCTGCACAGATCTTACCTGAC

CCCTGGCGACAGCAGCAGCGGCTGGACCGCCGGCGCCGCCGCTTACTACGTGGGCTA

CCTGCAGCCTAGAACCTTTCTGCTGAAGTACAACGAGAACGGCACCATCACTGATGC

CGTGGATTGCGCCCTGGACCCTCTGTCCGAAACCAAATGTACACTGAAGTCTTTTACC

GTGGAAAAAGGAATCTACCAGACTTCCAACTTCCGGGTGCAGCCGACCGAGAGCAT

CGTGCGGTTCCCTAACATCACAAACCTGTGCCCCTTTGGCGAGGTGTTCAACGCCAC

AAGATTTGCTAGCGTGTACGCCTGGAATAGAAAGAGAATCAGCAACTGCGTGGCCG

ATTACAGCGTGCTGTACAATAGCGCCTCTTTCAGCACCTTCAAATGCTACGGCGTGA

GCCCCACCAAGCTGAACGATCTGTGTTTTACAAACGTGTATGCCGACTCATTCGTAAT

CAGGGGCGATGAGGTGAGACAGATCGCTCCTGGACAGACAGGCAAAATCGCGGACT

ACAACTATAAGCTGCCTGATGACTTCACAGGATGTGTGATCGCATGGAACTCCAATA

ACCTCGACAGCAAGGTGGGCGGAAATTACAATTACCGCTACAGACTGTTTAGAAAG

AGCAATCTGAAACCTTTCGAGAGAGACATCAGCACAGAGATCTACCAGGCCGGCAG

CAAGCCCTGTAACGGCGTCGAGGGCTTCAACTGCTACTTCCCCCTGCAGAGCTACGG

CTTCCAGCCTACCAACGGCGTGGGATACCAGCCTTACAGAGTGGTGGTGCTGAGCTT

CGAGCTGCTGCATGCTCCTGCTACAGTGTGTGGTCCTAAGAAGAGCACCAACCTGGT

TAAGAACAAGTGCGTGAATTTTAACTTCAATGGACTGACCGGAACCGGCGTGCTGAC

CGAAAGCAACAAGAAATTCCTGCCTTTTCAGCAGTTTGGCAGAGACATCGCCGACAC

CACCGACGCCGTGAGAGATCCACAAACCCTGGAAATCCTGGACATCACACCTTGCTC

ATTTGGAGGGGTGTCGGTGATCACACCTGGCACCAACACCAGCAACCAGGTGGCCGT

GCTGTACCAGGGAGTGAATTGTACCGAGGTCCCCGTGGCCATTCACGCCGACCAGCT

GACCCCTACCTGGCGGGTGTACTCCACCGGCTCTAACGTATTCCAGACCAGAGCCGG

CTGTCTGATCGGCGCAGAACACGTGAACAATAGCTACGAGTGCGACATCCCTATCGG

AGCCGGGATCTGCGCTAGCTACCAGACCCAGACAAACTCCAGAAGCAGAGCCGGAA

GCGTGGCCAGCCAGTCTATCATCGCCTACACCATGAGCCTGGGCGCCGAAAACAGCG

TTGCCTACAGCAACAATTCTATCGCCATCCCTACAAACTTCACCATCTCCGTGACCAC

CGAGATCCTGCCTGTCAGCATGACAAAGACCAGCGTAGACTGCACAATGTACATCTG

CGGAGATTCCACCGAGTGTAGTAACCTCCTGCTGCAATACGGATCTTTCTGTACTCAG

CTGAACAGAGCCCTGACCGGCATCGCCGTTGAACAGGACAAGAACACCCAGGAGGT

TTTCGCCCAGGTTAAGCAGATCTACAAAACCCCTCCTATCAAGGACTTCGGAGGCTT

TAACTTCTCCCAGATCCTGCCCGACCCCAGCAAGCCCAGCAAGCGGAGCCCCATCGA

GGACCTGCTGTTCAACAAGGTGACCCTGGCCGACGCCGGCTTCATCAAACAGTACGG

CGATTGCCTGGGAGACATCGCCGCTAGAGATCTAATTTGCGCCCAAAAGTTTAACGG

CCTGACAGTGCTGCCTCCACTGCTGACAGACGAGATGATCGCCCAGTACACATCTGC

-continued

CCTGCTGGCTGGTACCATCACATCTGGCTGGACCTTTGGCGCCGGCCCCGCCCTCCAG

ATCCCTTTCCCCATGCAGATGGCCTACCGGTTCAACGGCATCGGCGTGACCCAGAAC

GTGCTGTACGAAAACCAGAAACTGATCGCCAACCAGTTCAATAGCGCGATCGGCAA

AATCCAGGATAGCCTCAGCTCTACACCCAGCGCTCTTGGCAAGCTGCAAAACGTGGT

GAACCAGAATGCCCAGGCCCTTAACACCCTGGTGAAGCAGCTATCCTCTAATTTCGG

TGCCATCAGCAGCGTGCTGAATGATATCCTGAGCAGACTGGACCCCCCTGAGGCCGA

AGTGCAGATCGACAGACTGATCACCGGAAGACTGCAGAGCCTGCAAACCTACGTGA

CCCAGCAACTGATCCGGGCCGCAGAAATCCGGGCCTCCGCTAACCTGGCCGCTACCA

AGATGAGCGAGTGCGTGCTGGGTCAAAGCAAGCGCGTGGACTTCTGTGGAAAAGGC

TACCACCTGATGAGCTTCCCTCAGAGCGCTCCACACGGCGTGGTGTTCCTGCATGTG

ACTTACGTGCCTGCCCAGGAAAAGAACTTCACCACCGCCCCTGCCATTTGTCACGAC

GGCAAGGCCCACTTCCCCCGGGAAGGCGTGTTTGTGTCTAACGGAACACACTGGTTT

GTGACTCAAAGAAACTTCTACGAGCCACAGATCATCACCACAGATAACACCTTCGTC

AGCGGCAACTGCGACGTGGTGATCGGCATCGTGAACAATACTGTGTACGACCCCCTG

CAGCCAGAGCTCGATTCTTTCAAAGAGGAACTGGATAAGTACTTCAAGAACCACACA

TCCCCCGACGTCGACCTGGGCGATATCAGCGGCATTAACGCCAGCGTGGTGAACATC

CAGAAGGAAATCGATAGACTGAACGAGGTGGCAAAGAACCTGAATGAGTCCCTGAT

TGACCTGCAAGAGCTCGGGAAGTACGAGCAGTATATCAAGTGGCCTTGGTACATCTG

GCTGGGCTTCATCGCGGGCCTGATCGCCATCGTTATGGTGACGATCATGCTGTGCTGC

ATGACCAGTTGCTGTAGCTGCCTGAAGGGCTGCTGCAGCTGCGGCAGCTGTTGCAAG

TTCGACGAGGACGACAGCGAGCCTGTGCTGAAGGGCGTTAAGCTGCACTACACCTGA

GCTCGCTTTCTTGCTGTCCAATTTCTATTAAAGGTTCCTTTGTTCCCTAAGTCCAACTA

CTAAACTGGGGGATATTATGAAGGGCCTTGAGCATCTGGATTCTGCCTAATAAAAAA

CATTTATTTTCATTGCCAATAGGCCGAAATCGGCAAGCGCGATCGCAAAAAAAAAAA

AAAAAAAAAAAAAAAAAAAAAAAAAAAAAAAAAAAAAAAGAAAAAAAAAAAAAA

AAAAAAAAAAAAAAAAAAAAAAAAAAAAAAAAAAAAAAAAAAAAA

SEQ ID NO: 32, RNA sequence of an exemplified
5'UTR-deltaC S6P-3' UTR-polyA:
GGACAUUUGCUUCUGACACAACUGUGUUCACUAGCAACCUCAAACAGACACCGCC

ACCAUGUUCGUGUUCCUGGUGCUGCUGCCUCUGGUCAGCAGCCAGUGCGUGAACC

UGAGAACAAGAACACAGCUUCCUCCAGCCUACACAAACUCUUUUACACGGGGCGU

GUACUAUCCUGACAAGGUGUUCCGGUCCAGCGUGCUGCACUCAACCCAAGACCUG

UUCCUGCCCUUCUUCAGCAACGUCACCUGGUUCCACGCCAUCCACGUGUCUGGCAC

CAAUGGCACAAAGCGAUUCGAUAACCCCGUGCUGCCUUUCAACGACGGCGUGUAC

UUUGCCUCCAUCGAGAAGUCCAACAUCAUCCGGGGCUGGAUCUUCGGGACCACAC

UGGAUAGCAAGACCCAGUCUCUGCUGAUCGUAAACAACGCCACCAACGUGGUCAU

CAAGGUGUGCGAGUUCCAGUUCUGCAACGACCCUUUCCUCGAUGUGUACUACCAC

AAGAACAACAAGUCUUGGAUGGAAUCGGGCGUGUAUAGCAGCGCCAACAACUGCA

CCUUCGAAUACGUGAGCCAGCCUUUCCUGAUGGACCUGGAAGGCAAACAAGGCAA

UUUUAAGAACCUGAGAGAAUUCGUGUUCAAAAAUAUAGACGGCUAUUUCAAGAU

CUACAGCAAGCACACCCCUAUUAAUCUGGUGCGGGAUCUGCCUCAGGGCUUCAGC

GCCCUCGAACCUCUGGUGGACCUGCCAAUCGGCAUCAACAUUACAAGAUUCCAGA

-continued

CGCUGCUCGCUCUGCACAGAUCUUACCUGACCCCUGGCGACAGCAGCAGCGGCUG

GACCGCCGGCGCCGCCGCUUACUACGUGGGCUACCUGCAGCCUAGAACCUUUCUGC

UGAAGUACAACGAGAACGGCACCAUCACUGAUGCCGUGGAUUGCGCCCUGGACCC

UCUGUCCGAAACCAAAUGUACACUGAAGUCUUUUACCGUGGAAAAAGGAAUCUAC

CAGACUUCCAACUUCCGGGUGCAGCCGACCGAGAGCAUCGUGCGGUUCCCUAACA

UCACAAACCUGUGCCCCUUUGGCGAGGUGUUCAACGCCACAAGAUUUGCUAGCGU

GUACGCCUGGAAUAGAAAGAGAAUCAGCAACUGCGUGGCCGAUUACAGCGUGCUG

UACAAUAGCGCCUCUUUCAGCACCUUCAAAUGCUACGGCGUGAGCCCCACCAAGC

UGAACGAUCUGUGUUUUACAAACGUGUAUGCCGACUCAUUCGUAAUCAGGGGCGA

UGAGGUGAGACAGAUCGCUCCUGGACAGACAGGCAAAAUCGCGGACUACAACUAU

AAGCUGCCUGAUGACUUCACAGGAUGUGUGAUCGCAUGGAACUCCAAUAACCUCG

ACAGCAAGGUGGGCGGAAAUUACAAUUACCGCUACAGACUGUUUAGAAAGAGCAA

UCUGAAACCUUUCGAGAGAGACAUCAGCACAGAGAUCUACCAGGCCGGCAGCAAG

CCCUGUAACGGCGUCGAGGGCUUCAACUGCUACUUCCCCCUGCAGAGCUACGGCU

UCCAGCCUACCAACGGCGUGGGAUACCAGCCUUACAGAGUGGUGGUGCUGAGCUU

CGAGCUGCUGCAUGCUCCUGCUACAGUGUGUGGUCCUAAGAAGAGCACCAACCUG

GUUAAGAACAAGUGCGUGAAUUUUAACUUCAAUGGACUGACCGGAACCGGCGUGC

UGACCGAAAGCAACAAGAAAUUCCUGCCUUUUCAGCAGUUUGGCAGAGACAUCGC

CGACACCACCGACGCCGUGAGAGAUCCACAAACCCUGGAAAUCCUGGACAUCACA

CCUUGCUCAUUUGGAGGGGUGUCGGUGAUCACACCUGGCACCAACACCAGCAACC

AGGUGGCCGUGCUGUACCAGGGAGUGAAUUGUACCGAGGUCCCCGUGGCCAUUCA

CGCCGACCAGCUGACCCCUACCUGGCGGGUGUACUCCACCGGCUCUAACGUAUUCC

AGACCAGAGCCGGCUGUCUGAUCGGCGCAGAACACGUGAACAAUAGCUACGAGUG

CGACAUCCCUAUCGGAGCCGGGAUCUGCGCUAGCUACCAGACCCAGACAAACUCC

AGAAGCAGAGCCGGAAGCGUGGCCAGCCAGUCUAUCAUCGCCUACACCAUGAGCC

UGGGCGCCGAAAACAGCGUUGCCUACAGCAACAAUUCUAUCGCCAUCCCUACAAA

CUUCACCAUCUCCGUGACCACCGAGAUCCUGCCUGUCAGCAUGACAAAGACCAGC

GUAGACUGCACAAUGUACAUCUGCGGAGAUUCCACCGAGUGUAGUAACCUCCUGC

UGCAAUACGGAUCUUUCUGUACUCAGCUGAACAGAGCCCUGACCGGCAUCGCCGU

UGAACAGGACAAGAACACCCAGGAGGUUUUCGCCCAGGUUAAGCAGAUCUACAAA

ACCCCUCCUAUCAAGGACUUCGGAGGCUUUAACUUCUCCCAGAUCCUGCCCGACCC

CAGCAAGCCCAGCAAGCGGAGCCCCAUCGAGGACCUGCUGUUCAACAAGGUGACC

CUGGCCGACGCCGGCUUCAUCAAACAGUACGGCGAUUGCCUGGGAGACAUCGCCG

CUAGAGAUCUAAUUUGCGCCCAAAAGUUUAACGGCCUGACAGUGCUGCCUCCACU

GCUGACAGACGAGAUGAUCGCCCAGUACACAUCUGCCCUGCUGGCUGGUACCAUC

ACAUCUGGCUGGACCUUUGGCGCCGGCCCCGCCCUCCAGAUCCCUUUCCCCAUGCA

GAUGGCCUACCGGUUCAACGGCAUCGGCGUGACCCAGAACGUGCUGUACGAAAAC

CAGAAACUGAUCGCCAACCAGUUCAAUAGCGCGAUCGGCAAAAUCCAGGAUAGCC

UCAGCUCUACACCCAGCGCUCUUGGCAAGCUGCAAAACGUGGUGAACCAGAAUGC

CCAGGCCCUUAACACCCUGGUGAAGCAGCUAUCCUCUAAUUUCGGUGCCAUCAGC

-continued

AGCGUGCUGAAUGAUAUCCUGAGCAGACUGGACCCCCCUGAGGCCGAAGUGCAGA

UCGACAGACUGAUCACCGGAAGACUGCAGAGCCUGCAAACCUACGUGACCCAGCA

ACUGAUCCGGGCCGCAGAAAUCCGGGCCUCCGCUAACCUGGCCGCUACCAAGAUG

AGCGAGUGCGUGCUGGGUCAAAGCAAGCGCGUGGACUUCUGUGGAAAAGGCUACC

ACCUGAUGAGCUUCCCUCAGAGCGCUCCACACGGCGUGGUGUUCCUGCAUGUGAC

UUACGUGCCUGCCCAGGAAAAGAACUUCACCACCGCCCCUGCCAUUUGUCACGAC

GGCAAGGCCCACUUCCCCCGGGAAGGCGUGUUUGUGUCUAACGGAACACACUGGU

UUGUGACUCAAAGAAACUUCUACGAGCCACAGAUCAUCACCACAGAUAACACCUU

CGUCAGCGGCAACUGCGACGUGGUGAUCGGCAUCGUGAACAAUACUGUGUACGAC

CCCCUGCAGCCAGAGCUCGAUUCUUUCAAAGAGGAACUGGAUAAGUACUUCAAGA

ACCACACAUCCCCCGACGUCGACCUGGGCGAUAUCAGCGGCAUUAACGCCAGCGU

GGUGAACAUCCAGAAGGAAAUCGAUAGACUGAACGAGGUGGCAAAGAACCUGAAU

GAGUCCCUGAUUGACCUGCAAGAGCUCGGGAAGUACGAGCAGUAUAUCAAGUGGC

CUUGGUACAUCUGGCUGGGCUUCAUCGCGGGCCUGAUCGCCAUCGUUAUGGUGAC

GAUCAUGCUGUGCUGCAUGACCAGUUGCUGUAGCUGCCUGAAGGGCUGCUGCAGC

UGCGGCAGCUGUUGCAAGUUCGACGAGGACGACAGCGAGCCUGUGCUGAAGGGCG

UUAAGCUGCACUACACCUGAGCUCGCUUUCUUGCUGUCCAAUUUCUAUUAAAGGU

UCCUUUGUUCCCUAAGUCCAACUACUAAACUGGGGGAUAUUAUGAAGGGCCUUGA

GCAUCUGGAUUCUGCCUAAUAAAAAACAUUUAUUUUCAUUGCCAAUAGGCCGAAA

UCGGCAAGCGCGAUCGCAAAAAAAAAAAAAAAAAAAAAAAAAAAAAAAAAAAAAA

AAAAAAAAAAAAGAAAAAAAAAAAAAAAAAAAAAAAAAAAAAAAAAAAAAAAAAAA

AAAAAAAAAAAAAAAAAA

SEQ ID NO: 33, plasmid DNA sequence:
TCGCGCGTTTCGGTGATGACGGTGAAAACCTCTGACACATGCAGCTCCCGGAGACGG

TCACAGCTTGTCTGTAAGCGGATGCCGGGAGCAGACAAGCCCGTCAGGGCGCGTCA

GCGGGTGTTGGCGGGTGTCGGGGCTGGCTTAACTATGCGGCATCAGAGCAGATTGTA

CTGAGAGTGCACCATATGCGGTGTGAAATACCGCACAGATGCGTAAGGAGAAAATA

CCGCATCAGGCGCCATTCGCCATTCAGGCTGCGCAACTGTTGGGAAGGGCGATCGGT

GCGGGCCTCTTCGCTATTACGCCAGCTGGCGAAAGGGGGATGTGCTGCAAGGCGATT

AAGTTGGGTAACGCCAGGGTTTTCCCAGTCACGACGTTGTAAAACGACGGCCAGTGA

ATTCGAGCTCGGTACCTCGCGAATGCATCTAGATATCGGATCCCGGGCCCGTCGACT

GCAGAGGCCTGCATGCAAGCTTTAATACGACTCACTATAAGGACATTTGCTTCTGAC

ACAACTGTGTTCACTAGCAACCTCAAACAGACACCGCCACCATGTTCGTGTTCCTGG

TGCTGCTGCCTCTGGTCAGCAGCCAGTGCGTGAACCTGAGAACAAGAACACAGCTTC

CTCCAGCCTACACAAACTCTTTTACACGGGGCGTGTACTATCCTGACAAGGTGTTCCG

GTCCAGCGTGCTGCACTCAACCCAAGACCTGTTCCTGCCCTTCTTCAGCAACGTCACC

TGGTTCCACGCCATCCACGTGTCTGGCACCAATGGCACAAAGCGATTCGATAACCCC

GTGCTGCCTTTCAACGACGGCGTGTACTTTGCCTCCATCGAGAAGTCCAACATCATCC

GGGGCTGGATCTTCGGGACCACACTGGATAGCAAGACCCAGTCTCTGCTGATCGTAA

ACAACGCCACCAACGTGGTCATCAAGGTGTGCGAGTTCCAGTTCTGCAACGACCCTT

TCCTCGATGTGTACTACCACAAGAACAACAAGTCTTGGATGGAATCGGGCGTGTATA

-continued

GCAGCGCCAACAACTGCACCTTCGAATACGTGAGCCAGCCTTTCCTGATGGACCTGG

AAGGCAAACAAGGCAATTTTAAGAACCTGAGAGAATTCGTGTTCAAAAATATAGAC

GGCTATTTCAAGATCTACAGCAAGCACACCCCTATTAATCTGGTGCGGGATCTGCCT

CAGGGCTTCAGCGCCCTCGAACCTCTGGTGGACCTGCCAATCGGCATCAACATTACA

AGATTCCAGACGCTGCTCGCTCTGCACAGATCTTACCTGACCCCTGGCGACAGCAGC

AGCGGCTGGACCGCCGGCGCCGCCGCTTACTACGTGGGCTACCTGCAGCCTAGAACC

TTTCTGCTGAAGTACAACGAGAACGGCACCATCACTGATGCCGTGGATTGCGCCCTG

GACCCTCTGTCCGAAACCAAATGTACACTGAAGTCTTTTACCGTGGAAAAAGGAATC

TACCAGACTTCCAACTTCCGGGTGCAGCCGACCGAGAGCATCGTGCGGTTCCCTAAC

ATCACAAACCTGTGCCCCTTTGGCGAGGTGTTCAACGCCACAAGATTTGCTAGCGTG

TACGCCTGGAATAGAAAGAGAATCAGCAACTGCGTGGCCGATTACAGCGTGCTGTAC

AATAGCGCCTCTTTCAGCACCTTCAAATGCTACGGCGTGAGCCCCACCAAGCTGAAC

GATCTGTGTTTTACAAACGTGTATGCCGACTCATTCGTAATCAGGGGCGATGAGGTG

AGACAGATCGCTCCTGGACAGACAGGCAAAATCGCGGACTACAACTATAAGCTGCC

TGATGACTTCACAGGATGTGTGATCGCATGGAACTCCAATAACCTCGACAGCAAGGT

GGGCGGAAATTACAATTACCGCTACAGACTGTTTAGAAAGAGCAATCTGAAACCTTT

CGAGAGAGACATCAGCACAGAGATCTACCAGGCCGGCAGCAAGCCCTGTAACGGCG

TCGAGGGCTTCAACTGCTACTTCCCCCTGCAGAGCTACGGCTTCCAGCCTACCAACG

GCGTGGGATACCAGCCTTACAGAGTGGTGGTGCTGAGCTTCGAGCTGCTGCATGCTC

CTGCTACAGTGTGTGGTCCTAAGAAGAGCACCAACCTGGTTAAGAACAAGTGCGTGA

ATTTTAACTTCAATGGACTGACCGGAACCGGCGTGCTGACCGAAAGCAACAAGAAAT

TCCTGCCTTTTCAGCAGTTTGGCAGAGACATCGCCGACACCACCGACGCCGTGAGAG

ATCCACAAACCCTGGAAATCCTGGACATCACACCTTGCTCATTTGGAGGGGTGTCGG

TGATCACACCTGGCACCAACACCAGCAACCAGGTGGCCGTGCTGTACCAGGGAGTG

AATTGTACCGAGGTCCCCGTGGCCATTCACGCCGACCAGCTGACCCCTACCTGGCGG

GTGTACTCCACCGGCTCTAACGTATTCCAGACCAGAGCCGGCTGTCTGATCGGCGCA

GAACACGTGAACAATAGCTACGAGTGCGACATCCCTATCGGAGCCGGGATCTGCGCT

AGCTACCAGACCCAGACAAACTCCAGAAGCAGAGCCGGAAGCGTGGCCAGCCAGTC

TATCATCGCCTACACCATGAGCCTGGGCGCCGAAAACAGCGTTGCCTACAGCAACAA

TTCTATCGCCATCCCTACAAACTTCACCATCTCCGTGACCACCGAGATCCTGCCTGTC

AGCATGACAAAGACCAGCGTAGACTGCACAATGTACATCTGCGGAGATTCCACCGA

GTGTAGTAACCTCCTGCTGCAATACGGATCTTTCTGTACTCAGCTGAACAGAGCCCTG

ACCGGCATCGCCGTTGAACAGGACAAGAACACCCAGGAGGTTTTCGCCCAGGTTAA

GCAGATCTACAAAACCCCTCCTATCAAGGACTTCGGAGGCTTTAACTTCTCCCAGAT

CCTGCCCGACCCCAGCAAGCCCAGCAAGCGGAGCCCCATCGAGGACCTGCTGTTCAA

CAAGGTGACCCTGGCCGACGCCGGCTTCATCAAACAGTACGGCGATTGCCTGGGAGA

CATCGCCGCTAGAGATCTAATTTGCGCCCAAAAGTTTAACGGCCTGACAGTGCTGCC

TCCACTGCTGACAGACGAGATGATCGCCCAGTACACATCTGCCCTGCTGGCTGGTAC

CATCACATCTGGCTGGACCTTTGGCGCCGGCCCCGCCCTCCAGATCCCTTTCCCCATG

CAGATGGCCTACCGGTTCAACGGCATCGGCGTGACCCAGAACGTGCTGTACGAAAAC

CAGAAACTGATCGCCAACCAGTTCAATAGCGCGATCGGCAAAATCCAGGATAGCCTC

-continued

AGCTCTACACCCAGCGCTCTTGGCAAGCTGCAAAACGTGGTGAACCAGAATGCCCAG

GCCCTTAACACCCTGGTGAAGCAGCTATCCTCTAATTTCGGTGCCATCAGCAGCGTG

CTGAATGATATCCTGAGCAGACTGGACCCCCCTGAGGCCGAAGTGCAGATCGACAG

ACTGATCACCGGAAGACTGCAGAGCCTGCAAACCTACGTGACCCAGCAACTGATCCG

GGCCGCAGAAATCCGGGCCTCCGCTAACCTGGCCGCTACCAAGATGAGCGAGTGCGT

GCTGGGTCAAAGCAAGCGCGTGGACTTCTGTGGAAAAGGCTACCACCTGATGAGCTT

CCCTCAGAGCGCTCCACACGGCGTGGTGTTCCTGCATGTGACTTACGTGCCTGCCCA

GGAAAAGAACTTCACCACCGCCCCTGCCATTTGTCACGACGGCAAGGCCCACTTCCC

CCGGGAAGGCGTGTTTGTGTCTAACGGAACACACTGGTTTGTGACTCAAAGAAACTT

CTACGAGCCACAGATCATCACCACAGATAACACCTTCGTCAGCGGCAACTGCGACGT

GGTGATCGGCATCGTGAACAATACTGTGTACGACCCCCTGCAGCCAGAGCTCGATTC

TTTCAAAGAGGAACTGGATAAGTACTTCAAGAACCACACATCCCCCGACGTCGACCT

GGGCGATATCAGCGGCATTAACGCCAGCGTGGTGAACATCCAGAAGGAAATCGATA

GACTGAACGAGGTGGCAAAGAACCTGAATGAGTCCCTGATTGACCTGCAAGAGCTC

GGGAAGTACGAGCAGTATATCAAGTGGCCTTGGTACATCTGGCTGGGCTTCATCGCG

GGCCTGATCGCCATCGTTATGGTGACGATCATGCTGTGCTGCATGACCAGTTGCTGTA

GCTGCCTGAAGGGCTGCTGCAGCTGCGGCAGCTGTTGCAAGTTCGACGAGGACGACA

GCGAGCCTGTGCTGAAGGGCGTTAAGCTGCACTACACCTGAGCTCGCTTTCTTGCTGT

CCAATTTCTATTAAAGGTTCCTTTGTTCCCTAAGTCCAACTACTAAACTGGGGGATAT

TATGAAGGGCCTTGAGCATCTGGATTCTGCCTAATAAAAAACATTTATTTTCATTGCC

AATAGGCCGAAATCGGCAAGCGCGATCGCAAAAAAAAAAAAAAAAAAAAAAAAAA

AAAAAAAAAAAAAAAAAAAAAAAAAGAAAAAAAAAAAAAAAAAAAAAAAAAAAAA

AAAAAAAAAAAAAAAAAAAAAAAAAAAAAAAGAATTCCTCGAGATTTAAATTCGC

GAGTACTATGCATATGGGCCCAATATTAATTAAGCGCTAGCACGCGTTTAAACAGGC

CTCGAGGCGCGCCCGCTTCCTCGCTCACTGACTCGCTGCGCTCGGTCGTTCGGCTGCG

GCGAGCGGTATCAGCTCACTCAAAGGCGGTAATACGGTTATCCACAGAATCAGGGG

ATAACGCAGGAAAGAACATGTGAGCAAAAGGCCAGCAAAAGGCCAGGAACCGTAA

AAAGGCCGCGTTGCTGGCGTTTTTCCATAGGCTCCGCCCCCCTGACGAGCATCACAA

AAATCGACGCTCAAGTCAGAGGTGGCGAAACCCGACAGGACTATAAAGATACCAGG

CGTTTCCCCCTGGAAGCTCCCTCGTGCGCTCTCCTGTTCCGACCCTGCCGCTTACCGG

ATACCTGTCCGCCTTTCTCCCTTCGGGAAGCGTGGCGCTTTCTCATAGCTCACGCTGT

AGGTATCTCAGTTCGGTGTAGGTCGTTCGCTCCAAGCTGGGCTGTGTGCACGAACCC

CCCGTTCAGCCCGACCGCTGCGCCTTATCCGGTAACTATCGTCTTGAGTCCAACCCGG

TAAGACACGACTTATCGCCACTGGCAGCAGCCACTGGTAACAGGATTAGCAGAGCG

AGGTATGTAGGCGGTGCTACAGAGTTCTTGAAGTGGTGGCCTAACTACGGCTACACT

AGAAGAACAGTATTTGGTATCTGCGCTCTGCTGAAGCCAGTTACCTTCGGAAAAAGA

GTTGGTAGCTCTTGATCCGGCAAACAAACCACCGCTGGTAGCGGTGGTTTTTTTGTTT

GCAAGCAGCAGATTACGCGCAGAAAAAAAGGATCTCAAGAAGATCCTTTGATCTTTT

CTACGGGGTCTGACGCTCAGTGGAACGAAAACTCACGTTAAGGGATTTTGGTCATGA

GATTATCAAAAAGGATCTTCACCTAGATCCTTTTAAATTAAAAATGAAGTTTTAAATC

-continued

AAGCCCAATCTGAATAATGTTACAACCAATTAACCAATTCTGATTAGAAAAACTCAT

CGAGCATCAAATGAAACTGCAATTTATTCATATCAGGATTATCAATACCATATTTTTG

AAAAAGCCGTTTCTGTAATGAAGGAGAAAACTCACCGAGGCAGTTCCATAGGATGG

CAAGATCCTGGTATCGGTCTGCGATTCCGACTCGTCCAACATCAATACAACCTATTA

ATTTCCCCTCGTCAAAAATAAGGTTATCAAGTGAGAAATCACCATGAGTGACGACTG

AATCCGGTGAGAATGGCAAAAGTTTATGCATTTCTTTCCAGACTTGTTCAACAGGCC

AGCCATTACGCTCGTCATCAAAATCACTCGCATCAACCAAACCGTTATTCATTCGTGA

TTGCGCCTGAGCGAGACGAAATACGCGATCGCTGTTAAAAGGACAATTACAAACAG

GAATCGAATGCAACCGGCGCAGGAACACTGCCAGCGCATCAACAATATTTTCACCTG

AATCAGGATATTCTTCTAATACCTGGAATGCTGTTTTTCCGGGGATCGCAGTGGTGAG

TAACCATGCATCATCAGGAGTACGGATAAAATGCTTGATGGTCGGAAGAGGCATAA

ATTCCGTCAGCCAGTTTAGTCTGACCATCTCATCTGTAACATCATTGGCAACGCTACC

TTTGCCATGTTTCAGAAACAACTCTGGCGCATCGGGCTTCCCATACAAGCGATAGAT

TGTCGCACCTGATTGCCCGACATTATCGCGAGCCCATTTATACCCATATAAATCAGCA

TCCATGTTGGAATTTAATCGCGGCCTCGACGTTTCCCGTTGAATATGGCTCATAACAC

CCCTTGTATTACTGTTTATGTAAGCAGACAGTTTTATTGTTCATGATGATATATTTTTA

TCTTGTGCAATGTAACATCAGAGATTTTGAGACACGGGCCAGAGCTGCA

SEQ ID NO: 34, HKP side chain:
KHKHKHKHK

SEQ ID NO: 35, HKP side chain:
HKHKHKHKHK

SEQ ID NO: 36, HKP side chain:
KHKHKHKHKH

SEQ ID NO: 37, HKP side chain:
HKHKHKHKHKH

SEQ ID NO: 38, HKP side chain:
KHKHHKHHKHHKHHKHHKHK

SEQ ID NO: 39, HKP side chain:
KHHHKHHHKHHHKHHHK

SEQ ID NO: 40, HKP side chain:
KHHHKHHHKHHHHKHHHK

SEQ ID NO: 41, HKP side chain:
KHHHKHHHKHHHHKHHHK,
wherein the $1^{st}$, $5^{th}$, $9^{th}$, $14^{th}$ and $18^{th}$ amino
acids are D-amino acids.

SEQ ID NO: 42, HKP side chain:
HKHHHKHHHKHHHHKHHHK

SEQ ID NO: 43, HKP side chain:
HHKHHHKHHHKHHHHKHHHK

SEQ ID NO: 44, HKP side chain:
KHHHHKHHHHKHHHHKHHHHK

SEQ ID NO: 45, HKP side chain:
KHHHKHHHKHHHKHHHHK

SEQ ID NO: 46, HKP side chain:
KHHHKHHHHKHHHKHHHK

SEQ ID NO: 47, HKP side chain:
KHHHKHHHHKHHHKHHHHK

SEQ ID NO: 48, furin-like cleavage site:
RRAR

-continued

SEQ ID NO: 49:
-HHHK-

RX(K/R)R

SEQ ID NO: 51:
TAATACGACTCACTATAA

SEQ ID NO: 52:
AGGACAUUUGCUUCUGACACAACUGUGUUCACUAGCAACCUCAAACAGACACC

GCCACCAUGUUCGUGUUCCUGGUGCUGCUGCCUCUGGUCAGCAGCCAGUGCGU

GAACCUGAGAACAAGAACACAGCUUCCUCCAGCCUACACAAACUCUUUUACAC

GGGGCGUGUACUAUCCUGACAAGGUGUUCCGGUCCAGCGUGCUGCACUCAACC

CAAGACCUGUUCCUGCCCUUCUUCAGCAACGUCACCUGGUUCCACGCCAUCCA

CGUGUCUGGCACCAAUGGCACAAAGCGAUUCGAUAACCCCGUGCUGCCUUUCA

ACGACGGCGUGUACUUUGCCUCCAUCGAGAAGUCCAACAUCAUCCGGGGCUGG

AUCUUCGGGACCACACUGGAUAGCAAGACCCAGUCUCUGCUGAUCGUAAACAA

CGCCACCAACGUGGUCAUCAAGGUGUGCGAGUUCCAGUUCUGCAACGACCCUU

UCCUCGAUGUGUACUACCACAAGAACAACAAGUCUUGGAUGGAAUCGGGCGU

GUAUAGCAGCGCCAACAACUGCACCUUCGAAUACGUGAGCCAGCCUUUCCUGA

UGGACCUGGAAGGCAAACAAGGCAAUUUUAAGAACCUGAGAGAAUUCGUGUU

CAAAAAUAUAGACGGCUAUUUCAAGAUCUACAGCAAGCACACCCCUAUUAAUC

UGGUGCGGGAUCUGCCUCAGGGCUUCAGCGCCCUCGAACCUCUGGUGGACCUG

CCAAUCGGCAUCAACAUUACAAGAUUCCAGACGCUGCUCGCUCUGCACAGAUC

UUACCUGACCCCUGGCGACAGCAGCAGCGGCUGGACCGCCGGCGCCGCCGCUU

ACUACGUGGGCUACCUGCAGCCUAGAACCUUUCUGCUGAAGUACAACGAGAAC

GGCACCAUCACUGAUGCCGUGGAUUGCGCCCUGGACCCUCUGUCCGAAACCAA

AUGUACACUGAAGUCUUUUACCGUGGAAAAAGGAAUCUACCAGACUUCCAAC

UUCCGGGUGCAGCCGACCGAGAGCAUCGUGCGGUUCCCUAACAUCACAAACCU

GUGCCCCUUUGGCGAGGUGUUCAACGCCACAAGAUUUGCUAGCGUGUACGCCU

GGAAUAGAAAGAGAAUCAGCAACUGCGUGGCCGAUUACAGCGUGCUGUACAA

UAGCGCCUCUUUCAGCACCUUCAAAUGCUACGGCGUGAGCCCCACCAAGCUGA

ACGAUCUGUGUUUUACAAACGUGUAUGCCGACUCAUUCGUAAUCAGGGGCGA

UGAGGUGAGACAGAUCGCUCCUGGACAGACAGGCAAAAUCGCGGACUACAACU

AUAAGCUGCCUGAUGACUUCACAGGAUGUGUGAUCGCAUGGAACUCCAAUAA

CCUCGACAGCAAGGUGGGCGGAAAUUACAAUUACCGCUACAGACUGUUUAGA

AAGAGCAAUCUGAAACCUUUCGAGAGAGACAUCAGCACAGAGAUCUACCAGGC

CGGCAGCAAGCCCUGUAACGGCGUCGAGGGCUUCAACUGCUACUUCCCCCUGC

AGAGCUACGGCUUCCAGCCUACCAACGGCGUGGGAUACCAGCCUUACAGAGUG

GUGGUGCUGAGCUUCGAGCUGCUGCAUGCUCCUGCUACAGUGUGUGGUCCUAA

GAAGAGCACCAACCUGGUUAAGAACAAGUGCGUGAAUUUUAACUUCAAUGGA

CUGACCGGAACCGGCGUGCUGACCGAAAGCAACAAGAAAUUCCUGCCUUUUCA

GCAGUUUGGCAGAGACAUCGCCGACACCACCGACGCCGUGAGAGAUCCACAAA

CCCUGGAAAUCCUGGACAUCACACCUUGCUCAUUUGGAGGGGUGUCGGUGAUC

ACACCUGGCACCAACACCAGCAACCAGGUGGCCGUGCUGUACCAGGGAGUGAA

-continued

UUGUACCGAGGUCCCCGUGGCCAUUCACGCCGACCAGCUGACCCCUACCUGGC
GGGUGUACUCCACCGGCUCUAACGUAUUCCAGACCAGAGCAGGCUGUCUGAUC
GGCGCAGAACACGUGAACAAUAGCUACGAGUGCGACAUCCCUAUCGGAGCCGG
GAUCUGCGCUAGCUACCAGACCCAGACAAACUCCAGAAGCAGAGCCGGAAGCG
UGGCCAGCCAGUCUAUCAUCGCCUACACCAUGAGCCUGGGCGCCGAAAACAGC
GUUGCCUACAGCAACAAUUCUAUCGCCAUCCCUACAAACUUCACCAUCUCCGU
GACCACCGAGAUCCUGCCUGUCAGCAUGACAAAGACCAGCGUAGACUGCACAA
UGUACAUCUGCGGAGAUUCCACCGAGUGUAGUAACCUCCUGCUGCAAUACGGA
UCUUUCUGUACUCAGCUGAACAGAGCCCUGACCGGCAUCGCCGUUGAACAGGA
CAAGAACACCCAGGAGGUUUUCGCCCAGGUUAAGCAGAUCUACAAAACCCCUC
CUAUCAAGGACUUCGGAGGCUUUAACUUCUCCCAGAUCCUGCCCGACCCCAGC
AAGCCCAGCAAGCGGAGCCCCAUCGAGGACCUGCUGUUCAACAAGGUGACCCU
GGCCGACGCCGGCUUCAUCAAACAGUACGGCGAUUGCCUGGGAGACAUCGCCG
CUAGAGAUCUAAUUUGCGCCCAAAAGUUUAACGGCCUGACAGUGCUGCCUCCA
CUGCUGACAGACGAGAUGAUCGCCCAGUACACAUCUGCCCUGCUGGCUGGUAC
CAUCACAUCUGGCUGGACCUUUGGCGCCGGCCCCGCCCUCCAGAUCCCUUUCC
CCAUGCAGAUGGCCUACCGGUUCAACGGCAUCGGCGUGACCCAGAACGUGCUG
UACGAAAACCAGAAACUGAUCGCCAACCAGUUCAAUAGCGCGAUCGGCAAAAU
CCAGGAUAGCCUCAGCUCUACACCCAGCGCUCUUGGCAAGCUGCAAAACGUGG
UGAACCAGAAUGCCCAGGCCCUUAACACCCUGGUGAAGCAGCUAUCCUCUAAU
UUCGGUGCCAUCAGCAGCGUGCUGAAUGAUAUCCUGAGCAGACUGGACCCCCC
UGAGGCCGAAGUGCAGAUCGACAGACUGAUCACCGGAAGACUGCAGAGCCUGC
AAACCUACGUGACCCAGCAACUGAUCCGGGCCGCAGAAAUCCGGGCCUCCGCU
AACCUGGCCGCUACCAAGAUGAGCGAGUGCGUGCUGGGUCAAAGCAAGCGCGU
GGACUUCUGUGGAAAAGGCUACCACCUGAUGAGCUUCCCUCAGAGCGCUCCAC
ACGGCGUGGUGUUCCUGCAUGUGACUUACGUGCCUGCCCAGGAAAAGAACUUC
ACCACCGCCCCUGCCAUUUGUCACGACGGCAAGGCCCACUUCCCCCGGGAAGG
CGUGUUUGUGUCUAACGGAACACACUGGUUUGUGACUCAAAGAAACUUCUAC
GAGCCACAGAUCAUCACCACAGAUAACACCUUCGUCAGCGGCAACUGCGACGU
GGUGAUCGGCAUCGUGAACAAUACUGUGUACGACCCCCUGCAGCCAGAGCUCG
AUUCUUUCAAAGAGGAACUGGAUAAGUACUUCAAGAACCACACAUCCCCCGAC
GUCGACCUGGGCGAUAUCAGCGGCAUUAACGCCAGCGUGGUGAACAUCCAGAA
GGAAAUCGAUAGACUGAACGAGGUGGCAAAGAACCUGAAUGAGUCCCUGAUU
GACCUGCAAGAGCUCGGGAAGUACGAGCAGUAUAUCAAGUGGCCUUGGUACA
UCUGGCUGGGCUUCAUCGCGGGCCUGAUCGCCAUCGUUAUGGUGACGAUCAUG
CUGUGCUGCAUGACCAGUUGCUGUAGCUGCCUGAAGGGCUGCUGCAGCUGCGG
CAGCUGUUGCAAGUUCGACGAGGACGACAGCGAGCCUGUGCUGAAGGGCGUU
AAGCUGCACUACACCUGAGCUCGCUUUCUUGCUGUCCAAUUUCUAUUAAAGGU
UCCUUUGUUCCCUAAGUCCAACUACUAAACUGGGGGAUAUUAUGAAGGGCCU
UGAGCAUCUGGAUUCUGCCUAAUAAAAAACAUUUAUUUUCAUUGCCAAUAGG
CCGAAAUCGGCAAGCGCGAUCGCAAAAAAAAAAAAAAAAAAAAAAAAAAAAA

-continued

AAAAAAAAAAAAAAAAGAAAAAAAAAAAAAAAAAAAAAAAAAAAAAAAAA

AAAAAAAAAAAAAAAAAAAAAAAGAAUUCC

SEQ ID NO: 53:
ttcctcgaggcgcgcccgcttcctcgctcactgactcgctgcgctcggtcgttcggctgcggc gagcggtatcagctcactcaaaggcggtaatacggttatccacagaatcaggggataacgcag gaaagaacatgtgagcaaaaggccagcaaaaggccaggaaccgtaaaaaggccgcgttgctgg cgtttttccataggctccgcccccctgacgagcatcacaaaaatcgacgctcaagtcagaggt ggcgaaacccgacaggactataaagataccaggcgtttccccctggaagctccctcgtgcgct ctcctgttccgaccctgccgcttaccggatacctgtccgcctttctcccttcgggaagcgtgg cgctttctcatagctcacgctgtaggtatctcagttcggtgtaggtcgttcgctccaagctgg gctgtgtgcacgaaccccccgttcagcccgaccgctgcgccttatccggtaactatcgtcttg agtccaacccggtaagacacgacttatcgccactggcagcagccactggtaacaggattagca gagcgaggtatgtaggcggtgctacagagttcttgaagtggtggcctaactacggctacacta gaagaacagtatttggtatctgcgctctgctgaagccagttaccttcggaaaaagagttggta gctcttgatccggcaaacaaaccaccgctggtagcggtggtttttttgtttgcaagcagcaga ttacgcgcagaaaaaaaggatctcaagaagatcctttgatcttttctacggggtctgacgctc agtggaacgaaaactcacgttaagggattttggtcattagattatcaaaaaggatcttcacct agatccttttaaattaaaaatgaagttttaaatcaatctaaagtatatatgagtaaacttggt ctgacagttagaaaaactcatcgagcatcaaatgaaactgcaatttattcatatcaggattat caataccatatttttgaaaaagccgtttctgtaatgaaggagaaaactcaccgaggcagttcc ataggatggcaagatcctggtatcggtctgcgattccgactcgtccaacatcaatacaaccta ttaatttcccctcgtcaaaaataaggttatcaagtgagaaatcaccatgagtgacgactgaat ccggtgagaatggcaaaagtttatgcatttctttccagacttgttcaacaggccagccattac gctcgtcatcaaaatcactcgcatcaaccaaaccgttattcattcgtgattgcgcctgagcga gacgaaatacgcgatcgctgttaaaaggacaattacaaacaggaatcgaatgcaaccggcgca ggaacactgccagcgcatcaacaatattttcacctgaatcatgatattcttctaatacctgga atgctgttttcccagggatcgcagtggtgagtaaccatgcatcatcaggagtacggataaaat gcttgatggtcggaagaggcataaattccgtcagccagtttagtctgaccatctcatctgtaa catcattggcaacgctacctttgccatgtttcagaaacaactctggcgcatcgggcttcccat acaatcgatagattgtcgcacctgattgccctacattatcgcgagcccatttatacccatata aatcagcatccatgttggaatttaatcgcggcctagagcaagacgtttcccgttgaatatggc tcatactcttcctttttcaatattattgaagcatttatcagggttattgtctcatgagcggat acatatttgaatgtatttagaaaaataaacaaataggggttccgcgcacatttccccgaaaag tgccacctgacgtctaagaaaccattattatcatgacattaacctataaaaataggcgtatca cgaggccctttcgtctcgcgcgtttcggtgatgacggtgaaaacctctgacacatgcagctcc cggagacggtcacagcttgtctgtaagcggatgccgggagcagacaagcccgtcagggcgcgt cagcgggtgttggcgggtgtcggggctggcttaactatgcggcatcagagcagattgtactga gagtgcaccatatgcggtgtgaaataccgcacagatgcgtaaggagaaaataccgcatcaggc gccattcgccattcaggctgcgcaactgttgggaagggcgatcggtgcgggcctcttcgctat tacgccagctggcgaaagggggatgtgctgcaaggcgattaagttgggtaacgccagggtttt cccagtcacgacgttgtaaaacgacggccagtgaattcgagctcggtacctcgcgaatgcatc -continued tagatatcggatcccgggcccgtcgactgcagaggcctgcatgcaagctttaatacgactcac tataaggacatttgcttctgacacaactgtgttcactagcaacctcaaacagacaccgccacc atgttcgtgttcctggtgctgctgcctctggtcagcagccagtgcgtgaacctgagaacaaga acacagcttcctccagcctacacaaactcttttacacggggcgtgtactatcctgacaaggtg ttccggtccagcgtgctgcactcaacccaagacctgttcctgcccttcttcagcaacgtcacc tggttccacgccatccacgtgtctggcaccaatggcacaaagcgattcgataaccccgtgctg cctttcaacgacggcgtgtactttgcctccatcgagaagtccaacatcatccggggctggatc ttcgggaccacactggatagcaagacccagtctctgctgatcgtaaacaacgccaccaacgtg gtcatcaaggtgtgcgagttccagttctgcaacgaccctttcctcgatgtgtactaccacaag aacaacaagtcttggatggaatcgggcgtgtatagcagcgccaacaactgcaccttcgaatac gtgagccagcctttcctgatggacctggaaggcaaacaaggcaattttaagaacctgagagaa ttcgtgttcaaaaatatagacggctatttcaagatctacagcaagcacacccctattaatctg gtgcgggatctgcctcagggcttcagcgccctcgaacctctggtggacctgccaatcggcatc aacattacaagattccagacgctgctcgctctgcacagatcttacctgacccctggcgacagc agcagcggctggaccgccggcgccgccgcttactacgtgggctacctgcagcctagaaccttt ctgctgaagtacaacgagaacggcaccatcactgatgccgtggattgcgccctggaccctctg tccgaaaccaaatgtacactgaagtcttttaccgtggaaaaaggaatctaccagacttccaac ttccgggtgcagccgaccgagagcatcgtgcggttccctaacatcacaaacctgtgccccttt ggcgaggtgttcaacgccacaagatttgctagcgtgtacgcctggaatagaaagagaatcagc aactgcgtggccgattacagcgtgctgtacaatagcgcctctttcagcaccttcaaatgctac ggcgtgagccccaccaagctgaacgatctgtgttttacaaacgtgtatgccgactcattcgta atcaggggcgatgaggtgagacagatcgctcctggacagacaggcaaaatcgcggactacaac tataagctgcctgatgacttcacaggatgtgtgatcgcatggaactccaataacctcgacagc aaggtgggcggaaattacaattaccgctacagactgtttagaaagagcaatctgaaacctttc gagagagacatcagcacagagatctaccaggccggcagcaagccctgtaacggcgtcgagggc ttcaactgctacttcccccctgcagagctacggcttccagcctaccaacggcgtgggataccag ccttacagagtggtggtgctgagcttcgagctgctgcatgctcctgctacagtgtgtggtcct aagaagagcaccaacctggttaagaacaagtgcgtgaattttaacttcaatggactgaccgga accggcgtgctgaccgaaagcaacaagaaattcctgccttttcagcagtttggcagagacatc gccgacaccaccgacgccgtgagagatccacaaaccctggaaatcctggacatcacaccttgc tcatttggaggggtgtcggtgatcacacctggcaccaacaccagcaaccaggtggccgtgctg taccagggagtgaattgtaccgaggtccccgtggccattcacgccgaccagctgacccctacc tggcgggtgtactccaccggctctaacgtattccagaccagagcaggctgtctgatcggcgca gaacacgtgaacaatagctacgagtgcgacatccctatcggagccgggatctgcgctagctac cagacccagacaaactccagaagcagagccggaagcgtggccagccagtctatcatcgcctac accatgagcctgggcgccgaaaacagcgttgcctacagcaacaattctatcgccatccctaca aacttcaccatctccgtgaccaccgagatcctgcctgtcagcatgacaaagaccagcgtagac tgcacaatgtacatctgcggagattccaccgagtgtagtaacctcctgctgcaatacggatct ttctgtactcagctgaacagagccctgaccggcatcgccgttgaacaggacaagaacacccag gaggttttcgcccaggttaagcagatctacaaaacccctcctatcaaggacttcggaggcttt -continued aacttctcccagatcctgcccgaccccagcaagcccagcaagcggagccccatcgaggacctg ctgttcaacaaggtgaccctggccgacgccggcttcatcaaacagtacggcgattgcctggga gacatcgccgctagagatctaatttgcgcccaaaagtttaacggcctgacagtgctgcctcca ctgctgacagacgagatgatcgcccagtacacatctgccctgctggctggtaccatcacatct ggctggacctttggcgccggccccgccctccagatccctttccccatgcagatggcctaccgg ttcaacggcatcggcgtgacccagaacgtgctgtacgaaaaccagaaactgatcgccaaccag ttcaatagcgcgatcggcaaaatccaggatagcctcagctctacacccagcgctcttggcaag ctgcaaaacgtggtgaaccagaatgcccaggcccttaacaccctggtgaagcagctatcctct aatttcggtgccatcagcagcgtgctgaatgatatcctgagcagactggacccccctgaggcc gaagtgcagatcgacagactgatcaccggaagactgcagagcctgcaaacctacgtgacccag caactgatccgggccgcagaaatccgggcctccgctaacctggccgctaccaagatgagcgag tgcgtgctgggtcaaagcaagcgcgtggacttctgtggaaaaggctaccacctgatgagcttc cctcagagcgctccacacggcgtggtgttcctgcatgtgacttacgtgcctgcccaggaaaag aacttcaccaccgcccctgccatttgtcacgacggcaaggcccacttcccccgggaaggcgtg tttgtgtctaacggaacacactggtttgtgactcaaagaaacttctacgagccacagatcatc accacagataacaccttcgtcagcggcaactgcgacgtggtgatcggcatcgtgaacaatact gtgtacgacccccctgcagccagagctcgattctttcaaagaggaactggataagtacttcaag aaccacacatcccccgacgtcgacctgggcgatatcagcggcattaacgccagcgtggtgaac atccagaaggaaatcgatagactgaacgaggtggcaaagaacctgaatgagtccctgattgac ctgcaagagctcgggaagtacgagcagtatatcaagtggccttggtacatctggctgggcttc atcgcgggcctgatcgccatcgttatggtgacgatcatgctgtgctgcatgaccagttgctgt agctgcctgaagggctgctgcagctgcggcagctgttgcaagttcgacgaggacgacagcgag cctgtgctgaagggcgttaagctgcactacacctgagctcgctttcttgctgtccaatttcta ttaaaggttcctttgttccctaagtccaactactaaactgggggatattatgaagggccttga gcatctggattctgcctaataaaaaacatttattttcattgccaataggccgaaatcggcaag cgcgatcgcaaaaaaaaaaaaaaaaaaaaaaaaaaaaaaaaaaaaaaagaaaaaaaaaaa aaaaaaaaaaaaaaaaaaaaaaaaaaaaaaaaaaaaaaaaaaaaa SEQ ID NO: 54:
Atgtttgtttttcttgttttattgccactagtctctagtcagtgtgttaattttacaaacaga actcaattaccctctgcatacactaattctttcacacgtggtgtttattaccctgacaaagtt ttcagatcctcagttttacattcaactcaggacttgttcttacctttcttttccaatgttact tggttccatgctatacatgtctctgggaccaatggtactaagaggtttgataaccctgtccta ccatttaatgatggtgtttattttgcttccactgagaagtctaacataataagaggctggatt tttggtactactttagattcgaagacccagtccctacttattgttaataacgctactaatgtt gttattaaagtctgtgaatttcaattttgtaattatccatttttgggtgtttattaccacaaa aacaacaaaagttggatggaaagtgagttcagagtttattctagtgcgaataattgcactttt gaatatgtctctcagccttttcttatggaccttgaaggaaaacagggtaatttcaaaaatctt agtgaatttgtgtttaagaatattgatggttattttaaaatatattctaagcacacgcctatt aatttagtgcgtgatctccctcagggtttttcggctttagaaccattggtagatttgccaata ggtattaacatcactaggtttcaaactttacttgctttacatagaagttatttgactcctggt gattcttcttcaggttggacagctggtgctgcagcttattatgtgggttatcttcaacctagg -continued acttttctattaaaatataatgaaaatggaaccattacagatgctgtagactgtgcacttgac cctctctcagaaacaaagtgtacgttgaaatccttcactgtagaaaaaggaatctatcaaact tctaactttagagtccaaccaacagaatctattgttagatttcctaatattacaaacttgtgc ccttttggtgaagtttttaacgccaccagatttgcatctgtttatgcttggaacaggaagaga atcagcaactgtgttgctgattattctgtcctatataattccgcatcattttccacttttaag tgttatggagtgtctcctactaaattaaatgatctctgctttactaatgtctatgcagattca tttgtaattagaggtgatgaagtcagacaaatcgctccagggcaaactggaaacattgctgat tataattataaattaccagatgattttacaggctgcgttatagcttggaattctaacaatctt gattctaaggttggtggtaattataattacctgtatagattgtttaggaagtctaatctcaaa ccttttgagagagatatttcaactgaaatctatcaggccggtagcacaccttgtaatggtgtt aaaggttttaattgttactttcctttacaatcatatggtttccaacccacttatggtgttggt taccaaccatacagagtagtagtactttcttttgaacttctacatgcaccagcaactgtttgt ggacctaaaaagtctactaatttggttaaaaacaaatgtgtcaatttcaacttcaatggttta acaggcacaggtgttcttactgagtctaacaaaaagtttctgcctttccaacaatttggcaga gacattgctgacactactgatgctgtccgtgatccacagacacttgagattcttgacattaca ccatgttcttttggtggtgtcagtgttataacaccaggaacaaatacttctaaccaggttgct gttctttatcagggtgttaactgcacagaagtccctgttgctattcatgcagatcaacttact cctacttggcgtgtttattctacaggttctaatgtttttcaaacacgtgcaggctgtttaata ggggctgaacatgtcaacaactcatatgagtgtgacatacccattggtgcaggtatatgcgct agttatcagactcagactaattctccttcgcgggcaggtagtgtagctagtcaatccatcatt gcctacactatgtcacttggtgcagaaaattcagttgcttactctaataactctattgccata cccacaaattttactattagtgttaccacagaaattctaccagtgtctatgaccaagacatca gtagattgtacaatgtacatttgtggtgattcaactgaatgcagcaatcttttgttgcaatat ggcagttttgtacacaattaaaccgtgctttaactggaatagctgttgaacaagacaaaaac acccaagaagtttttgcacaagtcaaacaaatttacaaaacaccaccaattaaagattttggt ggttttaatttttcacaaatattaccagatccatcaaaaccaagcaagaggtcacctattgaa gatctacttttcaacaaagtgacacttgcagatgctggcttcatcaaacaatatggtgattgc cttggtgatattgctgctagagacctcatttgtgcacaaaagtttaacggccttactgttttg ccacctttgctcacagatgaaatgattgctcaatacacttctgcactgttagcgggtacaatc acttctggttggacctttggtgcaggtcctgcattacaaataccatttcctatgcaaatggct tataggtttaatggtattggagttacacagaatgttctctatgagaaccaaaaattgattgcc aaccaatttaatagtgctattggcaaaattcaagactcactttcttccacaccaagtgcactt ggaaaacttcaagatgtggtcaaccaaaatgcacaagctttaaacacgcttgttaaacaactt agctccaattttggtgcaatttcaagtgttttaaatgatatcctttcacgtcttgacccacct gaggctgaagtgcaaattgataggttgatcacaggcagacttcaaagtttgcagacatatgtg actcaacaattaattagagctgcagaaatcagagcttctgctaatcttgctgctactaaaatg tcagagtgtgtacttggacaatcaaaaagagttgattttgtggaaagggctatcatcttatg tccttccctcagtcagcacctcatggtgtagtcttcttgcatgtgacttatgtccctgcacaa gaaaagaacttcacaactgctcctgccatttgtcatgatggaaaagcacactttcctcgtgaa ggtgtctttgtttcaaatggcacacactggtttgtaacacaaaggaattttttatgaaccacaa atcattactacagacaacacatttgtgtctggtaactgtgatgttgtaataggaattgtcaac -continued aacacagtttatgatcctttgcaacctgaattagactcattcaaggaggagttagataaatat tttaagaatcatacatcaccagatgttgatttaggtgacatctctggcattaatgcttcagtt gtaaacattcaaaaagaaattgaccgcctcaatgaggttgccaagaatttaaatgaatctctc atcgatctccaagaacttggaaagtatgagcagtatataaaatggccatggtacatttggcta ggttttatagctggcttgattgccatagtaatggtgacaattatgctttgctgtatgaccagt tgctgtagttgtctcaagggctgttgttcttgtggatcctgctgcaaatttgatgaagacgac tctgagccagtgctcaaaggagtcaaattacattacacataa SEQ ID NO: 55:
auguucguguuccuggugcugcugccucuggucagcagccagugcgugaaccugagaacaaga acacagcuuccuccagccuacacaaacucuuuuacacggggcguguacuauccugacaaggug uuccgguccagcgugcugcacucaacccaagaccuguuccugcccuucuucagcaacgucacc ugguuccacgccauccacgugucuggcaccaauggcacaaagcgauucgauaaccccgugcug ccuuucaacgacggcguguacuuugccuccaucgagaaguccaacaucauccggggcuggauc uucgggaccacacuggauagcaagacccagucucugcugaucguaaacaacgccaccaacgug gucaucaaggugugcgaguuccaguucugcaacgacccuuuccucgauguguacuaccacaag aacaacaagucuuggauggaaucgggcguguauagcagcgccaacaacugcaccuucgaauac gugagccagccuuuccugauggaccuggaaggcaaacaaggcaauuuuaagaaccugagagaa uucguguucaaaaauauagacggcuauuucaagaucuacagcaagcacaccccuauuaaucug gugcgggaucugccucagggcuucagcgcccucgaaccucugguggaccugccaaucggcauc aacauuacaagauuccagacgcugcucgcucugcacagaucuuaccugaccccuggcgacagc agcagcggcuggaccgccggcgccgccgcuuacuacgugggcuaccugcagccuagaaccuuu cugcugaaguacaacgagaacggcaccaucacugaugccguggauuggcccuggacccucugu ccgaaaccaaauguacacugaagucuuuuaccguggaaaaaggaaucuaccagacuuccaacu uccgggugcagccgaccgagagcaucgugcgguucccuaacaucacaaaccugugccccuuug gcgagguguucaacgccacaagauuugcuagcguguacgccuggaauagaaagagaaucagca acugcguggccgauuacagcgugcuguacaauagcgccucuuucagcaccuucaaaugcuacg gcgugagccccaccaagcugaacgaucuguguuuuacaaacguguaugccgacucauucguaa ucaggggcgaugaggugagacagaucgcuccuggacagacaggcaaaaucgcggacuacaacu auaagcugccugaugacuucacaggaugugugaucgcauggaacuccaauaaccucgacagca agguggggggaaauuacaauuaccgcuacagacuguuuagaaagagcaaucugaaaccuuucga gagagacaucagcacagagaucuaccaggccggcagcaagcccuguaacggcgucgagggcuu caacugcuacuuccccccugcagagcuacggcuuccagccuaccaacggcgugggauaccagcc uuacagagugguggugcugagcuucgagcugcugcaugcuccugcuacaguguguggguccuaa gaagagcaccaaccugguuaagaacaagugcgugaauuuuaacuucaauggacugaccggaac cggcgugcugaccgaaagcaacaagaaauuccugccuuuucagcaguuuggcagagacaucgc cgacaccaccgacgccgugagagauccacaaacccuggaaauccuggacaucacaccuugcuc auuuggagggggugucggugaucacaccuggcaccaacaccagcaaccagguggccgugcugua ccagggagugaauuguaccgagguccccguggccauucacgccgaccagcugaccccuaccug ggggguguacuccaccggcucuaacguauuccagaccagagcaggcugucugaucggcgcagaa cacgugaacaauagcuacgagugcgacaucccuaucggagccgggaucugcgcuagcuaccag acccagacaaacuccagaagcagagccggaagcguggccagccagucuaucaucgccuacacc -continued

```
augagccugggcgccgaaaacagcguugccuacagcaacaauucuaucgccaucccuacaaac
uucaccaucuccgugaccaccgagauccugccugucagcaugacaaagaccagcguagacugc
acaauguacaucugcggagauuccaccgaguguaguaaccuccugcugcaauacggaucuuuc
uguacucagcugaacagagcccugaccggcaucgccguugaacaggacaagaacacccaggag
guuuucgcccagguuaagcagaucuacaaaaccccuccuaucaaggacuucggaggcuuuaac
uucucccagauccugcccgaccccagcaagcccagcaagcggagccccaucgaggaccugcug
uucaacaaggugacccuggccgacgccggcuucaucaaacaguacggcgauugccugggagac
aucgccgcuagagaucuaauuugcgcccaaaaguuuaacggccugacagugcugccuccacug
cugacagacgagaugaucgcccaguacacaucugcccugcuggcugguaccaucacaucuggc
uggaccuuuggcgccggccccgcccuccagaucccuuuccccaugcagauggccuaccgguuc
aacggcaucggcgugacccagaacgugcuguacgaaaaccagaaacugaucgccaaccaguuc
aauagcgcgaucggcaaaauccaggauagccucagcucuacacccagcgcucuuggcaagcug
caaaacgugggugaaccagaaugcccaggcccuuaacacccuggugaagcagcuauccucuaau
uucggugccaucagcagcgugcugaaugauauccugagcagacuggacccccugaggccgaa
gugcagaucgacagacugaucaccggaagacugcagagccugcaaaccuacgugacccagcaa
cugauccgggccgcagaaauccgggccuccgcuaaccuggccgcuaccaagaugagcgagugc
gugcugggucaaagcaagcgcguggacuucuguggaaaaggcuaccaccugaugagcuucccu
cagagcgcuccacacggcgugguguuccugcaugugacuuacgugccugcccaggaaaagaac
uucaccaccgccccugccauuugucacgacggcaaggcccacuucccccgggaaggcguguuu
gugucuaacggaacacacugguuugugacucaaagaaacuucuacgagccacagaucaucacc
acagauaacaccuucgucagcggcaacugcgacguggugaucggcaucgugaacaauacugug
uacgacccccugcagccagagcucgauucuuucaaagaggaacuggauaaguacuucaagaac
cacacaucccccgacgucgaccugggcgauaucagcggcauuaacgccagcguggugaacauc
cagaaggaaaucgauagacugaacgagguggcaaagaaccugaaugagucccugauugaccug
caagagcucgggaaguacgagcaguauaucaaguggccuugguacaucuggcugggcuucauc
ggggccugaucgccaucguuauggugacgaucaugcugugcugcaugaccaguugcuguagcu
gccugaagggcugcugcagcugggcagcuguugcaaguucgacgaggacgacagcgagccugu
gcugaagggcguuaagcugcacuacaccuga
```

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of preferred aspects, are exemplary, and are not intended as limitations on the scope of the present technology.

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

The present technology has been described broadly and generically herein. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

What is claimed is:

1. A ribonucleic acid (RNA) encoding a spike(S) protein or an immunogenic fragment thereof of a severe acute respiratory syndrome coronavirus 2 (SARS-CoV-2), wherein the S protein or immunogenic fragment thereof comprises the polypeptide of SEQ ID NO: 5, the polypeptide of SEQ ID NO: 6, the polypeptide of SEQ ID NO: 7, the polypeptide of SEQ ID NO: 10, the polypeptide of SEQ ID NO: 11, or the polypeptide of SEQ ID NO: 14.

2. The RNA of claim 1, comprising
a polynucleotide encoding SEQ ID NO: 5 ,
a polynucleotide encoding SEQ ID NO: 6,
the polynucleotide of SEQ ID NO: 9,
a polynucleotide encoding SEQ ID NO: 10,
the polynucleotide of SEQ ID NO: 13, or
the polynucleotide of SEQ ID NO: 16.

3. The RNA of claim 1, further comprising
a 3' UTR, optionally wherein the 3' UTR comprises any one of SEQ ID NOs: 18, 22, or 24;
a 5' UTR, optionally wherein the 5' UTR comprises SEQ ID NO: 20 or 26; and
a polyA tail, optionally wherein the polyA tail comprises any one of SEQ ID NOs: 27, 28, or 30.

4. The RNA of claim 1, comprising or consisting of a UTR of SEQ ID NO: 32.

5. The RNA of claim 1, wherein the RNA is chemically modified and optionally comprises one or more of: an N1-methyl-pseudouridine residue or a pseudouridine residue.

6. The RNA of claim 5, wherein at least about 50%, or at least about 70%, or about 100% of the uridine residues in the RNA are N1-methyl pseudouridine or pseudouridine.

7. A polynucleotide encoding the RNA of claim 1, or a polynucleotide complementary thereto, optionally wherein the polynucleotide is selected from the group of: a deoxyribonucleic acid (DNA), an RNA, and a hybrid of DNA and RNA.

8. A polynucleotide encoding a spike(S) protein or an immunogenic fragment thereof of a severe acute respiratory syndrome coronavirus 2 (SARS-CoV-2), wherein the polynucleotide encoding the S protein or immunogenic fragment thereof comprises the sequence of SEQ ID NO: 55.

9. A polynucleotide encoding a spike(S) protein or an immunogenic fragment thereof of a severe acute respiratory syndrome coronavirus 2 (SARS-CoV-2), wherein the polynucleotide encoding the S protein or immunogenic fragment thereof comprises the sequence of SEQ ID NO: 52.

10. A vector or an isolated cell comprising the polynucleotide of claim 7.

11. A composition comprising a carrier and the RNA of claim 1.

12. The composition of claim 11, wherein the carrier is a pharmaceutically acceptable carrier.

13. A method of producing an RNA encoding an S protein or an immunogenic fragment thereof, wherein the S protein or immunogenic fragment thereof comprises the polypeptide of SEQ ID NO: 5, the polypeptide of SEQ ID NO: 6, the polypeptide of SEQ ID NO: 7, the polypeptide of SEQ ID NO: 10, the polypeptide of SEQ ID NO: 11, or the polypeptide of SEQ ID NO: 14, the method comprising culturing the isolated cell of claim 10 under conditions suitable for expressing the RNA.

14. A method of producing an RNA encoding an S protein or an immunogenic fragment thereof, wherein the S protein or immunogenic fragment thereof comprises the polypeptide of SEQ ID NO: 5, the polypeptide of SEQ ID NO: 6, the polypeptide of SEQ ID NO: 7, the polypeptide of SEQ ID NO: 10, the polypeptide of SEQ ID NO: 11, or the polypeptide of SEQ ID NO: 14, the method comprising contacting the polynucleotide of claim 7 with an RNA polymerase, adenosine triphosphate (ATP), cytidine triphosphate (CTP), guanosine-5'-triphosphate (GTP), and uridine triphosphate (UTP) or a chemically modified UTP under conditions suitable for expressing the RNA.

15. The composition of claim 12, wherein the pharmaceutically acceptable carrier comprises a lipid nanoparticle (LNP).

16. The composition of claim 15, wherein the LNP comprises a cationic or an ionizable lipid, a cholesterol, a pegylated lipid, and a helper lipid.

17. The composition of claim 12, wherein the pharmaceutically acceptable carrier comprises a polymeric nanoparticle that comprises a Histidine-Lysine co-polymer (HKP), optionally wherein the HKP comprises a side chain selected from SEQ ID NOs: 34-47, and optionally wherein the pharmaceutically acceptable carrier further comprises a lipid, optionally a cationic lipid, optionally wherein the cationic lipid is ionizable, or further optionally wherein the cationic lipid comprises Dlin-MC3-DMA (MC3) or dioleoyloxy-3-(trimethylammonio) propane (DOTAP) or both.

18. The composition of claim 17, wherein the lipid further comprises one or more of: a helper lipid, a cholesterol, or a PEGylated lipid, and optionally wherein the pharmaceutically acceptable carrier comprises a lipid nanoparticle (LNP) and optionally wherein the LNP comprises one or more of: 9-Heptadecanyl 8-{(2-hydroxyethyl) [6-oxo-6-(undecyloxy) hexyl]amino}octanoate (SM-102), 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), or an equivalent of each thereof, and optionally wherein the LNP further comprises one or more of: a helper lipid, a cholesterol, or a PEGylated lipid, and optionally wherein the helper lipid comprises one or more of: disteroylphosphatidyl choline (DSPC), Dipalmitoylphosphatidylcholine (DPPC), (2R)-3-(Hexadecanoyloxy)-2-{[(9Z)-octadec-9-enoyl]oxy}propyl 2-(trimethylazaniumyl)ethyl phosphate (POPC), or dioleoyl phosphatidylethanolamine (DOPE), and optionally wherein the cholesterol comprises a plant cholesterol or an animal cholesterol or both.

19. The composition of claim 18, wherein the PEGylated lipid comprises one or more of: PEG-c-DOMG (R-3-[(ω-methoxy-poly(ethyleneglycol)2000)carbamoyl)]-1,2-dimyristyloxypropyl-3-amine), PEG-DSG (1,2-Distearoyl-sn-glycerol, methoxypolyethylene glycol), PEG-DMG (1,2-Dimyristoyl-sn-glycerol) optionally PEG2000-DMG ((1,2-dimyristoyl-sn-glycero-3-phophoethanolamine-N-[methoxy (polyethylene glycol)-2000)], or PEG-DPG (1,2-Dipalmitoyl-sn-glycerol, methoxypolyethylene glycol), and optionally wherein the LNP comprises SM-102, DSPC, cholesterol and PEG2000-DMG, and further optionally wherein the mass ratio of the SM-102, DSPC, cholesterol and PEG200-DMG is about 1:1:1:1 and/or wherein the molar ratio of the SM-102, DSPC, cholesterol and PEG2000-DMG is about 50:10:38.5:1.5.

20. A method of producing the composition of claim 12, comprising contacting the RNA of claim 1 with an HKP, thereby the RNA and the HKP are self-assembled into nanoparticles, and optionally wherein the mass ratio of HKP and the RNA in the contacting step is about 10:1 to about 1:10, optionally 2.5:1, and optionally further comprising contacting the HKP and RNA with cationic lipid, optionally wherein the cationic lipid comprises Dlin-MC3-DMA (MC3) or DOTAP (dioleoyloxy-3-(trimethylammonio) propane) or both, and further optionally wherein the mass ratio of the cationic lipid and the RNA in the contacting step is about 10:1 to about 1:10, optionally 1:1, and optionally wherein the mass ratio of the HKP, the mRNA and the cationic lipid in the contacting step is about 4:1:1.

21. A method of producing a composition, comprising contacting the RNA of claim 1 with a lipid, thereby the RNA and the lipid are self-assembled into lipid nanoparticles (LNPs), and optionally wherein the LNPs comprise one or more of: 9-Heptadecanyl 8-{(2-hydroxyethyl) [6-oxo-6-(undecyloxy) hexyl]amino}octanoate (SM-102), 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), or an equivalent of each thereof, and further optionally wherein the LNPs further comprise one or more of: a helper lipid, a cholesterol, or a PEGylated lipid, optionally wherein the helper lipid comprises one or more of: disteroylphosphatidyl choline (DSPC), Dipalmitoylphosphatidylcholine (DPPC), (2R)-3-(Hexadecanoyloxy)-2-{[(9Z)-octadec-9-enoyl]oxy}propyl 2-(trimethylazaniumyl)ethyl phosphate (POPC), or dioleoyl phosphatidylethanolamine (DOPE), optionally wherein the cholesterol comprises a plant cholesterol or an animal cholesterol or both, and optionally wherein the PEGylated lipid comprises one or more of: PEG-c-DOMG (R-3-[(ω-methoxy-poly (ethyleneglycol)2000)carbamoyl)]-1,2-dimyristyloxypropyl-3-amine), PEG-DSG (1,2-Distearoyl-sn-glycerol, methoxypolyethylene glycol), PEG-DMG (1,2-Dimyristoyl-sn-glycerol) optionally PEG2000-DMG ((1,2-dimyristoyl-sn-glycero-3-phophoethanolamine-N-[methoxy(polyethylene glycol)-2000)], or PEG-DPG (1,2-Dipalmitoyl-sn-glycerol, methoxypolyethylene glycol), and optionally wherein the LNPs comprise SM-102, DSPC, cholesterol and PEG2000-DMG.

22. The method of claim 21, wherein the LNPs comprise SM-102, DSPC, cholesterol and PEG2000-DMG, optionally wherein the mass ratio of the SM-102, DSPC, cholesterol and PEG200-DMG is about 1:1:1:1 or optionally wherein the molar ratio of the SM-102, DSPC, cholesterol and PEG2000-DMG is about 50:10:38.5:1.5.

23. A method of one or more of:

(a) preventing a subject from having a symptomatic SARS-CoV-2 infection, (b) inducing an immune response to SARS-CoV-2 in a subject in need thereof, (c) reducing the binding of a SARS-CoV-2 or an S protein thereof with angiotensin converting enzyme 2 (ACE2) in a subject in need thereof, or (d) reducing a SARS-CoV-2 viral load in a subject in need thereof, comprising administering to the subject a composition comprising the RNA of claim 1 and a pharmaceutically acceptable carrier that is a lipid nanoparticle.

24. The method of claim 23, wherein the subject does not have a SARS-CoV-2 infection when administrated with the RNA.

25. The RNA of claim 3, wherein the RNA is chemically modified and optionally comprises one or more of: an N1-methyl-pseudouridine residue or a pseudouridine residue.

26. The RNA of claim 25, wherein at least about 50%, or at least about 70%, or about 100% of the uridine residues in the RNA are N1-methyl pseudouridine or pseudouridine.

27. A polynucleotide encoding the RNA of claim 25, or a polynucleotide complementary thereto, optionally wherein the polynucleotide is selected from the group of: a deoxyribonucleic acid (DNA), an RNA, and a hybrid of DNA and RNA.

28. The polynucleotide of claim 9, further comprising a 3' UTR, a 5' UTR, and a polyA tail.

29. A composition comprising the RNA of claim 25, and a pharmaceutically acceptable carrier, and optionally wherein the pharmaceutically acceptable carrier comprises a lipid, a lipid nanoparticle, or a polymeric nanoparticle that comprises a Histidine-Lysine co-polymer (HKP), and further optionally wherein the HKP comprises a side chain selected from SEQ ID NOs: 34-47.

30. A method of one or more of:

(a) preventing a subject from having a symptomatic SARS-CoV-2 infection, (b) inducing an immune response to SARS-CoV-2 in a subject in need thereof, (c) reducing the binding of a SARS-CoV-2 or an S protein thereof with angiotensin converting enzyme 2 (ACE2) in a subject in need thereof, or (d) reducing a SARS-CoV-2 viral load in a subject in need thereof, comprising administering to the subject a composition comprising the RNA of claim 25 and pharmaceutically acceptable carrier that is a lipid nanoparticle.

* * * * *

SEQUENCE LISTING

```
Sequence total quantity: 57
SEQ ID NO: 1            moltype = AA  length = 1273
FEATURE                 Location/Qualifiers
source                  1..1273
                        mol_type = protein
                        organism = Severe acute respiratory syndrome coronavirus 2
SEQUENCE: 1
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                    1273

SEQ ID NO: 2            moltype = AA  length = 1273
FEATURE                 Location/Qualifiers
source                  1..1273
                        mol_type = protein
                        organism = synthetic construct
SEQUENCE: 2
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQGVNCTEV PVAIHADQLT PTWRVYSTGS NVFQTRAGCL IGAEHVNNSY  660
ECDIPIGAGI CASYQTQTNS PSRAGSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSPIED LLFNKVTLAD AGFIKQYGDC  840
LGDIAARDLI CAQKFNGLTV LPPLLTDEMI AQYTSALLAG TITSGWTFGA GPALQIPFPM  900
QMAYRFNGIG VTQNVLYENQ KLIANQFNSA IGKIQDSLSS TPSALGKLQD VVNQNAQALN  960
TLVKQLSSNF GAISSVLNDI LSRLDPPEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                    1273

SEQ ID NO: 3            moltype = DNA  length = 3822
FEATURE                 Location/Qualifiers
source                  1..3822
                        mol_type = other DNA
                        organism = synthetic construct
SEQUENCE: 3
atgtttgttt ttcttgtttt attgccacta gtctctagtc agtgtgttaa tcttacaacc  60
agaactcaat tacccccctgc atacactaat tctttcacac gtggtgttta ttaccctgac  120
aaagttttca gatcctcagt tttacattca actcaggact tgttcttacc tttcttttcc  180
aatgttactt ggttccatgc tatacatgtc tctgggacca atggtactaa gaggtttgat  240
aaccctgtcc taccatttaa tgatggtgtt tattttgctt ccactgagaa gtctaacata  300
ataagaggct ggatttttgg tactacttta gattcgaaga cccagtccct acttattgtt  360
```

-continued

```
aataacgcta ctaatgttgt tattaaagtc tgtgaatttc aattttgtaa tgatccattt  420
ttgggtgttt attaccacaa aaacaacaaa agttggatgg aaagtgagtt cagagtttat  480
tctagtgcga ataattgcac ttttgaatat gtctctcagc cttttcttat ggaccttgaa  540
ggaaaacagg gtaatttcaa aaatcttagg gaatttgtgt ttaagaatat tgatggttat  600
tttaaaatat attctaagca cacgcctatt aatttagtgc gtgatctccc tcagggtttt  660
tcggctttag aaccattggt agatttgcca ataggtatta acatcactag gtttcaaact  720
ttacttgctt tacatagaag ttatttgact cctggtgatt cttcttcagg ttggacagct  780
ggtgctgcag cttattatgt gggttatctt caacctagga cttttctatt aaaatataat  840
gaaaatggaa ccattacaga tgctgtagac tgtgcacttg accctctctc agaaacaaag  900
tgtacgttga aatccttcac tgtagaaaaa ggaatctatc aaacttctaa ctttagagtc  960
caaccaacag aatctattgt tagatttcct aatattacaa acttgtgccc ttttggtgaa  1020
gtttttaacg ccaccagatt tgcatctgtt tatgcttgga acaggaagag aatcagcaac  1080
tgtgttgctg attattctgt cctatataat tccgcatcat tttccacttt taagtgttat  1140
ggagtgtctc ctactaaatt aaatgatctc tgctttacta atgtctatgc agattcattt  1200
gtaattagag gtgatgaagt cagacaaatc gctccagggc aaactggaaa gattgctgat  1260
tataattata aattaccaga tgattttaca ggctgcgtta tagcttggaa ttctaacaat  1320
cttgattcta aggttggtgg taattataat tacctgtata gattgtttag gaagtctaat  1380
ctcaaacctt ttgagagaga tatttcaact gaaatctatc aggccggtag cacaccttgt  1440
aatggtgttg aaggttttaa ttgttacttt cctttacaat catatggttt ccaacccact  1500
aatggtgttg gttaccaacc atacagagta gtagtacttt cttttgaact tctacatgca  1560
ccagcaactg tttgtggacc taaaaagtct actaatttgg ttaaaaacaa atgtgtcaat  1620
ttcaacttca atggtttaac aggcacaggt gttcttactg agtctaacaa aaagtttctg  1680
cctttccaac aatttggcag agacattgct gacactactg atgctgtccg tgatccacag  1740
acacttgaga ttcttgacat tacaccatgt tcttttggtg gtgtcagtgt tataacacca  1800
ggaacaaata cttctaacca ggttgctgtt ctttatcagg gtgttaactg cacagaagtc  1860
cctgttgcta ttcatgcaga tcaacttact cctacttggc gtgtttattc tacaggttct  1920
aatgtttttc aaacacgtgc aggctgttta ataggggctg aacatgtcaa caactcatat  1980
gagtgtgaca tacccattgg tgcaggtata tgcgctagtt atcagactca gactaattct  2040
ccttcgcggg caggtagtgt agctagtcaa tccatcattg cctacactat gtcacttggt  2100
gcagaaaatt cagttgctta ctctaataac tctattgcca tacccacaaa ttttactatt  2160
agtgttacca cagaaattct accagtgtct atgaccaaga catcagtaga ttgtacaatg  2220
tacatttgtg gtgattcaac tgaatgcagc aatcttttgt tgcaatatgg cagtttttgt  2280
acacaattaa accgtgcttt aactggaata gctgttgaac aagacaaaaa cacccaagaa  2340
gtttttgcac aagtcaaaca aatttacaaa acaccaccaa ttaaagattt tggtggtttt  2400
aatttttcac aaatattacc agatccatca aaaccaagca agaggtcacc tattgaagat  2460
ctacttttca acaaagtgac acttgcagat gctggcttca tcaaacaata tggtgattgc  2520
cttggtgata ttgctgctag agacctcatt tgtgcacaaa agtttaacgg ccttactgtt  2580
ttgccacctt tgctcacaga tgaaatgatt gctcaataca cttctgcact gttagcgggt  2640
acaatcactt ctggttggac ctttggtgca ggtcctgcat tacaaatacc atttcctatg  2700
caaatggctt ataggtttaa tggtattgga gttacacaga atgttctcta tgagaaccaa  2760
aaattgattg ccaaccaatt taatagtgct attggcaaaa ttcaagactc actttcttcc  2820
acaccaagtg cacttggaaa acttcaagat gtggtcaacc aaaatgcaca agctttaaac  2880
acgcttgtta aacaacttag ctccaatttt ggtgcaattt caagtgtttt aaatgatatc  2940
ctttcacgtc ttgacccacc tgaggctgaa gtgcaaattg ataggttgat cacaggcaga  3000
cttcaaagtt tgcagacata tgtgactcaa caattaatta gagctgcaga aatcagagct  3060
tctgctaatc ttgctgctac taaaatgtca gagtgtgtac ttggacaatc aaaaagagtt  3120
gatttttgtg gaaagggcta tcatcttatg tccttccctc agtcagcacc tcatggtgta  3180
gtcttcttgc atgtgactta tgtccctgca caagaaaaga acttcacaac tgctcctgcc  3240
atttgtcatg atggaaaagc acactttcct cgtgaaggtg tctttgtttc aaatggcaca  3300
cactggtttg taacacaaag gaatttttat gaaccacaaa tcattactac agacaacaca  3360
tttgtgtctg gtaactgtga tgttgtaata ggaattgtca acaacacagt ttatgatcct  3420
ttgcaacctg aattagactc attcaaggag gagttagata aatattttaa gaatcataca  3480
tcaccagatg ttgatttagg tgacatctct ggcattaatg cttcagttgt aaacattcaa  3540
aaagaaattg accgcctcaa tgaggttgcc aagaatttaa atgaatctct catcgatctc  3600
caagaacttg gaaagtatga gcagtatata aaatggccat ggtacatttg gctaggtttt  3660
atagctggct tgattgccat agtaatggtg acaattatgc tttgctgtat gaccagttgc  3720
tgtagttgtc tcaagggctg ttgttcttgt ggatcctgct gcaaatttga tgaagacgac  3780
tctgagccag tgctcaaagg agtcaaatta cattacacat aa                    3822

SEQ ID NO: 4           moltype = RNA  length = 3822
FEATURE                Location/Qualifiers
source                 1..3822
                       mol_type = other RNA
                       organism = synthetic construct
SEQUENCE: 4
atgtttgttt ttcttgtttt attgccacta gtctctagtc agtgtgttaa tcttacaacc  60
agaactcaat taccccctgc atacactaat tctttcacac gtggtgttta ttaccctgac  120
aaagttttca gatcctcagt tttacattca actcaggact tgttcttacc tttcttttcc  180
aatgttactt ggttccatgc tatacatgtc tctgggacca atggtactaa gaggtttgat  240
aaccctgtcc taccatttaa tgatggtgtt tattttgctt ccactgagaa gtctaacata  300
ataagaggct ggatttttgg tactacttta gattcgaaga cccagtccct acttattgtt  360
aataacgcta ctaatgttgt tattaaagtc tgtgaatttc aattttgtaa tgatccattt  420
ttgggtgttt attaccacaa aaacaacaaa agttggatgg aaagtgagtt cagagtttat  480
tctagtgcga ataattgcac ttttgaatat gtctctcagc cttttcttat ggaccttgaa  540
ggaaaacagg gtaatttcaa aaatcttagg gaatttgtgt ttaagaatat tgatggttat  600
tttaaaatat attctaagca cacgcctatt aatttagtgc gtgatctccc tcagggtttt  660
tcggctttag aaccattggt agatttgcca ataggtatta acatcactag gtttcaaact  720
ttacttgctt tacatagaag ttatttgact cctggtgatt cttcttcagg ttggacagct  780
ggtgctgcag cttattatgt gggttatctt caacctagga cttttctatt aaaatataat  840
```

-continued

```
gaaaatggaa ccattacaga tgctgtagac tgtgcacttg accctctctc agaaacaaag  900
tgtacgttga aatccttcac tgtagaaaaa ggaatctatc aaacttctaa ctttagagtc  960
caaccaacag aatctattgt tagatttcct aatattacaa acttgtgccc ttttggtgaa  1020
gtttttaacg ccaccagatt tgcatctgtt tatgcttgga acaggaagag aatcagcaac  1080
tgtgttgctg attattctgt cctatataat tccgcatcat tttccacttt taagtgttat  1140
ggagtgtctc ctactaaatt aaatgatctc tgctttacta atgtctatgc agattcattt  1200
gtaattagag gtgatgaagt cagacaaatc gctccagggc aaactggaaa gattgctgat  1260
tataattata aattaccaga tgattttaca ggctgcgtta tagcttggaa ttctaacaat  1320
cttgattcta aggttggtgg taattataat tacctgtata gattgtttag gaagtctaat  1380
ctcaaacctt ttgagagaga tatttcaact gaaatctatc aggccggtag cacaccttgt  1440
aatggtgttg aaggttttaa ttgttacttt cctttacaat catatggttt ccaacccact  1500
aatggtgttg gttaccaacc atacagagta gtagtacttt cttttgaact tctacatgca  1560
ccagcaactg tttgtggacc taaaaagtct actaatttgg ttaaaaacaa atgtgtcaat  1620
ttcaacttca atggtttaac aggcacaggt gttcttactg agtctaacaa aaagtttctg  1680
cctttccaac aatttggcag agacattgct gacactactg atgctgtccg tgatccacag  1740
acacttgaga ttcttgacat tacaccatgt tcttttggtg gtgtcagtgt tataacacca  1800
ggaacaaata cttctaacca ggttgctgtt ctttatcagg gtgttaactg cacagaagtc  1860
cctgttgcta ttcatgcaga tcaacttact cctacttggc gtgtttattc tacaggttct  1920
aatgtttttc aaacacgtgc aggctgttta atagggggctg aacatgtcaa caactcatat  1980
gagtgtgaca tacccattgg tgcaggtata tgcgctagtt atcagactca gactaattct  2040
ccttcgcggg caggtagtgt agctagtcaa tccatcattg cctacactat gtcacttggt  2100
gcagaaaatt cagttgctta ctctaataac tctattgcca tacccacaaa ttttactatt  2160
agtgttacca cagaaattct accagtgtct atgaccaaga catcagtaga ttgtacaatg  2220
tacatttgtg gtgattcaac tgaatgcagc aatcttttgt tgcaatatgg cagtttttgt  2280
acacaattaa accgtgcttt aactggaata gctgttgaac aagacaaaaa cacccaagaa  2340
gtttttgcac aagtcaaaca aatttacaaa acaccaccaa ttaaagattt tggtggtttt  2400
aatttttcac aaatattacc agatccatca aaaccaagca agaggtcacc tattgaagat  2460
ctacttttca acaaagtgac acttgcagat gctggcttca tcaaacaata tggtgattgc  2520
cttggtgata ttgctgctag agacctcatt tgtgcacaaa agtttaacgg ccttactgtt  2580
ttgccacctt tgctcacaga tgaaatgatt gctcaataca cttctgcact gttagcgggt  2640
acaatcactt ctggttggac ctttggtgca ggtcctgcat tacaaatacc atttcctatg  2700
caaatggctt ataggtttaa tggtattgga gttacacaga atgttctcta tgagaaccaa  2760
aaattgattg ccaaccaatt taatagtgct attggcaaaa ttcaagactc actttcttcc  2820
acaccaagtg cacttggaaa acttcaagat gtggtcaacc aaaatgcaca agctttaaac  2880
acgcttgtta aacaacttag ctccaatttt ggtgcaattt caagtgtttt aaatgatatc  2940
ctttcacgtc ttgacccacc tgaggctgaa gtgcaaattg ataggttgat cacaggcaga  3000
cttcaaagtt tgcagacata tgtgactcaa caattaatta gagctgcaga aatcagagct  3060
tctgctaatc ttgctgctac taaaatgtca gagtgtgtac ttggacaatc aaaaagagtt  3120
gatttttgtg gaaagggcta tcatcttatg tccttccctc agtcagcacc tcatggtgta  3180
gtcttcttgc atgtgactta tgtccctgca caagaaaaga acttcacaac tgctcctgcc  3240
atttgtcatg atggaaaagc acactttcct cgtgaaggtg tctttgtttc aaatggcaca  3300
cactggtttg taacacaaag gaatttttat gaaccacaaa tcattactac agacaacaca  3360
tttgtgtctg gtaactgtga tgttgtaata ggaattgtca acaacacagt ttatgatcct  3420
ttgcaacctg aattagactc attcaaggag gagttagata aatattttaa gaatcataca  3480
tcaccagatg ttgatttagg tgacatctct ggcattaatg cttcagttgt aaacattcaa  3540
aaagaaattg accgcctcaa tgaggttgcc aagaatttaa atgaatctct catcgatctc  3600
caagaacttg gaaagtatga gcagtatata aaatggccat ggtacatttg gctaggtttt  3660
atagctggct tgattgccat agtaatggtg acaattatgc tttgctgtat gaccagttgc  3720
tgtagttgtc tcaagggctg ttgttcttgt ggatcctgct gcaaatttga tgaagacgac  3780
tctgagccag tgctcaaagg agtcaaatta cattacacat aa                    3822

SEQ ID NO: 5              moltype = AA  length = 1271
FEATURE                   Location/Qualifiers
source                    1..1271
                          mol_type = protein
                          organism = synthetic construct
SEQUENCE: 5
MFVFLVLLPL VSSQCVNLRT RTQLPPAYTN SFTRGVYYPD KVFRSSVLHS TQDLFLPFFS  60
NVTWFHAIHV SGTNGTKRFD NPVLPFNDGV YFASIEKSNI IRGWIFGTTL DSKTQSLLIV  120
NNATNVVIKV CEFQFCNDPF LDVYYHKNNK SWMESGVYSS ANNCTFEYVS QPFLMDLEGK  180
QGNFKNLREF VFKNIDGYFK IYSKHTPINL VRDLPQGFSA LEPLVDLPIG INITRFQTLL  240
ALHRSYLTPG DSSSGWTAGA AAYYVGYLQP RTFLLKYNEN GTITDAVDCA LDPLSETKCT  300
LKSFTVEKGI YQTSNFRVQP TESIVRFPNI TNLCPFGEVF NATRFASVYA WNRKRISNCV  360
ADYSVLYNSA SFSTFKCYGV SPTKLNDLCF TNVYADSFVI RGDEVRQIAP GQTGKIADYN  420
YKLPDDFTGC VIAWNSNNLD SKVGGNYNYR YRLFRKSNLK PFERDISTEI YQAGSKPCNG  480
VEGFNCYFPL QSYGFQPTNG VGYQPYRVVV LSFELLHAPA TVCGPKKSTN LVKNKCVNFN  540
FNGLTGTGVL TESNKKFLPF QQFGRDIADT TDAVRDPQTL EILDITPCSF GGVSVITPGT  600
NTSNQVAVLY QGVNCTEVPV AIHADQLTPT WRVYSTGSNV FQTRAGCLIG AEHVNNSYEC  660
DIPIGAGICA SYQTQTNSRS RAGSVASQSI IAYTMSLGAE NSVAYSNNSI AIPTNFTISV  720
TTEILPVSMT KTSVDCTMYI CGDSTECSNL LLQYGSFCTQ LNRALTGIAV EQDKNTQEVF  780
AQVKQIYKTP PIKDFGGFNF SQILPDPSKP SKRSFIEDLL FNKVTLADAG FIKQYGDCLG  840
DIAARDLICA QKFNGLTVLP PLLTDEMIAQ YTSALLAGTI TSGWTFGAGA ALQIPFAMQM  900
AYRFNGIGVT QNVLYENQKL IANQFNSAIG KIQDSLSSTA SALGKLQNVV NQNAQALNTL  960
VKQLSSNFGA ISSVLNDILS RLDPPEAEVQ IDRLITGRLQ SLQTYVTQQL IRAAEIRASA  1020
NLAATKMSEC VLGQSKRVDF CGKGYHLMSF PQSAPHGVVF LHVTYVPAQE KNFTTAPAIC  1080
HDGKAHFPRE GVFVSNGTHW FVTQRNFYEP QIITTDNTFV SGNCDVVIGI VNNTVYDPLQ  1140
PELDSFKEEL DKYFKNHTSP DVDLGDISGI NASVVNIQKE IDRLNEVAKN LNESLIDLQE  1200
LGKYEQYIKW PWYIWLGFIA GLIAIVMVTI MLCCMTSCCS CLKGCCSCGS CCKFDEDDSE  1260
PVLKGVKLHY T                                                      1271
```

```
SEQ ID NO: 6            moltype = AA  length = 1271
FEATURE                 Location/Qualifiers
source                  1..1271
                        mol_type = protein
                        organism = synthetic construct
SEQUENCE: 6
MFVFLVLLPL VSSQCVNLRT RTQLPPAYTN SFTRGVYYPD KVFRSSVLHS TQDLFLPFFS  60
NVTWFHAIHV SGTNGTKRFD NPVLPFNDGV YFASIEKSNI IRGWIFGTTL DSKTQSLLIV  120
NNATNVVIKV CEFQFCNDPF LDVYYHKNNK SWMESGVYSS ANNCTFEYVS QPFLMDLEGK  180
QGNFKNLREF VFKNIDGYFK IYSKHTPINL VRDLPQGFSA LEPLVDLPIG INITRFQTLL  240
ALHRSYLTPG DSSSGWTAGA AAYYVGYLQP RTFLLKYNEN GTITDAVDCA LDPLSETKCT  300
LKSFTVEKGI YQTSNFRVQP TESIVRFPNI TNLCPFGEVF NATRFASVYA WNRKRISNCV  360
ADYSVLYNSA SFSTFKCYGV SPTKLNDLCF TNVYADSFVI RGDEVRQIAP GQTGKIADYN  420
YKLPDDFTGC VIAWNSNNLD SKVGGNYNYR YRLFRKSNLK PFERDISTEI YQAGSKPCNG  480
VEGFNCYFPL QSYGFQPTNG VGYQPYRVVV LSFELLHAPA TVCGPKKSTN LVKNKCVNFN  540
FNGLTGTGVL TESNKKFLPF QQFGRDIADT TDAVRDPQTL EILDITPCSF GGVSVITPGT  600
NTSNQVAVLY QGVNCTEVPV AIHADQLTPT WRVYSTGSNV FQTRAGCLIG AEHVNNSYEC  660
DIPIGAGICA SYQTQTNSPS RAGSVASQSI IAYTMSLGAE NSVAYSNNSI AIPTNFTISV  720
TTEILPVSMT KTSVDCTMYI CGDSTECSNL LLQYGSFCTQ LNRALTGIAV EQDKNTQEVF  780
AQVKQIYKTP PIKDFGGFNF SQILPDPSKP SKRSFIEDLL FNKVTLADAG FIKQYGDCLG  840
DIAARDLICA QKFNGLTVLP PLLTDEMIAQ YTSALLAGTI TSGWTFGAGA ALQIPFAMQM  900
AYRFNGIGVT QNVLYENQKL IANQFNSAIG KIQDSLSSTA SALGKLQNVV NQNAQALNTL  960
VKQLSSNFGA ISSVLNDILS RLDPPEAEVQ IDRLITGRLQ SLQTYVTQQL IRAAEIRASA  1020
NLAATKMSEC VLGQSKRVDF CGKGYHLMSF PQSAPHGVVF LHVTYVPAQE KNFTTAPAIC  1080
HDGKAHFPRE GVFVSNGTHW FVTQRNFYEP QIITTDNTFV SGNCDVVIGI VNNTVYDPLQ  1140
PELDSFKEEL DKYFKNHTSP DVDLGDISGI NASVVNIQKE IDRLNEVAKN LNESLIDLQE  1200
LGKYEQYIKW PWYIWLGFIA GLIAIVMVTI MLCCMTSCCS CLKGCCSCGS CCKFDEDDSE  1260
PVLKGVKLHY T                                                      1271

SEQ ID NO: 7            moltype = AA  length = 1271
FEATURE                 Location/Qualifiers
source                  1..1271
                        mol_type = protein
                        organism = synthetic construct
SEQUENCE: 7
MFVFLVLLPL VSSQCVNLRT RTQLPPAYTN SFTRGVYYPD KVFRSSVLHS TQDLFLPFFS  60
NVTWFHAIHV SGTNGTKRFD NPVLPFNDGV YFASIEKSNI IRGWIFGTTL DSKTQSLLIV  120
NNATNVVIKV CEFQFCNDPF LDVYYHKNNK SWMESGVYSS ANNCTFEYVS QPFLMDLEGK  180
QGNFKNLREF VFKNIDGYFK IYSKHTPINL VRDLPQGFSA LEPLVDLPIG INITRFQTLL  240
ALHRSYLTPG DSSSGWTAGA AAYYVGYLQP RTFLLKYNEN GTITDAVDCA LDPLSETKCT  300
LKSFTVEKGI YQTSNFRVQP TESIVRFPNI TNLCPFGEVF NATRFASVYA WNRKRISNCV  360
ADYSVLYNSA SFSTFKCYGV SPTKLNDLCF TNVYADSFVI RGDEVRQIAP GQTGKIADYN  420
YKLPDDFTGC VIAWNSNNLD SKVGGNYNYR YRLFRKSNLK PFERDISTEI YQAGSKPCNG  480
VEGFNCYFPL QSYGFQPTNG VGYQPYRVVV LSFELLHAPA TVCGPKKSTN LVKNKCVNFN  540
FNGLTGTGVL TESNKKFLPF QQFGRDIADT TDAVRDPQTL EILDITPCSF GGVSVITPGT  600
NTSNQVAVLY QGVNCTEVPV AIHADQLTPT WRVYSTGSNV FQTRAGCLIG AEHVNNSYEC  660
DIPIGAGICA SYQTQTNSRS RAGSVASQSI IAYTMSLGAE NSVAYSNNSI AIPTNFTISV  720
TTEILPVSMT KTSVDCTMYI CGDSTECSNL LLQYGSFCTQ LNRALTGIAV EQDKNTQEVF  780
AQVKQIYKTP PIKDFGGFNF SQILPDPSKP SKRSPIEDLL FNKVTLADAG FIKQYGDCLG  840
DIAARDLICA QKFNGLTVLP PLLTDEMIAQ YTSALLAGTI TSGWTFGAGP ALQIPFPMQM  900
AYRFNGIGVT QNVLYENQKL IANQFNSAIG KIQDSLSSTP SALGKLQNVV NQNAQALNTL  960
VKQLSSNFGA ISSVLNDILS RLDPPEAEVQ IDRLITGRLQ SLQTYVTQQL IRAAEIRASA  1020
NLAATKMSEC VLGQSKRVDF CGKGYHLMSF PQSAPHGVVF LHVTYVPAQE KNFTTAPAIC  1080
HDGKAHFPRE GVFVSNGTHW FVTQRNFYEP QIITTDNTFV SGNCDVVIGI VNNTVYDPLQ  1140
PELDSFKEEL DKYFKNHTSP DVDLGDISGI NASVVNIQKE IDRLNEVAKN LNESLIDLQE  1200
LGKYEQYIKW PWYIWLGFIA GLIAIVMVTI MLCCMTSCCS CLKGCCSCGS CCKFDEDDSE  1260
PVLKGVKLHY T                                                      1271

SEQ ID NO: 8            moltype = DNA  length = 3816
FEATURE                 Location/Qualifiers
source                  1..3816
                        mol_type = other DNA
                        organism = synthetic construct
SEQUENCE: 8
atgttcgtgt tcctggtgct gctgcctctg gtcagcagcc agtgcgtgaa cctgagaaca  60
agaacacagc ttcctccagc ctacacaaac tcttttacac ggggcgtgta ctatcctgac  120
aaggtgttcc ggtccagcgt gctgcactca acccaagacc tgttcctgcc cttcttcagc  180
aacgtcacct ggttccacgc catccacgtg tctggcacca atggcacaaa gcgattcgat  240
aaccccgtgc tgcctttcaa cgacggcgtg tactttgcct ccatcgagaa gtccaacatc  300
atccggggct ggatcttcgg gaccacactg gatagcaaga cccagtctct gctgatcgta  360
aacaacgcca ccaacgtggt catcaaggtg tgcgagttcc agttctgcaa cgaccctttc  420
ctcgatgtgt actaccacaa gaacaacaag tcttggatgg aatcgggcgt gtatagcagc  480
gccaacaact gcaccttcga atacgtgagc cagcctttcc tgatggacct ggaaggcaaa  540
caaggcaatt ttaagaacct gagagaattc gtgttcaaaa atatagacgg ctatttcaag  600
atctacagca agcacacccc tattaatctg gtgcgggatc tgcctcaggg cttcagcgcc  660
ctcgaacctc tggtggacct gccaatcggc atcaacatta caagattcca gacgctgctc  720
gctctgcaca gatcttacct gacccctggc gacagcagca gcggctggac cgccggcgcc  780
gccgcttact acgtgggcta cctgcagcct agaacctttc tgctgaagta caacgagaac  840
```

-continued

```
ggcaccatca ctgatgccgt ggattgcgcc ctggaccctc tgtccgaaac caaatgtaca  900
ctgaagtctt ttaccgtgga aaaggaatc taccagactt ccaacttccg ggtgcagccg  960
accgagagca tcgtgcggtt ccctaacatc acaaacctgt gccccttttgg cgaggtgttc  1020
aacgccacaa gatttgctag cgtgtacgcc tggaatagaa agagaatcag caactgcgtg  1080
gccgattaca gcgtgctgta caatagcgcc tctttcagca ccttcaaatg ctacggcgtg  1140
agccccacca agctgaacga tctgtgtttt acaaacgtgt atgccgactc attcgtaatc  1200
aggggcgatg aggtgagaca gatcgctcct ggacagacag gcaaaatcgc ggactacaac  1260
tataagctgc ctgatgactt cacaggatgt gtgatcgcat ggaactccaa taacctcgac  1320
agcaaggtgg gcggaaatta caattaccgc tacagactgt ttagaaagag caatctgaaa  1380
cctttcgaga gagacatcag cacagagatc taccaggccg gcagcaagcc ctgtaacggc  1440
gtcgagggct tcaactgcta cttccccctg cagagctacg gcttccagcc taccaacggc  1500
gtgggatacc agccttacag agtggtggtg ctgagcttcg agctgctgca tgctcctgct  1560
acagtgtgtg gtcctaagaa gagcaccaac ctggttaaga acaagtgcgt gaattttaac  1620
ttcaatggac tgaccggaac cggcgtgctg accgaaagca acaagaaatt cctgcctttt  1680
cagcagtttg gcagagacat cgccgacacc accgacgccg tgagagatcc acaaaccctg  1740
gaaatcctgg acatcacacc ttgctcattt ggaggggtgt cggtgatcac acctggcacc  1800
aacaccagca accaggtggc cgtgctgtac cagggagtga attgtaccga ggtccccgtg  1860
gccattcacg ccgaccagct gacccctacc tggcgggtgt actccaccgg ctctaacgta  1920
ttccagacca gagccggctg tctgatcggc gcagaacacg tgaacaatag ctacgagtgc  1980
gacatcccta tcggagccgg gatctgcgct agctaccaga cccagacaaa ctccagaagc  2040
agagccggaa gcgtggccag ccagtctatc atcgcctaca ccatgagcct gggcgccgaa  2100
aacagcgttg cctacagcaa caattctatc gccatcccta caaacttcac catctccgtg  2160
accaccgaga tcctgcctgt cagcatgaca aagaccagcg tagactgcac aatgtacatc  2220
tgcggagatt ccaccgagtg tagtaacctc ctgctgcaat acggatcttt ctgtactcag  2280
ctgaacagag ccctgaccgg catcgccgtt gaacaggaca agaacaccca ggaggttttc  2340
gcccaggtta agcagatcta caaaacccct cctatcaagg acttcggagg ctttaacttc  2400
tcccagatcc tgcccgaccc cagcaagccc agcaagcgga gccccatcga ggacctgctg  2460
ttcaacaagg tgaccctggc cgacgccggc ttcatcaaac agtacggcga ttgcctggga  2520
gacatcgccg ctagagatct aatttgcgcc caaaagttta acggcctgac agtgctgcct  2580
ccactgctga cagacgagat gatcgcccag tacacatctg ccctgctggc tggtaccatc  2640
acatctggct ggacctttgg cgccggcccc gccctccaga tccctttccc catgcagatg  2700
gcctaccggt tcaacggcat cggcgtgacc cagaacgtgc tgtacgaaaa ccagaaactg  2760
atcgccaacc agttcaatag cgcgatcggc aaaatccagg atagcctcag ctctacaccc  2820
agcgctcttg gcaagctgca aaacgtggtg aaccagaatg cccaggccct taacaccctg  2880
gtgaagcagc tatcctctaa tttcggtgcc atcagcagcg tgctgaatga tatcctgagc  2940
agactggacc cccctgaggc cgaagtgcag atcgacagac tgatcaccgg aagactgcag  3000
agcctgcaaa cctacgtgac ccagcaactg atccgggccg cagaaatccg ggcctccgct  3060
aacctggccg ctaccaagat gagcgagtgc gtgctgggtc aaagcaagcg cgtggacttc  3120
tgtggaaaag gctaccacct gatgagcttc cctcagagcg ctccacacgg cgtggtgttc  3180
ctgcatgtga cttacgtgcc tgcccaggaa aagaacttca ccaccgcccc tgccatttgt  3240
cacgacggca aggcccactt cccccgggaa ggcgtgtttg tgtctaacgg aacacactgg  3300
tttgtgactc aaagaaactt ctacgagcca cagatcatca ccacagataa caccttcgtc  3360
agcggcaact gcgacgtggt gatcggcatc gtgaacaata ctgtgtacga ccccctgcag  3420
ccagagctcg attctttcaa agaggaactg gataagtact tcaagaacca cacatccccc  3480
gacgtcgacc tgggcgatat cagcggcatt aacgccagcg tggtgaacat ccagaaggaa  3540
atcgatagac tgaacgaggt ggcaaagaac ctgaatgagt ccctgattga cctgcaagag  3600
ctcgggaagt acgagcagta tatcaagtgg ccttggtaca tctggctggg cttcatcgcg  3660
ggcctgatcg ccatcgttat ggtgacgatc atgctgtgct gcatgaccag ttgctgtagc  3720
tgcctgaagg gctgctgcag ctgcggcagc tgttgcaagt tcgacgagga cgacagcgag  3780
cctgtgctga agggcgttaa gctgcactac acctga                            3816

SEQ ID NO: 9            moltype = RNA  length = 3816
FEATURE                 Location/Qualifiers
source                  1..3816
                        mol_type = other RNA
                        organism = synthetic construct
SEQUENCE: 9
atgttcgtgt tcctggtgct gctgcctctg gtcagcagcc agtgcgtgaa cctgagaaca  60
agaacacagc ttcctccagc ctacacaaac tcttttacac ggggcgtgta ctatcctgac  120
aaggtgttcc ggtccagcgt gctgcactca acccaagacc tgttcctgcc cttcttcagc  180
aacgtcacct ggttccacgc catccacgtg tctggcacca atggcacaaa gcgattcgat  240
aaccccgtgc tgcctttcaa cgacggcgtg tactttgcct ccatcgagaa gtccaacatc  300
atccggggct ggatcttcgg gaccacactg gatagcaaga cccagtctct gctgatcgta  360
aacaacgcca ccaacgtggt catcaaggtg tgcgagttcc agttctgcaa cgaccctttc  420
ctcgatgtgt actaccacaa gaacaacaag tcttggatgg aatcgggcgt gtatagcagc  480
gccaacaact gcaccttcga atacgtgagc cagcctttcc tgatggacct ggaaggcaaa  540
caaggcaatt ttaagaacct gagagaattc gtgttcaaaa atatagacgg ctatttcaag  600
atctacagca agcacacccc tattaatctg gtgcgggatc tgcctcaggg cttcagcgcc  660
ctcgaacctc tggtggacct gccaatcggc atcaacatta caagattcca gacgctgctc  720
gctctgcaca gatcttacct gacccctggc gacagcagca gcggctggac cgccggcgcc  780
gccgcttact acgtgggcta cctgcagcct agaacctttc tgctgaagta caacgagaac  840
ggcaccatca ctgatgccgt ggattgcgcc ctggaccctc tgtccgaaac caaatgtaca  900
ctgaagtctt ttaccgtgga aaaggaatc taccagactt ccaacttccg ggtgcagccg  960
accgagagca tcgtgcggtt ccctaacatc acaaacctgt gccccttttgg cgaggtgttc  1020
aacgccacaa gatttgctag cgtgtacgcc tggaatagaa agagaatcag caactgcgtg  1080
gccgattaca gcgtgctgta caatagcgcc tctttcagca ccttcaaatg ctacggcgtg  1140
agccccacca agctgaacga tctgtgtttt acaaacgtgt atgccgactc attcgtaatc  1200
aggggcgatg aggtgagaca gatcgctcct ggacagacag gcaaaatcgc ggactacaac  1260
tataagctgc ctgatgactt cacaggatgt gtgatcgcat ggaactccaa taacctcgac  1320
```

-continued

```
agcaaggtgg gcggaaatta caattaccgc tacagactgt ttagaaagag caatctgaaa  1380
cctttcgaga gagacatcag cacagagatc taccaggccg gcagcaagcc ctgtaacggc  1440
gtcgagggct tcaactgcta cttcccctg cagagctacg gcttccagcc taccaacggc  1500
gtgggatacc agccttacag agtggtggtg ctgagcttcg agctgctgca tgctcctgct  1560
acagtgtgtg gtcctaagaa gagcaccaac ctggttaaga acaagtgcgt gaattttaac  1620
ttcaatggac tgaccggaac cggcgtgctg accgaaagca acaagaaatt cctgcctttt  1680
cagcagtttg gcagagacat cgccgacacc accgacgccg tgagagatcc acaaaccctg  1740
gaaatcctgg acatcacacc ttgctcattt ggaggggtgt cggtgatcac acctggcacc  1800
aacaccagca accaggtggc cgtgctgtac cagggagtga attgtaccga ggtccccgtg  1860
gccattcacg ccgaccagct gacccctacc tggcgggtgt actccaccgg ctctaacgta  1920
ttccagacca gagccggctg tctgatcggc gcagaacacg tgaacaatag ctacgagtgc  1980
gacatcccta tcggagccgg gatctgcgct agctaccaga cccagacaaa ctccagaagc  2040
agagccggaa gcgtggccag ccagtctatc atcgcctaca ccatgagcct gggcgccgaa  2100
aacagcgttg cctacagcaa caattctatc gccatcccta caaacttcac catctccgtg  2160
accaccgaga tcctgcctgt cagcatgaca aagaccagcg tagactgcac aatgtacatc  2220
tgcggagatt ccaccgagtg tagtaacctc ctgctgcaat acggatcttt ctgtactcag  2280
ctgaacagag ccctgaccgg catcgccgtt gaacaggaca agaacaccca ggaggttttc  2340
gcccaggtta agcagatcta caaaacccct cctatcaagg acttcggagg ctttaacttc  2400
tcccagatcc tgcccgaccc cagcaagccc agcaagcgga gccccatcga ggacctgctg  2460
ttcaacaagg tgaccctggc cgacgccggc ttcatcaaac agtacggcga ttgcctggga  2520
gacatcgccg ctagagatct aatttgcgcc caaaagttta acggcctgac agtgctgcct  2580
ccactgctga cagacgagat gatcgcccag tacacatctg ccctgctggc tggtaccatc  2640
acatctggct ggacctttgg cgccggcccc gccctccaga tccctttccc catgcagatg  2700
gcctaccggt tcaacggcat cggcgtgacc cagaacgtgc tgtacgaaaa ccagaaactg  2760
atcgccaacc agttcaatag cgcgatcggc aaaatccagg atagcctcag ctctacaccc  2820
agcgctcttg gcaagctgca aaacgtggtg aaccagaatg cccaggccct taacaccctg  2880
gtgaagcagc tatcctctaa tttcggtgcc atcagcagcg tgctgaatga tatcctgagc  2940
agactggacc cccctgaggc cgaagtgcag atcgacagac tgatcaccgg aagactgcag  3000
agcctgcaaa cctacgtgac ccagcaactg atccgggccg cagaaatccg ggcctccgct  3060
aacctggccg ctaccaagat gagcgagtgc gtgctgggtc aaagcaagcg cgtggacttc  3120
tgtggaaaag gctaccacct gatgagcttc cctcagagcg ctccacacgg cgtggtgttc  3180
ctgcatgtga cttacgtgcc tgcccaggaa aagaacttca ccaccgcccc tgccatttgt  3240
cacgacggca aggcccactt cccccgggaa ggcgtgtttg tgtctaacgg aacacactgg  3300
tttgtgactc aaagaaactt ctacgagcca cagatcatca ccacagataa caccttcgtc  3360
agcggcaact gcgacgtggt gatcggcatc gtgaacaata ctgtgtacga ccccctgcag  3420
ccagagctcg attctttcaa agaggaactg gataagtact tcaagaacca cacatccccc  3480
gacgtcgacc tgggcgatat cagcggcatt aacgccagcg tggtgaacat ccagaaggaa  3540
atcgatagac tgaacgaggt ggcaaagaac ctgaatgagt ccctgattga cctgcaagag  3600
ctcgggaagt acgagcagta tatcaagtgg ccttggtaca tctggctggg cttcatcgcg  3660
ggcctgatcg ccatcgttat ggtgacgatc atgctgtgct gcatgaccag ttgctgtagc  3720
tgcctgaagg gctgctgcag ctgcggcagc tgttgcaagt tcgacgagga cgacagcgag  3780
cctgtgctga agggcgttaa gctgcactac acctga                            3816
```

```
SEQ ID NO: 10          moltype = AA  length = 1271
FEATURE                Location/Qualifiers
source                 1..1271
                       mol_type = protein
                       organism = synthetic construct
SEQUENCE: 10
MFVFLVLLPL VSSQCVNLRT RTQLPPAYTN SFTRGVYYPD KVFRSSVLHS TQDLFLPFFS  60
NVTWFHAIHV SGTNGTKRFD NPVLPFNDGV YFASIEKSNI IRGWIFGTTL DSKTQSLLIV  120
NNATNVVIKV CEFQFCNDPF LDVYYHKNNK SWMESGVYSS ANNCTFEYVS QPFLMDLEGK  180
QGNFKNLREF VFKNIDGYFK IYSKHTPINL VRDLPQGFSA LEPLVDLPIG INITRFQTLL  240
ALHRSYLTPG DSSSGWTAGA AAYYVGYLQP RTFLLKYNEN GTITDAVDCA LDPLSETKCT  300
LKSFTVEKGI YQTSNFRVQP TESIVRFPNI TNLCPFGEVF NATRFASVYA WNRKRISNCV  360
ADYSVLYNSA SFSTFKCYGV SPTKLNDLCF TNVYADSFVI RGDEVRQIAP GQTGKIADYN  420
YKLPDDFTGC VIAWNSNNLD SKVGGNYNYR YRLFRKSNLK PFERDISTEI YQAGSKPCNG  480
VEGFNCYFPL QSYGFQPTNG VGYQPYRVVV LSFELLHAPA TVCGPKKSTN LVKNKCVNFN  540
FNGLTGTGVL TESNKKFLPF QQFGRDIADT TDAVRDPQTL EILDITPCSF GGVSVITPGT  600
NTSNQVAVLY QGVNCTEVPV AIHADQLTPT WRVYSTGSNV FQTRAGCLIG AEHVNNSYEC  660
DIPIGAGICA SYQTQTNSPS RAGSVASQSI IAYTMSLGAE NSVAYSNNSI AIPTNFTISV  720
TTEILPVSMT KTSVDCTMYI CGDSTECSNL LLQYGSFCTQ LNRALTGIAV EQDKNTQEVF  780
AQVKQIYKTP PIKDFGGFNF SQILPDPSKP SKRSPIEDLL FNKVTLADAG FIKQYGDCLG  840
DIAARDLICA QKFNGLTVLP PLLTDEMIAQ YTSALLAGTI TSGWTFGAGP ALQIPFPMQM  900
AYRFNGIGVT QNVLYENQKL IANQFNSAIG KIQDSLSSTP SALGKLQNVV NQNAQALNTL  960
VKQLSSNFGA ISSVLNDILS RLDPPEAEVQ IDRLITGRLQ SLQTYVTQQL IRAAEIRASA  1020
NLAATKMSEC VLGQSKRVDF CGKGYHLMSF PQSAPHGVVF LHVTYVPAQE KNFTTAPAIC  1080
HDGKAHFPRE GVFVSNGTHW FVTQRNFYEP QIITTDNTFV SGNCDVVIGI VNNTVYDPLQ  1140
PELDSFKEEL DKYFKNHTSP DVDLGDISGI NASVVNIQKE IDRLNEVAKN LNESLIDLQE  1200
LGKYEQYIKW PWYIWLGFIA GLIAIVMVTI MLCCMTSCCS CLKGCCSCGS CCKFDEDDSE  1260
PVLKGVKLHY T                                                       1271
```

```
SEQ ID NO: 11          moltype = AA  length = 1271
FEATURE                Location/Qualifiers
source                 1..1271
                       mol_type = protein
                       organism = synthetic construct
SEQUENCE: 11
MFVFLVLLPL VSSQCVNLRT RTQLPPAYTN SFTRGVYYPD KVFRSSVLHS TQDLFLPFFS  60
```

-continued

```
NVTWFHAIHF SGTNGTKRFD NPVLPFNDGV YFASIEKSNI IRGWIFGTTL DSKTQSLLIV  120
NNATNVVIKV CEFQFCNDPF LDVYYHKNNK SWMESGVYSS ANNCTFEYVS QPFLMDLEGK  180
QGNFKNLREF VFKNIDGYFK IYSKHTPINL VRDLPQGFSV LEPLVDLPIG INITRFQTLL  240
ALHRSYLTPG DSSSGLTAGA AAYYVGYLQP RTFLLKYNEN GTITDAVDCA LDPLSETKCT  300
LKSFTVEKGI YQTSNFRVQP TESIVRFPNI TNLCPFGEVF NATRFASVYA WNRKRISNCV  360
ADYSVLYNSA SFSTFKCYGV SPTKLNDLCF TNVYADSFVI RGDEVRQIAP GQTGNIADYN  420
YKLPDDFTGC VIAWNSNNLD SKVGGNYNYR YRLFRKSNLK PFERDISTEI YQAGSKPCNG  480
VEGFNCYFPL QSYGFQPTNG VGYQPYRVVV LSFELLHAPA TVCGPKKSTN LVKNKCVNFN  540
FNGLTGTGVL TESNKKFLPF QQFGRDIADT TDAVRDPQTL EILDITPCSF GGVSVITPGT  600
NTSNQVAVLY QGVNCTEVPV AIHADQLTPT WRVYSTGSNV FQTRAGCLIG AEHVNNSYEC  660
DIPIGAGICA SYQTQTNSRS RAGSVASQSI IAYTMSLGAE NSVAYSNNSI AIPTNFTISV  720
TTEILPVSMT KTSVDCTMYI CGDSTECSNL LLQYGSFCTQ LNRALTGIAV EQDKNTQEVF  780
AQVKQIYKTP PIKDFGGFNF SQILPDPSKP SKRSPIEDLL FNKVTLADAG FIKQYGDCLG  840
DIAARDLICA QKFNGLTVLP PLLTDEMIAQ YTSALLAGTI TSGWTFGAGP ALQIPFPMQM  900
AYRFNGIGVT QNVLYENQKL IANQFNSAIG KIQDSLSSTP SALGKLQNVV NQNAQALNTL  960
VKQLSSNFGA ISSVLNDILS RLDPPEAEVQ IDRLITGRLQ SLQTYVTQQL IRAAEIRASA  1020
NLAATKMSEC VLGQSKRVDF CGKGYHLMSF PQSAPHGVVF LHVTYVPAQE KNFTTAPAIC  1080
HDGKAHFPRE GVFVSNGTHW FVTQRNFYEP QIITTDNTFV SGNCDVVIGI VNNTVYDPLQ  1140
PELDSFKEEL DKYFKNHTSP DVDLGDISGI NASVVNIQKE IDRLNEVAKN LNESLIDLQE  1200
LGKYEQYIKW PWYIWLGFIA GLIAIVMVTI MLCCMTSCCS CLKGCCSCGS CCKFDEDDSE  1260
PVLKGVKLHY T                                                     1271

SEQ ID NO: 12          moltype = DNA  length = 3816
FEATURE                Location/Qualifiers
source                 1..3816
                       mol_type = other DNA
                       organism = synthetic construct
SEQUENCE: 12
atgttcgtgt tcctggtgct gctgcctctg gtcagcagcc agtgcgtgaa cctgagaaca  60
agaacacagc ttcctccagc ctacacaaac tcttttacac ggggcgtgta ctatcctgac  120
aaggtgttcc ggtccagcgt gctgcactca acccaagacc tgttcctgcc cttcttcagc  180
aacgtcacct ggttccacgc catccacttc tctggcacca atggcacaaa gcgattcgat  240
aaccccgtgc tgcctttcaa cgacggcgtg tactttgcct ccatcgagaa gtccaacatc  300
atccggggct ggatcttcgg gaccacactg gatagcaaga cccagtctct gctgatcgta  360
aacaacgcca ccaacgtggt catcaaggtg tgcgagttcc agttctgcaa cgacccctttc  420
ctcgatgtgt actaccacaa gaacaacaag tcttggatgg aatcgggcgt gtatagcagc  480
gccaacaact gcaccttcga atacgtgagc cagcctttcc tgatggacct ggaaggcaaa  540
caaggcaatt ttaagaacct gagagaattc gtgttcaaaa atatagacgg ctatttcaag  600
atctacagca agcacacccc tattaatctg gtgcgggatc tgcctcaggg cttcagcgtc  660
ctcgaacctc tggtggacct gccaatcggc atcaacatta caagattcca gacgctgctc  720
gctctgcaca gatcttacct gacccctggc gacagcagca gcggcctgac cgccggcgcc  780
gccgcttact acgtgggcta cctgcagcct agaacctttc tgctgaagta caacgagaac  840
ggcaccatca ctgatgccgt ggattgcgcc ctggaccctc tgtccgaaac caaatgtaca  900
ctgaagtctt ttaccgtgga aaaaggaatc taccagactt ccaacttccg ggtgcagccg  960
accgagagca tcgtgcggtt ccctaacatc acaaacctgt gcccctttgg cgaggtgttc  1020
aacgccacaa gatttgctag cgtgtacgcc tggaatagaa agagaatcag caactgcgtg  1080
gccgattaca gcgtgctgta caatagcgcc tctttcagca ccttcaaatg ctacggcgtg  1140
agccccacca agctgaacga tctgtgtttt acaaacgtgt atgccgactc attcgtaatc  1200
aggggcgatg aggtgagaca gatcgctcct ggacagacag gcaacatcgc ggactacaac  1260
tataagctgc ctgatgactt cacaggatgt gtgatcgcat ggaactccaa taacctcgac  1320
agcaaggtgg gcggaaatta caattaccgc tacagactgt ttagaaagag caatctgaaa  1380
cctttcgaga gagacatcag cacagagatc taccaggccg gcagcaagcc ctgtaacggc  1440
gtcgagggct tcaactgcta cttccccctg cagagctacg gcttccagcc taccaacggc  1500
gtgggatacc agccttacag agtggtggtg ctgagcttcg agctgctgca tgctcctgct  1560
acagtgtgtg gtcctaagaa gagcaccaac ctggttaaga acaagtgcgt gaattttaac  1620
ttcaatggac tgaccggaac cggcgtgctg accgaaagca acaagaaatt cctgcctttt  1680
cagcagtttg gcagagacat cgccgacacc accgacgccg tgagagatcc acaaaccctg  1740
gaaatcctgg acatcacacc ttgctcattt ggaggggtgt cggtgatcac acctggcacc  1800
aacaccagca accaggtggc cgtgctgtac caggggagtga attgtaccga ggtccccgtg  1860
gccattcacg ccgaccagct gacccctacc tggcgggtgt actccaccgg ctctaacgta  1920
ttccagacca gagccggctg tctgatcggc gcagaacacg tgaacaatag ctacgagtgc  1980
gacatcccta tcggagccgg gatctgcgct agctaccaga cccagacaaa ctccagaagc  2040
agagccggaa gcgtggccag ccagtctatc atcgcctaca ccatgagcct gggcgccgaa  2100
aacagcgttg cctacagcaa caattctatc gccatcccta caaacttcac catctccgtg  2160
accaccgaga tcctgcctgt cagcatgaca aagaccagcg tagactgcac aatgtacatc  2220
tgcggagatt ccaccgagtg tagtaacctc ctgctgcaat acggatcttt ctgtactcag  2280
ctgaacagag ccctgaccgg catcgccgtt gaacaggaca agaacaccca ggaggttttc  2340
gcccaggtta agcagatcta caaaaccccct cctatcaagg acttcggagg ctttaacttc  2400
tcccagatcc tgcccgaccc cagcaagccc agcaagcgga gccccatcga ggacctgctg  2460
ttcaacaagg tgaccctggc cgacgccggc ttcatcaaac agtacggcga ttgcctggga  2520
gacatcgccg ctagagatct aatttgcgcc caaaagttta acggcctgac agtgctgcct  2580
ccactgctga cagacgagat gatcgcccag tacacatctg ccctgctggc tggtaccatc  2640
acatctggct ggacctttgg cgccggcccc gccctccaga tccctttccc catgcagatg  2700
gcctaccggt tcaacggcat cggcgtgacc cagaacgtgc tgtacgaaaa ccagaaactg  2760
atcgccaacc agttcaatag cgcgatcggc aaaatccagg atagcctcag ctctacaccc  2820
agcgctcttg gcaagctgca aaacgtggtg aaccagaatg cccaggccct taacaccctg  2880
gtgaagcagc tatcctctaa tttcggtgcc atcagcagcg tgctgaatga tatcctgagc  2940
agactggacc cccctgaggc cgaagtgcag atcgacagac tgatcaccgg aagactgcag  3000
agcctgcaaa cctacgtgac ccagcaactg atccgggccg cagaaatccg ggcctccgct  3060
```

-continued

```
aacctggccg ctaccaagat gagcgagtgc gtgctgggtc aaagcaagcg cgtggacttc  3120
tgtggaaaag gctaccacct gatgagcttc cctcagagcg ctccacacgg cgtggtgttc  3180
ctgcatgtga cttacgtgcc tgcccaggaa aagaacttca ccaccgcccc tgccatttgt  3240
cacgacggca aggcccactt cccccgggaa ggcgtgtttg tgtctaacgg aacacactgg  3300
tttgtgactc aaagaaactt ctacgagcca cagatcatca ccacagataa caccttcgtc  3360
agcggcaact gcgacgtggt gatcggcatc gtgaacaata ctgtgtacga ccccctgcag  3420
ccagagctcg attctttcaa agaggaactg gataagtact tcaagaacca cacatccccc  3480
gacgtcgacc tgggcgatat cagcggcatt aacgccagcg tggtgaacat ccagaaggaa  3540
atcgatagac tgaacgaggt ggcaaagaac ctgaatgagt ccctgattga cctgcaagag  3600
ctcgggaagt acgagcagta tatcaagtgg ccttggtaca tctggctggg cttcatcgcg  3660
ggcctgatcg ccatcgttat ggtgacgatc atgctgtgct gcatgaccag ttgctgtagc  3720
tgcctgaagg gctgctgcag ctgcggcagc tgttgcaagt tcgacgagga cgacagcgag  3780
cctgtgctga agggcgttaa gctgcactac acctga                           3816

SEQ ID NO: 13          moltype = RNA  length = 3816
FEATURE                Location/Qualifiers
source                 1..3816
                       mol_type = other RNA
                       organism = synthetic construct
SEQUENCE: 13
atgttcgtgt tcctggtgct gctgcctctg gtcagcagcc agtgcgtgaa cctgagaaca  60
agaacacagc ttcctccagc ctacacaaac tcttttacac ggggcgtgta ctatcctgac  120
aaggtgttcc ggtccagcgt gctgcactca acccaagacc tgttcctgcc cttcttcagc  180
aacgtcacct ggttccacgc catccacttc tctggcacca atggcacaaa gcgattcgat  240
aaccccgtgc tgcctttcaa cgacggcgtg tactttgcct ccatcgagaa gtccaacatc  300
atccggggct ggatcttcgg gaccacactg gatagcaaga cccagtctct gctgatcgta  360
aacaacgcca ccaacgtggt catcaaggtg tgcgagttcc agttctgcaa cgaccctttc  420
ctcgatgtgt actaccacaa gaacaacaag tcttggatgg aatcgggcgt gtatagcagc  480
gccaacaact gcaccttcga atacgtgagc cagcctttcc tgatggacct ggaaggcaaa  540
caaggcaatt ttaagaacct gagagaattc gtgttcaaaa atatagacgg ctatttcaag  600
atctacagca agcacacccc tattaatctg gtgcgggatc tgcctcaggg cttcagcgtc  660
ctcgaacctc tggtggacct gccaatcggc atcaacatta caagattcca gacgctgctc  720
gctctgcaca gatcttacct gacccctggc gacagcagca gcggcctgac cgccggcgcc  780
gccgcttact acgtgggcta cctgcagcct agaacctttc tgctgaagta caacgagaac  840
ggcaccatca ctgatgccgt ggattgcgcc ctggaccctc tgtccgaaac caaatgtaca  900
ctgaagtctt ttaccgtgga aaaaggaatc taccagactt ccaacttccg ggtgcagccg  960
accgagagca tcgtgcggtt ccctaacatc acaaacctgt gcccctttgg cgaggtgttc  1020
aacgccacaa gatttgctag cgtgtacgcc tggaatagaa agagaatcag caactgcgtg  1080
gccgattaca gcgtgctgta caatagcgcc tctttcagca ccttcaaatg ctacggcgtg  1140
agccccacca agctgaacga tctgtgtttt acaaacgtgt atgccgactc attcgtaatc  1200
aggggcgatg aggtgagaca gatcgctcct ggacagacag gcaacatcgc ggactacaac  1260
tataagctgc ctgatgactt cacaggatgt gtgatcgcat ggaactccaa taacctcgac  1320
agcaaggtgg gcggaaatta caattaccgc tacagactgt ttagaaagag caatctgaaa  1380
cctttcgaga gagacatcag cacagagatc taccaggccg gcagcaagcc ctgtaacggc  1440
gtcgagggct tcaactgcta cttccccctg cagagctacg gcttccagcc taccaacggc  1500
gtgggatacc agccttacag agtggtggtg ctgagcttcg agctgctgca tgctcctgct  1560
acagtgtgtg gtcctaagaa gagcaccaac ctggttaaga acaagtgcgt gaattttaac  1620
ttcaatggac tgaccggaac cggcgtgctg accgaaagca acaagaaatt cctgcctttt  1680
cagcagtttg gcagagacat cgccgacacc accgacgccg tgagagatcc acaaaccctg  1740
gaaatcctgg acatcacacc ttgctcattt ggaggggtgt cggtgatcac acctggcacc  1800
aacaccagca accaggtggc cgtgctgtac cagggagtga attgtaccga ggtccccgtg  1860
gccattcacg ccgaccagct gacccctacc tggcgggtgt actccaccgg ctctaacgta  1920
ttccagacca gagccggctg tctgatcggc gcagaacacg tgaacaatag ctacgagtgc  1980
gacatcccta tcggagccgg gatctgcgct agctaccaga cccagacaaa ctccagaagc  2040
agagccggaa gcgtggccag ccagtctatc atcgcctaca ccatgagcct gggcgccgaa  2100
aacagcgttg cctacagcaa caattctatc gccatcccta caaacttcac catctccgtg  2160
accaccgaga tcctgcctgt cagcatgaca aagaccagcg tagactgcac aatgtacatc  2220
tgcggagatt ccaccgagtg tagtaacctc ctgctgcaat acggatcttt ctgtactcag  2280
ctgaacagag ccctgaccgg catcgccgtt gaacaggaca agaacaccca ggaggttttc  2340
gcccaggtta agcagatcta caaaacccct cctatcaagg acttcggagg ctttaacttc  2400
tcccagatcc tgcccgaccc cagcaagccc agcaagcgga gccccatcga ggacctgctg  2460
ttcaacaagg tgaccctggc cgacgccggc ttcatcaaac agtacggcga ttgcctggga  2520
gacatcgccg ctagagatct aatttgcgcc caaaagttta acggcctgac agtgctgcct  2580
ccactgctga cagacgagat gatcgcccag tacacatctg ccctgctggc tggtaccatc  2640
acatctggct ggacctttgg cgccggcccc gccctccaga tccctttccc catgcagatg  2700
gcctaccggt tcaacggcat cggcgtgacc cagaacgtgc tgtacgaaaa ccagaaactg  2760
atcgccaacc agttcaatag cgcgatcggc aaaatccagg atagcctcag ctctacaccc  2820
agcgctcttg gcaagctgca aaacgtggtg aaccagaatg cccaggccct taacaccctg  2880
gtgaagcagc tatcctctaa tttcggtgcc atcagcagcg tgctgaatga tatcctgagc  2940
agactggacc cccctgaggc cgaagtgcag atcgacagac tgatcaccgg aagactgcag  3000
agcctgcaaa cctacgtgac ccagcaactg atccgggccg cagaaatccg ggcctccgct  3060
aacctggccg ctaccaagat gagcgagtgc gtgctgggtc aaagcaagcg cgtggacttc  3120
tgtggaaaag gctaccacct gatgagcttc cctcagagcg ctccacacgg cgtggtgttc  3180
ctgcatgtga cttacgtgcc tgcccaggaa aagaacttca ccaccgcccc tgccatttgt  3240
cacgacggca aggcccactt cccccgggaa ggcgtgtttg tgtctaacgg aacacactgg  3300
tttgtgactc aaagaaactt ctacgagcca cagatcatca ccacagataa caccttcgtc  3360
agcggcaact gcgacgtggt gatcggcatc gtgaacaata ctgtgtacga ccccctgcag  3420
ccagagctcg attctttcaa agaggaactg gataagtact tcaagaacca cacatccccc  3480
gacgtcgacc tgggcgatat cagcggcatt aacgccagcg tggtgaacat ccagaaggaa  3540
```

-continued

```
atcgatagac tgaacgaggt ggcaaagaac ctgaatgagt ccctgattga cctgcaagag  3600
ctcgggaagt acgagcagta tatcaagtgg ccttggtaca tctggctggg cttcatcgcg  3660
ggcctgatcg ccatcgttat ggtgacgatc atgctgtgct gcatgaccag ttgctgtagc  3720
tgcctgaagg gctgctgcag ctgcggcagc tgttgcaagt tcgacgagga cgacagcgag  3780
cctgtgctga agggcgttaa gctgcactac acctga                            3816

SEQ ID NO: 14          moltype = AA  length = 1271
FEATURE                Location/Qualifiers
source                 1..1271
                       mol_type = protein
                       organism = synthetic construct
SEQUENCE: 14
MFVFLVLLPL VSSQCVNLRT RTQLPPAYTN SFTRGVYYPD KVFRSSVLHS TQDLFLPFFS  60
NVTWFHAIHF SGTNGTKRFD NPVLPFNDGV YFASIEKSNI IRGWIFGTTL DSKTQSLLIV  120
NNATNVVIKV CEFQFCNDPF LDVYYHKNNK SWMESGVYSS ANNCTFEYVS QPFLMDLEGK  180
QGNFKNLREF VFKNIDGYFK IYSKHTPINL VRDLPQGFSV LEPLVDLPIG INITRFQTLL  240
ALHRSYLTPG DSSSGLTAGA AAYYVGYLQP RTFLLKYNEN GTITDAVDCA LDPLSETKCT  300
LKSFTVEKGI YQTSNFRVQP TESIVRFPNI TNLCPFGEVF NATRFASVYA WNRKRISNCV  360
ADYSVLYNSA SFSTFKCYGV SPTKLNDLCF TNVYADSFVI RGDEVRQIAP GQTGNIADYN  420
YKLPDDFTGC VIAWNSNKLD SKVGGNYNYR YRLFRKSNLK PFERDISTEI YQAGSKPCNG  480
VKGFNCYFPL QSYGFQPTNG VGYQPYRVVV LSFELLHAPA TVCGPKKSTN LVKNKCVNFN  540
FNGLTGTGVL TESNKKFLPF QQFGRDIADT TDAVRDPQTL EILDITPCSF GGVSVITPGT  600
NTSNQVAVLY QGVNCTEVPV AIHADQLTPT WRVYSTGSNV FQTRAGCLIG AEHVNNSYEC  660
DIPIGAGICA SYQTQTNSRS RAGSVASQSI IAYTMSLGAE NSVAYSNNSI AIPTNFTISV  720
TTEILPVSMT KTSVDCTMYI CGDSTECSNL LLQYGSFCTQ LNRALTGIAV EQDKNTQEVF  780
AQVKQIYKTP PIKDFGGFNF SQILPDPSKP SKRSPIEDLL FNKVTLADAG FIKQYGDCLG  840
DIAARDLICA QKFNGLTVLP PLLTDEMIAQ YTSALLAGTI TSGWTFGAGP ALQIPFPMQM  900
AYRFNGIGVT QNVLYENQKL IANQFNSAIG KIQDSLSSTP SALGKLQNVV NQNAQALNTL  960
VKQLSSNFGA ISSVLNDILS RLDPPEAEVQ IDRLITGRLQ SLQTYVTQQL IRAAEIRASA  1020
NLAATKMSEC VLGQSKRVDF CGKGYHLMSF PQSAPHGVVF LHVTYVPAQE KNFTTAPAIC  1080
HDGKAHFPRE GVFVSNGTHW FVTQRNFYEP QIITTDNTFV SGNCDVVIGI VNNTVYDPLQ  1140
PELDSFKEEL DKYFKNHTSP DVDLGDISGI NASVVNIQKE IDRLNEVAKN LNESLIDLQE  1200
LGKYEQYIKW PWYIWLGFIA GLIAIVMVTI MLCCMTSCCS CLKGCCSCGS CCKFDEDDSE  1260
PVLKGVKLHY T                                                       1271

SEQ ID NO: 15          moltype = DNA  length = 3816
FEATURE                Location/Qualifiers
source                 1..3816
                       mol_type = other DNA
                       organism = synthetic construct
SEQUENCE: 15
atgttcgtgt tcctggtgct gctgcctctg gtcagcagcc agtgcgtgaa cctgagaaca  60
agaacacagc ttcctccagc ctacacaaac tcttttacac ggggcgtgta ctatcctgac  120
aaggtgttcc ggtccagcgt gctgcactca acccaagacc tgttcctgcc cttcttcagc  180
aacgtcacct ggttccacgc catccacttc tctggcacca atggcacaaa gcgattcgat  240
aaccccgtgc tgcctttcaa cgacggcgtg tactttgcct ccatcgagaa gtccaacatc  300
atccggggct ggatcttcgg gaccacactg gatagcaaga cccagtctct gctgatcgta  360
aacaacgcca ccaacgtggt catcaaggtg tgcgagttcc agttctgcaa cgacccttc   420
ctcgatgtgt actaccacaa gaacaacaag tcttggatgg aatcgggcgt gtatagcagc  480
gccaacaact gcaccttcga atacgtgagc cagcctttcc tgatggacct ggaaggcaaa  540
caaggcaatt ttaagaacct gagagaattc gtgttcaaaa atatagacgg ctatttcaag  600
atctacagca agcacacccc tattaatctg gtgcgggatc tgcctcaggg cttcagcgtc  660
ctcgaacctc tggtggacct gccaatcggc atcaacatta caagattcca gacgctgctc  720
gctctgcaca gatcttacct gacccctggc gacagcagca gcggcctgac cgccggcgcc  780
gccgcttact acgtgggcta cctgcagcct agaacctttc tgctgaagta caacgagaac  840
ggcaccatca ctgatgccgt ggattgcgcc ctggaccctc tgtccgaaac caaatgtaca  900
ctgaagtctt ttaccgtgga aaaaggaatc taccagactt ccaacttccg ggtgcagccg  960
accgagagca tcgtgcggtt ccctaacatc acaaacctgt gcccctttgg cgaggtgttc  1020
aacgccacaa gatttgctag cgtgtacgcc tggaatagaa agagaatcag caactgcgtg  1080
gccgattaca gcgtgctgta caatagcgcc tctttcagca ccttcaaatg ctacggcgtg  1140
agccccacca agctgaacga tctgtgtttt acaaacgtgt atgccgactc attcgtaatc  1200
aggggcgatg aggtgagaca gatcgctcct ggacagacag gcaacatcgc ggactacaac  1260
tataagctgc ctgatgactt cacaggatgt gtgatcgcat ggaactccaa taagctcgac  1320
agcaaggtgg gcggaaatta caattaccgc tacagactgt ttagaaagag caatctgaaa  1380
cctttcgaga gagacatcag cacagagatc taccaggccg gcagcaagcc ctgtaacggc  1440
gtcaagggct tcaactgcta cttccccctg cagagctacg gcttccagcc taccaacggc  1500
gtgggatacc agccttacag agtggtggtg ctgagcttcg agctgctgca tgctcctgct  1560
acagtgtgtg gtcctaagaa gagcaccaac ctggttaaga acaagtgcgt gaattttaac  1620
ttcaatggac tgaccggaac cggcgtgctg accgaaagca acaagaaatt cctgcctttt  1680
cagcagtttg gcagagacat cgccgacacc accgacgccg tgagagatcc acaaaccctg  1740
gaaatcctgg acatcacacc ttgctcattt ggaggggtgt cggtgatcac acctggcacc  1800
aacaccagca accaggtggc cgtgctgtac cagggagtga attgtaccga ggtccccgtg  1860
gccattcacg ccgaccagct gacccctacc tggcgggtgt actccaccgg ctctaacgta  1920
ttccagacca gagccggctg tctgatcggc gcagaacacg tgaacaatag ctacgagtgc  1980
gacatcccta tcggagccgg gatctgcgct agctaccaga cccagacaaa ctccagaagc  2040
agagccggaa gcgtggccag ccagtctatc atcgcctaca ccatgagcct gggcgccgaa  2100
aacagcgttg cctacagcaa caattctatc gccatcccta caaacttcac catctccgtg  2160
accaccgaga tcctgcctgt cagcatgaca aagaccagcg tagactgcac aatgtacatc  2220
tgcggagatt ccaccgagtg tagtaacctc ctgctgcaat acggatcttt ctgtactcag  2280
```

-continued

```
ctgaacagag ccctgaccgg catcgccgtt gaacaggaca agaacaccca ggaggttttc  2340
gcccaggtta agcagatcta caaaacccct cctatcaagg acttcggagg ctttaacttc  2400
tcccagatcc tgcccgaccc cagcaagccc agcaagcgga gccccatcga ggacctgctg  2460
ttcaacaagg tgaccctggc cgacgccggc ttcatcaaac agtacggcga ttgcctggga  2520
gacatcgccg ctagagatct aatttgcgcc caaaagttta acggcctgac agtgctgcct  2580
ccactgctga cagacgagat gatcgcccag tacacatctg ccctgctggc tggtaccatc  2640
acatctggct ggacctttgg cgccggcccc gccctccaga tccctttccc catgcagatg  2700
gcctaccggt tcaacggcat cggcgtgacc cagaacgtgc tgtacgaaaa ccagaaactg  2760
atcgccaacc agttcaatag cgcgatcggc aaaatccagg atagcctcag ctctacaccc  2820
agcgctcttg gcaagctgca aaacgtggtg aaccagaatg cccaggccct taacaccctg  2880
gtgaagcagc tatcctctaa tttcggtgcc atcagcagcg tgctgaatga tatcctgagc  2940
agactggacc cccctgaggc cgaagtgcag atcgacagac tgatcaccgg aagactgcag  3000
agcctgcaaa cctacgtgac ccagcaactg atccgggccg cagaaatccg ggcctccgct  3060
aacctggccg ctaccaagat gagcgagtgc gtgctgggtc aaagcaagcg cgtggacttc  3120
tgtggaaaag gctaccacct gatgagcttc cctcagagcg ctccacacgg cgtggtgttc  3180
ctgcatgtga cttacgtgcc tgcccaggaa aagaacttca ccaccgcccc tgccatttgt  3240
cacgacggca aggcccactt cccccgggaa ggcgtgtttg tgtctaacgg aacacactgg  3300
tttgtgactc aaagaaactt ctacgagcca cagatcatca ccacagataa caccttcgtc  3360
agcggcaact gcgacgtggt gatcggcatc gtgaacaata ctgtgtacga ccccctgcag  3420
ccagagctcg attctttcaa agaggaactg gataagtact tcaagaacca cacatccccc  3480
gacgtcgacc tgggcgatat cagcggcatt aacgccagcg tggtgaacat ccagaaggaa  3540
atcgatagac tgaacgaggt ggcaaagaac ctgaatgagt ccctgattga cctgcaagag  3600
ctcgggaagt acgagcagta tatcaagtgg ccttggtaca tctggctggg cttcatcgcg  3660
ggcctgatcg ccatcgttat ggtgacgatc atgctgtgct gcatgaccag ttgctgtagc  3720
tgcctgaagg gctgctgcag ctgcggcagc tgttgcaagt tcgacgagga cgacagcgag  3780
cctgtgctga agggcgttaa gctgcactac acctga                          3816

SEQ ID NO: 16          moltype = RNA  length = 3816
FEATURE                Location/Qualifiers
source                 1..3816
                       mol_type = other RNA
                       organism = synthetic construct
SEQUENCE: 16
atgttcgtgt tcctggtgct gctgcctctg gtcagcagcc agtgcgtgaa cctgagaaca  60
agaacacagc ttcctccagc ctacacaaac tcttttacac ggggcgtgta ctatcctgac  120
aaggtgttcc ggtccagcgt gctgcactca acccaagacc tgttcctgcc cttcttcagc  180
aacgtcacct ggttccacgc catccacttc tctggcacca atggcacaaa gcgattcgat  240
aaccccgtgc tgcctttcaa cgacggcgtg tactttgcct ccatcgagaa gtccaacatc  300
atccggggct ggatcttcgg gaccacactg gatagcaaga cccagtctct gctgatcgta  360
aacaacgcca ccaacgtggt catcaaggtg tgcgagttcc agttctgcaa cgaccctttc  420
ctcgatgtgt actaccacaa gaacaacaag tcttggatgg aatcgggcgt gtatagcagc  480
gccaacaact gcaccttcga atacgtgagc cagcctttcc tgatggacct ggaaggcaaa  540
caaggcaatt ttaagaacct gagagaattc gtgttcaaaa atatagacgg ctatttcaag  600
atctacagca agcacacccc tattaatctg gtgcgggatc tgcctcaggg cttcagcgtc  660
ctcgaacctc tggtggacct gccaatcggc atcaacatta caagattcca gacgctgctc  720
gctctgcaca gatcttacct gacccctggc gacagcagca gcggcctgac cgccggcgcc  780
gccgcttact acgtgggcta cctgcagcct agaacctttc tgctgaagta caacgagaac  840
ggcaccatca ctgatgccgt ggattgcgcc ctggaccctc tgtccgaaac caaatgtaca  900
ctgaagtctt ttaccgtgga aaaaggaatc taccagactt ccaacttccg ggtgcagccg  960
accgagagca tcgtgcggtt ccctaacatc acaaacctgt gcccctttgg cgaggtgttc  1020
aacgccacaa gatttgctag cgtgtacgcc tggaatagaa agagaatcag caactgcgtg  1080
gccgattaca gcgtgctgta caatagcgcc tctttcagca ccttcaaatg ctacggcgtg  1140
agccccacca agctgaacga tctgtgtttt acaaacgtgt atgccgactc attcgtaatc  1200
aggggcgatg aggtgagaca gatcgctcct ggacagacag gcaacatcgc ggactacaac  1260
tataagctgc ctgatgactt cacaggatgt gtgatcgcat ggaactccaa taagctcgac  1320
agcaaggtgg gcggaaatta caattaccgc tacagactgt ttagaaagag caatctgaaa  1380
cctttcgaga gagacatcag cacagagatc taccaggccg gcagcaagcc ctgtaacggc  1440
gtcaagggct tcaactgcta cttccccctg cagagctacg gcttccagcc taccaacggc  1500
gtgggatacc agccttacag agtggtggtg ctgagcttcg agctgctgca tgctcctgct  1560
acagtgtgtg gtcctaagaa gagcaccaac ctggttaaga acaagtgcgt gaattttaac  1620
ttcaatggac tgaccggaac cggcgtgctg accgaaagca acaagaaatt cctgcctttt  1680
cagcagtttg gcagagacat cgccgacacc accgacgccg tgagagatcc acaaaccctg  1740
gaaatcctgg acatcacacc ttgctcattt ggaggggtgt cggtgatcac acctggcacc  1800
aacaccagca accaggtggc cgtgctgtac cagggagtga attgtaccga ggtccccgtg  1860
gccattcacg ccgaccagct gaccccctacc tggcgggtgt actccaccgg ctctaacgta  1920
ttccagacca gagccggctg tctgatcggc gcagaacacg tgaacaatag ctacgagtgc  1980
gacatcccta tcggagccgg gatctgcgct agctaccaga cccagacaaa ctccagaagc  2040
agagccggaa gcgtggccag ccagtctatc atcgcctaca ccatgagcct gggcgccgaa  2100
aacagcgttg cctacagcaa caattctatc gccatcccta caaacttcac catctccgtg  2160
accaccgaga tcctgcctgt cagcatgaca aagaccagcg tagactgcac aatgtacatc  2220
tgcggagatt ccaccgagtg tagtaacctc ctgctgcaat acggatcttt ctgtactcag  2280
ctgaacagag ccctgaccgg catcgccgtt gaacaggaca agaacaccca ggaggttttc  2340
gcccaggtta agcagatcta caaaacccct cctatcaagg acttcggagg ctttaacttc  2400
tcccagatcc tgcccgaccc cagcaagccc agcaagcgga gccccatcga ggacctgctg  2460
ttcaacaagg tgaccctggc cgacgccggc ttcatcaaac agtacggcga ttgcctggga  2520
gacatcgccg ctagagatct aatttgcgcc caaaagttta acggcctgac agtgctgcct  2580
ccactgctga cagacgagat gatcgcccag tacacatctg ccctgctggc tggtaccatc  2640
acatctggct ggacctttgg cgccggcccc gccctccaga tccctttccc catgcagatg  2700
gcctaccggt tcaacggcat cggcgtgacc cagaacgtgc tgtacgaaaa ccagaaactg  2760
```

-continued

```
atcgccaacc agttcaatag cgcgatcggc aaaatccagg atagcctcag ctctacaccc  2820
agcgctcttg gcaagctgca aaacgtggtg aaccagaatg cccaggccct taacaccctg  2880
gtgaagcagc tatcctctaa tttcggtgcc atcagcagcg tgctgaatga tatcctgagc  2940
agactggacc cccctgaggc cgaagtgcag atcgacagac tgatcaccgg aagactgcag  3000
agcctgcaaa cctacgtgac ccagcaactg atccgggccg cagaaatccg ggcctccgct  3060
aacctggccg ctaccaagat gagcgagtgc gtgctgggtc aaagcaagcg cgtggacttc  3120
tgtggaaaag gctaccacct gatgagcttc cctcagagcg ctccacacgg cgtggtgttc  3180
ctgcatgtga cttacgtgcc tgcccaggaa aagaacttca ccaccgcccc tgccatttgt  3240
cacgacggca aggcccactt cccccgggaa ggcgtgtttg tgtctaacgg aacacactgg  3300
tttgtgactc aaagaaactt ctacgagcca cagatcatca ccacagataa caccttcgtc  3360
agcggcaact gcgacgtggt gatcggcatc gtgaacaata ctgtgtacga ccccctgcag  3420
ccagagctcg attctttcaa agaggaactg gataagtact tcaagaacca cacatccccc  3480
gacgtcgacc tgggcgatat cagcggcatt aacgccagcg tggtgaacat ccagaaggaa  3540
atcgatagac tgaacgaggt ggcaaagaac ctgaatgagt ccctgattga cctgcaagag  3600
ctcgggaagt acgagcagta tatcaagtgg ccttggtaca tctggctggg cttcatcgcg  3660
ggcctgatcg ccatcgttat ggtgacgatc atgctgtgct gcatgaccag ttgctgtagc  3720
tgcctgaagg gctgctgcag ctgcggcagc tgttgcaagt tcgacgagga cgacagcgag  3780
cctgtgctga agggcgttaa gctgcactac acctga                            3816

SEQ ID NO: 17          moltype = DNA  length = 132
FEATURE                Location/Qualifiers
source                 1..132
                       mol_type = other DNA
                       organism = synthetic construct
SEQUENCE: 17
gctcgctttc ttgctgtcca atttctatta aaggttcctt tgttccctaa gtccaactac  60
taaactgggg gatattatga agggccttga gcatctggat tctgcctaat aaaaaacatt  120
tattttcatt gc                                                      132

SEQ ID NO: 18          moltype = RNA  length = 132
FEATURE                Location/Qualifiers
source                 1..132
                       mol_type = other RNA
                       organism = synthetic construct
SEQUENCE: 18
gctcgctttc ttgctgtcca atttctatta aaggttcctt tgttccctaa gtccaactac  60
taaactgggg gatattatga agggccttga gcatctggat tctgcctaat aaaaaacatt  120
tattttcatt gc                                                      132

SEQ ID NO: 19          moltype = DNA  length = 50
FEATURE                Location/Qualifiers
source                 1..50
                       mol_type = other DNA
                       organism = synthetic construct
SEQUENCE: 19
acatttgctt ctgacacaac tgtgttcact agcaacctca aacagacacc             50

SEQ ID NO: 20          moltype = RNA  length = 50
FEATURE                Location/Qualifiers
source                 1..50
                       mol_type = other RNA
                       organism = synthetic construct
SEQUENCE: 20
acatttgctt ctgacacaac tgtgttcact agcaacctca aacagacacc             50

SEQ ID NO: 21          moltype = DNA  length = 55
FEATURE                Location/Qualifiers
source                 1..55
                       mol_type = other DNA
                       organism = synthetic construct
SEQUENCE: 21
ggcgctcgag caggttcaga aggagatcaa aaacccccaa ggatcaaacg ccacc       55

SEQ ID NO: 22          moltype = RNA  length = 55
FEATURE                Location/Qualifiers
source                 1..55
                       mol_type = other RNA
                       organism = synthetic construct
SEQUENCE: 22
ggcgctcgag caggttcaga aggagatcaa aaacccccaa ggatcaaacg ccacc       55

SEQ ID NO: 23          moltype = DNA  length = 50
FEATURE                Location/Qualifiers
source                 1..50
                       mol_type = other DNA
                       organism = synthetic construct
SEQUENCE: 23
gggcgctcga gcaggttcag aaggagatca aaaaccccca aggatcaaac             50
```

-continued

```
SEQ ID NO: 24          moltype = RNA  length = 50
FEATURE                Location/Qualifiers
source                 1..50
                       mol_type = other RNA
                       organism = synthetic construct
SEQUENCE: 24
gggcgctcga gcaggttcag aaggagatca aaaaccccca aggatcaaac             50

SEQ ID NO: 25          moltype = DNA  length = 55
FEATURE                Location/Qualifiers
source                 1..55
                       mol_type = other DNA
                       organism = synthetic construct
SEQUENCE: 25
ggcgcacgag cagggagaga aggagatcaa aaacccccaa ggatcaaacg ccacc       55

SEQ ID NO: 26          moltype = RNA  length = 55
FEATURE                Location/Qualifiers
source                 1..55
                       mol_type = other RNA
                       organism = synthetic construct
SEQUENCE: 26
ggcgcacgag cagggagaga aggagatcaa aaacccccaa ggatcaaacg ccacc       55

SEQ ID NO: 27          moltype = RNA  length = 40
FEATURE                Location/Qualifiers
source                 1..40
                       mol_type = other RNA
                       organism = synthetic construct
SEQUENCE: 27
aaaaaaaaaa aaaaaaaaaa aaaaaaaaaa aaaaaaaaaa                        40

SEQ ID NO: 28          moltype = RNA  length = 121
FEATURE                Location/Qualifiers
source                 1..121
                       mol_type = other RNA
                       organism = synthetic construct
SEQUENCE: 28
aaaaaaaaaa aaaaaaaaaa aaaaaaaaaa aaaaaaaaaa aaaaaaaaaa aaaaaaaaaa  60
gaaaaaaaaa aaaaaaaaaa aaaaaaaaaa aaaaaaaaaa aaaaaaaaaa aaaaaaaaaa  120
a                                                                  121

SEQ ID NO: 29          moltype = DNA  length = 48
FEATURE                Location/Qualifiers
source                 1..48
                       mol_type = other DNA
                       organism = synthetic construct
SEQUENCE: 29
cggcaataaa aagacagaat aaaacgcacg gtgttgggtc gtttgttc               48

SEQ ID NO: 30          moltype = RNA  length = 48
FEATURE                Location/Qualifiers
source                 1..48
                       mol_type = other RNA
                       organism = synthetic construct
SEQUENCE: 30
cggcaataaa aagacagaat aaaacgcacg gtgttgggtc gtttgttc               48

SEQ ID NO: 31          moltype = DNA  length = 4146
FEATURE                Location/Qualifiers
source                 1..4146
                       mol_type = other DNA
                       organism = synthetic construct
SEQUENCE: 31
ggacatttgc ttctgacaca actgtgttca ctagcaacct caaacagaca ccgccaccat  60
gttcgtgttc ctggtgctgc tgcctctggt cagcagccag tgcgtgaacc tgagaacaag  120
aacacagctt cctccagcct acacaaactc ttttacacgg ggcgtgtact atcctgacaa  180
ggtgttccgg tccagcgtgc tgcactcaac ccaagacctg ttcctgccct tcttcagcaa  240
cgtcacctgg ttccacgcca tccacgtgtc tggcaccaat ggcacaaagc gattcgataa  300
ccccgtgctg cctttcaacg acggcgtgta ctttgcctcc atcgagaagt ccaacatcat  360
ccggggctgg atcttcggga ccacactgga tagcaagacc cagtctctgc tgatcgtaaa  420
caacgccacc aacgtggtca tcaaggtgtg cgagttccag ttctgcaacg accctttcct  480
cgatgtgtac taccacaaga acaacaagtc ttggatggaa tcgggcgtgt atagcagcgc  540
caacaactgc accttcgaat acgtgagcca gcctttcctg atggacctgg aaggcaaaca  600
aggcaatttt aagaacctga gagaattcgt gttcaaaaat atagacggct atttcaagat  660
ctacagcaag cacaccccta ttaatctggt gcgggatctg cctcagggct tcagcgccct  720
cgaacctctg gtggacctgc caatcggcat caacattaca agattccaga cgctgctcgc  780
tctgcacaga tcttacctga cccctggcga cagcagcagc ggctggaccg ccggcgccgc  840
cgcttactac gtgggctacc tgcagcctag aacctttctg ctgaagtaca acgagaacgg  900
```

-continued

```
caccatcact gatgccgtgg attgcgccct ggaccctctg tccgaaacca aatgtacact  960
gaagtctttt accgtggaaa aaggaatcta ccagacttcc aacttccggg tgcagccgac  1020
cgagagcatc gtgcggttcc ctaacatcac aaacctgtgc cccttTggcg aggtgttcaa  1080
cgccacaaga tttgctagcg tgtacgcctg gaatagaaag agaatcagca actgcgtggc  1140
cgattacagc gtgctgtaca atagcgcctc tttcagcacc ttcaaatgct acggcgtgag  1200
ccccaccaag ctgaacgatc tgtgttttac aaacgtgtat gccgactcat tcgtaatcag  1260
gggcgatgag gtgagacaga tcgctcctgg acagacaggc aaaatcgcgg actacaacta  1320
taagctgcct gatgacttca caggatgtgt gatcgcatgg aactccaata acctcgacag  1380
caaggtgggc ggaaattaca attaccgcta cagactgttt agaaagagca atctgaaacc  1440
tttcgagaga gacatcagca cagagatcta ccaggccggc agcaagccct gtaacggcgt  1500
cgagggcttc aactgctact tcccccTgca gagctacggc ttccagccta ccaacggcgt  1560
gggataccag ccttacagag tggtggtgct gagcttcgag ctgctgcatg ctcctgctac  1620
agtgtgtggt cctaagaaga gcaccaacct ggttaagaac aagtgcgtga attttaactt  1680
caatggactg accggaaccg gcgtgctgac cgaaagcaac aagaaattcc tgccttttca  1740
gcagtttggc agagacatcg ccgacaccac cgacgccgtg agagatccac aaaccctgga  1800
aatcctggac atcacacctt gctcatttgg aggggtgtcg gtgatcacac ctggcaccaa  1860
caccagcaac caggtggccg tgctgtacca gggagtgaat tgtaccgagg tccccgtggc  1920
cattcacgcc gaccagctga cccctacctg gcgggtgtac tccaccggct ctaacgtatt  1980
ccagaccaga gccggctgtc tgatcggcgc agaacacgtg aacaatagct acgagtgcga  2040
catccctatc ggagccggga tctgcgctag ctaccagacc cagacaaact ccagaagcag  2100
agccggaagc gtggccagcc agtctatcat cgcctacacc atgagcctgg gcgccgaaaa  2160
cagcgttgcc tacagcaaca attctatcgc catccctaca aacttcacca tctccgtgac  2220
caccgagatc ctgcctgtca gcatgacaaa gaccagcgta gactgcacaa tgtacatctg  2280
cggagattcc accgagtgta gtaacctcct gctgcaatac ggatctttct gtactcagct  2340
gaacagagcc ctgaccggca tcgccgttga acaggacaag aacacccagg aggttttcgc  2400
ccaggttaag cagatctaca aaacccctcc tatcaaggac ttcggaggct ttaacttctc  2460
ccagatcctg cccgacccca gcaagcccag caagcggagc ccatcgagg acctgctgtt  2520
caacaaggtg accctggccg acgccggctt catcaaacag tacggcgatt gcctgggaga  2580
catcgccgct agagatctaa tttgcgccca aaagtttaac ggcctgacag tgctgcctcc  2640
actgctgaca gacgagatga tcgcccagta cacatctgcc ctgctggctg gtaccatcac  2700
atctggctgg acctttggcg ccggcccgc cctccagatc cctttcccca tgcagatggc  2760
ctaccggttc aacggcatcg gcgtgaccca gaacgtgctg tacgaaaacc agaaactgat  2820
cgccaaccag ttcaatagcg cgatcggcaa aatccaggat agcctcagct ctacacccag  2880
cgctcttggc aagctgcaaa acgtggtgaa ccagaatgcc caggccctta acaccctggt  2940
gaagcagcta tcctctaatt tcggtgccat cagcagcgtg ctgaatgata tcctgagcag  3000
actggacccc cctgaggccg aagtgcagat cgacagactg atcaccggaa gactgcagag  3060
cctgcaaacc tacgtgaccc agcaactgat ccgggccgca gaaatccggg cctccgctaa  3120
cctggccgct accaagatga gcgagtgcgt gctgggtcaa agcaagcgcg tggacttctg  3180
tggaaaaggc taccacctga tgagcttccc tcagagcgct ccacacggcg tggtgttcct  3240
gcatgtgact tacgtgcctg cccaggaaaa gaacttcacc accgcccctg ccatttgtca  3300
cgacggcaag gcccacttcc cccgggaagg cgtgtttgtg tctaacggaa cacactggtt  3360
tgtgactcaa agaaacttct acgagccaca gatcatcacc acagataaca ccttcgtcag  3420
cggcaactgc gacgtggtga tcggcatcgt gaacaatact gtgtacgacc ccctgcagcc  3480
agagctcgat tctttcaaag aggaactgga taagtacttc aagaaccaca catcccccga  3540
cgtcgacctg ggcgatatca gcggcattaa cgccagcgtg gtgaacatcc agaaggaaat  3600
cgatagactg aacgaggtgg caaagaacct gaatgagtcc ctgattgacc tgcaagagct  3660
cgggaagtac gagcagtata tcaagtggcc ttggtacatc tggctgggct tcatcgcggg  3720
cctgatcgcc atcgttatgg tgacgatcat gctgtgctgc atgaccagtt gctgtagctg  3780
cctgaagggc tgctgcagct gcggcagctg ttgcaagttc gacgaggacg acagcgagcc  3840
tgtgctgaag ggcgttaagc tgcactacac ctgagctcgc tttcttgctg tccaatttct  3900
attaaaggtt cctttgttcc ctaagtccaa ctactaaact gggggatatt atgaagggcc  3960
ttgagcatct ggattctgcc taataaaaaa catttatttt cattgccaat aggccgaaat  4020
cggcaagcgc gatcgcaaaa aaaaaaaaaa aaaaaaaaaa aaaaaaaaaa aaaaaaaaaa  4080
aaaaaagaaa aaaaaaaaaa aaaaaaaaaa aaaaaaaaaa aaaaaaaaaa aaaaaaaaaa  4140
aaaaaa                                                             4146

SEQ ID NO: 32          moltype = RNA  length = 4146
FEATURE                Location/Qualifiers
source                 1..4146
                       mol_type = other RNA
                       organism = synthetic construct
SEQUENCE: 32
ggacatttgc ttctgacaca actgtgttca ctagcaacct caaacagaca ccgccaccat  60
gttcgtgttc ctggtgctgc tgcctctggt cagcagccag tgcgtgaacc tgagaacaag  120
aacacagctt cctccagcct acacaaactc ttttacacgg ggcgtgtact atcctgacaa  180
ggtgttccgg tccagcgtgc tgcactcaac ccaagacctg ttcctgccct tcttcagcaa  240
cgtcacctgg ttccacgcca tccacgtgtc tggcaccaat ggcacaaagc gattcgataa  300
ccccgtgctg cctttcaacg acggcgtgta ctttgcctcc atcgagaagt ccaacatcat  360
ccggggctgg atcttcggga ccacactgga tagcaagacc cagtctctgc tgatcgtaaa  420
caacgccacc aacgtggtca tcaaggtgtg cgagttccag ttctgcaacg accctttcct  480
cgatgtgtac taccacaaga acaacaagtc ttggatggaa tcgggcgtgt atagcagcgc  540
caacaactgc accttcgaat acgtgagcca gcctttcctg atggacctgg aaggcaaaca  600
aggcaatttt aagaacctga gagaattcgt gttcaaaaat atagacggct atttcaagat  660
ctacagcaag cacaccccta ttaatctggt gcgggatctg cctcagggct tcagcgccct  720
cgaacctctg gtggacctgc caatcggcat caacattaca agattccaga cgctgctcgc  780
tctgcacaga tcttacctga cccctggcga cagcagcagc ggctggaccg ccggcgccgc  840
cgcttactac gtgggctacc tgcagcctag aacctttctg ctgaagtaca acgagaacgg  900
caccatcact gatgccgtgg attgcgccct ggaccctctg tccgaaacca aatgtacact  960
gaagtctttt accgtggaaa aaggaatcta ccagacttcc aacttccggg tgcagccgac  1020
```

-continued

```
cgagagcatc gtgcggttcc ctaacatcac aaacctgtgc ccctttggcg aggtgttcaa  1080
cgccacaaga tttgctagcg tgtacgcctg gaatagaaag agaatcagca actgcgtggc  1140
cgattacagc gtgctgtaca atagcgcctc tttcagcacc ttcaaatgct acggcgtgag  1200
ccccaccaag ctgaacgatc tgtgttttac aaacgtgtat gccgactcat tcgtaatcag  1260
gggcgatgag gtgagacaga tcgctcctgg acagacaggc aaaatcgcgg actacaacta  1320
taagctgcct gatgacttca caggatgtgt gatcgcatgg aactccaata acctcgacag  1380
caaggtgggc ggaaattaca attaccgcta cagactgttt agaaagagca atctgaaacc  1440
tttcgagaga gacatcagca cagagatcta ccaggccggc agcaagccct gtaacggcgt  1500
cgagggcttc aactgctact tcccccctgca gagctacggc ttccagccta ccaacggcgt  1560
gggataccag ccttacagag tggtggtgct gagcttcgag ctgctgcatg ctcctgctac  1620
agtgtgtggt cctaagaaga gcaccaacct ggttaagaac aagtgcgtga attttaactt  1680
caatggactg accggaaccg gcgtgctgac cgaaagcaac aagaaattcc tgccttttca  1740
gcagtttggc agagacatcg ccgacaccac cgacgccgtg agagatccac aaaccctgga  1800
aatcctggac atcacacctt gctcatttgg aggggtgtcg gtgatcacac ctggcaccaa  1860
caccagcaac caggtggccg tgctgtacca gggagtgaat tgtaccgagg tccccgtggc  1920
cattcacgcc gaccagctga cccctacctg gcgggtgtac tccaccggct ctaacgtatt  1980
ccagaccaga gccggctgtc tgatcggcgc agaacacgtg aacaatagct acgagtgcga  2040
catccctatc ggagccggga tctgcgctag ctaccagacc cagacaaact ccagaagcag  2100
agccggaagc gtggccagcc agtctatcat cgcctacacc atgagcctgg gcgccgaaaa  2160
cagcgttgcc tacagcaaca attctatcgc catccctaca aacttcacca tctccgtgac  2220
caccgagatc ctgcctgtca gcatgacaaa gaccagcgta gactgcacaa tgtacatctg  2280
cggagattcc accgagtgta gtaacctcct gctgcaatac ggatctttct gtactcagct  2340
gaacagagcc ctgaccggca tcgccgttga acaggacaag aacacccagg aggttttcgc  2400
ccaggttaag cagatctaca aaacccctcc tatcaaggac ttcggaggct ttaacttctc  2460
ccagatcctg cccgacccca gcaagcccag caagcggagc cccatcgagg acctgctgtt  2520
caacaaggtg accctggccg acgccggctt catcaaacag tacggcgatt gcctgggaga  2580
catcgccgct agagatctaa tttgcgccca aaagtttaac ggcctgacag tgctgcctcc  2640
actgctgaca gacgagatga tcgcccagta cacatctgcc ctgctggctg gtaccatcac  2700
atctggctgg acctttggcg ccggccccgc cctccagatc cctttcccca tgcagatggc  2760
ctaccggttc aacggcatcg gcgtgaccca gaacgtgctg tacgaaaacc agaaactgat  2820
cgccaaccag ttcaatagcg cgatcggcaa aatccaggat agcctcagct ctacacccag  2880
cgctcttggc aagctgcaaa acgtggtgaa ccagaatgcc caggccctta acaccctggt  2940
gaagcagcta tcctctaatt tcggtgccat cagcagcgtg ctgaatgata tcctgagcag  3000
actggacccc cctgaggccg aagtgcagat cgacagactg atcaccggaa gactgcagag  3060
cctgcaaacc tacgtgaccc agcaactgat ccgggccgca gaaatccggg cctccgctaa  3120
cctggccgct accaagatga gcgagtgcgt gctgggtcaa agcaagcgcg tggacttctg  3180
tggaaaaggc taccacctga tgagcttccc tcagagcgct ccacacggcg tggtgttcct  3240
gcatgtgact tacgtgcctg cccaggaaaa gaacttcacc accgcccctg ccatttgtca  3300
cgacggcaag gcccacttcc cccgggaagg cgtgtttgtg tctaacggaa cacactggtt  3360
tgtgactcaa agaaacttct acgagccaca gatcatcacc acagataaca ccttcgtcag  3420
cggcaactgc gacgtggtga tcggcatcgt gaacaatact gtgtacgacc ccctgcagcc  3480
agagctcgat tctttcaaag aggaactgga taagtacttc aagaaccaca catccccccga  3540
cgtcgacctg ggcgatatca gcggcattaa cgccagcgtg gtgaacatcc agaaggaaat  3600
cgatagactg aacgaggtgg caaagaacct gaatgagtcc ctgattgacc tgcaagagct  3660
cgggaagtac gagcagtata tcaagtggcc ttggtacatc tggctgggct tcatcgcggg  3720
cctgatcgcc atcgttatgg tgacgatcat gctgtgctgc atgaccagtt gctgtagctg  3780
cctgaagggc tgctgcagct gcggcagctg ttgcaagttc gacgaggacg acagcgagcc  3840
tgtgctgaag ggcgttaagc tgcactacac ctgagctcgc tttcttgctg tccaatttct  3900
attaaaggtt cctttgttcc ctaagtccaa ctactaaact gggggatatt atgaagggcc  3960
ttgagcatct ggattctgcc taataaaaaa catttatttt cattgccaat aggccgaaat  4020
cggcaagcgc gatcgcaaaa aaaaaaaaaa aaaaaaaaaa aaaaaaaaaa aaaaaaaaaa  4080
aaaaaagaaa aaaaaaaaaa aaaaaaaaaa aaaaaaaaaa aaaaaaaaaa aaaaaaaaaa  4140
aaaaaa                                                             4146

SEQ ID NO: 33          moltype = DNA  length = 6601
FEATURE                Location/Qualifiers
source                 1..6601
                       mol_type = other DNA
                       organism = synthetic construct
SEQUENCE: 33
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcaggcgcc  240
attcgccatt caggctgcgc aactgttggg aagggcgatc ggtgcgggcc tcttcgctat  300
tacgccagct ggcgaaaggg ggatgtgctg caaggcgatt aagttgggta acgccagggt  360
tttcccagtc acgacgttgt aaaacgacgg ccagtgaatt cgagctcggt acctcgcgaa  420
tgcatctaga tatcggatcc cgggcccgtc gactgcagag gcctgcatgc aagctttaat  480
acgactcact ataaggacat ttgcttctga cacaactgtg ttcactagca acctcaaaca  540
gacaccgcca ccatgttcgt gttcctggtg ctgctgcctc tggtcagcag ccagtgcgtg  600
aacctgagaa caagaacaca gcttcctcca gcctacacaa actcttttac acggggcgtg  660
tactatcctg acaaggtgtt ccggtccagc gtgctgcact caacccaaga cctgttcctg  720
cccttcttca gcaacgtcac ctggttccac gccatccacg tgtctggcac caatggcaca  780
aagcgattcg ataaccccgt gctgcctttc aacgacggcg tgtactttgc ctccatcgag  840
aagtccaaca tcatccgggg ctggatcttc gggaccacac tggatagcaa gacccagtct  900
ctgctgatcg taaacaacgc caccaacgtg gtcatcaagg tgtgcgagtt ccagttctgc  960
aacgaccctt tcctcgatgt gtactaccac aagaacaaca agtcttggat ggaatcgggc  1020
gtgtatagca gcgccaacaa ctgcaccttc gaatacgtga gccagccttt cctgatggac  1080
ctggaaggca aacaaggcaa ttttaagaac ctgagagaat tcgtgttcaa aaatatagac  1140
```

-continued

```
ggctatttca agatctacag caagcacacc cctattaatc tggtgcggga tctgcctcag  1200
ggcttcagcg ccctcgaacc tctggtggac ctgccaatcg gcatcaacat tacaagattc  1260
cagacgctgc tcgctctgca cagatcttac ctgacccctg gcgacagcag cagcggctgg  1320
accgccggcg ccgccgctta ctacgtgggc tacctgcagc ctagaacctt tctgctgaag  1380
tacaacgaga acggcaccat cactgatgcc gtggattgcg ccctggaccc tctgtccgaa  1440
accaaatgta cactgaagtc ttttaccgtg gaaaaaggaa tctaccagac ttccaacttc  1500
cgggtgcagc cgaccgagag catcgtgcgg ttccctaaca tcacaaacct gtgccccttt  1560
ggcgaggtgt tcaacgccac aagatttgct agcgtgtacg cctggaatag aaagagaatc  1620
agcaactgcg tggccgatta cagcgtgctg tacaatagcg cctctttcag caccttcaaa  1680
tgctacggcg tgagccccac caagctgaac gatctgtgtt ttacaaacgt gtatgccgac  1740
tcattcgtaa tcaggggcga tgaggtgaga cagatcgctc ctggacagac aggcaaaatc  1800
gcggactaca actataagct gcctgatgac ttcacaggat gtgtgatcgc atggaactcc  1860
aataacctcg acagcaaggt gggcggaaat tacaattacc gctacagact gtttagaaag  1920
agcaatctga aacctttcga gagagacatc agcacagaga tctaccaggc cggcagcaag  1980
ccctgtaacg gcgtcgaggg cttcaactgc tacttccccc tgcagagcta cggcttccag  2040
cctaccaacg gcgtgggata ccagccttac agagtggtgg tgctgagctt cgagctgctg  2100
catgctcctg ctacagtgtg tggtcctaag aagagcacca acctggttaa gaacaagtgc  2160
gtgaatttta acttcaatgg actgaccgga accggcgtgc tgaccgaaag caacaagaaa  2220
ttcctgcctt ttcagcagtt tggcagagac atcgccgaca ccaccgacgc cgtgagagat  2280
ccacaaaccc tggaaatcct ggacatcaca ccttgctcat ttggaggggt gtcggtgatc  2340
acacctggca ccaacaccag caaccaggtg gccgtgctgt accagggagt gaattgtacc  2400
gaggtccccg tggccattca cgccgaccag ctgaccccta cctggcgggt gtactccacc  2460
ggctctaacg tattccagac cagagccggc tgtctgatcg gcgcagaaca cgtgaacaat  2520
agctacgagt gcgacatccc tatcggagcc gggatctgcg ctagctacca gacccagaca  2580
aactccagaa gcagagccgg aagcgtggcc agccagtcta tcatcgccta caccatgagc  2640
ctgggcgccg aaaacagcgt tgcctacagc aacaattcta tcgccatccc tacaaacttc  2700
accatctccg tgaccaccga gatcctgcct gtcagcatga caaagaccag cgtagactgc  2760
acaatgtaca tctgcggaga ttccaccgag tgtagtaacc tcctgctgca atacggatct  2820
ttctgtactc agctgaacag agccctgacc ggcatcgccg ttgaacagga caagaacacc  2880
caggaggttt tcgcccaggt taagcagatc tacaaaaccc ctcctatcaa ggacttcgga  2940
ggctttaact tctcccagat cctgcccgac cccagcaagc ccagcaagcg gagccccatc  3000
gaggacctgc tgttcaacaa ggtgaccctg gccgacgccg gcttcatcaa acagtacggc  3060
gattgcctgg gagacatcgc cgctagagat ctaatttgcg cccaaaagtt taacggcctg  3120
acagtgctgc ctccactgct gacagacgag atgatcgccc agtacacatc tgccctgctg  3180
gctggtacca tcacatctgg ctggaccttt ggcgccggcc ccgccctcca gatccctttc  3240
cccatgcaga tggcctaccg gttcaacggc atcggcgtga cccagaacgt gctgtacgaa  3300
aaccagaaac tgatcgccaa ccagttcaat agcgcgatcg gcaaaatcca ggatagcctc  3360
agctctacac ccagcgctct tggcaagctg caaaacgtgg tgaaccagaa tgcccaggcc  3420
cttaacaccc tggtgaagca gctatcctct aatttcggtg ccatcagcag cgtgctgaat  3480
gatatcctga gcagactgga ccccccctgag gccgaagtgc agatcgacag actgatcacc  3540
ggaagactgc agagcctgca aacctacgtg acccagcaac tgatccgggc cgcagaaatc  3600
cgggcctccg ctaacctggc cgctaccaag atgagcgagt gcgtgctggg tcaaagcaag  3660
cgcgtggact tctgtggaaa aggctaccac ctgatgagct tccctcagag cgctccacac  3720
ggcgtggtgt tcctgcatgt gacttacgtg cctgcccagg aaaagaactt caccaccgcc  3780
cctgccattt gtcacgacgg caaggcccac ttcccccggg aaggcgtgtt tgtgtctaac  3840
ggaacacact ggtttgtgac tcaaagaaac ttctacgagc cacagatcat caccacagat  3900
aacaccttcg tcagcggcaa ctgcgacgtg gtgatcggca tcgtgaacaa tactgtgtac  3960
gacccccctgc agccagagct cgattctttc aaagaggaac tggataagta cttcaagaac  4020
cacacatccc ccgacgtcga cctgggcgat atcagcggca ttaacgccag cgtggtgaac  4080
atccagaagg aaatcgatag actgaacgag gtggcaaaga acctgaatga gtccctgatt  4140
gacctgcaag agctcgggaa gtacgagcag tatatcaagt ggccttggta catctggctg  4200
ggcttcatcg cgggcctgat cgccatcgtt atggtgacga tcatgctgtg ctgcatgacc  4260
agttgctgta gctgcctgaa gggctgctgc agctgcggca gctgttgcaa gttcgacgag  4320
gacgacagcg agcctgtgct gaagggcgtt aagctgcact acacctgagc tcgctttctt  4380
gctgtccaat ttctattaaa ggttcctttg ttccctaagt ccaactacta aactggggga  4440
tattatgaag ggccttgagc atctggattc tgcctaataa aaaacattta ttttcattgc  4500
caataggccg aaatcggcaa gcgcgatcgc aaaaaaaaaa aaaaaaaaaa aaaaaaaaaa  4560
aaaaaaaaaa aaaaaaaaaa gaaaaaaaaa aaaaaaaaaa aaaaaaaaaa aaaaaaaaaa  4620
aaaaaaaaaa aaaaaaaaaa agaattcctc gagatttaaa ttcgcgagta ctatgcatat  4680
gggcccaata ttaattaagc gctagcacgc gtttaaacag gcctcgaggc gcgcccgctt  4740
cctcgctcac tgactcgctg cgctcggtcg ttcggctgcg gcgagcggta tcagctcact  4800
caaaggcggt aatacggtta tccacagaat caggggataa cgcaggaaag aacatgtgag  4860
caaaaggcca gcaaaaggcc aggaaccgta aaaaggccgc gttgctggcg tttttccata  4920
ggctccgccc ccctgacgag catcacaaaa atcgacgctc aagtcagagg tggcgaaacc  4980
cgacaggact ataaagatac caggcgtttc cccctggaag ctccctcgtg cgctctcctg  5040
ttccgaccct gccgcttacc ggatacctgt ccgcctttct cccttcggga agcgtggcgc  5100
tttctcatag ctcacgctgt aggtatctca gttcggtgta ggtcgttcgc tccaagctgg  5160
gctgtgtgca cgaacccccc gttcagcccg accgctgcgc cttatccggt aactatcgtc  5220
ttgagtccaa cccggtaaga cacgacttat cgccactggc agcagccact ggtaacagga  5280
ttagcagagc gaggtatgta ggcggtgcta cagagttctt gaagtggtgg cctaactacg  5340
gctacactag aagaacagta tttggtatct gcgctctgct gaagccagtt accttcggaa  5400
aaagagttgg tagctcttga tccggcaaac aaaccaccgc tggtagcggt ggtttttttg  5460
tttgcaagca gcagattacg cgcagaaaaa aaggatctca agaagatcct ttgatctttt  5520
ctacggggtc tgacgctcag tggaacgaaa actcacgtta agggattttg gtcatgagat  5580
tatcaaaaag gatcttcacc tagatccttt taaattaaaa atgaagtttt aaatcaagcc  5640
caatctgaat aatgttacaa ccaattaacc aattctgatt agaaaaactc atcgagcatc  5700
aaatgaaact gcaatttatt catatcagga ttatcaatac catatttttg aaaaagccgt  5760
ttctgtaatg aaggagaaaa ctcaccgagg cagttccata ggatggcaag atcctggtat  5820
cggtctgcga ttccgactcg tccaacatca atacaaccta ttaatttccc ctcgtcaaaa  5880
```

-continued

```
ataaggttat caagtgagaa atcaccatga gtgacgactg aatccggtga gaatggcaaa  5940
agtttatgca tttctttcca gacttgttca acaggccagc cattacgctc gtcatcaaaa  6000
tcactcgcat caaccaaacc gttattcatt cgtgattgcg cctgagcgag acgaaatacg  6060
cgatcgctgt taaaaggaca attacaaaca ggaatcgaat gcaaccggcg caggaacact  6120
gccagcgcat caacaatatt ttcacctgaa tcaggatatt cttctaatac ctggaatgct  6180
gtttttccgg ggatcgcagt ggtgagtaac catgcatcat caggagtacg gataaaatgc  6240
ttgatggtcg gaagaggcat aaattccgtc agccagttta gtctgaccat ctcatctgta  6300
acatcattgg caacgctacc tttgccatgt ttcagaaaca actctggcgc atcgggcttc  6360
ccatacaagc gatagattgt cgcacctgat tgcccgacat tatcgcgagc ccatttatac  6420
ccatataaat cagcatccat gttggaattt aatcgcggcc tcgacgtttc ccgttgaata  6480
tggctcataa cacccccttgt attactgttt atgtaagcag acagttttat tgttcatgat  6540
gatatatttt tatcttgtgc aatgtaacat cagagatttt gagacacggg ccagagctgc  6600
a                                                                  6601

SEQ ID NO: 34          moltype = AA  length = 9
FEATURE                Location/Qualifiers
source                 1..9
                       mol_type = protein
                       organism = synthetic construct
SEQUENCE: 34
KHKHKHKHK                                                          9

SEQ ID NO: 35          moltype = AA  length = 10
FEATURE                Location/Qualifiers
source                 1..10
                       mol_type = protein
                       organism = synthetic construct
SEQUENCE: 35
HKHKHKHKHK                                                         10

SEQ ID NO: 36          moltype = AA  length = 10
FEATURE                Location/Qualifiers
source                 1..10
                       mol_type = protein
                       organism = synthetic construct
SEQUENCE: 36
KHKHKHKHKH                                                         10

SEQ ID NO: 37          moltype = AA  length = 11
FEATURE                Location/Qualifiers
source                 1..11
                       mol_type = protein
                       organism = synthetic construct
SEQUENCE: 37
HKHKHKHKHK H                                                       11

SEQ ID NO: 38          moltype = AA  length = 20
FEATURE                Location/Qualifiers
source                 1..20
                       mol_type = protein
                       organism = synthetic construct
SEQUENCE: 38
KHKHHKHHKH HKHHKHHKHK                                              20

SEQ ID NO: 39          moltype = AA  length = 17
FEATURE                Location/Qualifiers
source                 1..17
                       mol_type = protein
                       organism = synthetic construct
SEQUENCE: 39
KHHHKHHHKH HHKHHHK                                                 17

SEQ ID NO: 40          moltype = AA  length = 18
FEATURE                Location/Qualifiers
source                 1..18
                       mol_type = protein
                       organism = synthetic construct
SEQUENCE: 40
KHHHKHHHKH HHHKHHHK                                                18

SEQ ID NO: 41          moltype = AA  length = 18
FEATURE                Location/Qualifiers
source                 1..18
                       mol_type = protein
                       organism = synthetic construct
SITE                   1
                       note = D-lysine
SITE                   5
                       note = D-lysine
```

-continued

```
SITE                  9
                      note = D-lysine
SITE                  14
                      note = D-lysine
SITE                  18
                      note = D-lysine
SEQUENCE: 41
KHHHKHHHKH HHHKHHHK                                          18

SEQ ID NO: 42         moltype = AA  length = 19
FEATURE               Location/Qualifiers
source                1..19
                      mol_type = protein
                      organism = synthetic construct
SEQUENCE: 42
HKHHHKHHHK HHHHKHHHK                                         19

SEQ ID NO: 43         moltype = AA  length = 20
FEATURE               Location/Qualifiers
source                1..20
                      mol_type = protein
                      organism = synthetic construct
SEQUENCE: 43
HHKHHHKHHH KHHHHKHHHK                                        20

SEQ ID NO: 44         moltype = AA  length = 21
FEATURE               Location/Qualifiers
source                1..21
                      mol_type = protein
                      organism = synthetic construct
SEQUENCE: 44
KHHHHKHHHH KHHHHKHHHH K                                      21

SEQ ID NO: 45         moltype = AA  length = 18
FEATURE               Location/Qualifiers
source                1..18
                      mol_type = protein
                      organism = synthetic construct
SEQUENCE: 45
KHHHKHHHKH HHKHHHHK                                          18

SEQ ID NO: 46         moltype = AA  length = 18
FEATURE               Location/Qualifiers
source                1..18
                      mol_type = protein
                      organism = synthetic construct
SEQUENCE: 46
KHHHKHHHHK HHHKHHHK                                          18

SEQ ID NO: 47         moltype = AA  length = 19
FEATURE               Location/Qualifiers
source                1..19
                      mol_type = protein
                      organism = synthetic construct
SEQUENCE: 47
KHHHKHHHHK HHHKHHHHK                                         19

SEQ ID NO: 48         moltype = AA  length = 4
FEATURE               Location/Qualifiers
source                1..4
                      mol_type = protein
                      organism = synthetic construct
SEQUENCE: 48
RRAR                                                         4

SEQ ID NO: 49         moltype = AA  length = 4
FEATURE               Location/Qualifiers
source                1..4
                      mol_type = protein
                      organism = synthetic construct
SEQUENCE: 49
HHHK                                                         4

SEQ ID NO: 50         moltype =   length =
SEQUENCE: 50
000

SEQ ID NO: 51         moltype = DNA  length = 18
FEATURE               Location/Qualifiers
```

```
source                  1..18
                        mol_type = other DNA
                        organism = synthetic construct
SEQUENCE: 51
taatacgact cactataa                                                18

SEQ ID NO: 52           moltype = RNA  length = 4149
FEATURE                 Location/Qualifiers
source                  1..4149
                        mol_type = other RNA
                        organism = synthetic construct
SEQUENCE: 52
aggacatttg cttctgacac aactgtgttc actagcaacc tcaaacagac accgccacca  60
tgttcgtgtt cctggtgctg ctgcctctgg tcagcagcca gtgcgtgaac ctgagaacaa  120
gaacacagct tcctccagcc tacacaaact cttttacacg gggcgtgtac tatcctgaca  180
aggtgttccg gtccagcgtg ctgcactcaa cccaagacct gttcctgccc ttcttcagca  240
acgtcacctg gttccacgcc atccacgtgt ctggcaccaa tggcacaaag cgattcgata  300
accccgtgct gcctttcaac gacggcgtgt actttgcctc catcgagaag tccaacatca  360
tccggggctg gatcttcggg accacactgg atagcaagac ccagtctctg ctgatcgtaa  420
acaacgccac caacgtggtc atcaaggtgt gcgagttcca gttctgcaac gaccctttcc  480
tcgatgtgta ctaccacaag aacaacaagt cttggatgga atcgggcgtg tatagcagcg  540
ccaacaactg caccttcgaa tacgtgagcc agcctttcct gatggacctg gaaggcaaac  600
aaggcaattt taagaacctg agagaattcg tgttcaaaaa tatagacggc tatttcaaga  660
tctacagcaa gcacacccct attaatctgg tgcgggatct gcctcagggc ttcagcgccc  720
tcgaacctct ggtggacctg ccaatcggca tcaacattac aagattccag acgctgctcg  780
ctctgcacag atcttacctg acccctggcg acagcagcag cggctggacc gccggcgccg  840
ccgcttacta cgtgggctac ctgcagccta gaacctttct gctgaagtac aacgagaacg  900
gcaccatcac tgatgccgtg gattgcgccc tggaccctct gtccgaaacc aaatgtacac  960
tgaagtcttt taccgtggaa aaaggaatct accagacttc caacttccgg gtgcagccga  1020
ccgagagcat cgtgcggttc cctaacatca caaacctgtg ccccttttggc gaggtgttca  1080
acgccacaag atttgctagc gtgtacgcct ggaatagaaa gagaatcagc aactgcgtgg  1140
ccgattacag cgtgctgtac aatagcgcct ctttcagcac cttcaaatgc tacggcgtga  1200
gccccaccaa gctgaacgat ctgtgtttta caaacgtgta tgccgactca ttcgtaatca  1260
ggggcgatga ggtgagacag atcgctcctg gacagacagg caaaatcgcg gactacaact  1320
ataagctgcc tgatgacttc acaggatgtg tgatcgcatg gaactccaat aacctcgaca  1380
gcaaggtggg cggaaattac aattaccgct acagactgtt tagaaagagc aatctgaaac  1440
ctttcgagag agacatcagc acagagatct accaggccgg cagcaagccc tgtaacggcg  1500
tcgagggctt caactgctac ttccccctgc agagctacgg cttccagcct accaacggcg  1560
tgggatacca gccttacaga gtggtggtgc tgagcttcga gctgctgcat gctcctgcta  1620
cagtgtgtgg tcctaagaag agcaccaacc tggttaagaa caagtgcgtg aattttaact  1680
tcaatggact gaccggaacc ggcgtgctga ccgaaagcaa caagaaattc ctgccttttc  1740
agcagtttgg cagagacatc gccgacacca ccgacgccgt gagagatcca caaaccctgg  1800
aaatcctgga catcacacct tgctcatttg gaggggtgtc ggtgatcaca cctggcacca  1860
acaccagcaa ccaggtggcc gtgctgtacc agggagtgaa ttgtaccgag gtccccgtgg  1920
ccattcacgc cgaccagctg acccctacct ggcgggtgta ctccaccggc tctaacgtat  1980
tccagaccag agcaggctgt ctgatcggcg cagaacacgt gaacaatagc tacgagtgcg  2040
acatccctat cggagccggg atctgcgcta gctaccagac ccagacaaac tccagaagca  2100
gagccggaag cgtggccagc cagtctatca tcgcctacac catgagcctg ggcgccgaaa  2160
acagcgttgc ctacagcaac aattctatcg ccatccctac aaacttcacc atctccgtga  2220
ccaccgagat cctgcctgtc agcatgacaa agaccagcgt agactgcaca atgtacatct  2280
gcggagattc caccgagtgt agtaacctcc tgctgcaata cggatctttc tgtactcagc  2340
tgaacagagc cctgaccggc atcgccgttg aacaggacaa gaacacccag gaggttttcg  2400
cccaggttaa gcagatctac aaaacccctc ctatcaagga cttcggaggc tttaacttct  2460
cccagatcct gcccgacccc agcaagccca gcaagcggag ccccatcgag gacctgctgt  2520
tcaacaaggt gaccctggcc gacgccggct tcatcaaaca gtacggcgat tgcctgggag  2580
acatcgccgc tagagatcta atttgcgccc aaaagtttaa cggcctgaca gtgctgcctc  2640
cactgctgac agacgagatg atcgcccagt acacatctgc cctgctggct ggtaccatca  2700
catctggctg gacctttggc gccggccccg ccctccagat ccctttcccc atgcagatgg  2760
cctaccggtt caacggcatc ggcgtgaccc agaacgtgct gtacgaaaac cagaaactga  2820
tcgccaacca gttcaatagc gcgatcggca aaatccagga tagcctcagc tctacaccca  2880
gcgctcttgg caagctgcaa aacgtggtga accagaatgc ccaggccctt aacaccctgg  2940
tgaagcagct atcctctaat ttcggtgcca tcagcagcgt gctgaatgat atcctgagca  3000
gactggaccc ccctgaggcc gaagtgcaga tcgacagact gatcaccgga agactgcaga  3060
gcctgcaaac ctacgtgacc cagcaactga tccgggccgc agaaatccgg gcctccgcta  3120
acctggccgc taccaagatg agcgagtgcg tgctgggtca aagcaagcgc gtggacttct  3180
gtggaaaagg ctaccacctg atgagcttcc ctcagagcgc tccacacggc gtggtgttcc  3240
tgcatgtgac ttacgtgcct gcccaggaaa agaacttcac caccgcccct gccatttgtc  3300
acgacggcaa ggcccacttc ccccgggaag gcgtgtttgt gtctaacgga acacactggt  3360
ttgtgactca aagaaacttc tacgagccac agatcatcac cacagataac accttcgtca  3420
gcggcaactg cgacgtggtg atcggcatcg tgaacaatac tgtgtacgac cccctgcagc  3480
cagagctcga ttctttcaaa gaggaactgg ataagtactt caagaaccac acatcccccg  3540
acgtcgacct gggcgatatc agcggcatta acgccagcgt ggtgaacatc cagaaggaaa  3600
tcgatagact gaacgaggtg gcaaagaacc tgaatgagtc cctgattgac ctgcaagagc  3660
tcgggaagta cgagcagtat atcaagtggc cttggtacat ctggctgggc ttcatcgcgg  3720
gcctgatcgc catcgttatg gtgacgatca tgctgtgctg catgaccagt tgctgtagct  3780
gcctgaaggg ctgctgcagc tgcggcagct gttgcaagtt cgacgaggac gacagcgagc  3840
ctgtgctgaa gggcgttaag ctgcactaca cctgagctcg ctttcttgct gtccaatttc  3900
tattaaaggt tcctttgttc cctaagtcca actactaaac tgggggatat tatgaagggc  3960
cttgagcatc tggattctgc ctaataaaaa acatttattt tcattgccaa taggccgaaa  4020
```

-continued

```
tcggcaagcg cgatcgcaaa aaaaaaaaaa aaaaaaaaaa aaaaaaaaaa aaaaaaaaaa  4080
aagaaaaaaa aaaaaaaaaa aaaaaaaaaa aaaaaaaaaa aaaaaaaaaa aaaaaaaaaa  4140
aagaattcc                                                          4149

SEQ ID NO: 53          moltype = DNA  length = 6599
FEATURE                Location/Qualifiers
source                 1..6599
                       mol_type = other DNA
                       organism = synthetic construct
SEQUENCE: 53
ttcctcgagg cgcgcccgct tcctcgctca ctgactcgct gcgctcggtc gttcggctgc  60
ggcgagcggt atcagctcac tcaaaggcgg taatacggtt atccacagaa tcaggggata  120
acgcaggaaa gaacatgtga gcaaaaggcc agcaaaaggc caggaaccgt aaaaaggccg  180
cgttgctggc gtttttccat aggctccgcc cccctgacga gcatcacaaa aatcgacgct  240
caagtcagag gtggcgaaac ccgacaggac tataaagata ccaggcgttt ccccctggaa  300
gctccctcgt gcgctctcct gttccgaccc tgccgcttac cggatacctg tccgcctttc  360
tcccttcggg aagcgtggcg ctttctcata gctcacgctg taggtatctc agttcggtgt  420
aggtcgttcg ctccaagctg ggctgtgtgc acgaaccccc cgttcagccc gaccgctgcg  480
ccttatccgg taactatcgt cttgagtcca acccggtaag acacgactta tcgccactgg  540
cagcagccac tggtaacagg attagcagag cgaggtatgt aggcggtgct acagagttct  600
tgaagtggtg gcctaactac ggctacacta gaagaacagt atttggtatc tgcgctctgc  660
tgaagccagt taccttcgga aaaagagttg gtagctcttg atccggcaaa caaaccaccg  720
ctggtagcgg tggttttttt gtttgcaagc agcagattac gcgcagaaaa aaaggatctc  780
aagaagatcc tttgatcttt tctacggggt ctgacgctca gtggaacgaa aactcacgtt  840
aagggatttt ggtcattaga ttatcaaaaa ggatcttcac ctagatcctt ttaaattaaa  900
aatgaagttt taaatcaatc taaagtatat atgagtaaac ttggtctgac agttagaaaa  960
actcatcgag catcaaatga aactgcaatt tattcatatc aggattatca ataccatatt  1020
tttgaaaaag ccgtttctgt aatgaaggag aaaactcacc gaggcagttc cataggatgg  1080
caagatcctg gtatcggtct gcgattccga ctcgtccaac atcaatacaa cctattaatt  1140
tcccctcgtc aaaaataagg ttatcaagtg agaaatcacc atgagtgacg actgaatccg  1200
gtgagaatgg caaaagttta tgcatttctt tccagacttg ttcaacaggc cagccattac  1260
gctcgtcatc aaaatcactc gcatcaacca aaccgttatt cattcgtgat tgcgcctgag  1320
cgagacgaaa tacgcgatcg ctgttaaaag gacaattaca aacaggaatc gaatgcaacc  1380
ggcgcaggaa cactgccagc gcatcaacaa tattttcacc tgaatcatga tattcttcta  1440
atacctggaa tgctgttttc ccagggatcg cagtggtgag taaccatgca tcatcaggag  1500
tacggataaa atgcttgatg gtcggaagag gcataaattc cgtcagccag tttagtctga  1560
ccatctcatc tgtaacatca ttggcaacgc tacctttgcc atgtttcaga aacaactctg  1620
gcgcatcggg cttcccatac aatcgataga ttgtcgcacc tgattgccct acattatcgc  1680
gagcccattt atacccatat aaatcagcat ccatgttgga atttaatcgc ggcctagagc  1740
aagacgtttc ccgttgaata tggctcatac tcttcctttt tcaatattat tgaagcattt  1800
atcagggtta ttgtctcatg agcggataca tatttgaatg tatttagaaa aataaacaaa  1860
taggggttcc gcgcacattt ccccgaaaag tgccacctga cgtctaagaa accattatta  1920
tcatgacatt aacctataaa aataggcgta tcacgaggcc ctttcgtctc gcgcgtttcg  1980
gtgatgacgg tgaaaacctc tgacacatgc agctcccgga gacggtcaca gcttgtctgt  2040
aagcggatgc cgggagcaga caagcccgtc agggcgcgtc agcgggtgtt ggcgggtgtc  2100
ggggctggct taactatgcg gcatcagagc agattgtact gagagtgcac catatgcggt  2160
gtgaaatacc gcacagatgc gtaaggagaa aataccgcat caggcgccat tcgccattca  2220
ggctgcgcaa ctgttgggaa gggcgatcgg tgcgggcctc ttcgctatta cgccagctgg  2280
cgaaaggggg atgtgctgca aggcgattaa gttgggtaac gccagggttt tcccagtcac  2340
gacgttgtaa aacgacggcc agtgaattcg agctcggtac ctcgcgaatg catctagata  2400
tcggatcccg ggcccgtcga ctgcagaggc ctgcatgcaa gctttaatac gactcactat  2460
aaggacattt gcttctgaca caactgtgtt cactagcaac ctcaaacaga caccgccacc  2520
atgttcgtgt tcctggtgct gctgcctctg gtcagcagcc agtgcgtgaa cctgagaaca  2580
agaacacagc ttcctccagc ctacacaaac tcttttacac ggggcgtgta ctatcctgac  2640
aaggtgttcc ggtccagcgt gctgcactca acccaagacc tgttcctgcc cttcttcagc  2700
aacgtcacct ggttccacgc catccacgtg tctggcacca atggcacaaa gcgattcgat  2760
aaccccgtgc tgcctttcaa cgacggcgtg tactttgcct ccatcgagaa gtccaacatc  2820
atccggggct ggatcttcgg gaccacactg gatagcaaga cccagtctct gctgatcgta  2880
aacaacgcca ccaacgtggt catcaaggtg tgcgagttcc agttctgcaa cgaccctttc  2940
ctcgatgtgt actaccacaa gaacaacaag tcttggatgg aatcgggcgt gtatagcagc  3000
gccaacaact gcaccttcga atacgtgagc cagcctttcc tgatggacct ggaaggcaaa  3060
caaggcaatt ttaagaacct gagagaattc gtgttcaaaa atatagacgg ctatttcaag  3120
atctacagca agcacacccc tattaatctg gtgcgggatc tgcctcaggg cttcagcgcc  3180
ctcgaacctc tggtggacct gccaatcggc atcaacatta caagattcca gacgctgctc  3240
gctctgcaca gatcttacct gacccctggc gacagcagca gcggctggac cgccggcgcc  3300
gccgcttact acgtgggcta cctgcagcct agaacctttc tgctgaagta caacgagaac  3360
ggcaccatca ctgatgccgt ggattgcgcc ctggaccctc tgtccgaaac caaatgtaca  3420
ctgaagtctt ttaccgtgga aaaaggaatc taccagactt ccaacttccg ggtgcagccg  3480
accgagagca tcgtgcggtt ccctaacatc acaaacctgt gcccctttgg cgaggtgttc  3540
aacgccacaa gatttgctag cgtgtacgcc tggaatagaa agagaatcag caactgcgtg  3600
gccgattaca gcgtgctgta caatagcgcc tctttcagca ccttcaaatg ctacggcgtg  3660
agccccacca agctgaacga tctgtgtttt acaaacgtgt atgccgactc attcgtaatc  3720
aggggcgatg aggtgagaca gatcgctcct ggacagacag gcaaaatcgc ggactacaac  3780
tataagctgc ctgatgactt cacaggatgt gtgatcgcat ggaactccaa taacctcgac  3840
agcaaggtgg gcggaaatta caattaccgc tacagactgt ttagaaagag caatctgaaa  3900
cctttcgaga gagacatcag cacagagatc taccaggccg gcagcaagcc ctgtaacggc  3960
gtcgagggct tcaactgcta cttcccccctg cagagctacg gcttccagcc taccaacggc  4020
gtgggatacc agccttacag agtggtggtg ctgagcttcg agctgctgca tgctcctgct  4080
acagtgtgtg gtcctaagaa gagcaccaac ctggttaaga acaagtgcgt gaattttaac  4140
```

-continued

```
ttcaatggac tgaccggaac cggcgtgctg accgaaagca acaagaaatt cctgcctttt  4200
cagcagtttg gcagagacat cgccgacacc accgacgccg tgagagatcc acaaaccctg  4260
gaaatcctgg acatcacacc ttgctcattt ggaggggtgt cggtgatcac acctggcacc  4320
aacaccagca accaggtggc cgtgctgtac cagggagtga attgtaccga ggtccccgtg  4380
gccattcacg ccgaccagct gacccctacc tggcgggtgt actccaccgg ctctaacgta  4440
ttccagacca gagcaggctg tctgatcggc gcagaacacg tgaacaatag ctacgagtgc  4500
gacatcccta tcggagccgg gatctgcgct agctaccaga cccagacaaa ctccagaagc  4560
agagccggaa gcgtggccag ccagtctatc atcgcctaca ccatgagcct gggcgccgaa  4620
aacagcgttg cctacagcaa caattctatc gccatcccta caaacttcac catctccgtg  4680
accaccgaga tcctgcctgt cagcatgaca aagaccagcg tagactgcac aatgtacatc  4740
tgcggagatt ccaccgagtg tagtaacctc ctgctgcaat acggatcttt ctgtactcag  4800
ctgaacagag ccctgaccgg catcgccgtt gaacaggaca agaacaccca ggaggttttc  4860
gcccaggtta agcagatcta caaaacccct cctatcaagg acttcggagg ctttaacttc  4920
tcccagatcc tgcccgaccc cagcaagccc agcaagcgga gccccatcga ggacctgctg  4980
ttcaacaagg tgaccctggc cgacgccggc ttcatcaaac agtacggcga ttgcctggga  5040
gacatcgccg ctagagatct aatttgcgcc caaaagttta acggcctgac agtgctgcct  5100
ccactgctga cagacgagat gatcgcccag tacacatctg ccctgctggc tggtaccatc  5160
acatctggct ggacctttgg cgccggcccc gccctccaga tccctttccc catgcagatg  5220
gcctaccggt tcaacggcat cggcgtgacc cagaacgtgc tgtacgaaaa ccagaaactg  5280
atcgccaacc agttcaatag cgcgatcggc aaaatccagg atagcctcag ctctacaccc  5340
agcgctcttg gcaagctgca aaacgtggtg aaccagaatg cccaggccct taacaccctg  5400
gtgaagcagc tatcctctaa tttcggtgcc atcagcagcg tgctgaatga tatcctgagc  5460
agactggacc cccctgaggc cgaagtgcag atcgacagac tgatcaccgg aagactgcag  5520
agcctgcaaa cctacgtgac ccagcaactg atccgggccg cagaaatccg ggcctccgct  5580
aacctggccg ctaccaagat gagcgagtgc gtgctgggtc aaagcaagcg cgtggacttc  5640
tgtggaaaag gctaccacct gatgagcttc cctcagagcg ctccacacgg cgtggtgttc  5700
ctgcatgtga cttacgtgcc tgcccaggaa aagaacttca ccaccgcccc tgccatttgt  5760
cacgacggca aggcccactt cccccgggaa ggcgtgtttg tgtctaacgg aacacactgg  5820
tttgtgactc aaagaaactt ctacgagcca cagatcatca ccacagataa caccttcgtc  5880
agcggcaact gcgacgtggt gatcggcatc gtgaacaata ctgtgtacga ccccctgcag  5940
ccagagctcg attctttcaa agaggaactg gataagtact tcaagaacca cacatccccc  6000
gacgtcgacc tgggcgatat cagcggcatt aacgccagcg tggtgaacat ccagaaggaa  6060
atcgatagac tgaacgaggt ggcaaagaac ctgaatgagt ccctgattga cctgcaagag  6120
ctcgggaagt acgagcagta tatcaagtgg ccttggtaca tctggctggg cttcatcgcg  6180
ggcctgatcg ccatcgttat ggtgacgatc atgctgtgct gcatgaccag ttgctgtagc  6240
tgcctgaagg gctgctgcag ctgcggcagc tgttgcaagt tcgacgagga cgacagcgag  6300
cctgtgctga agggcgttaa gctgcactac acctgagctc gctttcttgc tgtccaattt  6360
ctattaaagg ttcctttgtt ccctaagtcc aactactaaa ctgggggata ttatgaaggg  6420
ccttgagcat ctggattctg cctaataaaa aacatttatt ttcattgcca ataggccgaa  6480
atcggcaagc gcgatcgcaa aaaaaaaaaa aaaaaaaaaa aaaaaaaaaa aaaaaaaaga  6540
aaaaaaaaaa aaaaaaaaaa aaaaaaaaaa aaaaaaaaaa aaaaaaaaaa aaaaaaaaa   6599

SEQ ID NO: 54           moltype = DNA  length = 3822
FEATURE                 Location/Qualifiers
source                  1..3822
                        mol_type = other DNA
                        organism = synthetic construct
SEQUENCE: 54
atgtttgttt ttcttgtttt attgccacta gtctctagtc agtgtgttaa ttttacaaac  60
agaactcaat taccctctgc atacactaat tctttcacac gtggtgttta ttaccctgac  120
aaagttttca gatcctcagt tttacattca actcaggact tgttcttacc tttcttttcc  180
aatgttactt ggttccatgc tatacatgtc tctgggacca atggtactaa gaggtttgat  240
aaccctgtcc taccatttaa tgatggtgtt tattttgctt ccactgagaa gtctaacata  300
ataagaggct ggatttttgg tactacttta gattcgaaga cccagtccct acttattgtt  360
aataacgcta ctaatgttgt tattaaagtc tgtgaatttc aattttgtaa ttatccattt  420
ttgggtgttt attaccacaa aaacaacaaa agttggatgg aaagtgagtt cagagtttat  480
tctagtgcga ataattgcac ttttgaatat gtctctcagc cttttcttat ggaccttgaa  540
ggaaaacagg gtaatttcaa aaatcttagt gaatttgtgt ttaagaatat tgatggttat  600
tttaaaatat attctaagca cacgcctatt aatttagtgc gtgatctccc tcagggtttt  660
tcggctttag aaccattggt agatttgcca ataggtatta acatcactag gtttcaaact  720
ttacttgctt tacatagaag ttatttgact cctggtgatt cttcttcagg ttggacagct  780
ggtgctgcag cttattatgt gggttatctt caacctagga cttttctatt aaaatataat  840
gaaaatggaa ccattacaga tgctgtagac tgtgcacttg accctctctc agaaacaaag  900
tgtacgttga aatccttcac tgtagaaaaa ggaatctatc aaacttctaa ctttagagtc  960
caaccaacag aatctattgt tagatttcct aatattacaa acttgtgccc ttttggtgaa  1020
gtttttaacg ccaccagatt tgcatctgtt tatgcttgga acaggaagag aatcagcaac  1080
tgtgttgctg attattctgt cctatataat tccgcatcat tttccacttt taagtgttat  1140
ggagtgtctc ctactaaatt aaatgatctc tgctttacta atgtctatgc agattcattt  1200
gtaattagag gtgatgaagt cagacaaatc gctccagggc aaactggaaa cattgctgat  1260
tataattata aattaccaga tgattttaca ggctgcgtta tagcttggaa ttctaacaat  1320
cttgattcta aggttggtgg taattataat tacctgtata gattgtttag gaagtctaat  1380
ctcaaacctt ttgagagaga tatttcaact gaaatctatc aggccggtag cacaccttgt  1440
aatggtgtta aaggttttaa ttgttacttt cctttacaat catatggttt ccaacccact  1500
tatggtgttg gttaccaacc atacagagta gtagtacttt cttttgaact tctacatgca  1560
ccagcaactg tttgtggacc taaaaagtct actaatttgg ttaaaaacaa atgtgtcaat  1620
ttcaacttca atggtttaac aggcacaggt gttcttactg agtctaacaa aaagtttctg  1680
cctttccaac aatttggcag agacattgct gacactactg atgctgtccg tgatccacag  1740
acacttgaga ttcttgacat tacaccatgt tcttttggtg gtgtcagtgt tataacacca  1800
ggaacaaata cttctaacca ggttgctgtt ctttatcagg gtgttaactg cacagaagtc  1860
```

-continued

```
cctgttgcta ttcatgcaga tcaacttact cctacttggc gtgtttattc tacaggttct  1920
aatgtttttc aaacacgtgc aggctgttta ataggggctg aacatgtcaa caactcatat  1980
gagtgtgaca tacccattgg tgcaggtata tgcgctagtt atcagactca gactaattct  2040
ccttcgcggg caggtagtgt agctagtcaa tccatcattg cctacactat gtcacttggt  2100
gcagaaaatt cagttgctta ctctaataac tctattgcca tacccacaaa ttttactatt  2160
agtgttacca cagaaattct accagtgtct atgaccaaga catcagtaga ttgtacaatg  2220
tacatttgtg gtgattcaac tgaatgcagc aatctttttgt tgcaatatgg cagtttttgt  2280
acacaattaa accgtgcttt aactggaata gctgttgaac aagacaaaaa cacccaagaa  2340
gtttttgcac aagtcaaaca aatttacaaa acaccaccaa ttaaagattt tggtggtttt  2400
aatttttcac aaatattacc agatccatca aaaccaagca agaggtcacc tattgaagat  2460
ctacttttca acaaagtgac acttgcagat gctggcttca tcaaacaata tggtgattgc  2520
cttggtgata ttgctgctag agacctcatt tgtgcacaaa agtttaacgg ccttactgtt  2580
ttgccacctt tgctcacaga tgaaatgatt gctcaataca cttctgcact gttagcgggt  2640
acaatcactt ctggttggac ctttggtgca ggtcctgcat tacaaatacc atttcctatg  2700
caaatggctt ataggtttaa tggtattgga gttacacaga atgttctcta tgagaaccaa  2760
aaattgattg ccaaccaatt taatagtgct attggcaaaa ttcaagactc actttcttcc  2820
acaccaagtg cacttggaaa acttcaagat gtggtcaacc aaaatgcaca agctttaaac  2880
acgcttgtta aacaacttag ctccaatttt ggtgcaattt caagtgtttt aaatgatatc  2940
ctttcacgtc ttgacccacc tgaggctgaa gtgcaaattg ataggttgat cacaggcaga  3000
cttcaaagtt tgcagacata tgtgactcaa caattaatta gagctgcaga aatcagagct  3060
tctgctaatc ttgctgctac taaaatgtca gagtgtgtac ttggacaatc aaaaagagtt  3120
gatttttgtg gaaagggcta tcatcttatg tccttccctc agtcagcacc tcatggtgta  3180
gtcttcttgc atgtgactta tgtccctgca caagaaaaga acttcacaac tgctcctgcc  3240
atttgtcatg atggaaaagc acactttcct cgtgaaggtg tctttgtttc aaatggcaca  3300
cactggtttg taacacaaag gaatttttat gaaccacaaa tcattactac agacaacaca  3360
tttgtgtctg gtaactgtga tgttgtaata ggaattgtca acaacacagt ttatgatcct  3420
ttgcaacctg aattagactc attcaaggag gagttagata aatattttaa gaatcataca  3480
tcaccagatg ttgatttagg tgacatctct ggcattaatg cttcagttgt aaacattcaa  3540
aaagaaattg accgcctcaa tgaggttgcc aagaatttaa atgaatctct catcgatctc  3600
caagaacttg gaaagtatga gcagtatata aaatggccat ggtacatttg gctaggtttt  3660
atagctggct tgattgccat agtaatggtg acaattatgc tttgctgtat gaccagttgc  3720
tgtagttgtc tcaagggctg ttgttcttgt ggatcctgct gcaaatttga tgaagacgac  3780
tctgagccag tgctcaaagg agtcaaatta cattacacat aa                    3822

SEQ ID NO: 55          moltype = RNA  length = 3816
FEATURE                Location/Qualifiers
source                 1..3816
                       mol_type = other RNA
                       organism = synthetic construct
SEQUENCE: 55
atgttcgtgt tcctggtgct gctgcctctg gtcagcagcc agtgcgtgaa cctgagaaca  60
agaacacagc ttcctccagc ctacacaaac tcttttacac ggggcgtgta ctatcctgac  120
aaggtgttcc ggtccagcgt gctgcactca acccaagacc tgttcctgcc cttcttcagc  180
aacgtcacct ggttccacgc catccacgtg tctggcacca atggcacaaa gcgattcgat  240
aaccccgtgc tgcctttcaa cgacggcgtg tactttgcct ccatcgagaa gtccaacatc  300
atccggggct ggatcttcgg gaccacactg gatagcaaga cccagtctct gctgatcgta  360
aacaacgcca ccaacgtggt catcaaggtg tgcgagttcc agttctgcaa cgaccctttc  420
ctcgatgtgt actaccacaa gaacaacaag tcttggatgg aatcgggcgt gtatagcagc  480
gccaacaact gcaccttcga atacgtgagc cagcctttcc tgatggacct ggaaggcaaa  540
caaggcaatt ttaagaacct gagagaattc gtgttcaaaa atatagacgg ctatttcaag  600
atctacagca agcacacccc tattaatctg gtgcgggatc tgcctcaggg cttcagcgcc  660
ctcgaacctc tggtggacct gccaatcggc atcaacatta caagattcca gacgctgctc  720
gctctgcaca gatcttacct gacccctggc gacagcagca gcggctggac cgccggcgcc  780
gccgcttact acgtgggcta cctgcagcct agaacctttc tgctgaagta caacgagaac  840
ggcaccatca ctgatgccgt ggattgcgcc ctggaccctc tgtccgaaac caaatgtaca  900
ctgaagtctt ttaccgtgga aaaggaatc taccagactt ccaacttccg ggtgcagccg  960
accgagagca tcgtgcggtt ccctaacatc acaaacctgt gcccctttgg cgaggtgttc  1020
aacgccacaa gatttgctag cgtgtacgcc tggaatagaa agagaatcag caactgcgtg  1080
gccgattaca gcgtgctgta caatagcgcc tctttcagca ccttcaaatg ctacggcgtg  1140
agccccacca agctgaacga tctgtgtttt acaaacgtgt atgccgactc attcgtaatc  1200
aggggcgatg aggtgagaca gatcgctcct ggacagacag gcaaaatcgc ggactacaac  1260
tataagctgc ctgatgactt cacaggatgt gtgatcgcat ggaactccaa taacctcgac  1320
agcaaggtgg gcggaaatta caattaccgc tacagactgt ttagaaagag caatctgaaa  1380
cctttcgaga gagacatcag cacagagatc taccaggccg gcagcaagcc ctgtaacggc  1440
gtcgagggct tcaactgcta cttccccctg cagagctacg gcttccagcc taccaacggc  1500
gtgggatacc agccttacag agtggtggtg ctgagcttcg agctgctgca tgctcctgct  1560
acagtgtgtg gtcctaagaa gagcaccaac ctggttaaga acaagtgcgt gaattttaac  1620
ttcaatggac tgaccggaac cggcgtgctg accgaaagca acaagaaatt cctgcctttt  1680
cagcagtttg gcagagacat cgccgacacc accgacgccg tgagagatcc acaaaccctg  1740
gaaatcctgg acatcacacc ttgctcattt ggaggggtgt cggtgatcac acctggcacc  1800
aacaccagca accaggtggc cgtgctgtac cagggagtga attgtaccga ggtccccgtg  1860
gccattcacg ccgaccagct gacccctacc tggcgggtgt actccaccgg ctctaacgta  1920
ttccagacca gagcaggctg tctgatcggc gcagaacacg tgaacaatag ctacgagtgc  1980
gacatcccta tcggagccgg gatctgcgct agctaccaga cccagacaaa ctccagaagc  2040
agagccggaa gcgtggccag ccagtctatc atcgcctaca ccatgagcct gggcgccgaa  2100
aacagcgttg cctacagcaa caattctatc gccatcccta caaacttcac catctccgtg  2160
accaccgaga tcctgcctgt cagcatgaca aagaccagcg tagactgcac aatgtacatc  2220
tgcggagatt ccaccgagtg tagtaacctc ctgctgcaat acggatcttt ctgtactcag  2280
ctgaacagag ccctgaccgg catcgccgtt gaacaggaca agaacaccca ggaggttttc  2340
```

-continued

```
gcccaggtta agcagatcta caaaacccct cctatcaagg acttcggagg ctttaacttc  2400
tcccagatcc tgcccgaccc cagcaagccc agcaagcgga gccccatcga ggacctgctg  2460
ttcaacaagg tgaccctggc cgacgccggc ttcatcaaac agtacggcga ttgcctggga  2520
gacatcgccg ctagagatct aatttgcgcc caaaagttta acggcctgac agtgctgcct  2580
ccactgctga cagacgagat gatcgcccag tacacatctg ccctgctggc tggtaccatc  2640
acatctggct ggacctttgg cgccggcccc gccctccaga tccctttccc catgcagatg  2700
gcctaccggt tcaacggcat cggcgtgacc cagaacgtgc tgtacgaaaa ccagaaactg  2760
atcgccaacc agttcaatag cgcgatcggc aaaatccagg atagcctcag ctctacaccc  2820
agcgctcttg gcaagctgca aaacgtggtg aaccagaatg cccaggccct taacaccctg  2880
gtgaagcagc tatcctctaa tttcggtgcc atcagcagcg tgctgaatga tatcctgagc  2940
agactggacc cccctgaggc cgaagtgcag atcgacagac tgatcaccgg aagactgcag  3000
agcctgcaaa cctacgtgac ccagcaactg atccgggccg cagaaatccg ggcctccgct  3060
aacctggccg ctaccaagat gagcgagtgc gtgctgggtc aaagcaagcg cgtggacttc  3120
tgtggaaaag gctaccacct gatgagcttc cctcagagcg ctccacacgg cgtggtgttc  3180
ctgcatgtga cttacgtgcc tgcccaggaa aagaacttca ccaccgcccc tgccatttgt  3240
cacgacggca aggcccactt cccccgggaa ggcgtgtttg tgtctaacgg aacacactgg  3300
tttgtgactc aaagaaactt ctacgagcca cagatcatca ccacagataa caccttcgtc  3360
agcggcaact gcgacgtggt gatcggcatc gtgaacaata ctgtgtacga ccccctgcag  3420
ccagagctcg attctttcaa agaggaactg gataagtact tcaagaacca cacatccccc  3480
gacgtcgacc tgggcgatat cagcggcatt aacgccagcg tggtgaacat ccagaaggaa  3540
atcgatagac tgaacgaggt ggcaaagaac ctgaatgagt ccctgattga cctgcaagag  3600
ctcgggaagt acgagcagta tatcaagtgg ccttggtaca tctggctggg cttcatcgcg  3660
ggcctgatcg ccatcgttat ggtgacgatc atgctgtgct gcatgaccag ttgctgtagc  3720
tgcctgaagg gctgctgcag ctgcggcagc tgttgcaagt tcgacgagga cgacagcgag  3780
cctgtgctga agggcgttaa gctgcactac acctga                            3816

SEQ ID NO: 56          moltype = DNA  length = 40
FEATURE                Location/Qualifiers
source                 1..40
                       mol_type = other DNA
                       organism = synthetic construct
SEQUENCE: 56
aaaaaaaaaa aaaaaaaaaa aaaaaaaaaa aaaaaaaaaa                        40

SEQ ID NO: 57          moltype = DNA  length = 121
FEATURE                Location/Qualifiers
source                 1..121
                       mol_type = other DNA
                       organism = synthetic construct
SEQUENCE: 57
aaaaaaaaaa aaaaaaaaaa aaaaaaaaaa aaaaaaaaaa aaaaaaaaaa aaaaaaaaaa  60
gaaaaaaaaa aaaaaaaaaa aaaaaaaaaa aaaaaaaaaa aaaaaaaaaa aaaaaaaaaa  120
a                                                                  121
```